US012564640B2

(12) United States Patent
Baum et al.

(10) Patent No.: US 12,564,640 B2
(45) **Date of Patent: *Mar. 3, 2026**

(54) PROTEIN-ANTIVIRAL COMPOUND CONJUGATES

(71) Applicant: REGENERON PHARMACEUTICALS, INC., Tarrytown, NY (US)

(72) Inventors: Alina Baum, Pleasantville, NY (US); Thomas Nittoli, Pearl River, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/225,567

(22) Filed: Jul. 24, 2023

(65) Prior Publication Data

US 2024/0100179 A1 Mar. 28, 2024

Related U.S. Application Data

(63) Continuation of application No. 17/156,525, filed on Jan. 23, 2021, now Pat. No. 11,752,214.

(60) Provisional application No. 63/094,285, filed on Oct. 20, 2020, provisional application No. 62/965,735, filed on Jan. 24, 2020.

(51) Int. Cl.

| | |
|---|---|
| ***A61K 31/519*** | (2006.01) |
| ***A61K 31/506*** | (2006.01) |
| ***A61K 31/5383*** | (2006.01) |
| ***A61K 47/68*** | (2017.01) |

(52) U.S. Cl.
CPC ........ *A61K 47/6801* (2017.08); *A61K 31/506* (2013.01); *A61K 31/5383* (2013.01); *A61K 47/6803* (2017.08); *A61K 47/6841* (2017.08)

(58) Field of Classification Search
None
See application file for complete search history.

(56) References Cited

U.S. PATENT DOCUMENTS

| | | | |
|---|---|---|---|
| 2015/0274812 A1 | 10/2015 | Swem et al. | |
| 2016/0176953 A1 | 6/2016 | Shishido et al. | |
| 2017/0189529 A1 | 7/2017 | Estelles et al. | |
| 2018/0118760 A1* | 5/2018 | Kawai | A61K 9/0014 |

(Continued)

FOREIGN PATENT DOCUMENTS

| | | |
|---|---|---|
| CN | 106589126 A | 4/2017 |
| WO | 90/14361 A1 | 11/1990 |

(Continued)

OTHER PUBLICATIONS

International Search Report and written opinion of PCT/US2021/014802 mailed May 3, 2021; 15 pages.

(Continued)

*Primary Examiner* — Karl J Puttlitz
(74) *Attorney, Agent, or Firm* — Troutman Pepper Locke LLP

(57) ABSTRACT

Provided herein are compounds, compositions, and methods for the treatment of diseases and disorders associated with influenza, including VX-787 and derivatives thereof, baloxavir and derivatives thereof, and baloxavir marboxil and derivatives thereof, and protein (e.g., antibody) drug conjugates thereof.

19 Claims, 13 Drawing Sheets

Specification includes a Sequence Listing.

(56) References Cited

U.S. PATENT DOCUMENTS

| | | | | |
|---|---|---|---|---|
| 2020/0261481 | A1* | 8/2020 | Shishido | A61K 31/5383 |
| 2021/0220478 | A1* | 7/2021 | Balkovec | A61P 31/16 |
| 2021/0393786 | A1* | 12/2021 | Low | A61K 47/54 |

FOREIGN PATENT DOCUMENTS

| | | | |
|---|---|---|---|
| WO | 2005/108418 | A1 | 11/2005 |
| WO | 2015/073476 | A1 | 5/2015 |
| WO | WO 2015/120097 | A2 | 8/2015 |
| WO | 2016/100807 | A2 | 6/2016 |
| WO | WO 2016/175224 | A1 | 11/2016 |
| WO | WO 2017/104691 | A1 | 6/2017 |
| WO | 2019/147831 | A1 | 8/2019 |
| WO | WO 2020/023323 | A1 | 1/2020 |

OTHER PUBLICATIONS

Jain et al., "Current ADC Linker Chemistry", Pharm Res (2015) 32:3526-3540; DOI 10.1007/s11095-015-1657-7.

Tan et al., "Universal influenza virus vaccines and therapeutics: where do we stand with influenza B virus?", Current Opinion In Immunology, Elsevier, Oxford, GB, vol. 53, Apr. 17, 2018, pp. 45-50, XP085474567, ISSN: 0952-7915, DOI: 10.1016/J.COI.2018.04.002.

PubChem database—«Baloxavir Marboxil», CID 124081896, Feb. 17, 2017.

Nareshkumar Jain et al.: «Current ADC Linker Chemistry», Pharm Res. Mar. 11, 2015, 32: pp. 3526-3540; doi: 10.1007/s11095-015-1657-7.

Fu et al., "Comparative Immunogenicity Evaluations of Influenza A Virus M2 Peptide as Recombinant Virus Like Particle or Conjugate Vaccines in Mice and Monkeys," Vaccine 27:1440-1447 (2009).

Strop et al., "Location Matters: Site of Conjugation Modulates Stability and Pharmacokinetics of Antibody Drug Conjugates," Chemistry & Biology 20:161-167 (2013).

CAS Registry No. 1777814-32-0, entered Jun. 10, 2015.

Zhou et al., "Advances in the Development of Site-Specific Antibody-Drug Conjugation," Anti-Cancer Agents in Medicinal Chemistry 15(7):828-836 (2015).

* cited by examiner

Conjugation of LP to Cterm of HC and LC and Nterm of LC retains binding to influenza A/H1N1/PR8 infected cells. Conjugation of LP to Nterm of HC results in loss of binding to influenza A/H1N1/PR8 infected cells Conjugation of LP to Cterm of HC and LC and Nterm of LCs enhanced antiviral activity of the ADCs over parental antibody against influenza A/H1/N1/PR8 virus by 3- to 163-fold Conjugation of LP to Cterm of HC increased antiviral activity of ADCs over parental antibody against influenza A/H1/N1/Cal09 virus by 10-fold Conjugation of LP to Cterm of HC increased antiviral activity of ADCs over parental antibody against influenza A/H1/N1/PR8 virus by 51-fold. Conjugation of LP to Cterm of LC did not increase antiviral activity over parental mAb Conjugation of LPs to Cterm of HC increased antiviral activity of ADCs over parental antibody against influenza A/H1/N1/PR8 virus by 7- and 31-fold. Conjugation of LPs to Cterm of LC did not increase antiviral activity over parental mAb Conjugation of LPs to Cterm of LC and HC increased antiviral activity of ADCs over parental antibody against influenza A/H3/N2/HK68X31 virus by 3- to 10-fold Conjugation of LP to Cterm of HC increased antiviral activity of ADCs over parental antibody against influenza A/H1/N1/PR8 virus by 71-fold Conjugation of LP to Cterm of HC retains binding to influenza A/H1N1/PR8 infected cells

SEQUENCE LISTING

```
Sequence total quantity: 296
SEQ ID NO: 1            moltype = DNA  length = 375
FEATURE                 Location/Qualifiers
misc_feature            1..375
                        note = synthetic
source                  1..375
                        mol_type = other DNA
                        organism = synthetic construct
SEQUENCE: 1
caggtgcagc tggtgcagtc tggggctgag gtgaagaagc ctgggtcctc ggtgaaggtc  60
tcctgcaagg cttctggagg caccttcagc aactatgcta tcagctgggt gcgacaggcc  120
cctggacaag ggcttgagag gatgggaggg atcatcccta tctttggtac agcaaactac  180
gcacagaagt tccagggcag agtcacgatt accacggacg aatccacgag cacagcctac  240
atggagctgg gcagcctgag atctgaggac acggccgtgt attactgtgc gagagggaag  300
gatttctatg gttcggggag ttattataac ctctttgact actggggcca gggaaccctg  360
gtcaccgtct cctca                                                   375

SEQ ID NO: 2            moltype = AA  length = 125
FEATURE                 Location/Qualifiers
REGION                  1..125
                        note = synthetic
source                  1..125
                        mol_type = protein
                        organism = synthetic construct
SEQUENCE: 2
QVQLVQSGAE VKKPGSSVKV SCKASGGTFS NYAISWVRQA PGQGLERMGG IIPIFGTANY  60
AQKFQGRVTI TTDESTSTAY MELGSLRSED TAVYYCARGK DFYGSGSYYN LFDYWGQGTL  120
VTVSS                                                              125

SEQ ID NO: 3            moltype = DNA  length = 24
FEATURE                 Location/Qualifiers
misc_feature            1..24
                        note = synthetic
source                  1..24
                        mol_type = other DNA
                        organism = synthetic construct
SEQUENCE: 3
ggaggcacct tcagcaacta tgct                                         24

SEQ ID NO: 4            moltype = AA  length = 8
FEATURE                 Location/Qualifiers
REGION                  1..8
                        note = synthetic
source                  1..8
                        mol_type = protein
                        organism = synthetic construct
SEQUENCE: 4
GGTFSNYA                                                           8

SEQ ID NO: 5            moltype = DNA  length = 24
FEATURE                 Location/Qualifiers
misc_feature            1..24
                        note = synthetic
source                  1..24
                        mol_type = other DNA
                        organism = synthetic construct
SEQUENCE: 5
atcatcccta tctttggtac agca                                         24

SEQ ID NO: 6            moltype = AA  length = 8
FEATURE                 Location/Qualifiers
REGION                  1..8
                        note = synthetic
source                  1..8
                        mol_type = protein
                        organism = synthetic construct
SEQUENCE: 6
IIPIFGTA                                                           8

SEQ ID NO: 7            moltype = DNA  length = 54
FEATURE                 Location/Qualifiers
misc_feature            1..54
                        note = synthetic
source                  1..54
                        mol_type = other DNA
                        organism = synthetic construct
SEQUENCE: 7
gcgagaggga aggatttcta tggttcgggg agttattata acctctttga ctac        54
```

```
SEQ ID NO: 8            moltype = AA  length = 18
FEATURE                 Location/Qualifiers
REGION                  1..18
                        note = synthetic
source                  1..18
                        mol_type = protein
                        organism = synthetic construct
SEQUENCE: 8
ARGKDFYGSG SYYNLFDY                                                18

SEQ ID NO: 9            moltype = DNA  length = 321
FEATURE                 Location/Qualifiers
misc_feature            1..321
                        note = synthetic
source                  1..321
                        mol_type = other DNA
                        organism = synthetic construct
SEQUENCE: 9
gacatccaga tgacccagtc tccttccacc ctgtctgcat ctgtaggaga catagtcacc  60
atcacttgcc gggccagtca gagtattagt agctggttgg cctggtatca gcagaaacca  120
gggaaagccc ctaagctcct gatctataag gcgtctagtt tacaaagtgg ggtcccatca  180
aggttcagcg gcagtggatc tgggacagaa ttcactctca ccatcagcag cctgcagcct  240
gatgattttg caacttttta ctgccaacac tataatactt attcgtggac gttcggccaa  300
gggaccaagg tggaaatcaa a                                            321

SEQ ID NO: 10           moltype = AA  length = 107
FEATURE                 Location/Qualifiers
REGION                  1..107
                        note = synthetic
source                  1..107
                        mol_type = protein
                        organism = synthetic construct
SEQUENCE: 10
DIQMTQSPST LSASVGDIVT ITCRASQSIS SWLAWYQQKP GKAPKLLIYK ASSLQSGVPS  60
RFSGSGSGTE FTLTISSLQP DDFATFYCQH YNTYSWTFGQ GTKVEIK                107

SEQ ID NO: 11           moltype = DNA  length = 18
FEATURE                 Location/Qualifiers
misc_feature            1..18
                        note = synthetic
source                  1..18
                        mol_type = other DNA
                        organism = synthetic construct
SEQUENCE: 11
cagagtatta gtagctgg                                                18

SEQ ID NO: 12           moltype = AA  length = 6
FEATURE                 Location/Qualifiers
REGION                  1..6
                        note = synthetic
source                  1..6
                        mol_type = protein
                        organism = synthetic construct
SEQUENCE: 12
QSISSW                                                             6

SEQ ID NO: 13           moltype =   length =
SEQUENCE: 13
000

SEQ ID NO: 14           moltype =   length =
SEQUENCE: 14
000

SEQ ID NO: 15           moltype = DNA  length = 27
FEATURE                 Location/Qualifiers
misc_feature            1..27
                        note = synthetic
source                  1..27
                        mol_type = other DNA
                        organism = synthetic construct
SEQUENCE: 15
caacactata atacttattc gtggacg                                      27

SEQ ID NO: 16           moltype = AA  length = 9
FEATURE                 Location/Qualifiers
REGION                  1..9
                        note = synthetic
```

-continued

```
source                  1..9
                        mol_type = protein
                        organism = synthetic construct
SEQUENCE: 16
QHYNTYSWT                                                         9

SEQ ID NO: 17           moltype = DNA  length = 360
FEATURE                 Location/Qualifiers
misc_feature            1..360
                        note = synthetic
source                  1..360
                        mol_type = other DNA
                        organism = synthetic construct
SEQUENCE: 17
caggtgcagc tggtgcagtc tggggctgag gtgaagaagt ctgggtcctc ggtgaaggtc  60
tcctgcaagg cttctggagg caccttcagc agctatgcta ttagctgggt gcgccaggcc  120
cctggacaag ggcttgagtg gatgggaggg atcatcccta tttttggtac accaagctat  180
gcacagaagt tccaggacag agtcacgatt accacggacg aatccacgag cacagtttac  240
atggagctga gcagcctgag atctgaagac acggccgtgt attactgtgc gagacagcag  300
cccgtctacc agtacaatat ggacgtctgg ggccaaggga ccacggtcac cgtctcctca  360

SEQ ID NO: 18           moltype = AA  length = 120
FEATURE                 Location/Qualifiers
REGION                  1..120
                        note = synthetic
source                  1..120
                        mol_type = protein
                        organism = synthetic construct
SEQUENCE: 18
QVQLVQSGAE VKKSGSSVKV SCKASGGTFS SYAISWVRQA PGQGLEWMGG IIPIFGTPSY  60
AQKFQDRVTI TTDESTSTVY MELSSLRSED TAVYYCARQQ PVYQYNMDVW GQGTTVTVSS  120

SEQ ID NO: 19           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 19
ggaggcacct tcagcagcta tgct                                        24

SEQ ID NO: 20           moltype = AA  length = 8
FEATURE                 Location/Qualifiers
REGION                  1..8
                        note = synthetic
source                  1..8
                        mol_type = protein
                        organism = synthetic construct
SEQUENCE: 20
GGTFSSYA                                                          8

SEQ ID NO: 21           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 21
atcatcccta tttttggtac acca                                        24

SEQ ID NO: 22           moltype = AA  length = 8
FEATURE                 Location/Qualifiers
REGION                  1..8
                        note = synthetic
source                  1..8
                        mol_type = protein
                        organism = synthetic construct
SEQUENCE: 22
IIPIFGTP                                                          8

SEQ ID NO: 23           moltype = DNA  length = 39
FEATURE                 Location/Qualifiers
misc_feature            1..39
                        note = synthetic
source                  1..39
                        mol_type = other DNA
                        organism = synthetic construct
```

-continued

```
SEQUENCE: 23
gcgagacagc agcccgtcta ccagtacaat atggacgtc                       39

SEQ ID NO: 24          moltype = AA  length = 13
FEATURE                Location/Qualifiers
REGION                 1..13
                       note = synthetic
source                 1..13
                       mol_type = protein
                       organism = synthetic construct
SEQUENCE: 24
ARQQPVYQYN MDV                                                   13

SEQ ID NO: 25          moltype = DNA  length = 321
FEATURE                Location/Qualifiers
misc_feature           1..321
                       note = synthetic
source                 1..321
                       mol_type = other DNA
                       organism = synthetic construct
SEQUENCE: 25
gacatccaga tgacccagtc tccatcctcc ctgtctgcat ctgtaggaga cagagtcacc  60
atcacttgcc gggcaagtca gggcattaga aataatttag gctggtatca gcagaaacca  120
ctgaaagccc ctaagcgcct gatctatgct gcgtccagtt tgcaaagtgg ggtcccatca  180
aggttcagcg gcagtggatc tgggacagaa ttcactctca caatcagcag cctgcagcct  240
gaagattttg caacttatta ctgtctacaa tataataatt acccgtggac gttcggccaa  300
gggaccaagg tggaaatcaa a                                          321

SEQ ID NO: 26          moltype = AA  length = 107
FEATURE                Location/Qualifiers
REGION                 1..107
                       note = synthetic
source                 1..107
                       mol_type = protein
                       organism = synthetic construct
SEQUENCE: 26
DIQMTQSPSS LSASVGDRVT ITCRASQGIR NNLGWYQQKP LKAPKRLIYA ASSLQSGVPS  60
RFSGSGSGTE FTLTISSLQP EDFATYYCLQ YNNYPWTFGQ GTKVEIK              107

SEQ ID NO: 27          moltype = DNA  length = 18
FEATURE                Location/Qualifiers
misc_feature           1..18
                       note = synthetic
source                 1..18
                       mol_type = other DNA
                       organism = synthetic construct
SEQUENCE: 27
cagggcatta gaaataat                                              18

SEQ ID NO: 28          moltype = AA  length = 6
FEATURE                Location/Qualifiers
REGION                 1..6
                       note = synthetic
source                 1..6
                       mol_type = protein
                       organism = synthetic construct
SEQUENCE: 28
QGIRNN                                                           6

SEQ ID NO: 29          moltype =   length =
SEQUENCE: 29
000

SEQ ID NO: 30          moltype =   length =
SEQUENCE: 30
000

SEQ ID NO: 31          moltype = DNA  length = 27
FEATURE                Location/Qualifiers
misc_feature           1..27
                       note = synthetic
source                 1..27
                       mol_type = other DNA
                       organism = synthetic construct
SEQUENCE: 31
ctacaatata ataattaccc gtggacg                                    27

SEQ ID NO: 32          moltype = AA  length = 9
FEATURE                Location/Qualifiers
```

```
REGION                  1..9
                        note = synthetic
source                  1..9
                        mol_type = protein
                        organism = synthetic construct
SEQUENCE: 32
LQYNNYPWT                                                            9

SEQ ID NO: 33           moltype = DNA  length = 366
FEATURE                 Location/Qualifiers
misc_feature            1..366
                        note = synthetic
source                  1..366
                        mol_type = other DNA
                        organism = synthetic construct
SEQUENCE: 33
caggtgcagc tggtgcagtc tggggctgaa gtgaagaagc ctgggtcctc ggtgaaggtc  60
tcctgcaagg cttctggagg caccttcaac agctatgcta tcagctgggt gcgacaggcc  120
cctggacaag ggcttgagtg gatgggaggc atcatcccta tctttgctac aacaaacttc  180
gcacagaagt tccagggcag agtcacgatt acctcggacg aatccacgaa cacagcctac  240
atggagctga ccagcctgag atctgaggac acggccgcgt attactgtgc aaggggggggt  300
tggtataact ggcagtacgt ggggtttgac tcctggggcc aagggaccac ggtcaccgtc  360
tcctca                                                               366

SEQ ID NO: 34           moltype = AA  length = 122
FEATURE                 Location/Qualifiers
REGION                  1..122
                        note = synthetic
source                  1..122
                        mol_type = protein
                        organism = synthetic construct
SEQUENCE: 34
QVQLVQSGAE VKKPGSSVKV SCKASGGTFN SYAISWVRQA PGQGLEWMGG IIPIFATTNF  60
AQKFQGRVTI TSDESTNTAY MELTSLRSED TAAYYCARGG WYNWQYVGFD SWGQGTTVTV  120
SS                                                                   122

SEQ ID NO: 35           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 35
ggaggcacct tcaacagcta tgct                                           24

SEQ ID NO: 36           moltype = AA  length = 8
FEATURE                 Location/Qualifiers
REGION                  1..8
                        note = synthetic
source                  1..8
                        mol_type = protein
                        organism = synthetic construct
SEQUENCE: 36
GGTFNSYA                                                             8

SEQ ID NO: 37           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 37
atcatcccta tctttgctac aaca                                           24

SEQ ID NO: 38           moltype = AA  length = 8
FEATURE                 Location/Qualifiers
REGION                  1..8
                        note = synthetic
source                  1..8
                        mol_type = protein
                        organism = synthetic construct
SEQUENCE: 38
IIPIFATT                                                             8

SEQ ID NO: 39           moltype = DNA  length = 45
FEATURE                 Location/Qualifiers
misc_feature            1..45
```

```
                         note = synthetic
source                   1..45
                         mol_type = other DNA
                         organism = synthetic construct
SEQUENCE: 39
gcaagggggg gttggtataa ctggcagtac gtggggtttg actcc                 45

SEQ ID NO: 40            moltype = AA  length = 15
FEATURE                  Location/Qualifiers
REGION                   1..15
                         note = synthetic
source                   1..15
                         mol_type = protein
                         organism = synthetic construct
SEQUENCE: 40
ARGGWYNWQY VGFDS                                                  15

SEQ ID NO: 41            moltype = DNA  length = 321
FEATURE                  Location/Qualifiers
misc_feature             1..321
                         note = synthetic
source                   1..321
                         mol_type = other DNA
                         organism = synthetic construct
SEQUENCE: 41
gacatccaga tgacccagtc tccttccacc ctgtctgcat ctgtaggaga cagagtcgcc  60
atcacttgcc gggccagtca gagtattagt acctggttgg cctggtatca gcagaaacca  120
gggaaagccc ctaagctcct gatctataag gcgtctagtt tagaaaatgg ggtcccttca  180
aggttcagcg gcagtggatc tgggacagat ttcactctca ccatcagcag cctgcaggct  240
gatgattttg caacttatta ctgccaaaag tataatagta attcgtggac gttcggccaa  300
gggaccaagg tggatatcaa a                                           321

SEQ ID NO: 42            moltype = AA  length = 107
FEATURE                  Location/Qualifiers
REGION                   1..107
                         note = synthetic
source                   1..107
                         mol_type = protein
                         organism = synthetic construct
SEQUENCE: 42
DIQMTQSPST LSASVGDRVA ITCRASQSIS TWLAWYQQKP GKAPKLLIYK ASSLENGVPS  60
RFSGSGSGTD FTLTISSLQA DDFATYYCQK YNSNSWTFGQ GTKVDIK               107

SEQ ID NO: 43            moltype = DNA  length = 18
FEATURE                  Location/Qualifiers
misc_feature             1..18
                         note = synthetic
source                   1..18
                         mol_type = other DNA
                         organism = synthetic construct
SEQUENCE: 43
cagagtatta gtacctgg                                               18

SEQ ID NO: 44            moltype = AA  length = 6
FEATURE                  Location/Qualifiers
REGION                   1..6
                         note = synthetic
source                   1..6
                         mol_type = protein
                         organism = synthetic construct
SEQUENCE: 44
QSISTW                                                            6

SEQ ID NO: 45            moltype =   length =
SEQUENCE: 45
000

SEQ ID NO: 46            moltype =   length =
SEQUENCE: 46
000

SEQ ID NO: 47            moltype = DNA  length = 27
FEATURE                  Location/Qualifiers
misc_feature             1..27
                         note = synthetic
source                   1..27
                         mol_type = other DNA
                         organism = synthetic construct
SEQUENCE: 47
```

```
caaaagtata atagtaattc gtggacg                                          27

SEQ ID NO: 48          moltype = AA  length = 9
FEATURE                Location/Qualifiers
REGION                 1..9
                       note = synthetic
source                 1..9
                       mol_type = protein
                       organism = synthetic construct
SEQUENCE: 48
QKYNSNSWT                                                              9

SEQ ID NO: 49          moltype = DNA  length = 360
FEATURE                Location/Qualifiers
misc_feature           1..360
                       note = synthetic
source                 1..360
                       mol_type = other DNA
                       organism = synthetic construct
SEQUENCE: 49
caggtccacc tggtgcagtc tgggccagag gtgaagaagc ctgggtcctc ggtgaaggtc  60
tcctgcaagg cttctggagt caccttcatc agtcatgcta tcagctgggt gcgacaggcc  120
cctggacaag ggcttgaatg ggtgggagga atcatcgcta tctttggtac aacaaactac  180
gcacagaagt tccagggcag agtcacggtt acaacggaca aatccacgaa cacagtctac  240
atggaattga gcagactgag atctgaggac acggccattt attactgtgc gcgaggtgag  300
acctactacg agggaaactt tgacttctgg ggccagggaa ccctggtcac cgtctcctca  360

SEQ ID NO: 50          moltype = AA  length = 120
FEATURE                Location/Qualifiers
REGION                 1..120
                       note = synthetic
source                 1..120
                       mol_type = protein
                       organism = synthetic construct
SEQUENCE: 50
QVHLVQSGPE VKKPGSSVKV SCKASGVTFI SHAISWVRQA PGQGLEWVGG IIAIFGTTNY  60
AQKFQGRVTV TTDKSTNTVY MELSRLRSED TAIYYCARGE TYYEGNFDFW GQGTLVTVSS  120

SEQ ID NO: 51          moltype = DNA  length = 24
FEATURE                Location/Qualifiers
misc_feature           1..24
                       note = synthetic
source                 1..24
                       mol_type = other DNA
                       organism = synthetic construct
SEQUENCE: 51
ggagtcacct tcatcagtca tgct                                             24

SEQ ID NO: 52          moltype = AA  length = 8
FEATURE                Location/Qualifiers
REGION                 1..8
                       note = synthetic
source                 1..8
                       mol_type = protein
                       organism = synthetic construct
SEQUENCE: 52
GVTFISHA                                                               8

SEQ ID NO: 53          moltype = DNA  length = 24
FEATURE                Location/Qualifiers
misc_feature           1..24
                       note = synthetic
source                 1..24
                       mol_type = other DNA
                       organism = synthetic construct
SEQUENCE: 53
atcatcgcta tctttggtac aaca                                             24

SEQ ID NO: 54          moltype = AA  length = 8
FEATURE                Location/Qualifiers
REGION                 1..8
                       note = synthetic
source                 1..8
                       mol_type = protein
                       organism = synthetic construct
SEQUENCE: 54
IIAIFGTT                                                               8

SEQ ID NO: 55          moltype = DNA  length = 39
```

-continued

```
FEATURE                Location/Qualifiers
misc_feature           1..39
                       note = synthetic
source                 1..39
                       mol_type = other DNA
                       organism = synthetic construct
SEQUENCE: 55
gcgcgaggtg agacctacta cgagggaaac tttgacttc                      39

SEQ ID NO: 56          moltype = AA  length = 13
FEATURE                Location/Qualifiers
REGION                 1..13
                       note = synthetic
source                 1..13
                       mol_type = protein
                       organism = synthetic construct
SEQUENCE: 56
ARGETYYEGN FDF                                                  13

SEQ ID NO: 57          moltype = DNA  length = 324
FEATURE                Location/Qualifiers
misc_feature           1..324
                       note = synthetic
source                 1..324
                       mol_type = other DNA
                       organism = synthetic construct
SEQUENCE: 57
gtcatccaga tgacccagtc tccatcctcc ctgtctgcat ctgtaggaga cagagtcacc  60
atcacttgcc gggccagtca gagcgttagg agtaatttaa attggtatca gcagacacca  120
gggaaagccc ctaggctcct gatctatgct gcatccagtt tgcaaagtgg ggtcccatca  180
aggttcagtg gcagtggatc tgggacagat ttcactctca ccatcagcag tctgcaacct  240
gaagattttg caacttatta ctgtcaacag agttacagta cccctccgat caccttcggc  300
caagggacac gactggagat taaa                                      324

SEQ ID NO: 58          moltype = AA  length = 108
FEATURE                Location/Qualifiers
REGION                 1..108
                       note = synthetic
source                 1..108
                       mol_type = protein
                       organism = synthetic construct
SEQUENCE: 58
VIQMTQSPSS LSASVGDRVT ITCRASQSVR SNLNWYQQTP GKAPRLLIYA ASSLQSGVPS  60
RFSGSGSGTD FTLTISSLQP EDFATYYCQQ SYSTPPITFG QGTRLEIK            108

SEQ ID NO: 59          moltype = DNA  length = 18
FEATURE                Location/Qualifiers
misc_feature           1..18
                       note = synthetic
source                 1..18
                       mol_type = other DNA
                       organism = synthetic construct
SEQUENCE: 59
cagagcgtta ggagtaat                                             18

SEQ ID NO: 60          moltype = AA  length = 6
FEATURE                Location/Qualifiers
REGION                 1..6
                       note = synthetic
source                 1..6
                       mol_type = protein
                       organism = synthetic construct
SEQUENCE: 60
QSVRSN                                                          6

SEQ ID NO: 61          moltype =   length =
SEQUENCE: 61
000

SEQ ID NO: 62          moltype =   length =
SEQUENCE: 62
000

SEQ ID NO: 63          moltype = DNA  length = 30
FEATURE                Location/Qualifiers
misc_feature           1..30
                       note = synthetic
source                 1..30
                       mol_type = other DNA
```

```
                       organism = synthetic construct
SEQUENCE: 63
caacagagtt acagtacccc tccgatcacc                         30

SEQ ID NO: 64          moltype = AA  length = 10
FEATURE                Location/Qualifiers
REGION                 1..10
                       note = synthetic
source                 1..10
                       mol_type = protein
                       organism = synthetic construct
SEQUENCE: 64
QQSYSTPPIT                                               10

SEQ ID NO: 65          moltype = DNA  length = 324
FEATURE                Location/Qualifiers
misc_feature           1..324
                       note = synthetic
source                 1..324
                       mol_type = other DNA
                       organism = synthetic construct
SEQUENCE: 65
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                               324

SEQ ID NO: 66          moltype = AA  length = 108
FEATURE                Location/Qualifiers
REGION                 1..108
                       note = synthetic
source                 1..108
                       mol_type = protein
                       organism = synthetic construct
SEQUENCE: 66
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK         108

SEQ ID NO: 67          moltype = DNA  length = 18
FEATURE                Location/Qualifiers
misc_feature           1..18
                       note = synthetic
source                 1..18
                       mol_type = other DNA
                       organism = synthetic construct
SEQUENCE: 67
cagagcatta gcagctat                                      18

SEQ ID NO: 68          moltype = AA  length = 6
FEATURE                Location/Qualifiers
REGION                 1..6
                       note = synthetic
source                 1..6
                       mol_type = protein
                       organism = synthetic construct
SEQUENCE: 68
QSISSY                                                   6

SEQ ID NO: 69          moltype =   length =
SEQUENCE: 69
000

SEQ ID NO: 70          moltype =   length =
SEQUENCE: 70
000

SEQ ID NO: 71          moltype = DNA  length = 30
FEATURE                Location/Qualifiers
misc_feature           1..30
                       note = synthetic
source                 1..30
                       mol_type = other DNA
                       organism = synthetic construct
SEQUENCE: 71
caacagagtt acagtacccc tccgatcacc                         30

SEQ ID NO: 72          moltype = AA  length = 10
```

-continued

```
FEATURE                Location/Qualifiers
REGION                 1..10
                       note = synthetic
source                 1..10
                       mol_type = protein
                       organism = synthetic construct
SEQUENCE: 72
QQSYSTPPIT                                                             10

SEQ ID NO: 73          moltype = DNA  length = 369
FEATURE                Location/Qualifiers
misc_feature           1..369
                       note = synthetic
source                 1..369
                       mol_type = other DNA
                       organism = synthetic construct
SEQUENCE: 73
caggtgcagc tggtgcagtc tggagcagag gtgaggaagc ctgggtcctc ggtgaaggtc  60
tcctgcaagg cttctggagg aaccttcacc ggccatgcta tcagctgggt gcgacaggcc  120
cctggacaag gccttgagtg gatgggaggg gtcgtcccta tctttggttc agcaaactac  180
gcacagaagt tccagggcag agtcacgatg accatggacg aatccacgag tacagcctac  240
atggacctga gcagcctgag atctgaggac acggccgttt attattgtgt gagagatccg  300
ggcaactcgg gatactacta ctacggtatg gacgtctggg gccaagggac cacggtcacc  360
gtctcctca                                                              369

SEQ ID NO: 74          moltype = AA  length = 123
FEATURE                Location/Qualifiers
REGION                 1..123
                       note = synthetic
source                 1..123
                       mol_type = protein
                       organism = synthetic construct
SEQUENCE: 74
QVQLVQSGAE VRKPGSSVKV SCKASGGTFT GHAISWVRQA PGQGLEWMGG VVPIFGSANY  60
AQKFQGRVTM TMDESTSTAY MDLSSLRSED TAVYYCVRDP GNSGYYYYGM DVWGQGTTVT  120
VSS                                                                    123

SEQ ID NO: 75          moltype = DNA  length = 24
FEATURE                Location/Qualifiers
misc_feature           1..24
                       note = synthetic
source                 1..24
                       mol_type = other DNA
                       organism = synthetic construct
SEQUENCE: 75
ggaggaacct tcaccggcca tgct                                             24

SEQ ID NO: 76          moltype = AA  length = 8
FEATURE                Location/Qualifiers
REGION                 1..8
                       note = synthetic
source                 1..8
                       mol_type = protein
                       organism = synthetic construct
SEQUENCE: 76
GGTFTGHA                                                               8

SEQ ID NO: 77          moltype = DNA  length = 24
FEATURE                Location/Qualifiers
misc_feature           1..24
                       note = synthetic
source                 1..24
                       mol_type = other DNA
                       organism = synthetic construct
SEQUENCE: 77
gtcgtcccta tctttggttc agca                                             24

SEQ ID NO: 78          moltype = AA  length = 8
FEATURE                Location/Qualifiers
REGION                 1..8
                       note = synthetic
source                 1..8
                       mol_type = protein
                       organism = synthetic construct
SEQUENCE: 78
VVPIFGSA                                                               8

SEQ ID NO: 79          moltype = DNA  length = 48
FEATURE                Location/Qualifiers
```

-continued

```
misc_feature          1..48
                      note = synthetic
source                1..48
                      mol_type = other DNA
                      organism = synthetic construct
SEQUENCE: 79
gtgagagatc cgggcaactc gggatactac tactacggta tggacgtc              48

SEQ ID NO: 80         moltype = AA  length = 16
FEATURE               Location/Qualifiers
REGION                1..16
                      note = synthetic
source                1..16
                      mol_type = protein
                      organism = synthetic construct
SEQUENCE: 80
VRDPGNSGYY YYGMDV                                                 16

SEQ ID NO: 81         moltype = DNA  length = 324
FEATURE               Location/Qualifiers
misc_feature          1..324
                      note = synthetic
source                1..324
                      mol_type = other DNA
                      organism = synthetic construct
SEQUENCE: 81
gacatccaga tgacccagtc tccatcctcc ctgtctgcat ctgtaggaga cagagtcacc  60
atcacttgcc gggcaagtca gagcattagc agctatttaa attggtttca gcagaaacca  120
gggaaagccc ctaagctcct gatctatact gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagtt cccctccgat caccttcggc  300
caagggacac gactggagat taaa                                         324

SEQ ID NO: 82         moltype = AA  length = 108
FEATURE               Location/Qualifiers
REGION                1..108
                      note = synthetic
source                1..108
                      mol_type = protein
                      organism = synthetic construct
SEQUENCE: 82
DIQMTQSPSS LSASVGDRVT ITCRASQSIS SYLNWFQQKP GKAPKLLIYT ASSLQSGVPS  60
RFSGSGSGTD FTLTISSLQP EDFATYYCQQ SYSSPPITFG QGTRLEIK               108

SEQ ID NO: 83         moltype = DNA  length = 18
FEATURE               Location/Qualifiers
misc_feature          1..18
                      note = synthetic
source                1..18
                      mol_type = other DNA
                      organism = synthetic construct
SEQUENCE: 83
cagagcatta gcagctat                                               18

SEQ ID NO: 84         moltype = AA  length = 6
FEATURE               Location/Qualifiers
REGION                1..6
                      note = synthetic
source                1..6
                      mol_type = protein
                      organism = synthetic construct
SEQUENCE: 84
QSISSY                                                            6

SEQ ID NO: 85         moltype =   length =
SEQUENCE: 85
000

SEQ ID NO: 86         moltype =   length =
SEQUENCE: 86
000

SEQ ID NO: 87         moltype = DNA  length = 30
FEATURE               Location/Qualifiers
misc_feature          1..30
                      note = synthetic
source                1..30
                      mol_type = other DNA
                      organism = synthetic construct
```

-continued

```
SEQUENCE: 87
caacagagtt acagttcccc tccgatcacc                                30

SEQ ID NO: 88          moltype = AA  length = 10
FEATURE                Location/Qualifiers
REGION                 1..10
                       note = synthetic
source                 1..10
                       mol_type = protein
                       organism = synthetic construct
SEQUENCE: 88
QQSYSSPPIT                                                      10

SEQ ID NO: 89          moltype = DNA  length = 369
FEATURE                Location/Qualifiers
misc_feature           1..369
                       note = synthetic
source                 1..369
                       mol_type = other DNA
                       organism = synthetic construct
SEQUENCE: 89
caggtccacc tggtgcagtc tggggctgag gtgaagaagc ctgggtcgtc ggtgaaggtc  60
tcctgcaagg cttctggagg caccttcagc acctatgcta tcacctgggt gcgacaggcc  120
cctggacaag ggcttgagtg gataggaggg atcagccgtt tctttggttc agcaaactac  180
gcacagaagt ttcagggcag agtcacaatt accacggacg aatccacgaa cacagcctac  240
atggaactaa gcagcctgag atctgaggac acggccgtat attattgtgc gagagatcct  300
ggaaacacgg gctattattt ttacggtatg gacgtctggg gccaagggac cacggtcacc  360
gtctcctca                                                       369

SEQ ID NO: 90          moltype = AA  length = 123
FEATURE                Location/Qualifiers
REGION                 1..123
                       note = synthetic
source                 1..123
                       mol_type = protein
                       organism = synthetic construct
SEQUENCE: 90
QVHLVQSGAE VKKPGSSVKV SCKASGGTFS TYAITWVRQA PGQGLEWIGG ISRFFGSANY  60
AQKFQGRVTI TTDESTNTAY MELSSLRSED TAVYYCARDP GNTGYYFYGM DVWGQGTTVT  120
VSS                                                             123

SEQ ID NO: 91          moltype = DNA  length = 24
FEATURE                Location/Qualifiers
misc_feature           1..24
                       note = synthetic
source                 1..24
                       mol_type = other DNA
                       organism = synthetic construct
SEQUENCE: 91
ggaggcacct tcagcaccta tgct                                      24

SEQ ID NO: 92          moltype = AA  length = 8
FEATURE                Location/Qualifiers
REGION                 1..8
                       note = synthetic
source                 1..8
                       mol_type = protein
                       organism = synthetic construct
SEQUENCE: 92
GGTFSTYA                                                        8

SEQ ID NO: 93          moltype = DNA  length = 24
FEATURE                Location/Qualifiers
misc_feature           1..24
                       note = synthetic
source                 1..24
                       mol_type = other DNA
                       organism = synthetic construct
SEQUENCE: 93
atcagccgtt tctttggttc agca                                      24

SEQ ID NO: 94          moltype = AA  length = 8
FEATURE                Location/Qualifiers
REGION                 1..8
                       note = synthetic
source                 1..8
                       mol_type = protein
                       organism = synthetic construct
SEQUENCE: 94
```

```
ISRFFGSA                                                    8

SEQ ID NO: 95          moltype = DNA  length = 48
FEATURE                Location/Qualifiers
misc_feature           1..48
                       note = synthetic
source                 1..48
                       mol_type = other DNA
                       organism = synthetic construct
SEQUENCE: 95
gcgagagatc ctggaaacac gggctattat ttttacggta tggacgtc        48

SEQ ID NO: 96          moltype = AA  length = 16
FEATURE                Location/Qualifiers
REGION                 1..16
                       note = synthetic
source                 1..16
                       mol_type = protein
                       organism = synthetic construct
SEQUENCE: 96
ARDPGNTGYY FYGMDV                                           16

SEQ ID NO: 97          moltype = DNA  length = 324
FEATURE                Location/Qualifiers
misc_feature           1..324
                       note = synthetic
source                 1..324
                       mol_type = other DNA
                       organism = synthetic construct
SEQUENCE: 97
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatggt gcatccagtt tgcaaagtgg ggtcccatca  180
aggttcagtg gcagtggatc tgggacagat ttcactctca ccatcagcag tctgcaacct  240
gaagattttg caacttacta ctgtcaacag agtaagagta attctccgat caccttcggc  300
caagggacac gactggagat taaa                                  324

SEQ ID NO: 98          moltype = AA  length = 108
FEATURE                Location/Qualifiers
REGION                 1..108
                       note = synthetic
source                 1..108
                       mol_type = protein
                       organism = synthetic construct
SEQUENCE: 98
DIQMTQSPSS LSASVGDRVT ITCRASQSIS SYLNWYQQKP GKAPKLLIYG ASSLQSGVPS  60
RFSGSGSGTD FTLTISSLQP EDFATYYCQQ SKSNSPITFG QGTRLEIK        108

SEQ ID NO: 99          moltype = DNA  length = 18
FEATURE                Location/Qualifiers
misc_feature           1..18
                       note = synthetic
source                 1..18
                       mol_type = other DNA
                       organism = synthetic construct
SEQUENCE: 99
cagagcatta gcagctat                                         18

SEQ ID NO: 100         moltype = AA  length = 6
FEATURE                Location/Qualifiers
REGION                 1..6
                       note = synthetic
source                 1..6
                       mol_type = protein
                       organism = synthetic construct
SEQUENCE: 100
QSISSY                                                      6

SEQ ID NO: 101         moltype =   length =
SEQUENCE: 101
000

SEQ ID NO: 102         moltype =   length =
SEQUENCE: 102
000

SEQ ID NO: 103         moltype = DNA  length = 30
FEATURE                Location/Qualifiers
misc_feature           1..30
```

```
                        note = synthetic
source                  1..30
                        mol_type = other DNA
                        organism = synthetic construct
SEQUENCE: 103
caacagagta agagtaattc tccgatcacc                                30

SEQ ID NO: 104          moltype = AA  length = 10
FEATURE                 Location/Qualifiers
REGION                  1..10
                        note = synthetic
source                  1..10
                        mol_type = protein
                        organism = synthetic construct
SEQUENCE: 104
QQSKSNSPIT                                                      10

SEQ ID NO: 105          moltype = DNA  length = 369
FEATURE                 Location/Qualifiers
misc_feature            1..369
                        note = synthetic
source                  1..369
                        mol_type = other DNA
                        organism = synthetic construct
SEQUENCE: 105
caggtccagc tggtgcagtc tggggctgag gtgaagaagc ctgggtcctc ggtgaaggtc  60
tcctgcaagg cttctggagg caccttcatc acctatgcta tcagctgggt gcgacaggcc  120
cctggacaag ggcttgagtg gatgggaggt gtcatcccta tctttggtac tccaaggtac  180
gcacagaagt tccagggcag agtcacgatt accacggacg attccacgac cacagcctac  240
atggagctga gcagcctgag atctgacgac acggccgtgt attattgtgc gacaaggagc  300
agctcgtctc cctattatta ctacggtatg gacgtctggg gccaagggac cacggtcacc  360
gtctcctca                                                       369

SEQ ID NO: 106          moltype = AA  length = 123
FEATURE                 Location/Qualifiers
REGION                  1..123
                        note = synthetic
source                  1..123
                        mol_type = protein
                        organism = synthetic construct
SEQUENCE: 106
QVQLVQSGAE VKKPGSSVKV SCKASGGTFI TYAISWVRQA PGQGLEWMGG VIPIFGTPRY  60
AQKFQGRVTI TTDDSTTTAY MELSSLRSDD TAVYYCATRS SSSPYYYYGM DVWGQGTTVT  120
VSS                                                             123

SEQ ID NO: 107          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 107
ggaggcacct tcatcaccta tgct                                      24

SEQ ID NO: 108          moltype = AA  length = 8
FEATURE                 Location/Qualifiers
REGION                  1..8
                        note = synthetic
source                  1..8
                        mol_type = protein
                        organism = synthetic construct
SEQUENCE: 108
GGTFITYA                                                        8

SEQ ID NO: 109          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 109
gtcatcccta tctttggtac tcca                                      24

SEQ ID NO: 110          moltype = AA  length = 8
FEATURE                 Location/Qualifiers
REGION                  1..8
                        note = synthetic
```

-continued

```
source                  1..8
                        mol_type = protein
                        organism = synthetic construct
SEQUENCE: 110
VIPIFGTP                                                                     8

SEQ ID NO: 111          moltype = DNA  length = 48
FEATURE                 Location/Qualifiers
misc_feature            1..48
                        note = synthetic
source                  1..48
                        mol_type = other DNA
                        organism = synthetic construct
SEQUENCE: 111
gcgacaagga gcagctcgtc tccctattat tactacggta tggacgtc                        48

SEQ ID NO: 112          moltype = AA  length = 16
FEATURE                 Location/Qualifiers
REGION                  1..16
                        note = synthetic
source                  1..16
                        mol_type = protein
                        organism = synthetic construct
SEQUENCE: 112
ATRSSSSPYY YYGMDV                                                            16

SEQ ID NO: 113          moltype = DNA  length = 336
FEATURE                 Location/Qualifiers
misc_feature            1..336
                        note = synthetic
source                  1..336
                        mol_type = other DNA
                        organism = synthetic construct
SEQUENCE: 113
gatattgtga tgacccagac tccactctcc tcacctgtca cccttggaca gccggcctcc  60
atctcctgca ggtctagtca aagcctcgta cacagtgatg gaaacaccta tttgagttgg  120
cttcagcaga ggccaggcca gcctccaaga ctcctaattt ataagatttc taaccggttc  180
tctggggtcc cagacagatt cagtggcagt ggggcaggga cagatttcac actgaaaatc  240
agcagggtgg aagctgagga tgtcgggatt tattactgca ttcaagctac acaatttccg  300
tacacttttg gccaggggac caagctggag atcaaa                             336

SEQ ID NO: 114          moltype = AA  length = 112
FEATURE                 Location/Qualifiers
REGION                  1..112
                        note = synthetic
source                  1..112
                        mol_type = protein
                        organism = synthetic construct
SEQUENCE: 114
DIVMTQTPLS SPVTLGQPAS ISCRSSQSLV HSDGNTYLSW LQQRPGQPPR LLIYKISNRF  60
SGVPDRFSGS GAGTDFTLKI SRVEAEDVGI YYCIQATQFP YTFGQGTKLE IK          112

SEQ ID NO: 115          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 115
caaagcctcg tacacagtga tggaaacacc tat                                         33

SEQ ID NO: 116          moltype = AA  length = 11
FEATURE                 Location/Qualifiers
REGION                  1..11
                        note = synthetic
source                  1..11
                        mol_type = protein
                        organism = synthetic construct
SEQUENCE: 116
QSLVHSDGNT Y                                                                 11

SEQ ID NO: 117          moltype =   length =
SEQUENCE: 117
000

SEQ ID NO: 118          moltype =   length =
SEQUENCE: 118
000
```

```
SEQ ID NO: 119         moltype = DNA  length = 27
FEATURE                Location/Qualifiers
misc_feature           1..27
                       note = synthetic
source                 1..27
                       mol_type = other DNA
                       organism = synthetic construct
SEQUENCE: 119
attcaagcta cacaatttcc gtacact                                        27

SEQ ID NO: 120         moltype = AA  length = 9
FEATURE                Location/Qualifiers
REGION                 1..9
                       note = synthetic
source                 1..9
                       mol_type = protein
                       organism = synthetic construct
SEQUENCE: 120
IQATQFPYT                                                            9

SEQ ID NO: 121         moltype = DNA  length = 372
FEATURE                Location/Qualifiers
misc_feature           1..372
                       note = synthetic
source                 1..372
                       mol_type = other DNA
                       organism = synthetic construct
SEQUENCE: 121
caggtgcagc tggtgcagtc tggggctgag gtgaagaagc ctggggcctc agtgacggtc  60
tcctgcaagg cttctggata caccttcacc aattatgata tcaactgggt gcgacaggcc  120
actggacaag gacttgagtg gttgggatgg atgagcccta acagtggtaa caaaggctat  180
gcacagaagt tccagggcag agtctccatg actttgaata ccgccttaag cacagcctac  240
atggaactga gcagcctgag atctgaggac acggccgtgt attactgtgc gagatggtat  300
tgtagtgatg ccagttgcta tcccgatgct tttgatatct ggggccaagg gacaatggtc  360
accgtctctt ca                                                        372

SEQ ID NO: 122         moltype = AA  length = 124
FEATURE                Location/Qualifiers
REGION                 1..124
                       note = synthetic
source                 1..124
                       mol_type = protein
                       organism = synthetic construct
SEQUENCE: 122
QVQLVQSGAE VKKPGASVTV SCKASGYTFT NYDINWVRQA TGQGLEWLGW MSPNSGNKGY  60
AQKFQGRVSM TLNTALSTAY MELSSLRSED TAVYYCARWY CSDASCYPDA FDIWGQGTMV  120
TVSS                                                                 124

SEQ ID NO: 123         moltype = DNA  length = 24
FEATURE                Location/Qualifiers
misc_feature           1..24
                       note = synthetic
source                 1..24
                       mol_type = other DNA
                       organism = synthetic construct
SEQUENCE: 123
ggatacacct tcaccaatta tgat                                           24

SEQ ID NO: 124         moltype = AA  length = 8
FEATURE                Location/Qualifiers
REGION                 1..8
                       note = synthetic
source                 1..8
                       mol_type = protein
                       organism = synthetic construct
SEQUENCE: 124
GYTFTNYD                                                             8

SEQ ID NO: 125         moltype = DNA  length = 24
FEATURE                Location/Qualifiers
misc_feature           1..24
                       note = synthetic
source                 1..24
                       mol_type = other DNA
                       organism = synthetic construct
SEQUENCE: 125
atgagcccta acagtggtaa caaa                                           24
```

```
SEQ ID NO: 126         moltype = AA  length = 8
FEATURE                Location/Qualifiers
REGION                 1..8
                       note = synthetic
source                 1..8
                       mol_type = protein
                       organism = synthetic construct
SEQUENCE: 126
MSPNSGNK                                                          8

SEQ ID NO: 127         moltype = DNA  length = 51
FEATURE                Location/Qualifiers
misc_feature           1..51
                       note = synthetic
source                 1..51
                       mol_type = other DNA
                       organism = synthetic construct
SEQUENCE: 127
gcgagatggt attgtagtga tgccagttgc tatcccgatg cttttgatat c          51

SEQ ID NO: 128         moltype = AA  length = 17
FEATURE                Location/Qualifiers
REGION                 1..17
                       note = synthetic
source                 1..17
                       mol_type = protein
                       organism = synthetic construct
SEQUENCE: 128
ARWYCSDASC YPDAFDI                                                17

SEQ ID NO: 129         moltype = DNA  length = 321
FEATURE                Location/Qualifiers
misc_feature           1..321
                       note = synthetic
source                 1..321
                       mol_type = other DNA
                       organism = synthetic construct
SEQUENCE: 129
gacatccaga tgacccagtc tccatcttcc gtgtctgcat ctgtaggaga cagagtcacc  60
atcacttgtc gggcgagtca ggatttttcc gactggttag cctggtatca gcagaaacct  120
gggaaagccc ctgagctcct gatctatgct acatccagtt tgcatactgg ggtcccatca  180
aggttcagcg gcagtggatc tgggacagat ttcactctca ccatcagcac cctgcagcct  240
gaagattttg ctacttacta ttgtctacag gctaacaatt tcccgctcac tttcggcgga  300
gggaccaagg tggagatcaa a                                            321

SEQ ID NO: 130         moltype = AA  length = 107
FEATURE                Location/Qualifiers
REGION                 1..107
                       note = synthetic
source                 1..107
                       mol_type = protein
                       organism = synthetic construct
SEQUENCE: 130
DIQMTQSPSS VSASVGDRVT ITCRASQDFS DWLAWYQQKP GKAPELLIYA TSSLHTGVPS  60
RFSGSGSGTD FTLTISTLQP EDFATYYCLQ ANNFPLTFGG GTKVEIK                107

SEQ ID NO: 131         moltype = DNA  length = 18
FEATURE                Location/Qualifiers
misc_feature           1..18
                       note = synthetic
source                 1..18
                       mol_type = other DNA
                       organism = synthetic construct
SEQUENCE: 131
caggattttt ccgactgg                                               18

SEQ ID NO: 132         moltype = AA  length = 6
FEATURE                Location/Qualifiers
REGION                 1..6
                       note = synthetic
source                 1..6
                       mol_type = protein
                       organism = synthetic construct
SEQUENCE: 132
QDFSDW                                                            6

SEQ ID NO: 133         moltype =   length =
SEQUENCE: 133
000
```

```
SEQ ID NO: 134         moltype =   length =
SEQUENCE: 134
000

SEQ ID NO: 135         moltype = DNA  length = 27
FEATURE                Location/Qualifiers
misc_feature           1..27
                       note = synthetic
source                 1..27
                       mol_type = other DNA
                       organism = synthetic construct
SEQUENCE: 135
ctacaggcta acaatttccc gctcact                                      27

SEQ ID NO: 136         moltype = AA  length = 9
FEATURE                Location/Qualifiers
REGION                 1..9
                       note = synthetic
source                 1..9
                       mol_type = protein
                       organism = synthetic construct
SEQUENCE: 136
LQANNFPLT                                                          9

SEQ ID NO: 137         moltype = DNA  length = 366
FEATURE                Location/Qualifiers
misc_feature           1..366
                       note = synthetic
source                 1..366
                       mol_type = other DNA
                       organism = synthetic construct
SEQUENCE: 137
caggtgcagc tggtggagtc tgggggaggc gtggcccagc ctgggaggtc cctgagactc  60
tcctgtgcag cctctggaat caccttcaat aactatggca tgcactgggt ccgccaggct  120
ccaggcaagg ggctggagtg ggtggcattt atttcagatg aaggaagaaa taaacactat  180
ggagactccg tgaagggccg attcaccatc gacagagaca attccaagaa cacactgtat  240
ctgcaaatga atagcctgag agctgaggac acggctgtat attactgtgc gaaattgggg  300
gataatagga atcaccacta cggtttggac gtctggggcc aagggaccac ggtcaccgtc  360
tcctca                                                             366

SEQ ID NO: 138         moltype = AA  length = 122
FEATURE                Location/Qualifiers
REGION                 1..122
                       note = synthetic
source                 1..122
                       mol_type = protein
                       organism = synthetic construct
SEQUENCE: 138
QVQLVESGGG VAQPGRSLRL SCAASGITFN NYGMHWVRQA PGKGLEWVAF ISDEGRNKHY  60
GDSVKGRFTI DRDNSKNTLY LQMNSLRAED TAVYYCAKLG DNRNHHYGLD VWGQGTTVTV  120
SS                                                                 122

SEQ ID NO: 139         moltype = DNA  length = 24
FEATURE                Location/Qualifiers
misc_feature           1..24
                       note = synthetic
source                 1..24
                       mol_type = other DNA
                       organism = synthetic construct
SEQUENCE: 139
ggaatcacct tcaataacta tggc                                         24

SEQ ID NO: 140         moltype = AA  length = 8
FEATURE                Location/Qualifiers
REGION                 1..8
                       note = synthetic
source                 1..8
                       mol_type = protein
                       organism = synthetic construct
SEQUENCE: 140
GITFNNYG                                                           8

SEQ ID NO: 141         moltype = DNA  length = 24
FEATURE                Location/Qualifiers
misc_feature           1..24
                       note = synthetic
source                 1..24
                       mol_type = other DNA
```

```
                         organism = synthetic construct
SEQUENCE: 141
atttcagatg aaggaagaaa taaa                                  24

SEQ ID NO: 142           moltype = AA  length = 8
FEATURE                  Location/Qualifiers
REGION                   1..8
                         note = synthetic
source                   1..8
                         mol_type = protein
                         organism = synthetic construct
SEQUENCE: 142
ISDEGRNK                                                    8

SEQ ID NO: 143           moltype = DNA  length = 45
FEATURE                  Location/Qualifiers
misc_feature             1..45
                         note = synthetic
source                   1..45
                         mol_type = other DNA
                         organism = synthetic construct
SEQUENCE: 143
gcgaaattgg gggataatag gaatcaccac tacggtttgg acgtc           45

SEQ ID NO: 144           moltype = AA  length = 15
FEATURE                  Location/Qualifiers
REGION                   1..15
                         note = synthetic
source                   1..15
                         mol_type = protein
                         organism = synthetic construct
SEQUENCE: 144
AKLGDNRNHH YGLDV                                            15

SEQ ID NO: 145           moltype = DNA  length = 321
FEATURE                  Location/Qualifiers
misc_feature             1..321
                         note = synthetic
source                   1..321
                         mol_type = other DNA
                         organism = synthetic construct
SEQUENCE: 145
gacatccagt tgacccagtc tccatccttc ctgtctgcat ctgtaggaga cagagtcacc  60
atcacttgct gggccagtca gggcattacc aattatttag cctggtatca gcaaaaacca  120
gggaaagccc ctagcctcct gatctatgct gcatccactt tgcaaagtgg ggtcccatca  180
aggttcagcg gcagtggaca tgggacagaa ttcactctca cagtcagcag cctgcagcct  240
gaagattttg taacttatta ctgtcaacag tttaatagtt acccgatcac cttcggccaa  300
gggacacgac tggagattaa a                                     321

SEQ ID NO: 146           moltype = AA  length = 107
FEATURE                  Location/Qualifiers
REGION                   1..107
                         note = synthetic
source                   1..107
                         mol_type = protein
                         organism = synthetic construct
SEQUENCE: 146
DIQLTQSPSF LSASVGDRVT ITCWASQGIT NYLAWYQQKP GKAPSLLIYA ASTLQSGVPS  60
RFSGSGHGTE FTLTVSSLQP EDFVTYYCQQ FNSYPITFGQ GTRLEIK          107

SEQ ID NO: 147           moltype = DNA  length = 18
FEATURE                  Location/Qualifiers
misc_feature             1..18
                         note = synthetic
source                   1..18
                         mol_type = other DNA
                         organism = synthetic construct
SEQUENCE: 147
cagggcatta ccaattat                                         18

SEQ ID NO: 148           moltype = AA  length = 6
FEATURE                  Location/Qualifiers
REGION                   1..6
                         note = synthetic
source                   1..6
                         mol_type = protein
                         organism = synthetic construct
SEQUENCE: 148
QGITNY                                                      6
```

```
SEQ ID NO: 149          moltype =   length =
SEQUENCE: 149
000

SEQ ID NO: 150          moltype =   length =
SEQUENCE: 150
000

SEQ ID NO: 151          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 151
caacagttta atagttaccc gatcacc                                       27

SEQ ID NO: 152          moltype = AA  length = 9
FEATURE                 Location/Qualifiers
REGION                  1..9
                        note = synthetic
source                  1..9
                        mol_type = protein
                        organism = synthetic construct
SEQUENCE: 152
QQFNSYPIT                                                           9

SEQ ID NO: 153          moltype = DNA  length = 366
FEATURE                 Location/Qualifiers
misc_feature            1..366
                        note = synthetic
source                  1..366
                        mol_type = other DNA
                        organism = synthetic construct
SEQUENCE: 153
caggtccagc tggtgcagtc tggggctgag gtgaagaagc ctgggtcctc ggtgaaggtc  60
tcctgtaagg cttctggagg caccttcagc aactatgata tcagctgggt gcgacaggcc  120
cctggacaag gacttgagtg gatgggaggg atcatcccca tcattggtac agcaaactac  180
gcacagaagt tccagggcag agtcacgatt acaacggacg aatccacgag cacagcctac  240
atggagctga gcagcctgag atctgaggac acggccgtgt attactgtgc gagagatccg  300
ggtatagcag tggctggttc gagctttgac tactggggcc agggaaccct ggtcaccgtc  360
tcctca                                                              366

SEQ ID NO: 154          moltype = AA  length = 122
FEATURE                 Location/Qualifiers
REGION                  1..122
                        note = synthetic
source                  1..122
                        mol_type = protein
                        organism = synthetic construct
SEQUENCE: 154
QVQLVQSGAE VKKPGSSVKV SCKASGGTFS NYDISWVRQA PGQGLEWMGG IIPIIGTANY  60
AQKFQGRVTI TTDESTSTAY MELSSLRSED TAVYYCARDP GIAVAGSSFD YWGQGTLVTV  120
SS                                                                  122

SEQ ID NO: 155          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 155
ggaggcacct tcagcaacta tgat                                          24

SEQ ID NO: 156          moltype = AA  length = 8
FEATURE                 Location/Qualifiers
REGION                  1..8
                        note = synthetic
source                  1..8
                        mol_type = protein
                        organism = synthetic construct
SEQUENCE: 156
GGTFSNYD                                                            8

SEQ ID NO: 157          moltype = DNA  length = 24
FEATURE                 Location/Qualifiers
```

```
misc_feature          1..24
                      note = synthetic
source                1..24
                      mol_type = other DNA
                      organism = synthetic construct
SEQUENCE: 157
atcatcccca tcattggtac agca                                        24

SEQ ID NO: 158        moltype = AA  length = 8
FEATURE               Location/Qualifiers
REGION                1..8
                      note = synthetic
source                1..8
                      mol_type = protein
                      organism = synthetic construct
SEQUENCE: 158
IIPIIGTA                                                          8

SEQ ID NO: 159        moltype = DNA  length = 45
FEATURE               Location/Qualifiers
misc_feature          1..45
                      note = synthetic
source                1..45
                      mol_type = other DNA
                      organism = synthetic construct
SEQUENCE: 159
gcgagagatc cgggtatagc agtggctggt tcgagctttg actac                 45

SEQ ID NO: 160        moltype = AA  length = 15
FEATURE               Location/Qualifiers
REGION                1..15
                      note = synthetic
source                1..15
                      mol_type = protein
                      organism = synthetic construct
SEQUENCE: 160
ARDPGIAVAG SSFDY                                                  15

SEQ ID NO: 161        moltype = DNA  length = 321
FEATURE               Location/Qualifiers
misc_feature          1..321
                      note = synthetic
source                1..321
                      mol_type = other DNA
                      organism = synthetic construct
SEQUENCE: 161
gccatccaga tgacccagtc tccatcctcc ctgtctgcat ctgttggaga cagagtcacc  60
atcacttgcc gggcaagtca gggcattaga catgatttag gctggtatca gcagaaacca  120
gggaaagccc ctaagctcct gatctatgct gcatccaatt tacaaagtgg ggtcccatca  180
aggttcagcg gcagtggatc tggcacagat ttcactctca ccatcagcag cctgcagcct  240
gaagattttg caacttatta ctgtctacaa gattacaatt accctcggac gttcggccaa  300
gggaccaagg tggaaatcaa a                                           321

SEQ ID NO: 162        moltype = AA  length = 107
FEATURE               Location/Qualifiers
REGION                1..107
                      note = synthetic
source                1..107
                      mol_type = protein
                      organism = synthetic construct
SEQUENCE: 162
AIQMTQSPSS LSASVGDRVT ITCRASQGIR HDLGWYQQKP GKAPKLLIYA ASNLQSGVPS  60
RFSGSGSGTD FTLTISSLQP EDFATYYCLQ DYNYPRTFGQ GTKVEIK               107

SEQ ID NO: 163        moltype = DNA  length = 18
FEATURE               Location/Qualifiers
misc_feature          1..18
                      note = synthetic
source                1..18
                      mol_type = other DNA
                      organism = synthetic construct
SEQUENCE: 163
cagggcatta gacatgat                                               18

SEQ ID NO: 164        moltype = AA  length = 6
FEATURE               Location/Qualifiers
REGION                1..6
                      note = synthetic
source                1..6
```

```
                        mol_type = protein
                        organism = synthetic construct
SEQUENCE: 164
QGIRHD                                                                6

SEQ ID NO: 165          moltype =   length =
SEQUENCE: 165
000

SEQ ID NO: 166          moltype =   length =
SEQUENCE: 166
000

SEQ ID NO: 167          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 167
ctacaagatt acaattaccc tcggacg                                         27

SEQ ID NO: 168          moltype = AA  length = 9
FEATURE                 Location/Qualifiers
REGION                  1..9
                        note = synthetic
source                  1..9
                        mol_type = protein
                        organism = synthetic construct
SEQUENCE: 168
LQDYNYPRT                                                             9

SEQ ID NO: 169          moltype = DNA  length = 348
FEATURE                 Location/Qualifiers
misc_feature            1..348
                        note = synthetic
source                  1..348
                        mol_type = other DNA
                        organism = synthetic construct
SEQUENCE: 169
caggtgcagc tggtgcagtc tggggctgag gtgaggacgc ctgggtcctc ggtgaaggtc  60
tcctgcaagg cttctggagg caccttcagc agctatgctg tcacctgggt gcgacaggcc  120
cctggacaag ggcttgagtg gatgggaggg ctcatccctt tctttggtcc agcaaactac  180
gcacagagat tccagggcag agtctcgatt accacggacg aatccacgaa catagcctac  240
ttggagctga gcagcctgag atccgaggac tcggccgttt attactgtgc gagagggcgg  300
aacttcggtg actactgggg ccagggaacc ctggtcaccg tctcctca                 348

SEQ ID NO: 170          moltype = AA  length = 116
FEATURE                 Location/Qualifiers
REGION                  1..116
                        note = synthetic
source                  1..116
                        mol_type = protein
                        organism = synthetic construct
SEQUENCE: 170
QVQLVQSGAE VRTPGSSVKV SCKASGGTFS SYAVTWVRQA PGQGLEWMGG LIPFFGPANY  60
AQRFQGRVSI TTDESTNIAY LELSSLRSED SAVYYCARGR NFGDYWGQGT LVTVSS      116

SEQ ID NO: 171          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 171
ggaggcacct tcagcagcta tgct                                            24

SEQ ID NO: 172          moltype = AA  length = 8
FEATURE                 Location/Qualifiers
REGION                  1..8
                        note = synthetic
source                  1..8
                        mol_type = protein
                        organism = synthetic construct
SEQUENCE: 172
GGTFSSYA                                                              8
```

```
SEQ ID NO: 173          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 173
ctcatccctt tctttggtcc agca                                          24

SEQ ID NO: 174          moltype = AA  length = 8
FEATURE                 Location/Qualifiers
REGION                  1..8
                        note = synthetic
source                  1..8
                        mol_type = protein
                        organism = synthetic construct
SEQUENCE: 174
LIPFFGPA                                                            8

SEQ ID NO: 175          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 175
gcgagagggc ggaacttcgg tgactac                                       27

SEQ ID NO: 176          moltype = AA  length = 9
FEATURE                 Location/Qualifiers
REGION                  1..9
                        note = synthetic
source                  1..9
                        mol_type = protein
                        organism = synthetic construct
SEQUENCE: 176
ARGRNFGDY                                                           9

SEQ ID NO: 177          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 177
gacatccaga tgacccagtc tccatcctca ctgtctgcat ctataggaga cagagtcacc  60
atcacttgtc gggcgagtca ggacattagc aattatttag cctggtttca gcagaaacca  120
gggaaagtcc ctaagtccct gatctatgct gcatccaatt tgcaaagtgg ggtcccatca  180
aagttcagcg gcagtggatc tgggacagat ttcactctca ccatcagtac cctgcagcct  240
gaagattttg caacttatta ctgccaacag tatagtagtt atccattcac tttcggccct  300
gggaccaaag tggatatcaa a                                             321

SEQ ID NO: 178          moltype = AA  length = 107
FEATURE                 Location/Qualifiers
REGION                  1..107
                        note = synthetic
source                  1..107
                        mol_type = protein
                        organism = synthetic construct
SEQUENCE: 178
DIQMTQSPSS LSASIGDRVT ITCRASQDIS NYLAWFQQKP GKVPKSLIYA ASNLQSGVPS  60
KFSGSGSGTD FTLTISTLQP EDFATYYCQQ YSSYPFTFGP GTKVDIK                107

SEQ ID NO: 179          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 179
caggacatta gcaattat                                                 18

SEQ ID NO: 180          moltype = AA  length = 6
FEATURE                 Location/Qualifiers
REGION                  1..6
```

```
                        note = synthetic
source                  1..6
                        mol_type = protein
                        organism = synthetic construct
SEQUENCE: 180
QDISNY                                                                      6

SEQ ID NO: 181          moltype =   length =
SEQUENCE: 181
000

SEQ ID NO: 182          moltype =   length =
SEQUENCE: 182
000

SEQ ID NO: 183          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 183
caacagtata gtagttatcc attcact                                               27

SEQ ID NO: 184          moltype = AA  length = 9
FEATURE                 Location/Qualifiers
REGION                  1..9
                        note = synthetic
source                  1..9
                        mol_type = protein
                        organism = synthetic construct
SEQUENCE: 184
QQYSSYPFT                                                                   9

SEQ ID NO: 185          moltype = DNA  length = 351
FEATURE                 Location/Qualifiers
misc_feature            1..351
                        note = synthetic
source                  1..351
                        mol_type = other DNA
                        organism = synthetic construct
SEQUENCE: 185
caggtgcagc tggtgcagtc tggggctgag gtgaagaagc ctgggtcctc ggtgaaggtc  60
tcctgcaagg cttctggagg caccttcagc agctatgcta tcagctgggt gcgacaggcc  120
cctggacaag ggcttgagtg gatgggaggg atcatcccta tctttggtac aacaaactac  180
gcacagaagt tccagggcag agtcacgatt accacggacg aatccacgag cacagcctac  240
atggagctga gcagcctgag atctgaggac acggccgtgt attactgtgc gagaaggcac  300
ggtatatcct ttgactactg gggccaggga accctggtca ccgtctcctc a           351

SEQ ID NO: 186          moltype = AA  length = 117
FEATURE                 Location/Qualifiers
REGION                  1..117
                        note = synthetic
source                  1..117
                        mol_type = protein
                        organism = synthetic construct
SEQUENCE: 186
QVQLVQSGAE VKKPGSSVKV SCKASGGTFS SYAISWVRQA PGQGLEWMGG IIPIFGTTNY  60
AQKFQGRVTI TTDESTSTAY MELSSLRSED TAVYYCARRH GISFDYWGQG TLVTVSS     117

SEQ ID NO: 187          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 187
ggaggcacct tcagcagcta tgct                                                  24

SEQ ID NO: 188          moltype = AA  length = 8
FEATURE                 Location/Qualifiers
REGION                  1..8
                        note = synthetic
source                  1..8
                        mol_type = protein
                        organism = synthetic construct
SEQUENCE: 188
```

```
GGTFSSYA                                                8

SEQ ID NO: 189          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 189
atcatcccta tctttggtac aaca                              24

SEQ ID NO: 190          moltype = AA  length = 8
FEATURE                 Location/Qualifiers
REGION                  1..8
                        note = synthetic
source                  1..8
                        mol_type = protein
                        organism = synthetic construct
SEQUENCE: 190
IIPIFGTT                                                8

SEQ ID NO: 191          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 191
gcgagaaggc acggtatatc ctttgactac                        30

SEQ ID NO: 192          moltype = AA  length = 10
FEATURE                 Location/Qualifiers
REGION                  1..10
                        note = synthetic
source                  1..10
                        mol_type = protein
                        organism = synthetic construct
SEQUENCE: 192
ARRHGISFDY                                              10

SEQ ID NO: 193          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 193
gacatccaga tgacccagtc tccatcctcc ctgtctgcat ctgtaggaga cagagtcacc  60
gtcacttgcc gggcaagtca gggcattaga aatgatttgg cctggtatca gcagaaacca  120
gggaaagccc ctaagcgcct gatctatgct gcatccagtt tgcaaagtgg ggtcccatca  180
aggttcagcg gcagtggatc tgggacagaa ttcactctca caatcagcag cctgcagcct  240
gaagattttg caacttatta ctgtctacag cataatagtt atccgtggac gttcggccta  300
gggaccaagg tggaaatcaa a                                 321

SEQ ID NO: 194          moltype = AA  length = 107
FEATURE                 Location/Qualifiers
REGION                  1..107
                        note = synthetic
source                  1..107
                        mol_type = protein
                        organism = synthetic construct
SEQUENCE: 194
DIQMTQSPSS LSASVGDRVT VTCRASQGIR NDLAWYQQKP GKAPKRLIYA ASSLQSGVPS  60
RFSGSGSGTE FTLTISSLQP EDFATYYCLQ HNSYPWTFGL GTKVEIK     107

SEQ ID NO: 195          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 195
cagggcatta gaaatgat                                     18

SEQ ID NO: 196          moltype = AA  length = 6
```

-continued

```
FEATURE                Location/Qualifiers
REGION                 1..6
                       note = synthetic
source                 1..6
                       mol_type = protein
                       organism = synthetic construct
SEQUENCE: 196
QGIRND                                                                     6

SEQ ID NO: 197         moltype =   length =
SEQUENCE: 197
000

SEQ ID NO: 198         moltype =   length =
SEQUENCE: 198
000

SEQ ID NO: 199         moltype = DNA  length = 27
FEATURE                Location/Qualifiers
misc_feature           1..27
                       note = synthetic
source                 1..27
                       mol_type = other DNA
                       organism = synthetic construct
SEQUENCE: 199
ctacagcata atagttatcc gtggacg                                              27

SEQ ID NO: 200         moltype = AA  length = 9
FEATURE                Location/Qualifiers
REGION                 1..9
                       note = synthetic
source                 1..9
                       mol_type = protein
                       organism = synthetic construct
SEQUENCE: 200
LQHNSYPWT                                                                  9

SEQ ID NO: 201         moltype = DNA  length = 366
FEATURE                Location/Qualifiers
misc_feature           1..366
                       note = synthetic
source                 1..366
                       mol_type = other DNA
                       organism = synthetic construct
SEQUENCE: 201
caggtgcagc tggtgcagtc tggggctgag gtgaagaagc ctgggtcctc ggtgaaggtc  60
tcctgcaagg cttctggagg caccttcagc agctatacta tcagctgggt tcgacaggcc  120
cctggacaag ggcttgagtg gatgggaggg atcagcccta tctttggtac agcaaactac  180
gcacagaagt tccagggcag agtcacgatt accacggacg aatccacgag cacagcctac  240
atggagctga gcagcctgag atctgaggac acggccgtgt attactgtgc gagagagtcc  300
ccgtataact ggaaccaaaa atacttccag tattggggcc agggcaccct ggtcaccgtc  360
tcctca                                                                     366

SEQ ID NO: 202         moltype = AA  length = 122
FEATURE                Location/Qualifiers
REGION                 1..122
                       note = synthetic
source                 1..122
                       mol_type = protein
                       organism = synthetic construct
SEQUENCE: 202
QVQLVQSGAE VKKPGSSVKV SCKASGGTFS SYTISWVRQA PGQGLEWMGG ISPIFGTANY  60
AQKFQGRVTI TTDESTSTAY MELSSLRSED TAVYYCARES PYNWNQKYFQ YWGQGTLVTV  120
SS                                                                         122

SEQ ID NO: 203         moltype = DNA  length = 24
FEATURE                Location/Qualifiers
misc_feature           1..24
                       note = synthetic
source                 1..24
                       mol_type = other DNA
                       organism = synthetic construct
SEQUENCE: 203
ggaggcacct tcagcagcta tact                                                 24

SEQ ID NO: 204         moltype = AA  length = 8
FEATURE                Location/Qualifiers
REGION                 1..8
                       note = synthetic
```

```
source                  1..8
                        mol_type = protein
                        organism = synthetic construct
SEQUENCE: 204
GGTFSSYT                                                    8

SEQ ID NO: 205          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 205
atcagcccta tctttggtac agca                                  24

SEQ ID NO: 206          moltype = AA  length = 8
FEATURE                 Location/Qualifiers
REGION                  1..8
                        note = synthetic
source                  1..8
                        mol_type = protein
                        organism = synthetic construct
SEQUENCE: 206
ISPIFGTA                                                    8

SEQ ID NO: 207          moltype = DNA  length = 45
FEATURE                 Location/Qualifiers
misc_feature            1..45
                        note = synthetic
source                  1..45
                        mol_type = other DNA
                        organism = synthetic construct
SEQUENCE: 207
gcgagagagt ccccgtataa ctggaaccaa aaatacttcc agtat           45

SEQ ID NO: 208          moltype = AA  length = 15
FEATURE                 Location/Qualifiers
REGION                  1..15
                        note = synthetic
source                  1..15
                        mol_type = protein
                        organism = synthetic construct
SEQUENCE: 208
ARESPYNWNQ KYFQY                                            15

SEQ ID NO: 209          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 209
gacatccaga tgacccagtc tccttccacc ctgtctgcat ctgtaggaga cagagtcacc  60
atcacttgcc gggccagtca gagtattagt agctggttgg cctggtatca gcagaaacca  120
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgccaacag tataatagtt attcgtacac ttttggccag  300
gggaccaagc tggagatcaa a                                     321

SEQ ID NO: 210          moltype = AA  length = 107
FEATURE                 Location/Qualifiers
REGION                  1..107
                        note = synthetic
source                  1..107
                        mol_type = protein
                        organism = synthetic construct
SEQUENCE: 210
DIQMTQSPST LSASVGDRVT ITCRASQSIS SWLAWYQQKP GKAPKLLIYK ASSLESGVPS  60
RFSGSGSGTE FTLTISSLQP DDFATYYCQQ YNSYSYTFGQ GTKLEIK         107

SEQ ID NO: 211          moltype = DNA  length = 18
FEATURE                 Location/Qualifiers
misc_feature            1..18
                        note = synthetic
source                  1..18
                        mol_type = other DNA
                        organism = synthetic construct
```

```
SEQUENCE: 211
cagagtatta gtagctgg                                              18

SEQ ID NO: 212         moltype = AA  length = 6
FEATURE                Location/Qualifiers
REGION                 1..6
                       note = synthetic
source                 1..6
                       mol_type = protein
                       organism = synthetic construct
SEQUENCE: 212
QSISSW                                                           6

SEQ ID NO: 213         moltype =   length =
SEQUENCE: 213
000

SEQ ID NO: 214         moltype =   length =
SEQUENCE: 214
000

SEQ ID NO: 215         moltype = DNA  length = 27
FEATURE                Location/Qualifiers
misc_feature           1..27
                       note = synthetic
source                 1..27
                       mol_type = other DNA
                       organism = synthetic construct
SEQUENCE: 215
caacagtata atagttattc gtacact                                    27

SEQ ID NO: 216         moltype = AA  length = 9
FEATURE                Location/Qualifiers
REGION                 1..9
                       note = synthetic
source                 1..9
                       mol_type = protein
                       organism = synthetic construct
SEQUENCE: 216
QQYNSYSYT                                                        9

SEQ ID NO: 217         moltype = DNA  length = 363
FEATURE                Location/Qualifiers
misc_feature           1..363
                       note = synthetic
source                 1..363
                       mol_type = other DNA
                       organism = synthetic construct
SEQUENCE: 217
caggtccagc tggtgcagtc tgggtctgag gtgaagaagc ctgggtcctc ggtgaaggtc  60
tcctgcaagg cgtctggagg gaccctcagc ctctatgctg tcagctgggt gcgacaggcc  120
cctggacagg ggcttgagtg gatggggggg atcatcccta tctttggtac aacaaaatac  180
gcacaggagt tccagggcag agtcacgttt tccacggacg agtccacgag cacagcctac  240
atggagctga acagcctgcg atctgaggac acggccgtgt attactgtgc gagacaatgg  300
actatgacta gaaccttgga ttttgacatc tggggccagg gaaccctggt caccgtctcc  360
tca                                                              363

SEQ ID NO: 218         moltype = AA  length = 121
FEATURE                Location/Qualifiers
REGION                 1..121
                       note = synthetic
source                 1..121
                       mol_type = protein
                       organism = synthetic construct
SEQUENCE: 218
QVQLVQSGSE VKKPGSSVKV SCKASGGTLS LYAVSWVRQA PGQGLEWMGG IIPIFGTTKY  60
AQEFQGRVTF STDESTSTAY MELNSLRSED TAVYYCARQW TMTRTLDFDI WGQGTLVTVS  120
S                                                                121

SEQ ID NO: 219         moltype = DNA  length = 24
FEATURE                Location/Qualifiers
misc_feature           1..24
                       note = synthetic
source                 1..24
                       mol_type = other DNA
                       organism = synthetic construct
SEQUENCE: 219
ggagggaccc tcagcctcta tgct                                       24
```

```
SEQ ID NO: 220          moltype = AA  length = 8
FEATURE                 Location/Qualifiers
REGION                  1..8
                        note = synthetic
source                  1..8
                        mol_type = protein
                        organism = synthetic construct
SEQUENCE: 220
GGTLSLYA                                                                8

SEQ ID NO: 221          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 221
atcatcccta tctttggtac aaca                                              24

SEQ ID NO: 222          moltype = AA  length = 8
FEATURE                 Location/Qualifiers
REGION                  1..8
                        note = synthetic
source                  1..8
                        mol_type = protein
                        organism = synthetic construct
SEQUENCE: 222
IIPIFGTT                                                                8

SEQ ID NO: 223          moltype = DNA  length = 42
FEATURE                 Location/Qualifiers
misc_feature            1..42
                        note = synthetic
source                  1..42
                        mol_type = other DNA
                        organism = synthetic construct
SEQUENCE: 223
gcgagacaat ggactatgac tagaaccttg gattttgaca tc                          42

SEQ ID NO: 224          moltype = AA  length = 14
FEATURE                 Location/Qualifiers
REGION                  1..14
                        note = synthetic
source                  1..14
                        mol_type = protein
                        organism = synthetic construct
SEQUENCE: 224
ARQWTMTRTL DFDI                                                         14

SEQ ID NO: 225          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 225
gacatccaga tgacccagtc tccatcctcc ctgtctgcat ctgtaggaga cagagtcacc  60
atcacttgcc ggacaagtca gggcattaga aatgatttag gctggtatca gcagaaaccg  120
gggaaagccc ctaagcgcct gatctatggt gcatccagtt tgcaaagtgg ggtcccatca  180
agattcagcg gcagtggatc tgggacagaa ttcactctca caatcagcag cctgcagcct  240
gaagattttg caagttatta ctgtctacaa cataataatt atccgtggac gttcggccaa  300
gggaccaagg tggaaatcaa a                                                 321

SEQ ID NO: 226          moltype = AA  length = 107
FEATURE                 Location/Qualifiers
REGION                  1..107
                        note = synthetic
source                  1..107
                        mol_type = protein
                        organism = synthetic construct
SEQUENCE: 226
DIQMTQSPSS LSASVGDRVT ITCRTSQGIR NDLGWYQQKP GKAPKRLIYG ASSLQSGVPS  60
RFSGSGSGTE FTLTISSLQP EDFASYYCLQ HNNYPWTFGQ GTKVEIK                107

SEQ ID NO: 227          moltype = DNA  length = 18
FEATURE                 Location/Qualifiers
misc_feature            1..18
```

```
                        note = synthetic
source                  1..18
                        mol_type = other DNA
                        organism = synthetic construct
SEQUENCE: 227
cagggcatta gaaatgat                                            18

SEQ ID NO: 228          moltype = AA  length = 6
FEATURE                 Location/Qualifiers
REGION                  1..6
                        note = synthetic
source                  1..6
                        mol_type = protein
                        organism = synthetic construct
SEQUENCE: 228
QGIRND                                                         6

SEQ ID NO: 229          moltype =   length =
SEQUENCE: 229
000

SEQ ID NO: 230          moltype =   length =
SEQUENCE: 230
000

SEQ ID NO: 231          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 231
ctacaacata ataattatcc gtggacg                                  27

SEQ ID NO: 232          moltype = AA  length = 9
FEATURE                 Location/Qualifiers
REGION                  1..9
                        note = synthetic
source                  1..9
                        mol_type = protein
                        organism = synthetic construct
SEQUENCE: 232
LQHNNYPWT                                                      9

SEQ ID NO: 233          moltype = DNA  length = 369
FEATURE                 Location/Qualifiers
misc_feature            1..369
                        note = synthetic
source                  1..369
                        mol_type = other DNA
                        organism = synthetic construct
SEQUENCE: 233
caggtgcagc tggtggagtc tgggggaggc gtggtccagc ctgggaggtc cctgagactc  60
tcctgtgtag cctccggatt caccttcagt gtctatggca tgaactgggt ccgccaggct  120
ccaggcaagg gtctggactg ggtggcagtc atatcaaatg atggaagtta taaatactat  180
gcggactccg tgaagggccg attcaccatc tccagagaca attccaagaa cacggtgtat  240
ctgcaaatga acagcctgag aggtgaggac acggctattt attactgtgc gaaaaggaat  300
gaatgggagc tagaggaata ctacggtatg gacgtctggg gccaagggac cacggtcacc  360
gtctcctca                                                      369

SEQ ID NO: 234          moltype = AA  length = 123
FEATURE                 Location/Qualifiers
REGION                  1..123
                        note = synthetic
source                  1..123
                        mol_type = protein
                        organism = synthetic construct
SEQUENCE: 234
QVQLVESGGG VVQPGRSLRL SCVASGFTFS VYGMNWVRQA PGKGLDWVAV ISNDGSYKYY  60
ADSVKGRFTI SRDNSKNTVY LQMNSLRGED TAIYYCAKRN EWELEEYYGM DVWGQGTTVT  120
VSS                                                            123

SEQ ID NO: 235          moltype = DNA  length = 24
FEATURE                 Location/Qualifiers
misc_feature            1..24
                        note = synthetic
source                  1..24
                        mol_type = other DNA
```

```
                         organism = synthetic construct
SEQUENCE: 235
ggattcacct tcagtgtcta tggc                                       24

SEQ ID NO: 236           moltype = AA  length = 8
FEATURE                  Location/Qualifiers
REGION                   1..8
                         note = synthetic
source                   1..8
                         mol_type = protein
                         organism = synthetic construct
SEQUENCE: 236
GFTFSVYG                                                         8

SEQ ID NO: 237           moltype = DNA  length = 24
FEATURE                  Location/Qualifiers
misc_feature             1..24
                         note = synthetic
source                   1..24
                         mol_type = other DNA
                         organism = synthetic construct
SEQUENCE: 237
atatcaaatg atggaagtta taaa                                       24

SEQ ID NO: 238           moltype = AA  length = 8
FEATURE                  Location/Qualifiers
REGION                   1..8
                         note = synthetic
source                   1..8
                         mol_type = protein
                         organism = synthetic construct
SEQUENCE: 238
ISNDGSYK                                                         8

SEQ ID NO: 239           moltype = DNA  length = 48
FEATURE                  Location/Qualifiers
misc_feature             1..48
                         note = synthetic
source                   1..48
                         mol_type = other DNA
                         organism = synthetic construct
SEQUENCE: 239
gcgaaaagga atgaatggga gctagaggaa tactacggta tggacgtc             48

SEQ ID NO: 240           moltype = AA  length = 16
FEATURE                  Location/Qualifiers
REGION                   1..16
                         note = synthetic
source                   1..16
                         mol_type = protein
                         organism = synthetic construct
SEQUENCE: 240
AKRNEWELEE YYGMDV                                                16

SEQ ID NO: 241           moltype = DNA  length = 363
FEATURE                  Location/Qualifiers
misc_feature             1..363
                         note = synthetic
source                   1..363
                         mol_type = other DNA
                         organism = synthetic construct
SEQUENCE: 241
gaggtgcagc tggtggagtc tgggggagga ttggtacagt ctggagggtc cctgagactc  60
tcctgtgtag cctctggatt caccttcaat aattatgaga tgaattgggt ccgccaggct  120
ccagggaagg ggctggagtg gatttcatac attgatatta atggtggaag taccatctac  180
tatgcagact ctgtgaaggg ccgattcacc atctccagag acaatgccaa gaagtcactg  240
tatctgcaaa tgaacagcct gagagccgag gacacggcta tttactactg tgcgagcgcc  300
tttggttcgg gtggttttct ttttgactat tggggccagg gaaccctggt cactgtctcc  360
tca                                                               363

SEQ ID NO: 242           moltype = AA  length = 121
FEATURE                  Location/Qualifiers
REGION                   1..121
                         note = synthetic
source                   1..121
                         mol_type = protein
                         organism = synthetic construct
SEQUENCE: 242
EVQLVESGGG LVQSGGSLRL SCVASGFTFN NYEMNWVRQA PGKGLEWISY IDINGGSTIY  60
```

-continued

```
YADSVKGRFT ISRDNAKKSL YLQMNSLRAE DTAIYYCASA FGSGGFLFDY WGQGTLVTVS  120
S                                                                 121

SEQ ID NO: 243          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 243
ggattcacct tcaataatta tgag                                       24

SEQ ID NO: 244          moltype = AA  length = 8
FEATURE                 Location/Qualifiers
REGION                  1..8
                        note = synthetic
source                  1..8
                        mol_type = protein
                        organism = synthetic construct
SEQUENCE: 244
GFTFNNYE                                                         8

SEQ ID NO: 245          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 245
attgatatta atggtggaag taccatc                                    27

SEQ ID NO: 246          moltype = AA  length = 9
FEATURE                 Location/Qualifiers
REGION                  1..9
                        note = synthetic
source                  1..9
                        mol_type = protein
                        organism = synthetic construct
SEQUENCE: 246
IDINGGSTI                                                        9

SEQ ID NO: 247          moltype = DNA  length = 39
FEATURE                 Location/Qualifiers
misc_feature            1..39
                        note = synthetic
source                  1..39
                        mol_type = other DNA
                        organism = synthetic construct
SEQUENCE: 247
gcgagcgcct ttggttcggg tggttttctt tttgactat                       39

SEQ ID NO: 248          moltype = AA  length = 13
FEATURE                 Location/Qualifiers
REGION                  1..13
                        note = synthetic
source                  1..13
                        mol_type = protein
                        organism = synthetic construct
SEQUENCE: 248
ASAFGSGGFL FDY                                                   13

SEQ ID NO: 249          moltype = DNA  length = 366
FEATURE                 Location/Qualifiers
misc_feature            1..366
                        note = synthetic
source                  1..366
                        mol_type = other DNA
                        organism = synthetic construct
SEQUENCE: 249
caggtgcagc tggtggagtc tgggggaggc gtggtccagc ctgggatgtc cctgagactc  60
tcctgtatag cgtctggatt caccttcagt gactatgtca tacactgggt ccgccaggct  120
ccaggcaagg ggctggagtg ggtggcaatt atatggtatg atggaagtaa taaatactat  180
gcagactccg tgaagggccg attcaccatc tccagagaca attccaagaa cacgctgtat  240
cttgaaatga atagactgag agtcgaggac acggctgtgt tttactgtgc gaggggtctg  300
gggatcgaag attacaatta cggtatggac gtctggggcc aagggaccac ggtcaccgtc  360
tcctca                                                            366
```

-continued

```
SEQ ID NO: 250         moltype = AA  length = 122
FEATURE                Location/Qualifiers
REGION                 1..122
                       note = synthetic
source                 1..122
                       mol_type = protein
                       organism = synthetic construct
SEQUENCE: 250
QVQLVESGGG VVQPGMSLRL SCIASGFTFS DYVIHWVRQA PGKGLEWVAI IWYDGSNKYY  60
ADSVKGRFTI SRDNSKNTLY LEMNRLRVED TAVFYCARGL GIEDYNYGMD VWGQGTTVTV  120
SS                                                                 122

SEQ ID NO: 251         moltype = DNA  length = 24
FEATURE                Location/Qualifiers
misc_feature           1..24
                       note = synthetic
source                 1..24
                       mol_type = other DNA
                       organism = synthetic construct
SEQUENCE: 251
ggattcacct tcagtgacta tgtc                                        24

SEQ ID NO: 252         moltype = AA  length = 8
FEATURE                Location/Qualifiers
REGION                 1..8
                       note = synthetic
source                 1..8
                       mol_type = protein
                       organism = synthetic construct
SEQUENCE: 252
GFTFSDYV                                                           8

SEQ ID NO: 253         moltype = DNA  length = 24
FEATURE                Location/Qualifiers
misc_feature           1..24
                       note = synthetic
source                 1..24
                       mol_type = other DNA
                       organism = synthetic construct
SEQUENCE: 253
atatggtatg atggaagtaa taaa                                        24

SEQ ID NO: 254         moltype = AA  length = 8
FEATURE                Location/Qualifiers
REGION                 1..8
                       note = synthetic
source                 1..8
                       mol_type = protein
                       organism = synthetic construct
SEQUENCE: 254
IWYDGSNK                                                           8

SEQ ID NO: 255         moltype = DNA  length = 45
FEATURE                Location/Qualifiers
misc_feature           1..45
                       note = synthetic
source                 1..45
                       mol_type = other DNA
                       organism = synthetic construct
SEQUENCE: 255
gcgaggggtc tggggatcga agattacaat tacggtatgg acgtc                 45

SEQ ID NO: 256         moltype = AA  length = 15
FEATURE                Location/Qualifiers
REGION                 1..15
                       note = synthetic
source                 1..15
                       mol_type = protein
                       organism = synthetic construct
SEQUENCE: 256
ARGLGIEDYN YGMDV                                                  15

SEQ ID NO: 257         moltype = DNA  length = 357
FEATURE                Location/Qualifiers
misc_feature           1..357
                       note = synthetic
source                 1..357
                       mol_type = other DNA
                       organism = synthetic construct
```

```
SEQUENCE: 257
gaggtgcagc tggtgcagtc tggagcagag gtgaaaaagc ccggggagtc tctgaagatc  60
tcctgtaagg gttctggata cagctttacc agctactgga tcggctgggt gcgccagatg  120
cccgggaaag gcctggagtg gatggggatc atctatcctg gtgactctga taccagatac  180
agcccgtcct tccaaggcca ggtcaccatc tcagccgaca agtccatcag caccgcctac  240
ctgcagtgga gcagcctgaa ggcctcggac accgccatgt attactgtgc gagacactgg  300
accgacgagg atgcttttga tatctggggc caagggacaa tggtcaccgt ctcttca     357

SEQ ID NO: 258         moltype = AA  length = 119
FEATURE                Location/Qualifiers
REGION                 1..119
                       note = synthetic
source                 1..119
                       mol_type = protein
                       organism = synthetic construct
SEQUENCE: 258
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARHW TDEDAFDIWG QGTMVTVSS   119

SEQ ID NO: 259         moltype = DNA  length = 24
FEATURE                Location/Qualifiers
misc_feature           1..24
                       note = synthetic
source                 1..24
                       mol_type = other DNA
                       organism = synthetic construct
SEQUENCE: 259
ggatacagct ttaccagcta ctgg                                         24

SEQ ID NO: 260         moltype = AA  length = 8
FEATURE                Location/Qualifiers
REGION                 1..8
                       note = synthetic
source                 1..8
                       mol_type = protein
                       organism = synthetic construct
SEQUENCE: 260
GYSFTSYW                                                           8

SEQ ID NO: 261         moltype = DNA  length = 24
FEATURE                Location/Qualifiers
misc_feature           1..24
                       note = synthetic
source                 1..24
                       mol_type = other DNA
                       organism = synthetic construct
SEQUENCE: 261
atctatcctg gtgactctga tacc                                         24

SEQ ID NO: 262         moltype = AA  length = 8
FEATURE                Location/Qualifiers
REGION                 1..8
                       note = synthetic
source                 1..8
                       mol_type = protein
                       organism = synthetic construct
SEQUENCE: 262
IYPGDSDT                                                           8

SEQ ID NO: 263         moltype = DNA  length = 36
FEATURE                Location/Qualifiers
misc_feature           1..36
                       note = synthetic
source                 1..36
                       mol_type = other DNA
                       organism = synthetic construct
SEQUENCE: 263
gcgagacact ggaccgacga ggatgctttt gatatc                            36

SEQ ID NO: 264         moltype = AA  length = 12
FEATURE                Location/Qualifiers
REGION                 1..12
                       note = synthetic
source                 1..12
                       mol_type = protein
                       organism = synthetic construct
SEQUENCE: 264
ARHWTDEDAF DI                                                      12
```

-continued

```
SEQ ID NO: 265          moltype = DNA  length = 369
FEATURE                 Location/Qualifiers
misc_feature            1..369
                        note = synthetic
source                  1..369
                        mol_type = other DNA
                        organism = synthetic construct
SEQUENCE: 265
caggtccagc tggtgcagtc tggggactgag gtgaagaagc ctgggtcttc ggtgaaggtc  60
tcctgcaagg cttctggagg caccttcggc agttatccta tcagctgggt gcgacaggcc  120
cctggacaag ggcttgagtg gatgggaggg atcatcccta tctttggtac agcaaactcc  180
gcacagaagt tccagggcag agtcacgatt accacggacg aacccacgag cacagccttc  240
atggagctga gcagcctgag atctgaggac acggccgtgt attactgtgc gagaccgtat  300
tacgatattt tgactgacta ctacggtatg gacgtctggg gtcaagggac cacggtcacc  360
gtctcctca                                                          369

SEQ ID NO: 266          moltype = AA  length = 123
FEATURE                 Location/Qualifiers
REGION                  1..123
                        note = synthetic
source                  1..123
                        mol_type = protein
                        organism = synthetic construct
SEQUENCE: 266
QVQLVQSGTE VKKPGSSVKV SCKASGGTFG SYPISWVRQA PGQGLEWMGG IIPIFGTANS  60
AQKFQGRVTI TTDEPTSTAF MELSSLRSED TAVYYCARPY YDILTDYYGM DVWGQGTTVT  120
VSS                                                                123

SEQ ID NO: 267          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 267
ggaggcacct tcggcagtta tcct                                         24

SEQ ID NO: 268          moltype = AA  length = 8
FEATURE                 Location/Qualifiers
REGION                  1..8
                        note = synthetic
source                  1..8
                        mol_type = protein
                        organism = synthetic construct
SEQUENCE: 268
GGTFGSYP                                                           8

SEQ ID NO: 269          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 269
atcatcccta tctttggtac agca                                         24

SEQ ID NO: 270          moltype = AA  length = 8
FEATURE                 Location/Qualifiers
REGION                  1..8
                        note = synthetic
source                  1..8
                        mol_type = protein
                        organism = synthetic construct
SEQUENCE: 270
IIPIFGTA                                                           8

SEQ ID NO: 271          moltype = DNA  length = 48
FEATURE                 Location/Qualifiers
misc_feature            1..48
                        note = synthetic
source                  1..48
                        mol_type = other DNA
                        organism = synthetic construct
SEQUENCE: 271
gcgagaccgt attacgatat tttgactgac tactacggta tggacgtc               48

SEQ ID NO: 272          moltype = AA  length = 16
```

```
FEATURE                Location/Qualifiers
REGION                 1..16
                       note = synthetic
source                 1..16
                       mol_type = protein
                       organism = synthetic construct
SEQUENCE: 272
ARPYYDILTD YYGMDV                                                16

SEQ ID NO: 273         moltype = DNA  length = 354
FEATURE                Location/Qualifiers
misc_feature           1..354
                       note = synthetic
source                 1..354
                       mol_type = other DNA
                       organism = synthetic construct
SEQUENCE: 273
caggtccagc tggtgcagtc tggggctgag gtgaagaagc ctgggtcctc ggtgaaggtc  60
tcctgcaagg cttctggagg caccttcagc agctatgcta tcagctgggt gcgacaggcc  120
cctggacaag ggcttgagtg gatgggaggg atcatcccta tctttggtac agcaaactac  180
gcacagaagt tccagggcag agtcacgatt accacggacg aatccacgag cacagcctac  240
atggagctga gcagtctgag atctgaggac acggccgtgt attactgtgc gacagaaggg  300
tacaactgga actatgacta ttggggccag ggaaccctgg tcaccgtctc ctca        354

SEQ ID NO: 274         moltype = AA  length = 118
FEATURE                Location/Qualifiers
REGION                 1..118
                       note = synthetic
source                 1..118
                       mol_type = protein
                       organism = synthetic construct
SEQUENCE: 274
QVQLVQSGAE VKKPGSSVKV SCKASGGTFS SYAISWVRQA PGQGLEWMGG IIPIFGTANY  60
AQKFQGRVTI TTDESTSTAY MELSSLRSED TAVYYCATEG YNWNYDYWGQ GTLVTVSS    118

SEQ ID NO: 275         moltype = DNA  length = 24
FEATURE                Location/Qualifiers
misc_feature           1..24
                       note = synthetic
source                 1..24
                       mol_type = other DNA
                       organism = synthetic construct
SEQUENCE: 275
ggaggcacct tcagcagcta tgct                                       24

SEQ ID NO: 276         moltype = AA  length = 8
FEATURE                Location/Qualifiers
REGION                 1..8
                       note = synthetic
source                 1..8
                       mol_type = protein
                       organism = synthetic construct
SEQUENCE: 276
GGTFSSYA                                                         8

SEQ ID NO: 277         moltype = DNA  length = 24
FEATURE                Location/Qualifiers
misc_feature           1..24
                       note = synthetic
source                 1..24
                       mol_type = other DNA
                       organism = synthetic construct
SEQUENCE: 277
atcatcccta tctttggtac agca                                       24

SEQ ID NO: 278         moltype = AA  length = 8
FEATURE                Location/Qualifiers
REGION                 1..8
                       note = synthetic
source                 1..8
                       mol_type = protein
                       organism = synthetic construct
SEQUENCE: 278
IIPIFGTA                                                         8

SEQ ID NO: 279         moltype = DNA  length = 33
FEATURE                Location/Qualifiers
misc_feature           1..33
                       note = synthetic
```

```
source                1..33
                      mol_type = other DNA
                      organism = synthetic construct
SEQUENCE: 279
gcgacagaag ggtacaactg gaactatgac tat                              33

SEQ ID NO: 280        moltype = AA  length = 11
FEATURE               Location/Qualifiers
REGION                1..11
                      note = synthetic
source                1..11
                      mol_type = protein
                      organism = synthetic construct
SEQUENCE: 280
ATEGYNWNYD Y                                                      11

SEQ ID NO: 281        moltype = DNA  length = 363
FEATURE               Location/Qualifiers
misc_feature          1..363
                      note = synthetic
source                1..363
                      mol_type = other DNA
                      organism = synthetic construct
SEQUENCE: 281
caggtccagc tggtgcagtc tggggctgag gtgaagaagc ctgggtcctc ggtgaaggtc  60
tcctgcaagg cttctggagg caccttcagc agctatgtta tcacctgggt gcgacaggtc  120
cctggacaag ggcttgagtg gatgggaggg atcatcccta tctttggtac agcaaactac  180
gcacagaagt tccagggcag agtcacgatt accacggacg aatccacgag cacagcctac  240
atggacctga gcagcctgag atctgaggac acggcctttt attattgtgc gagaaggagg  300
tctaactggg gatctcatgc ttttgatatc tggggccaag ggacaatggt caccgtctct  360
tca                                                               363

SEQ ID NO: 282        moltype = AA  length = 121
FEATURE               Location/Qualifiers
REGION                1..121
                      note = synthetic
source                1..121
                      mol_type = protein
                      organism = synthetic construct
SEQUENCE: 282
QVQLVQSGAE VKKPGSSVKV SCKASGGTFS SYVITWVRQV PGQGLEWMGG IIPIFGTANY  60
AQKFQGRVTI TTDESTSTAY MDLSSLRSED TAFYYCARRR SNWGSHAFDI WGQGTMVTVS  120
S                                                                 121

SEQ ID NO: 283        moltype = DNA  length = 24
FEATURE               Location/Qualifiers
misc_feature          1..24
                      note = synthetic
source                1..24
                      mol_type = other DNA
                      organism = synthetic construct
SEQUENCE: 283
ggaggcacct tcagcagcta tgtt                                        24

SEQ ID NO: 284        moltype = AA  length = 8
FEATURE               Location/Qualifiers
REGION                1..8
                      note = synthetic
source                1..8
                      mol_type = protein
                      organism = synthetic construct
SEQUENCE: 284
GGTFSSYV                                                          8

SEQ ID NO: 285        moltype = DNA  length = 24
FEATURE               Location/Qualifiers
misc_feature          1..24
                      note = synthetic
source                1..24
                      mol_type = other DNA
                      organism = synthetic construct
SEQUENCE: 285
atcatcccta tctttggtac agca                                        24

SEQ ID NO: 286        moltype = AA  length = 8
FEATURE               Location/Qualifiers
REGION                1..8
                      note = synthetic
source                1..8
```

-continued

```
                        mol_type = protein
                        organism = synthetic construct
SEQUENCE: 286
IIPIFGTA                                                                8

SEQ ID NO: 287          moltype = DNA  length = 42
FEATURE                 Location/Qualifiers
misc_feature            1..42
                        note = synthetic
source                  1..42
                        mol_type = other DNA
                        organism = synthetic construct
SEQUENCE: 287
gcgagaagga ggtctaactg gggatctcat gcttttgata tc                          42

SEQ ID NO: 288          moltype = AA  length = 14
FEATURE                 Location/Qualifiers
REGION                  1..14
                        note = synthetic
source                  1..14
                        mol_type = protein
                        organism = synthetic construct
SEQUENCE: 288
ARRRSNWGSH AFDI                                                         14

SEQ ID NO: 289          moltype = DNA  length = 387
FEATURE                 Location/Qualifiers
misc_feature            1..387
                        note = synthetic
source                  1..387
                        mol_type = other DNA
                        organism = synthetic construct
SEQUENCE: 289
gaagtgcagc tggtggagtc tgggggaggc ttggtacagc ctggcaggtc cctgagactc  60
tcctgtgcag cctctggaat cacctttgat gattatgcca tgtactgggt ccggcaagct  120
ccagggaagg gcctggagtg ggtctcaggt attagttgga atagtggtag cataggctat  180
gcggactctg tgaagggccg attcaccatc tccagagaca acgccaagaa ctccctgtat  240
ctgcaaatga acagtctgag agttgaggac acggccttgt attattgtgc aaaagataag  300
gggtattacg atattttgac tggagattac tactactact acggtatgga cgtctggggc  360
caagggacca cggtcaccgt ctcctca                                          387

SEQ ID NO: 290          moltype = AA  length = 129
FEATURE                 Location/Qualifiers
REGION                  1..129
                        note = synthetic
source                  1..129
                        mol_type = protein
                        organism = synthetic construct
SEQUENCE: 290
EVQLVESGGG LVQPGRSLRL SCAASGITFD DYAMYWVRQA PGKGLEWVSG ISWNSGSIGY  60
ADSVKGRFTI SRDNAKNSLY LQMNSLRVED TALYYCAKDK GYYDILTGDY YYYYGMDVWG  120
QGTTVTVSS                                                              129

SEQ ID NO: 291          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 291
ggaatcacct ttgatgatta tgcc                                              24
```

-continued

```
SEQ ID NO: 292          moltype = AA  length = 8
FEATURE                 Location/Qualifiers
REGION                  1..8
                        note = synthetic
source                  1..8
                        mol_type = protein
                        organism = synthetic construct
SEQUENCE: 292
GITFDDYA                                                          8

SEQ ID NO: 293          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 293
attagttgga atagtggtag cata                                        24

SEQ ID NO: 294          moltype = AA  length = 8
FEATURE                 Location/Qualifiers
REGION                  1..8
                        note = synthetic
source                  1..8
                        mol_type = protein
                        organism = synthetic construct
SEQUENCE: 294
ISWNSGSI                                                          8

SEQ ID NO: 295          moltype = DNA  length = 66
FEATURE                 Location/Qualifiers
misc_feature            1..66
                        note = synthetic
source                  1..66
                        mol_type = other DNA
                        organism = synthetic construct
SEQUENCE: 295
gcaaaagata aggggtatta cgatattttg actggagatt actactacta ctacggtatg  60
gacgtc                                                            66

SEQ ID NO: 296          moltype = AA  length = 22
FEATURE                 Location/Qualifiers
REGION                  1..22
                        note = synthetic
source                  1..22
                        mol_type = protein
                        organism = synthetic construct
SEQUENCE: 296
AKDKGYYDIL TGDYYYYYGM DV                                          22
```

PROTEIN-ANTIVIRAL COMPOUND CONJUGATES

CROSS REFERENCE TO RELATED APPLICATIONS

This application is a continuation of U.S. application Ser. No. 17/156,525, filed Jan. 23, 2021, which claims priority to, and the benefit of, U.S. Provisional Application No. 62/965,735, filed Jan. 24, 2020, and U.S. Provisional Application No. 63/094,285 filed Oct. 20, 2020, the entire contents of each of which are herein incorporated by reference in their entirety for all purposes.

GOVERNMENT LICENSE RIGHTS

This invention was made with Government support under Agreement HHS0100201700020C, awarded by the U.S. Department of Health and Human Services. The Government has certain rights in the invention.

SEQUENCE LISTING

This application includes a Sequence Listing XML file with the title “Sequence Listing XML,” created on Nov. 14, 2023, with a size of 347 KB, the contents of which are herein incorporated by reference in its entirety for all purposes.

FIELD

Provided herein are antiviral compounds and protein conjugates thereof, and methods for treating a variety of diseases, disorders, and conditions including administering the antiviral compounds, and protein conjugates thereof.

BACKGROUND

Influenza is a highly contagious disease, which has a long history characterized by waves of pandemics, epidemics, resurgences, and outbreaks. In spite of annual vaccination efforts, influenza infections result in substantial morbidity and mortality.

Influenza viruses consist of three main types, A, B, and C. Influenza A viruses can be classified into subtypes based on allelic variations in antigenic regions of two genes that encode the surface glycoproteins, hemagglutinin (HA) and neuraminidase (NA), which are required for viral attachment and entry into the host cell.

Hemagglutinin is a trimeric glycoprotein that contains two structural domains, a globular head domain that consists of the receptor-binding site (that is subject to frequent antigenic drift) and the stem region (more conserved among various strains of influenza virus). The HA protein is synthesized as a precursor (HA0), which undergoes proteolytic processing to produce two subunits (HA1 and HA2), which associate with one another to form the stem/globular head structure. The HA1 peptide is responsible for the attachment of virus to the cell surface. The HA2 peptide forms a stem-like structure that mediates the fusion of viral and cell membranes in endosomes, allowing the release of the ribonucleoprotein complex into the cytoplasm.

Currently, there are eighteen subtypes defined by their hemagglutinin proteins (H1-H18). The eighteen HAs can be classified into two groups. Group 1 consists of H1, H2, H5, H6, H8, H9, H11, H12, H13, H16, H17, and H18 subtypes, and group 2 includes H3, H4, H7, H10, H14, and H15 subtypes.

Despite decades of research, there are no marketed antibodies or antibody-drug conjugates (ADCs) that broadly neutralize or inhibit influenza A virus infection or attenuate disease caused by influenza A virus. Therefore, there is a need to identify new antibodies and ADCs that neutralize multiple subtypes of influenza A virus and can be used as medicaments for prevention or therapy of influenza A infection.

SUMMARY

Provided herein are compounds useful, for example, in antiviral treatments. In certain embodiments, the compounds include VX-787 and derivatives thereof, baloxavir and derivatives thereof, and/or baloxavir marboxil and derivatives thereof. In one embodiment, provided is an antibody-drug conjugate including an anti-influenza antibody or antigen-binding fragment thereof conjugated to a payload (e.g., an antiviral compound), linker-payload (e.g., linker-antiviral compound), and/or compound as described herein.

In certain embodiments, provided are compounds having the following structure

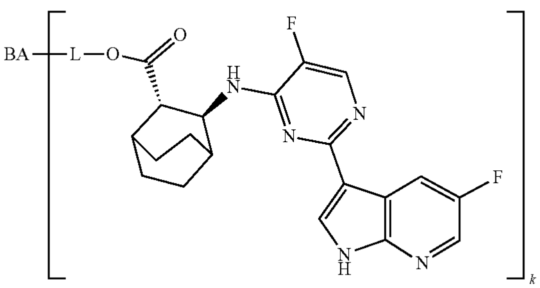

or

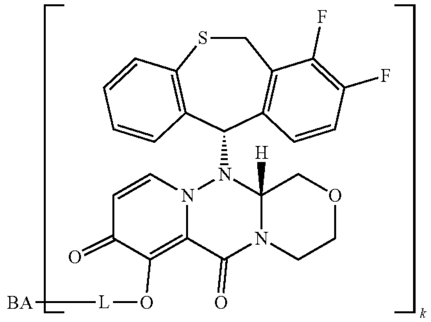

wherein L is a linker; BA is a binding agent; and k is an integer from one to thirty.

In certain embodiments, provided are linker-payloads (e.g., linker-antiviral compounds) having the following structure

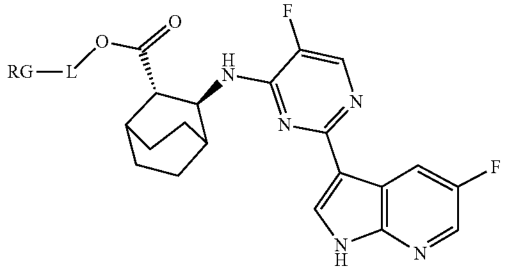

or

-continued

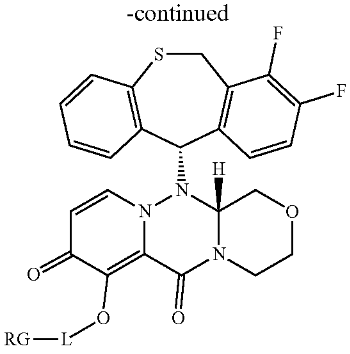

or a pharmaceutically acceptable salt thereof, wherein L is a linker; and RG is a reactive moiety.

In another embodiment, set forth herein are methods for making the payloads or compounds, linker-payloads, or antibody-drug conjugates, and compositions described herein.

In another embodiment, provided herein are methods for the treatment, prophylaxis, reduction, or inhibition of a disease, disorder, or condition associated with an infection, as described herein, in a subject including administering to the subject an effective amount of a payload (e.g., antiviral compound), linker-payload (e.g., linker-antiviral compound), antibody-drug conjugate, or pharmaceutical composition as described herein.

BRIEF DESCRIPTIONS OF THE DRAWINGS

DESCRIPTION OF EXEMPLARY EMBODIMENTS

Figure 1A:
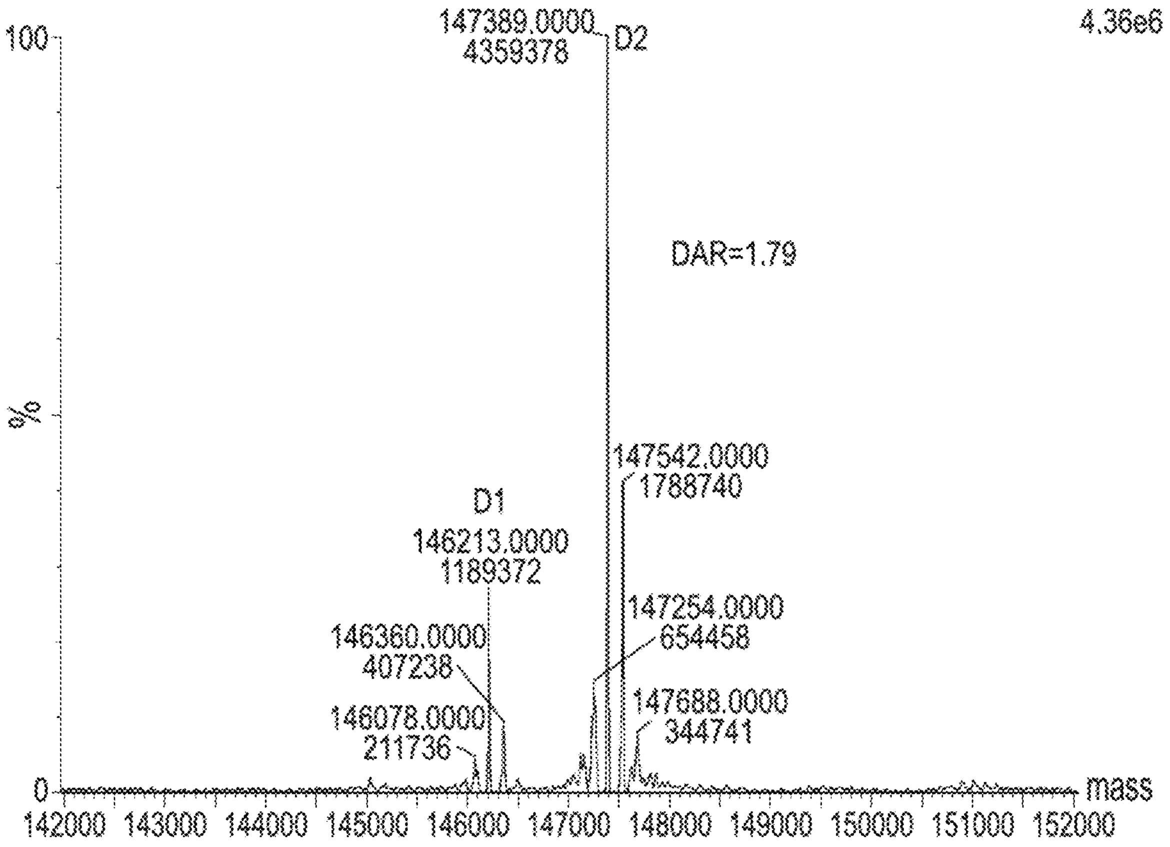
FIG. 1A shows the intensity-weighted average linker-payload (e.g., linker-antiviral compound) loadings as measured by LC-MS for 11729-Q295-11.

Provided herein are compounds, compositions, and methods useful for treating, for example, influenza infections in a subject.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term provided herein, these Definitions prevail unless stated otherwise.

The phrase "influenza hemagglutinin," also called "influenza HA" is a trimeric glycoprotein found on the surface of influenza virions, which mediates viral attachment (via HA1 binding to a-2,3- and a-2,6-sialic acids) and entry (through conformational change) into host cells. The HA is comprised of two structural domains: a globular head domain containing the receptor binding site (subject to high frequency of antigenic mutations) and the stem region (more conserved among various strains of influenza virus). The influenza HA is synthesized as a precursor (HA0) that undergoes proteolytic processing to produce two subunits (HA1 and HA2) which associate with one another to form the stem/globular head structure. The viral HA is the most variable antigen on the virus (eighteen subtypes can be classified into two groups), but the stem (HA2) is highly conserved within each group.

The amino acid sequence of full-length Influenza HA is exemplified by the amino acid sequence of influenza isolate H1N1 A/California/04/2009 provided in GenBank as accession number FJ966082.1. The phrase "influenza-HA" also includes protein variants of influenza HA isolated from different influenza isolates, e.g., GQ149237.1, NC 002017, KM972981.1, etc. The phrase "influenza-HA" also includes recombinant influenza HA or a fragment thereof. The phrase also encompasses influenza HA or a fragment thereof coupled to, for example, histidine tag, mouse or human Fc, or a signal sequence.

The phrase "influenza infection," as used herein, also characterized as "flu" refers to the severe acute respiratory illness caused by influenza virus. The phrase includes respiratory tract infection and the symptoms that include high fever, headache, general aches and pains, fatigue and weakness, in some instances extreme exhaustion, stuffy nose, sneezing, sore throat, chest discomfort, cough, shortness of breath, bronchitis, pneumonia, and death in severe cases.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those radicals having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to, methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl. A pentyl moiety includes, but is not limited to, n-pentyl and i-pentyl. A hexyl moiety includes, but is not limited to, n-hexyl.

As used herein, "alkylene" refers to a divalent alkyl group. Unless specified otherwise, alkylene includes, but is not limited to, 1-20 carbon atoms. The alkylene group is optionally substituted as described herein for alkyl. In some embodiments, alkylene is unsubstituted.

Designation of an amino acid or amino acid residue without specifying its stereochemistry is intended to encompass the L-form of the amino acid, the D-form of the amino acid, or a racemic mixture thereof.

As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, $—CF_3$, $—CH_2CF_3$, $—CCl_2F$, and $—CCl_3$.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those radicals having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to, vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those radicals having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2—O—$ for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to, methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to, those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are limited to, phenyl, naphthyl, fluorenyl, azulenyl, anthryl, phenanthryl, and pyrenyl.

As used herein, "arylalkyl" refers to a monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

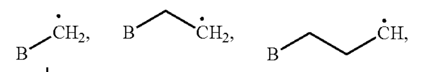

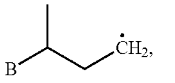

or

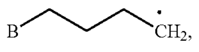

wherein B is an aromatic moiety, e.g., aryl or phenyl. Arylalkyl is optionally substituted, i.e., the aryl group and/or the alkyl group, can be substituted as disclosed herein. Examples of arylalkyl include, but are not limited to, benzyl.

As used herein, "alkylaryl" refers to a monovalent moiety that is a radical of an aryl compound, wherein the aryl compound is substituted with an alkyl substituent, i.e., the aryl compound includes a single bond to an alkyl group and wherein the radical is localized on the aryl group. An alkylaryl group bonds to the illustrated chemical structure via the aryl group. An alkylaryl can be represented by the structure, e.g.,

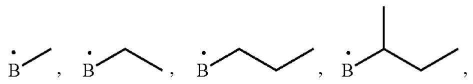

or

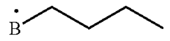

wherein B is an aromatic moiety, e.g., phenyl. Alkylaryl is optionally substituted, i.e., the aryl group and/or the alkyl group, can be substituted as disclosed herein. Examples of alkylaryl include, but are not limited to, toluyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g.,

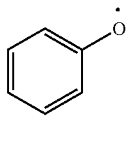

for phenoxy. Aryloxy substituents bond to the compound which they substitute through this oxygen atom. Aryloxy is optionally substituted. Aryloxy includes, but is not limited to, those radicals having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to, phenoxy, naphthoxy, and anthroxy.

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl, heteroalkenyl, and heteroalkynyl are optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to a divalent heteroaryl in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "Lewis acid" refers to a molecule or ion that accepts an electron lone pair. The Lewis acids used in the methods described herein are those other than protons. Lewis acids include, but are not limited to, non-metal acids, metal acids, hard Lewis acids, and soft Lewis acids. Lewis acids include, but are not limited to, Lewis acids of aluminum, boron, iron, tin, titanium, magnesium, copper, antimony, phosphorus, silver, ytterbium, scandium, nickel, and zinc. Illustrative Lewis acids include, but are not limited to, $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl), $Zn(OTf)_2$, $ZnCl_2$, $Yb(OTf)_3$, $Sc(OTf)_3$, $MgBr_2$, $NiCl_2$, $Sn(OTf)_2$, $Ni(OTf)_2$, and $Mg(OTf)_2$.

As used herein, "N-containing heterocycloalkyl," refers to a cycloalkyl in which one or more carbon atoms are replaced by heteroatoms and wherein at least one replacing heteroatom is a nitrogen atom. Suitable heteroatoms in addition to nitrogen, include, but are not limited to, oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety, for example, optionally substituted alkyl, means that such moiety is optionally bonded to one or more substituents. Examples of such substituents include, but are not limited to, halo, cyano, nitro, amino, hydroxyl, optionally substituted haloalkyl, aminoalkyl, hydroxyalkyl, azido, epoxy, optionally substituted heteroaryl, optionally substituted heterocycloalkyl,

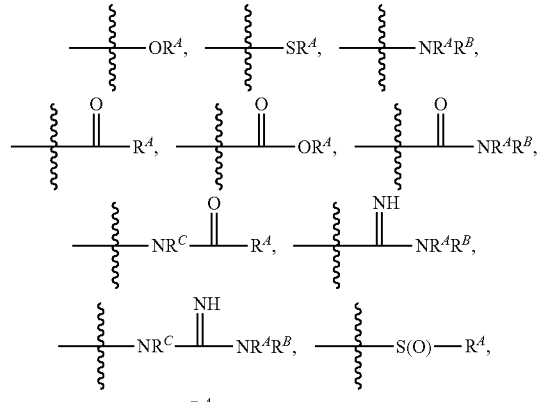

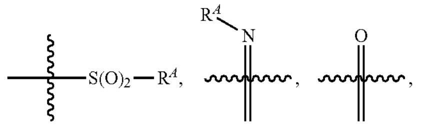

or

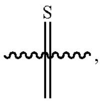

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic ring, wherein the ring is optionally substituted, and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "binding agent" refers to any molecule, e.g., protein, antibody, or fragment thereof, capable of binding with specificity to a given binding partner, e.g., antigen.

As used herein, "linker" refers to a divalent, trivalent, or multivalent moiety that covalently links, or is capable of covalently linking (e.g., via a reactive group), the binding agent to one or more compounds described herein, for instance, payload or antiviral compounds and enhancement agents.

As used herein, “amide synthesis conditions” refers to reaction conditions suitable to effect the formation of an amide, e.g., by the reaction of a carboxylic acid, activated carboxylic acid, or acyl halide with an amine. In some examples, amide synthesis conditions refers to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dim ethyl amino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dim ethylamino)methyl ene]-1H-1,2,3-triazolo[4,5-b]pyridinium 3-oxide hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), carbonyldiimidazole (CDI), and 1-Cyano-2-ethoxy-2-oxoethylidenaminooxy)dimethylamino-morpholino-carbenium hexafluorophosphate (COMU). In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forms a product complex with the deprotonated carboxylic acid as a result of nucleophilic attack by the deprotonated carboxylic acid onto the protonated reagent. The activated carboxylic esters of certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, the term “residue” refers to the chemical moiety within a compound that remains after a chemical reaction. For example, the term “amino acid residue” or “N-alkyl amino acid residue” refers to the product of an amide coupling or peptide coupling of an amino acid or a N-alkyl amino acid to a suitable coupling partner; wherein, for example, a water molecule is expelled after the amide or peptide coupling of the amino acid or the N-alkylamino acid, resulting in the product having the amino acid residue or N-alkyl amino acid residue incorporated therein.

As used herein, “constitutional isomers” refers to compounds that have the same molecular formula, but different chemical structures resulting from the way the atoms are arranged. Exemplary constitutional isomers include n-propyl and isopropyl; n-butyl, sec-butyl, and tert-butyl; and n-pentyl, isopentyl, and neopentyl, and the like.

Certain groups, moieties, substituents, and atoms are depicted with a wiggly line that intersects a bond or bonds to indicate the atom through which the groups, moieties, substituents, atoms are bonded. For example, a phenyl group that is substituted with an isopropyl group depicted as:

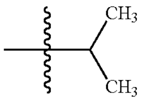 or 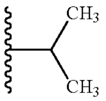

has the following structure:

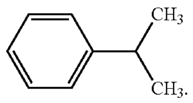

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

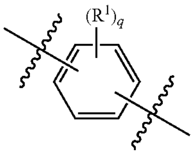 or 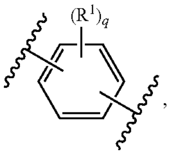, wherein subscript q is an integer from 0 to 4 and in which the positions of substituent $R^1$ are described generically, i.e., not directly attached to any vertex of the bond line structure, i.e., specific ring carbon atom, includes the following, non-limiting examples of groups in which the substituent $R^1$ is bonded to a specific ring carbon atom:

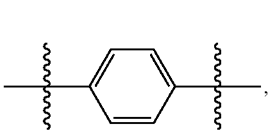, 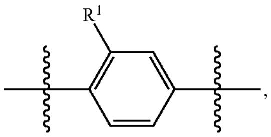,

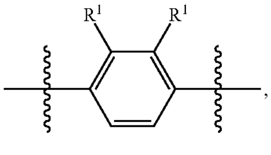, 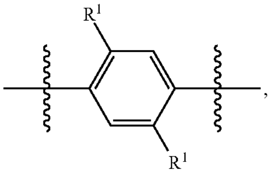,

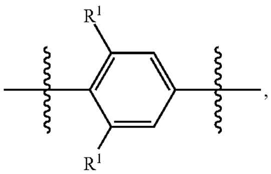, 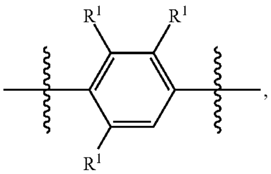,

-continued

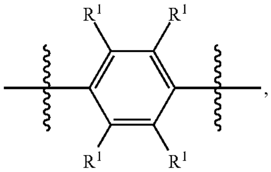,
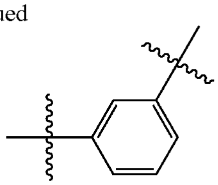,
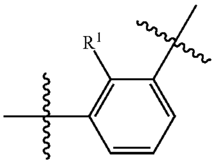,
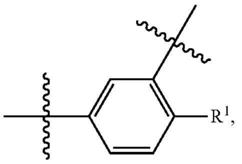
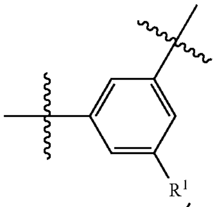,
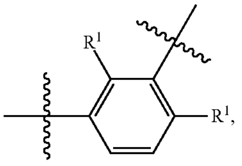
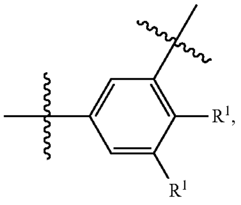
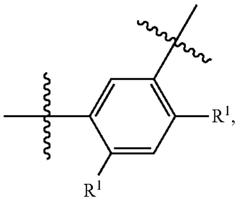
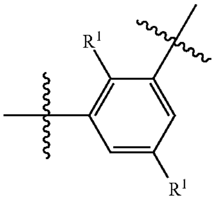,
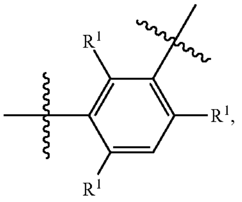
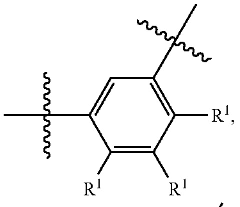
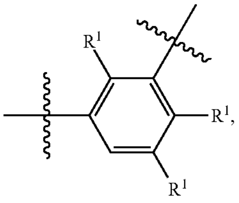
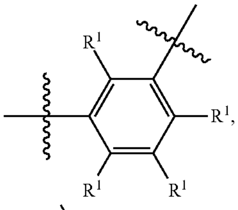
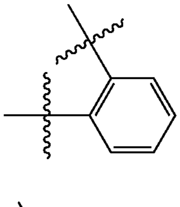,
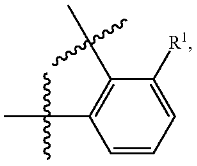
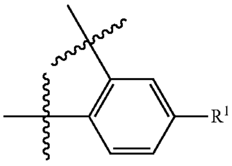,
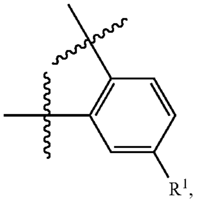
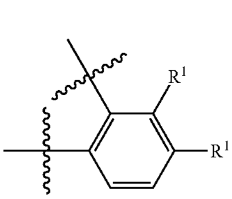, -continued

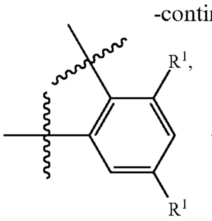
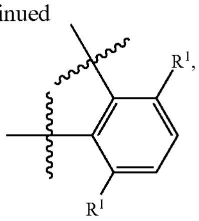
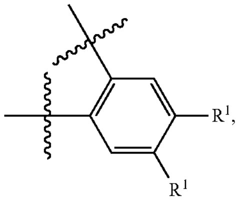
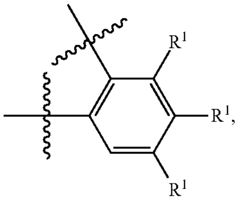
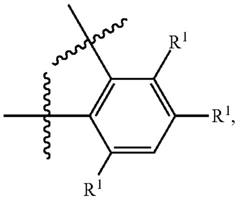
and
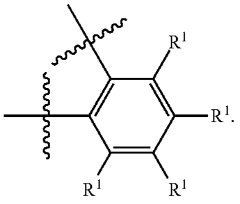

As used herein, the phrase "reactive linker," or the abbreviation "RL" refers to a monovalent group that includes a reactive group ("RG") and spacer group ("SP"), depicted for example as

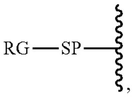, wherein RG is the reactive group and SP is the spacer group. As described herein, a reactive linker may include more than one reactive group and more than one spacer group. The spacer group is any divalent moiety that bridges the reactive group to another group, such as a payload (e.g., antiviral compound). The reactive linkers (RLs), together with the payloads (e.g., antiviral compounds) to which they are bonded, provide intermediates ("linker-payloads" (LPs) (e.g., linker-antiviral compounds)) useful as synthetic precursors for the preparation of the antibody conjugates described herein. As used herein, payloads can be antivral compounds, and linker-payloads incorporating those antiviral compounds can be referred to as "linker-antiviral compounds." The reactive linker includes a reactive group, which is a functional group or moiety that is capable of reacting with a reactive portion of another group, for instance, an antibody, modified antibody, or antigen binding fragment thereof. The moiety resulting from the reaction of the reactive group with the antibody, modified antibody, or antigen binding fragment thereof, together with the linking group, include the "binding agent linker" ("BL") portion of the conjugate, described herein. In certain embodiments, the "reactive group" is a functional group or moiety (e.g., maleimide or N-hydroxysuccinimide (NETS) ester) that reacts with a cysteine or lysine residue of an antibody or antigen-binding fragment thereof. In some examples, the reactive group is a functional group, e.g.,

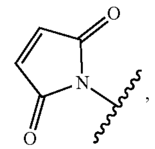 [SMILES: *N1C(=O)C=CC1=O], which reacts with a cysteine residue on an antibody or antigen-binding fragment thereof, to form a carbon-sulfur bond thereto, e.g.,

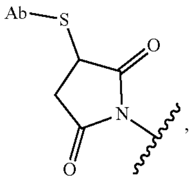, wherein Ab refers to an antibody or antigen-binding fragment thereof and S refers to the S atom on a cysteine residue through which the functional group bonds to the Ab. In some examples, the reactive group is a functional group, e.g.,

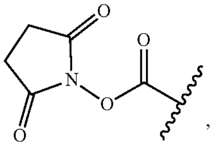 [SMILES: *C(=O)ON1C(=O)CCC1=O], which reacts with a lysine residue on an antibody or antigen-binding fragment thereof, to form an amide bond thereto, e.g.,

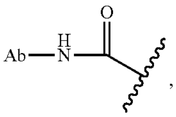, wherein Ab refers to an antibody or antigen-binding fragment thereof and NH refers to the NH atom on a lysine side chain residue through which the functional group bonds to the Ab.

As used herein, the phrase "biodegradable moiety" refers to a moiety that degrades in vivo to non-toxic, biocompatible components which can be cleared from the body by ordinary biological processes. In some embodiments, a biodegradable moiety completely or substantially degrades in vivo over the course of about 90 days or less, about 60 days or less, or about 30 days or less, where the extent of degradation is based on percent mass loss of the biodegradable moiety, and wherein complete degradation corresponds to 100% mass loss. Exemplary biodegradable moieties include, without limitation, aliphatic polyesters such as poly(s-caprolactone) (PCL), poly(3-hydroxybutyrate) (PHB), poly(glycolic acid) (PGA), poly(lactic acid) (PLA) and its copolymers with glycolic acid (i.e., poly(D,L-lactide-coglycolide) (PLGA) (Vert M, Schwach G, Engel R and Coudane J (1998) J Control Release 53(1-3):85-92; Jain R A (2000) Biomaterials 21(23):2475-2490; Uhrich K E, Cannizzaro S M, Langer R S and Shakesheff K M (1999) Chemical Reviews 99(11): 3181-3198; and Park T G (1995) Biomaterials 16(15):1123-1130, each of which are incorporated herein by reference in their entirety).

As used herein, the phrase "binding agent linker," or "BL" refers to any divalent, trivalent, or multi-valent group or moiety that links, connects, or bonds a binding agent (e.g., an antibody or an antigen-binding fragment thereof) with a payload compound set forth herein (e.g., VX-787 and derivatives thereof, and/or baloxavir and derivatives thereof (such as baloxavir marboxil)) and, optionally, with one or more side chain compounds. Generally, suitable binding agent linkers for the antibody conjugates described herein are those that are sufficiently stable to exploit the circulating half-life of the antibody conjugates and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolytically-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyloxycarbonyl (PABC), para-aminobenzyl (PAB) units. In some embodiments, the binding agent linker (BL) includes a moiety that is formed by the reaction of the reactive group (RG) of a reactive linker (RL) and reactive portion of the binding agent, e.g., antibody, modified antibody, or antigen binding fragment thereof.

In some examples, the BL includes the following moiety:

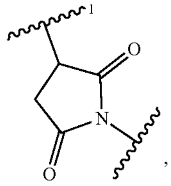, wherein is the bond to the cysteine of the antibody or antigen-binding fragment thereof. In some examples, the BL includes the following moiety:

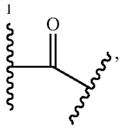, wherein is the bond to the lysine of the antibody or antigen-binding fragment thereof.

In some embodiments, the binding agent is an antibody or an antigen-binding fragment thereof. The antibody can be in any form known to those of skill in the art.

The term "antibody," as used herein, refers to any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds (i.e., full antibody molecules), as well as multimers thereof (e.g., IgM) or antigen-binding fragments thereof. Each heavy chain comprises a heavy chain variable region (abbreviated herein as HCVR or $V_H$) and a heavy chain constant region. The heavy chain constant region comprises three domains, $C_H1$, $C_H2$, and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments disclosed herein, the FRs of the antibodies (or antigen-binding portion thereof) suitable for the compounds herein may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding domain" or "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. In certain embodiments, the term "antigen-binding fragment" refers to a polypeptide fragment of a multi-specific antigen-binding molecule. The terms "antigen-binding fragment" of an antibody, or "antibody fragment," as used herein, refers to one or more fragments of an antibody that retain the ability to bind to an antigen such as influenza HA. Antigen-binding fragments of an antibody may be derived, e.g., from full antibody molecules using any suitable, standard technique(s) such as proteolytic digestion or recombinant genetic engineering technique(s) involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Non-limiting examples of antigen-binding fragments include: (i) Fab fragments; (ii) $F(ab')_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., a fragment containing a CDR, or an isolated CDR such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$, or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of this disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60, or more) amino acids which result in a flexible or semi-flexible linkage between adjacent variable and/or constant domains in a single polypeptide molecule. Moreover, an antigen-binding fragment of an antibody herein may comprise a homo-dimer or hetero-dimer (or other multimer) of any of the variable and constant domain configurations listed above in non-covalent association with one another and/or with one or more monomeric $V_H$ or $V_L$, domain (e.g., by disulfide bond(s)). As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art. In certain embodiments described herein, antibodies described herein are human antibodies.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan et al. also found many antibodies in which one or two CDRs had no amino acids in contact with an antigen (see also, Vajdos et al. 2002 J Mol Biol 320:415-428).

CDR residues not contacting antigen can be identified based on previous studies (for example, residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-influenza-HA monoclonal antibodies disclosed herein may comprise one or more amino acid substitutions, insertions, and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. This disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2, or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of this disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired properties such as, improved binding specificity, increased binding affinity, improved or enhanced antagonistic or agonistic biological properties (as the case may be), reduced immunogenicity, etc. Antibodies and antigen-binding fragments obtained in this general manner are encompassed within this disclosure.

This disclosure also includes fully human anti-influenza-HA monoclonal antibodies comprising variants of any of the HCVR, LCVR, and/or CDR amino acid sequences disclosed herein having one or more conservative substitutions. For example, this disclosure includes anti-influenza-HA antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody," as used herein, is intended to include antibodies having variable and constant regions derived from human germline immunoglobulin sequences. The human mAbs of this disclosure may include amino acid residues not encoded by human germline immunoglobulin sequences (e.g., mutations introduced by random or site-specific mutagenesis in vitro or by somatic mutation in vivo), for example, in the CDRs and in particular CDR3. However, the term "human antibody," as used herein, is not intended to include mAbs in which CDR sequences derived from the germline of another mammalian species (e.g., mouse) have been grafted onto human FR sequences. The term includes antibodies recombinantly produced in a non-human mammal, or in cells of a non-human mammal. The term is not intended to include antibodies isolated from or generated in a human subject. The term does not include naturally occurring antibodies that normally exist without modification or human intervention/manipulation, in a naturally occurring, unmodified living organism.

The term "recombinant," as used herein, refers to antibodies or antigen-binding fragments thereof, created, expressed, isolated, or obtained by technologies or methods known in the art as recombinant DNA technology which include, e.g., DNA splicing and transgenic expression. The term refers to antibodies expressed in a non-human mammal (including transgenic non-human mammals (e.g., transgenic mice), or a cell (e.g., CHO cells) expression system, or isolated from a recombinant combinatorial human antibody library. The phrase "recombinant human antibody," as used herein, is intended to include all human antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created, or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$, or $C_H3$ region which may be desirable, for example, in production, to improve the yield of the desired antibody form.

An "isolated antibody," as used herein, is intended to refer to an antibody that is substantially free of other antibodies (Abs) having different antigenic specificities (e.g., an isolated antibody that specifically binds influenza-HA, or a fragment thereof, is substantially free of Abs that specifically bind antigens other than influenza-HA). The antibodies described herein may be isolated antibodies. An "isolated antibody," as used herein, further refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the instant disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals. The antibodies used herein can comprise one or more amino acid substitutions, insertions, and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof.

A "blocking antibody," "neutralizing antibody," or "antagonist antibody," as used herein is intended to refer to an antibody whose binding to an antigen results in inhibition of at least one biological activity associated with the antigen. For example, an antibody or antibody-drug conjugate of this disclosure may prevent or block influenza attachment to, or entry into, a host cell. In addition, a "neutralizing antibody" is one that can neutralize, i.e., prevent, inhibit, reduce, impede, or interfere with, the ability of a pathogen to initiate and/or perpetuate an infection in a host. Such an antibody or antibody-drug conjugate, when possessing neutralizing ability via binding to influenza HA, can be referred to as an "antibody that neutralizes influenza-HA activity." The terms "neutralizing antibody" and "an antibody that neutralizes" or "antibodies that neutralize" are used interchangeably herein. These antibodies can be used, alone or in combination, as prophylactic or therapeutic agents with other anti-viral agents upon appropriate formulation, or in association with active vaccination, or as a diagnostic tool. As used herein, an "anti-influenza antibody" can refer to an antibody whose binding to an antigen (e.g., HA) results in inhibition of at least one biological activity associated with influenza virus.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "surface plasmon resonance," refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J).

Bio-layer interferometry is a label-free technology for measuring biomolecular interactions. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time (Abdiche, Y. N., et al. Analytical Biochemistry, (2008), 377(2), 209-217). In certain embodiments, a "real-time bio-layer interferometer based biosensor (Octet HTX assay)" was used to assess the binding characteristics of certain of the anti-influenza HA antibodies.

The term "$K_D$," as used herein, is intended to refer to the equilibrium dissociation constant of a particular antibody-antigen interaction.

The phrase "cross-competes," as used herein, means an antibody or antigen-binding fragment thereof that binds to an antigen and inhibits or blocks the binding of another antibody or antigen-binding fragment thereof. The phrase also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., by steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies are the same antibody). Cross-competition between two antibodies may be expressed, for example, as % binding of the second antibody that is less than the baseline self-self background binding (wherein first and second antibodies are the same antibody).

The term “substantial identity” or “substantially identical,” when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98%, or 99% of the nucleotide bases, as measured by any well-known algorithm of sequence identity, such as FASTA, BLAST, or GAP, as discussed in WO 2016/100807 or US 2016/0176953 A1, each of which are incorporated herein by reference in their entirety. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the phrase “substantial similarity” or “substantially similar” means that two peptide sequences, when optimally aligned, such as by the programs GAP or BESTFIT using default gap weights, share at least 90% sequence identity, even more preferably at least 95%, 98%, or 99% sequence identity. Preferably, residue positions, which are not identical, differ by conservative amino acid substitutions. A “conservative amino acid substitution” is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. (See, e.g., Pearson (1994) Methods Mol. Biol. 24: 307-331). Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45. A “moderately conservative” replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions, and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, and BLOSUM matrix of 62. Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402.

The phrase “therapeutically effective amount” refers to an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term “subject” refers to an animal, preferably a mammal, more preferably a human, in need of amelioration, prevention, and/or treatment of a disease or disorder such as a viral infection. The subject may have an influenza infection or is predisposed to developing an influenza virus infection. Subjects “predisposed to developing an influenza virus infection,” or subjects “who may be at elevated risk for contracting an influenza virus infection,” are those subjects with compromised immune systems because of autoimmune disease, those persons receiving immunosuppressive therapy (e.g., following organ transplant), those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subject of extreme young or old age are at increased risk. Any person who comes into physical contact or close physical proximity with an infected individual has an increased risk of developing an Influenza virus infection. Moreover, a subject is at risk of contracting an influenza infection due to proximity to an outbreak of the disease, e.g., subject resides in a densely-populated city or in close proximity to subjects having confirmed or suspected infections of Influenza virus, or choice of employment, e.g., hospital worker, pharmaceutical researcher, traveler to infected area, or frequent flier.

As used herein, the terms "treat," "treating," or "treatment" refer to the reduction or amelioration of the severity of at least one symptom or indication of influenza infection due to the administration of a therapeutic agent such as a disclosed antibody to a subject in need thereof. The terms include inhibition of progression of disease or of worsening of infection. The terms also include positive prognosis of disease, i.e., the subject may be free of infection or may have reduced or no viral titers upon administration of a therapeutic agent such as a disclosed antibody or antibody-drug conjugate. The therapeutic agent may be administered at a therapeutic dose to the subject.

The terms "prevent," "preventing," or "prevention" refer to inhibition of manifestation of influenza infection or any symptoms or indications of influenza infection upon administration of a disclosed antibody or antibody-drug conjugate. The term includes prevention of the spread of infection in a subject exposed to the virus or at risk of having influenza infection.

As used herein a "protective effect" may be demonstrated by any standard procedure known in the art to determine whether an agent such as an anti-viral agent, or an antibody such as an anti-influenza-HA antibody, or an antibody-drug conjugate disclosed herein can demonstrate any one or more of the following: e.g., an increase in survival after exposure to an infectious agent, a decrease in viral load, or amelioration of at least one symptom associated with the infectious agent.

As used herein, the phrases "antiviral drug" "anti-viral," "antiviral compound," and "anti-viral compound" apply to an anti-infective drug or therapy used to treat, prevent, or ameliorate a viral infection (e.g., influenza infection) in a subject. The term "anti-viral drug" (or its synonyms "antiviral drug," "anti-viral compound," and "antiviral compound") includes, but is not limited to, TAMIFLU® (Oseltamivir), RELENZA® (Zanamivir), ribavirin, or interferon-alpha2b. Anti-viral drugs include influenza inhibitors. As used herein, an "influenza inhibitor" refers to a drug used to inhibit influenza virus infection, and includes, but is not limited to, oseltamivir. As used herein, a polymerase inhibitor can refer to an inhibitor of a nucleic acid polymerase, such as influenza polymerase. An exemplary polymerase inhibitor is VX-787. Without wishing to be bound by any particular theory, influenza inhibitors can function by targeting the influenza virus itself or by targeting a host cell that may be targeted by an influenza virus. For example, an influenza inhibitor that targets a host cell may inhibit translation in the cell, thereby reducing viral replication.

The phrase "specifically binds," or "binds specifically to," or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes tighter binding). Methods for determining whether two molecules specifically bind are well known in the art and include, for example, equilibrium dialysis, surface plasmon resonance, and the like. As described herein, antibodies have been identified by real-time, label free bio-layer interferometry assay on an Octet® HTX biosensor, which bind specifically to influenza-HA. Moreover, multi-specific antibodies that bind to one domain in influenza-HA and one or more additional antigens or a bi-specific that binds to two different regions of influenza-HA are nonetheless considered antibodies that "specifically bind", as used herein. In addition to neutralizing antibodies, antibodies that bind specifically to HA, but are non-neutralizing, also can be used within the scope of the present disclosure to generate antibody-drug conjugates. Such antibodies may function, for example, to deliver a payload to influenza-infected cells.

The term "high affinity" antibody refers to those mAbs having a binding affinity to influenza-HA, expressed as $K_D$, of at least $10^{-8}$ M; preferably $10^{-9}$ M; more preferably $10^{-10}$ M, even more preferably $10^{-11}$ M, even more preferably $10^{-12}$ M, as measured by real-time, label free bio-layer interferometry assay, e.g., an Octet® HTX biosensor, or by surface plasmon resonance, e.g., BIACORE™, or by solution-affinity ELISA.

The phrase or term "slow off rate," "$K_{off}$," or "$k_d$" refers to an antibody that dissociates from influenza-HA, with a rate constant of $1\times10^{-3}$ $s^{-1}$ or less, preferably $1\times10^{-4}$ $s^{-1}$ or less, as determined by real-time, label free bio-layer interferometry assay, e.g., an Octet® HTX biosensor, or by surface plasmon resonance, e.g., BIACORE™.

The phrase "antigen-binding domain" or "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

In specific embodiments, antibody or antibody fragments of this disclosure may be conjugated to a moiety such a ligand or a therapeutic moiety ("antibody-drug conjugate" or "immunoconjugate"), such as an anti-viral drug, a linker-payload including an anti-viral drug, a second anti-influenza antibody, or any other therapeutic moiety useful for treating an infection caused by influenza-HA.

As used herein, "sequentially administering" means that each dose of the compound is administered to the subject at a different point in time, e.g., on different days separated by a predetermined interval (e.g., hours, days, weeks, or months).

The phrases "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all include the same amount the compound described herein, but generally can differ from one another in terms of frequency of administration.

The phrase "the immediately preceding dose," as used herein, means, in a sequence of multiple administrations, the dose of the compound which is administered to a patient prior to the administration of the very next dose in the sequence with no intervening doses.

As used herein, the term "payload" refers to a small molecule active ingredient (e.g., an antiviral compound), optionally conjugated to an antibody or antigen-binding fragment thereof, directly or via a linker, that provides a desired biological effect (e.g., inhibiting influenza virus infection or replication). A payload can be less than or equal to 2,000 Da, less than or equal to 1,500 Da, or less than or equal to 900 Da.

Compounds or Payloads

Provided herein are antiviral compounds or payloads. Without being bound by any particular theory of operation, the antiviral compounds include (1) VX-787 and derivatives thereof; and (2) baloxavir and derivatives thereof (e.g., baloxavir marboxil). In certain embodiments, the antiviral compounds can be delivered to cells as part of a conjugate.

In certain embodiments, the antiviral compounds are capable of carrying out any activity of VX-787, baloxavir, and/or baloxavir marboxil and each of their derivatives at or in a target, for instance, a target cell. Certain antiviral compounds can have one or more additional activities.

In certain embodiments, set forth herein is a compound having the structure of Formula I:

Formula I

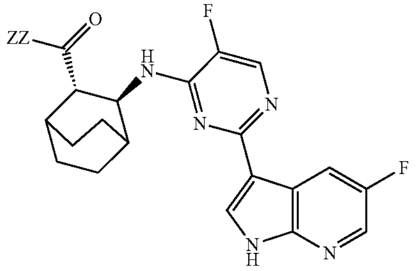

or a pharmaceutically acceptable salt thereof. In Formula I, in certain embodiments, ZZ is —$OR^1$ or —NHOH. In one embodiment, ZZ is —NHOH. In one embodiment, ZZ is —$OR^1$. In Formula I, when ZZ is —$OR^1$, useful $R^1$ groups include hydrogen and

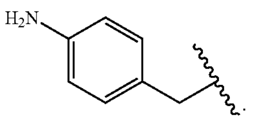 [SMILES: *Cc1ccc(N)cc1]

In one embodiment, $R^1$ is hydrogen. In one embodiment, $R^1$ is

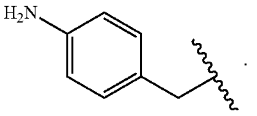 [SMILES: *Cc1ccc(N)cc1]

In one embodiment, the compound is VX-787 or

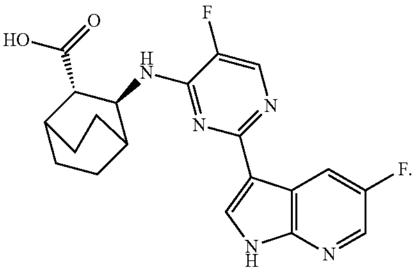 [SMILES: O=C(O)[C@H]1C2CCC(CC2)[C@@H]1Nc1nc(-c2c[nH]c3ncc(F)cc23)ncc1F]

In certain embodiments, set forth herein is a compound having the structure of Formula II:

Formula II

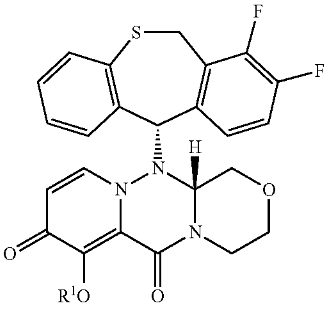

or a pharmaceutically acceptable salt thereof. In one embodiment, $R^1$ is hydrogen. In one embodiment, $R^1$ is $—C_{H}2OC(O)OCH_3$. In one embodiment, $R^1$ is

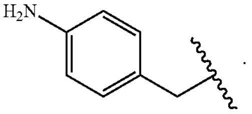 [SMILES: *Cc1ccc(N)cc1]

In one embodiment, the compound is baloxavir marboxil or

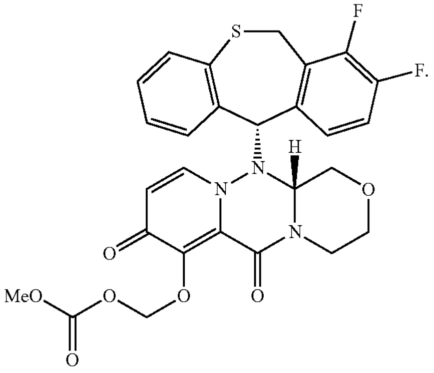 [SMILES: COC(=O)OCOc1c2n(ccc1=O)N([C@@H]1c3ccccc3SCc3c1ccc(F)c3F)[C@@H]1COCCN1C2=O]

In one embodiment, the compound is baloxavir or

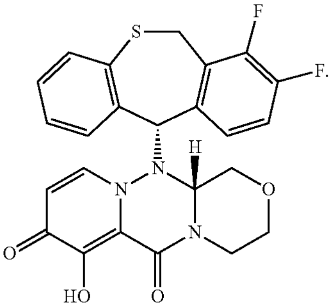 [SMILES: O=C1c2c(O)c(=O)ccn2N([C@@H]2c3ccccc3SCc3c2ccc(F)c3F)[C@@H]2COCCN12]

Binding Agents

Suitable binding agents for any of the conjugates provided in the instant disclosure include, but are not limited to, antibodies, viral receptors, or any other cell binding or peptide binding molecules or substances. The full-length amino acid sequence of an exemplary Influenza HA is shown in GenBank as accession number ACP44150.1.

Suitable binding agents include antibodies (e.g., fully human antibodies) and antigen-binding fragments thereof that specifically bind to influenza virus proteins, such as the surface proteins hemagglutinin (HA), neuraminidase (NA), and Matrix-2 (M2). In some embodiments, these binding agents modulate the interaction of influenza virus with host cells. In some embodiments, the antibodies or antigen-binding fragments thereof bind to mature hemagglutinin. In some embodiments, the antibodies or antigen-binding fragments thereof bind to an HA0 hemagglutinin precursor protein. The anti-influenza HA antibodies may bind to the influenza virus HA with high affinity. In certain embodiments, the antibodies herein are blocking antibodies wherein the antibodies may bind to influenza HA and block the attachment to and/or entry of the virus into host cells. In some embodiments, the blocking antibodies herein may block the binding of influenza virus to cells and as such may inhibit or neutralize viral infectivity of host cells. In some embodiments, the blocking antibodies may be useful for treating a subject suffering from an influenza virus infection. The antibodies when administered to a subject in need thereof may reduce the infection by a virus such as influenza in the subject. They may be used to decrease viral loads in a subject. They may be used alone or as adjunct therapy with other therapeutic moieties or modalities known in the art for treating a viral infection. In certain embodiments, these antibodies may bind to an epitope in the stem region of the viral HA, the head region of the viral HA, or both. Furthermore, the identified antibodies can be used prophylactically (before infection) to protect a mammal from infection, or can be used therapeutically (after infection is established) to ameliorate a previously established infection, or to ameliorate at least one symptom associated with the infection.

In certain embodiments, the antibodies are obtained from mice immunized with a primary immunogen, such as a full length influenza HA or with a recombinant form of influenza HA or fragments thereof followed by immunization with a secondary immunogen, or with an immunogenically active fragment of influenza HA. In certain embodiments, the antibodies are obtained from mice immunized with an influenza vaccine composition followed by booster immunization with one or more recombinantly produced HA peptides. In certain embodiments, the antibodies are obtained from humans. In certain embodiments, the antibodies are obtained from mammals (e.g., non-human mammals). In certain embodiments, the antibodies are obtained from non-human primates.

The immunogen may be a biologically active and/or immunogenic fragment of influenza HA or DNA encoding the active fragment thereof. The fragment may be derived from the stem region of the HA protein. (See, Sui et al. Nature Struct, and Mol. Biol. Published online 22 Feb. 2009; Pages 1-9), the head region of the HA protein, or a combination thereof.

The peptides may be modified to include addition or substitution of certain residues for tagging or for purposes of conjugation to carrier molecules, such as, keyhole limpet hemocyanin (KLH). For example, a cysteine may be added at either the N-terminal or C-terminal end of a peptide, or a linker sequence may be added to prepare the peptide for conjugation to, for example, KLH for immunization.

Certain anti-influenza antibodies, anti-influenza-HA antibodies, or ADCs herein have antiviral activity, such as being able to bind to and neutralize the activity of influenza-HA, as determined by in vitro or in vivo assays. Certain anti-influenza antibodies, anti-influenza-HA antibodies, or ADCs herein are able to bind to HA but do not have neutralizing activity, as determined by in vitro or in vivo assays. The ability of the antibodies or ADCs herein to bind to and neutralize the activity of influenza-HA and thus the attachment and/or entry of the virus into a host cell followed by the ensuing viral infection, may be measured using any standard method known to those skilled in the art, including binding assays, or activity assays, as described herein.

The antibodies or ADCs specific for influenza-HA may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye, or a MRI-detectable label. In certain embodiments, such labeled antibodies may be used in diagnostic assays including imaging assays. In one embodiment, the additional moiety is a peptide tag. In one embodiment, an ADC includes an antibody heavy chain and further includes a peptide tag at the C-terminus of the antibody heavy chain. In one embodiment, an ADC includes an antibody heavy chain and further includes a peptide tag (e.g., a pentapeptide) at the C-terminus of the antibody heavy chain, wherein the peptide tag is the pentapeptide sequence LLQGA (e.g., for use in conjugating a linker-payload via transglutaminase). In one embodiment, an ADC includes two antibody heavy chains and further includes a peptide tag at the C-terminus of each antibody heavy chain. In one embodiment, an ADC includes two antibody heavy chains and further includes a peptide tag at the C-terminus of each antibody heavy chain, wherein the peptide tag is the pentapeptide sequence LLQGA.

In certain embodiments, the antibody comprises a light chain. In certain embodiments, the light chain is a kappa light chain. In certain embodiments, the light chain is a lambda light chain. In certain embodiments, the antibody comprises a heavy chain. In some embodiments, the heavy chain is an IgA. In some embodiments, the heavy chain is an IgD. In some embodiments, the heavy chain is an IgE. In some embodiments, the heavy chain is an IgG. In some embodiments, the heavy chain is an IgM. In some embodiments, the heavy chain is an IgG1. In some embodiments, the heavy chain is an IgG2. In some embodiments, the heavy chain is an IgG3. In some embodiments, the heavy chain is an IgG4. In some embodiments, the heavy chain is an IgA1. In some embodiments, the heavy chain is an IgA2.

In some embodiments, the antibody is an antibody fragment. In some embodiments, the antibody fragment is an Fv fragment. In some embodiments, the antibody fragment is a Fab fragment. In some embodiments, the antibody fragment is a $F(ab')_2$ fragment. In some embodiments, the antibody fragment is a Fab' fragment. In some embodiments, the antibody fragment is an scFv (sFv) fragment. In some embodiments, the antibody fragment is an scFv-Fc fragment.

In some embodiments, the antibody is a monoclonal antibody. In some embodiments, the antibody is a polyclonal antibody. In some embodiments, the antibody is a bispecific antibody including a first antigen-binding domain, and a second antigen-binding domain.

In some embodiments, the antibody is a chimeric antibody. In some embodiments, the antibody is a humanized antibody. In some embodiments, the antibody is a human antibody.

In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. Identification of residue Q295 can be accomplished readily with standard sequence alignment tools, including those described herein. In other useful embodiments, the antibody can be engineered to comprise a glutamine residue. In certain embodiments, the antibody comprises one or more N297Q mutations. Techniques for modifying an antibody sequence to include a glutamine residue are within the skill of those in the art (see, e.g., Ausubel et al. *Current Protoc. Mol. Biol.*). In one embodiment, the antibody includes an antibody heavy chain and further includes a peptide tag at the C-terminus of the antibody heavy chain. In one embodiment, the antibody includes an antibody heavy chain and further includes a peptide tag, e.g., transglutaminase recognition sequence or pentapeptide tag, at the C-terminus of the antibody heavy chain, wherein the peptide tag is the pentapeptide sequence LLQGA.

Preparation of Human Antibodies

Methods for generating human antibodies in transgenic mice are known in the art. Any such known methods can be used in the context of this disclosure to make human antibodies that specifically bind to Influenza-HA. An immunogen comprising any one of the following can be used to generate antibodies to Influenza HA. In certain embodiments, the antibodies herein are obtained from mice immunized with a full length, native influenza HA (See, e.g., GenBank accession number FJ966082.1), or with a live attenuated or inactivated virus, or with DNA encoding the protein or fragment thereof. Alternatively, the influenza-HA protein or a fragment thereof may be produced using standard biochemical techniques and modified and used as immunogen. In one embodiment, the immunogen is a recombinantly produced influenza-HA protein or fragment thereof. In certain embodiments herein, the immunogen may be an influenza virus vaccine. In certain embodiments, one or more booster injections may be administered. In certain embodiments, the booster injections may comprise one or more influenza virus strains, or hemagglutinins derived from these strains, e.g., see Protein Sciences H1 A/New Caledonia/20/1999, H5 A/Indonesia/05/2005, H3 A/Victoria/361/2011, H7 A/Netherlands/219/2003, or H9 A/Hong Kong/1073/1988, or the influenza B virus strains B/Victoria/2/87, B/Nanchang/3451/93, B/Singapore/11/1994, B/Florida/4/2006, or B/Yamagata/16/88. In certain embodiments, the booster injections may contain a 1:1 mixture of the influenza strains, or a 1:1 mixture of the hemagglutinins derived from the strains. In certain embodiments, the immunogen may be a recombinant Influenza HA peptide expressed in *E. coli* or in any other eukaryotic or mammalian cells such as Chinese hamster ovary (CHO) cells or influenza virus itself.

Using VELOCIIVIMUNE® technology (see, e.g., U.S. Pat. No. 6,596,541, Regeneron Pharmaceuticals, VELOCIIVIMUNE®) or any other known method for generating monoclonal antibodies, high affinity chimeric antibodies to influenza-HA are initially isolated having a human variable region and a mouse constant region. The VELOCIIVIMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIIVIMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As described in WO 2016/100807 or US 2016/0176953 A1, each of which are incorporated by reference in their entirety, the antibodies are characterized and selected for desirable characteristics, including affinity, selectivity, epitope, etc. The mouse constant regions are replaced with a desired human constant region to generate the fully human antibody herein, for example, wild-type or modified IgG1 or IgG4. While the constant region selected may vary according to specific use, high affinity antigen-binding and target specificity characteristics reside in the variable region.

Bioequivalents

The anti-influenza-HA antibodies and antibody fragments herein encompass proteins having amino acid sequences that vary from those of the described antibodies, but that retain the ability to bind Influenza HA. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment herein. Other bioequivalent anti-influenza-HA antibodies and antibody fragments are as described in WO 2016/100807 or US 2016/0176953 A1, each of which are incorporated by reference in their entirety.

Biological Characteristics of the Antibodies

In general, the antibodies herein function by binding to Influenza HA. For example, provided herein are antibodies and antigen-binding fragments of antibodies that bind Influenza HA (e.g., at 25° C. or at 37° C.) with a $K_D$ of less than 10 nM, as measured by real-time bio-layer interferometer based biosensor (Octet HTX assay), or by surface plasmon resonance. In certain embodiments, the antibodies or antigen-binding fragments thereof bind influenza-HA with a $K_D$ of less than about 5 nM, less than about 2 nM, less than about 1 nM, less than about 500 pM, less than 250 pM, or less than 100 pM, as measured by surface plasmon resonance, e.g., using the assay format as described in WO 2016/100807 or US 2016/0176953 A1, each of which are incorporated by reference in their entirety, or a substantially similar assay.

Non-limiting, exemplary in vitro assays for measuring binding activity are illustrated in Example 3 of WO 2016/100807 or US 2016/0176953 A1, each of which is incorporated herein by reference in their entirety. In WO 2016/100807 or US 2016/0176953 A1 Example 3, the binding affinity and dissociation constants of anti-influenza-HA antibodies for influenza-HA were determined by real-time bio-layer interferometer based biosensor (Octet HTX assay). In Examples 4 and 5 of WO 2016/100807 or US 2016/0176953 A1, neutralization assays were used to determine infectivity of diverse group 1 strains of influenza virus. In Example 6 of WO 2016/100807 or US 2016/0176953 A1, certain antibodies were shown to mediate complement dependent cytotoxicity (CDC) of virus-infected cells in vitro. Examples 7 and 10 of WO 2016/100807 or US 2016/0176953 A1 demonstrate that certain antibodies of the disclosure are capable of neutralizing an influenza A infection in vivo when administered either prophylactically or therapeutically.

Also provided herein are antibodies and antigen-binding fragments thereof that bind Influenza HA with a dissociative half-life (t½) of greater than about 100 minutes as measured by surface plasmon resonance at 25° C., e.g., using an assay format as defined in WO 2016/100807 or US 2016/0176953 A1, each of which are incorporated herein by reference in their entirety, or a substantially similar assay. In certain embodiments, the antibodies or antigen-binding fragments herein bind Influenza HA with a t½ of greater than about 200 minutes, greater than about 300 minutes, greater than about 400 minutes, greater than about 500 minutes, greater than about 600 minutes, greater than about 700 minutes, greater than about 800 minutes, greater than about 900 minutes, or greater than about 1000 minutes as measured by surface plasmon resonance at 25° C., e.g., using an assay format as defined in WO 2016/100807 or US 2016/0176953 A1, each of which is incorporated herein by reference in their entirety (e.g., imAb-capture or antigen-capture format), or a substantially similar assay. In one embodiment, the antibodies and antigen-binding fragments herein bind Influenza HA with a dissociative half-life (t½) of greater than 300 minutes. In one embodiment, an antibody herein provides for about a 1.5 to 2-fold increase in dissociative half life as compared to a comparator antibody designated Control I mAb, when tested in monkeys and mice.

Also provided herein are antibodies or antigen-binding fragments thereof that neutralize the infectivity of influenza virus for its host cells. In some embodiments, the antibodies exhibit a neutralization potency against various representative group 1 influenza viruses (H1N1 A/Puerto Rico/08/1934; H5N1 A/Vietnam/1203/2004; H1N1 A California/07/2009; H1N1 A/Wisconsin/1933; H1N1 A/Brisbane/59/1997, H9N2 A Hong Kong/33982/2009, H13N6 a/gull/Maryland/704/1977 and H16N3 A/shorebird/Delaware/172/2006) with an $IC_{50}$ ranging from about 1.6 nM to about 130 nM in a microneutralization assay, e.g., as shown in Examples 4 and 5 of WO 2016/100807 or US 2016/0176953 A1, each of which is incorporated herein by reference in their entirety, or a substantially similar assay. In one embodiment, the antibodies or antigen-binding fragments thereof that neutralize the infectivity of influenza virus for its host cells do so with an $IC_{50}$ of less than 130 nM.

Also provided herein are antibodies or antigen-binding fragments thereof that mediate complement dependent cytotoxicity of infected cells, with an $EC_{50}$ ranging from about 20 nM to about 66 nM (see example 6 in WO 2016/100807 or US 2016/0176953 A1, each of which is incorporated herein by reference in their entirety). In one embodiment, the antibodies or antigen-binding fragments thereof mediate complement-dependent cytotoxicity of infected cells, with an $EC_{50}$ less than 66 nM.

Described herein are anti-influenza-A HA antibodies that demonstrate an increase in protection, or neutralization of influenza A infection in vivo, as compared to a control antibody. Certain antibodies show neutralization when administered either prophylactically (prior to infection) or therapeutically (after infection); see example 7 in WO 2016/100807 or US 2016/0176953 A1, each of which is incorporated herein by reference in their entirety.

In one embodiment, provided herein is an isolated recombinant antibody or antigen-binding fragment thereof that binds specifically to Influenza HA, wherein the antibody or fragment thereof exhibits two or more of the following characteristics: (a) is a fully human monoclonal antibody; (b) binds to influenza HA with a dissociation constant ($K_D$) of less than $10^{-9}$ M, as measured in a surface plasmon resonance assay; (c) demonstrates a dissociative half-life (t½) ranging from about 370 minutes to greater than 1000 minutes; (d) demonstrates neutralization of group 1 influenza A viruses selected from H1N1, H5N1, H9N2, H13N6, and H16N3, with an $IC_{50}$ ranging from about 1.6 nM to about 130 nM; (e) demonstrates complement mediated lysis of influenza virus infected cells with an $EC_{50}$ of about 20 nM to about 66 nM; or (f) demonstrates protection, as measured by increased survival in an animal model of influenza virus infection when administered either before or after virus challenge.

The antibodies herein may possess two or more of the aforementioned biological characteristics, or any combinations thereof. Other biological characteristics of the antibodies herein will be evident to a person of ordinary skill in the art from a review of the present disclosure including the working Examples herein.

Heavy and Light Chain Variable Region Amino Acid and Nucleotide Sequences

In some embodiments, the antibody, or antigen-binding fragment thereof, conjugated to the linker-payload or payload can be an antibody that targets Influenza HA. Exemplary Influenza HA antibodies can be found, for example, in WO 2016/100807 or US 2016/0176953 A1, each of which are incorporated herein by reference in their entirety. In some embodiments, an Influenza HA antibody comprises a heavy chain complementarity determining region (HCDR)-1 comprising SEQ ID NO: 20; an HCDR2 comprising SEQ ID NO: 22; an HCDR3 comprising SEQ ID NO: 24; a light chain complementarity determining region (LCDR)-1 comprising SEQ ID NO: 28; an LCDR2 comprising SEQ ID NO: 30; and an LCDR3 comprising SEQ ID NO: 32. In some embodiments, an Influenza HA antibody comprises a heavy chain variable region (HCVR) comprising SEQ ID NO: 18 and a light chain variable region (LCVR) comprising SEQ ID NO: 26. In any of the foregoing embodiments, the Influenza HA antibody can be prepared by site-directed mutagenesis to insert a glutamine residue at a site without resulting in disabled antibody function or binding. For example, in any of the foregoing embodiments, the Influenza HA antibody can comprise an Asn297Gln (N297Q) mutation. Such antibodies having an N297Q mutation can also contain one or more additional naturally occurring glutamine residues in their variable regions, which can be accessible to transglutaminase and therefore capable of conjugation to a payload or a linker-payload. In one embodiment, the antibody includes a HCVR and further includes a peptide tag at the C-terminus of the HCVR. In one embodiment, the antibody includes a HCVR and further includes a peptide tag at the C-terminus of the HCVR, wherein the peptide tag is the pentapeptide sequence LLQGA. In one embodiment, the antibody includes two HCVRs and further includes a peptide tag at the C-terminus of each HCVR. In one embodiment, the antibody includes two HCVRs and further includes a peptide tag at the C-terminus of the HCVRs, wherein the peptide tag is the pentapeptide sequence LLQGA.

Table 1 sets forth the amino acid sequence identifiers of the heavy and light chain variable regions and CDRs of selected anti-influenza HA antibodies. The corresponding nucleic acid sequence identifiers are set forth in Table 2.

TABLE 1

| | Amino Acid Sequence Identifiers SEQ ID NOs: | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| mAb11723 | 2 | 4 | 6 | 8 | 10 | 12 | 14 | 16 |
| mAb11729 | 18 | 20 | 22 | 24 | 26 | 28 | 30 | 32 |
| mAb11820 | 34 | 36 | 38 | 40 | 42 | 44 | 46 | 48 |
| mAb11829 | 50 | 52 | 54 | 56 | 58 | 60 | 62 | 64 |
| mAb11829* | 50 | 52 | 54 | 56 | 66 | 68 | 70 | 72 |
| mAb11829 | 50 | 52 | 54 | 56 | 58 | 60 | 62 | 64 |
| mAb11830 | 74 | 76 | 78 | 80 | 82 | 84 | 86 | 88 |
| mAb11830* | 74 | 76 | 78 | 80 | 66 | 68 | 70 | 72 |
| mAb11903 | 90 | 92 | 94 | 96 | 98 | 100 | 102 | 104 |
| mAb14571 | 106 | 108 | 110 | 112 | 114 | 116 | 118 | 120 |
| mAb14571 | 106 | 108 | 110 | 112 | 114 | 116 | 118 | 120 |
| mAb11704 | 122 | 124 | 126 | 128 | 130 | 132 | 134 | 136 |
| mAb11711 | 138 | 140 | 142 | 144 | 146 | 148 | 150 | 152 |
| mAb11714 | 154 | 156 | 158 | 160 | 162 | 164 | 166 | 168 |
| mAb11717 | 170 | 172 | 174 | 176 | 178 | 180 | 182 | 184 |
| mAb11724 | 186 | 188 | 190 | 192 | 194 | 196 | 198 | 200 |
| mAb11727 | 202 | 204 | 206 | 208 | 210 | 212 | 214 | 216 |
| mAb11730* | 218 | 220 | 222 | 224 | 226 | 228 | 230 | 232 |
| mAb11731* | 234 | 236 | 238 | 240 | 66 | 68 | 70 | 72 |
| mAb11734* | 242 | 244 | 246 | 248 | 66 | 68 | 70 | 72 |
| mAb11736* | 250 | 252 | 254 | 256 | 66 | 68 | 70 | 72 |
| mAb11742* | 258 | 260 | 262 | 264 | 66 | 68 | 70 | 72 |
| mAb11744* | 266 | 268 | 270 | 272 | 66 | 68 | 70 | 72 |
| mAb11745* | 274 | 276 | 278 | 280 | 66 | 68 | 70 | 72 |
| mAb11747* | 282 | 284 | 286 | 288 | 66 | 68 | 70 | 72 |
| mAb11748* | 290 | 292 | 294 | 296 | 66 | 68 | 70 | 72 |
| mAb5385 | 298 | 299 | 300 | 301 | 302 | 303 | 304 | 305 |

*mAb contains one or more mutations in the constant region

TABLE 2

| | Nucleic Acid Sequence Identifiers SEQ ID NOs: | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| mAb11723 | 1 | 3 | 5 | 7 | 9 | 11 | 13 | 15 |
| mAb11729 | 17 | 19 | 21 | 23 | 25 | 27 | 29 | 31 |
| mAb11820 | 33 | 35 | 37 | 39 | 41 | 43 | 45 | 47 |
| mAb11829 | 49 | 51 | 53 | 55 | 57 | 59 | 61 | 63 |
| mAb11829* | 49 | 51 | 53 | 55 | 65 | 67 | 69 | 71 |
| mAb11829 | 49 | 51 | 53 | 55 | 57 | 59 | 61 | 63 |
| mAb11830 | 73 | 75 | 77 | 79 | 81 | 83 | 85 | 87 |
| mAb11830* | 73 | 75 | 77 | 79 | 65 | 67 | 69 | 71 |
| mAb11903 | 89 | 91 | 93 | 95 | 97 | 99 | 101 | 103 |
| mAb14571 | 105 | 107 | 109 | 111 | 113 | 115 | 117 | 119 |
| mAb14571 | 105 | 107 | 109 | 111 | 113 | 115 | 117 | 119 |
| mAb11704 | 121 | 123 | 125 | 127 | 129 | 131 | 133 | 135 |
| mAb11711 | 137 | 139 | 141 | 143 | 145 | 147 | 149 | 151 |
| mAb11714 | 153 | 155 | 157 | 159 | 161 | 163 | 165 | 167 |
| mAb11717 | 169 | 171 | 173 | 175 | 177 | 179 | 181 | 183 |
| mAb11724 | 185 | 187 | 189 | 191 | 193 | 195 | 197 | 199 |
| mAb11727 | 201 | 203 | 205 | 207 | 209 | 211 | 213 | 215 |
| mAb11730* | 217 | 219 | 221 | 223 | 225 | 227 | 229 | 231 |
| mAb11731* | 233 | 235 | 237 | 239 | 65 | 67 | 69 | 71 |
| mAb11734* | 241 | 243 | 245 | 247 | 65 | 67 | 69 | 71 |
| mAb11736* | 249 | 251 | 253 | 255 | 65 | 67 | 69 | 71 |
| mAb11742* | 257 | 259 | 261 | 263 | 65 | 67 | 69 | 71 |
| mAb11744* | 265 | 267 | 269 | 271 | 65 | 67 | 69 | 71 |

TABLE 2-continued

| Nucleic Acid Sequence Identifiers SEQ ID NOs: | | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| mAb11745* | 273 | 275 | 277 | 279 | 65 | 67 | 69 | 71 |
| mAb11747* | 281 | 283 | 285 | 287 | 65 | 67 | 69 | 71 |
| mAb11748* | 289 | 291 | 293 | 295 | 65 | 67 | 69 | 71 |

*mAb contains one or more mutations in the constant region.

The binding agent linkers can be bonded to the binding agent, e.g., antibody or antigen-binding molecule, through an attachment at a particular amino acid within the antibody or antigen-binding molecule. Exemplary amino acid attachments that can be used in the context of this embodiment of the disclosure include, e.g., lysine (see, e.g., U.S. Pat. No. 5,208,020; US 2010/0129314; Hollander et al., *Bioconjugate Chem.,* 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, Ryan et al., *Food & Agriculture Immunol.,* 2001, 13:127-130, and Jeger et al., *Angew Chem Int Ed Engl.,* 2010, 49:9995-9997).

In some examples, the binding agent is an antibody or antigen binding molecule, and the antibody is bonded to the linker through a lysine residue. In some embodiments, the antibody or antigen binding molecule is bonded to the linker through a cysteine residue.

Linkers can also be conjugated to one or more glutamine residues via transglutaminase-based chemo-enzymatic conjugation (see, e.g., Jeger et al., *Angew Chem Int Ed Engl.,* 2010, 49:9995-9997 and Dennler et al., *Bioconjugate Chem.* 2014, 25:569-578). For example, in the presence of transglutaminase, one or more glutamine residues of an antibody can be coupled to a primary amine compound. Primary amine compounds include, e.g., payloads or linker-payloads, which directly provide antibody drug conjugates via transglutaminase-mediated coupling. Primary amine compounds also include linkers and spacers that are functionalized with reactive groups that can be subsequently reacted with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody or a glutaminyl-modified antibody or antigen binding molecule comprises at least one glutamine residue in at least one polypeptide chain sequence. In certain embodiments, the antibody or a glutaminyl-modified antibody or antigen binding molecule comprises two heavy chain polypeptides, each with one Gln295 or Q295 residue. In further embodiments, the antibody or a glutaminyl-modified antibody or antigen binding molecule comprises one or more glutamine residues at a site other than a heavy chain 295. Included herein are antibodies of this section bearing N297Q mutation(s) described herein.

In one embodiment, the antibody or a glutaminyl-modified antibody or antigen binding molecule includes an antibody heavy chain and further includes a peptide tag at the C-terminus of the antibody heavy chain. In one embodiment, the antibody or a glutaminyl-modified antibody or antigen binding molecule includes an antibody heavy chain and further includes a peptide tag at the C-terminus of the antibody heavy chain, wherein the peptide tag is the pentapeptide sequence LLQGA. In one embodiment, the antibody or a glutaminyl-modified antibody or antigen binding molecule includes two antibody heavy chains and further includes a peptide tag at the C-terminus of each antibody heavy chain. In one embodiment, the antibody or a glutaminyl-modified antibody or antigen binding molecule includes two antibody heavy chains and further includes a peptide tag at the C-terminus of each antibody heavy chain, wherein the peptide tag is the pentapeptide sequence LLQGA.

Linkers

In certain embodiments, the linker L portion of the conjugates described herein is a moiety, for instance a divalent moiety, that covalently links a binding agent to a payload compound described herein. In other instances, the linker L is a trivalent or multivalent moiety that covalently links a binding agent to a payload compound described herein. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. In certain embodiments, the linker L portion of the linker-payloads described herein is a moiety covalently linked to a payload compound described herein, capable of divalently and covalently linking a binding agent to a payload compound described herein. In other instances, the linker L portion of the linker-payloads described herein is a moiety covalently linked to a payload compound described herein, capable of covalently linking, as a trivalent or multivalent moiety, a binding agent to a payload compound described herein. Payload compounds include compounds of Formulae I and II above, and their residues following bonding to or incorporation of linker L are linker-payloads. The linker-payloads can be further bonded to binding agents such as antibodies or antigen binding fragments thereof to form antibody-drug conjugates. Those of skill in the art will recognize that certain functional groups of payload moieties are convenient for linking to linkers and/or binding agents. For example, in certain embodiments, the linker is absent and payloads are directly bonded to binding agents. In another embodiment, payloads include carboxylic acids and binding agents include lysines, where each carboxylic acid and lysine participate in amide bond formation to bind payload residues directly to binding agent residues. Payload functional groups further include hydroxyls (e.g., baloxavir, and derivatives thereof, such as a baloxavir marboxil derivative), and carboxylic acids (e.g., in the form of esters upon linking to L, as in VX-787 and derivatives thereof).

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety. In some embodiments, the non-cleavable linker is derived from

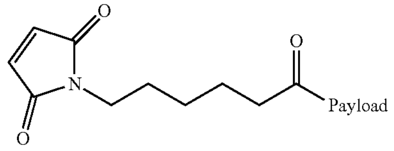

or a residue thereof. In some embodiments, the non-cleavable linker-payload residue is

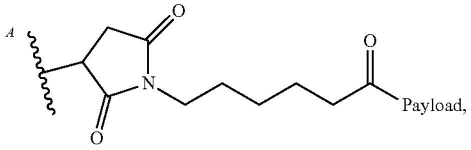

or a regioisomer thereof. In some embodiments, the non-cleavable linker is derived from

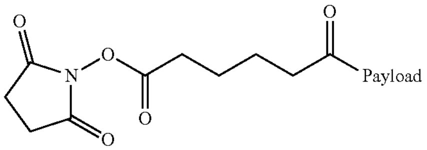

embodiments, the non-cleavable linker-payload residue is or a residue thereof. In some

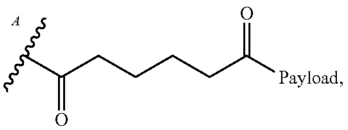

or a regioisomer thereof. In one embodiment, the linker is maleimide cyclohexane carboxylate or 4-(N-maleimidomethyl)cyclohexanecarboxylic acid (MCC). In the structures,

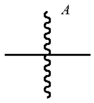

indicates a bond to a binding agent. In the structures,

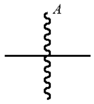

in some examples, indicates a click chemistry residue which results from the reaction of, for example, a binding agent having an azide or alkyne functionality and a linker-payload having a complementary alkyne or azide functionality. In the structures, in other examples,

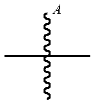

indicates a divalent sulfide which results from the reaction of, for example, one or more binding agent cysteines with one or more linkers or linker-payloads having maleimide functionality via Michael addition reactions. In the structures, in other examples,

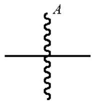

indicates an amide bond which results from the reaction of, for example, one or more binding agent lysines with one or more linkers or linker-payloads having activated or unactivated carboxyl functionality, as would be appreciated by a person of skill in the art. In one embodiment,

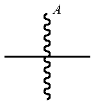

indicates an amide bond which results from the reaction of, for example, one or more binding agent lysines with one or more linkers or linker-payloads having activated carboxyl functionality, as would be appreciated by a person of skill in the art.

In some embodiments, suitable linkers include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L- or D- α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or any combination thereof (e.g., dipeptides, tripeptides, oligopeptides, polypeptides, and the like). In certain embodiments, one or more side chains of the amino acids are linked to a side chain group, described below. In some embodiments, the linker is a peptide comprising or consisting of the amino acids valine and citrulline (e.g., divalent -Val-Cit- or divalent -VCit-). In some embodiments, the linker is a peptide comprising or consisting of the amino acids alanine and alanine, or divalent -AA-. In some embodiments, the linker is a peptide comprising or consisting of the amino acids glutamic acid and alanine, or -EA-. In some embodiments, the linker is a peptide comprising or consisting of the amino acids glutamic acid and glycine, or -EG-. In some embodiments, the linker is a peptide comprising or consisting of the amino acids glycine and glycine, or -GG-. In some embodiments, the linker is a peptide comprising or consisting of the amino acids glutamine, valine, and citrulline, or -Q-V-Cit- or -QVCit-. In some embodiments, the linker is a peptide comprising or consisting of the amino acids glutamic acid, valine, and citrulline, or -E-V-Cit- or -EVCit-. In some embodiments, the linker is a peptide comprising or consisting of the amino acids -GGGGS-. In some embodiments, the linker is a peptide comprising or consisting of the amino acids -GGGGG-. In some embodiments, the linker is a peptide comprising or consisting of the amino acids -GGGGK-. In some embodiments, the linker is a peptide comprising or consisting of the amino acids -GFGG-. In some embodiments, the linker is a peptide comprising or consisting of the amino acids lysine, valine, and citrulline, or -KVCit-. In some embodiments, the linker is a peptide comprising or consisting of the amino acids -KVA-. In some embodiments, the linker is a peptide comprising or consisting of the amino acids -VA-. In any of the embodiments in this paragraph, and throughout this disclosure, the standard three-letter or one-letter amino acid designations are used, as would be appreciated by a person of skill in the art. Exemplary single-letter amino acid designations include, G for glycine, K for lysine, S for serine, V for valine, A for alanine, and F for phenylalanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

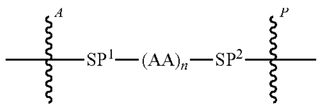

wherein:

$SP^1$ is a spacer;

$SP^2$ is a spacer;

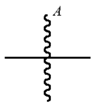

is one or more bonds to the binding agent;

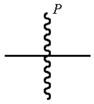

is one or more bonds to the payload;

each AA is an amino acid residue; and n is an integer from zero to ten.

The $SP^1$ spacer is a moiety that connects the $(AA)_n$ moiety or residue to the binding agent (BA) or to a reactive group residue which is bonded to BA. Suitable $SP^1$ spacers include, but are not limited to, those comprising alkylene or polyether, or both. The ends of the spacers, for example, the portion of the spacer bonded to the BA or an AA, can be moieties derived from reactive moieties that are used for purposes of coupling the antibody or an AA to the spacer during chemical synthesis of the conjugate. In certain embodiments, n is 0, 1, 2, 3, or 4 (i.e., when n is 0, AA is absent). In particular embodiments, n is 2. In particular embodiments, n is 3. In particular embodiments, n is 4.

In some embodiments, the $SP^1$ spacer comprises an alkylene. In some embodiments, the $SP^1$ spacer comprises a $C_{5-7}$ alkylene. In some embodiments, the $SP^1$ spacer comprises a polyether. In some embodiments, the $SP^1$ spacer comprises a polymer of ethylene oxide such as polyethylene glycol (PEG). Polymeric units of polyethyene glycol are commonly represented as $-(OCH_2C_H2)_p-$, where p could be an integer from one to one hundred. For example, $-(OCH_2C_H2)_2-$ can also be represented as $-OCH_2CH_2-OCH_2CH_2-$ or $PEG_2$. In certain embodiments, the polyethylene glycol is $PEG_1$. In certain embodiments, the polyethylene glycol is $PEG_2$. In certain embodiments, the polyethylene glycol is $PEG_3$. In certain embodiments, the polyethylene glycol is $PEG_4$. In certain embodiments, the polyethylene glycol is $PEG_5$. In certain embodiments, the polyethylene glycol is $PEG_6$. In certain embodiments, the polyethylene glycol is $PEG_2$. In certain embodiments, the polyethylene glycol is $PEG_3$. In certain embodiments, the polyethylene glycol is $PEG_4$. In certain embodiments, the polyethylene glycol is $PEG_{10}$. In certain embodiments, the polyethylene glycol is $PEG_{11}$. In certain embodiments, the polyethylene glycol is $PEG_{12}$. In certain embodiments, the polyethylene glycol is $PEG_{13}$. In certain embodiments, the polyethylene glycol is $PEG_{14}$. In certain embodiments, the polyethylene glycol is $PEG_{15}$. In certain embodiments, the polyethylene glycol is $PEG_{16}$. In certain embodiments, the polyethylene glycol is $PEG_{17}$. In certain embodiments, the polyethylene glycol is $PEG_{15}$. In certain embodiments, the polyethylene glycol is $PEG_{19}$. In certain embodiments, the polyethylene glycol is $PEG_{20}$. In certain embodiments, the polyethylene glycol is $PEG_{21}$. In certain embodiments, the polyethylene glycol is $PEG_{22}$. In certain embodiments, the polyethylene glycol is $PEG_{23}$. In certain embodiments, the polyethylene glycol is $PEG_{24}$. In certain embodiments, the polyethylene glycol is $PEG_{25}$. In certain embodiments, the polyethylene glycol is $PEG_{26}$. In certain embodiments, the polyethylene glycol is $PEG_{27}$. In certain embodiments, the polyethylene glycol is $PEG_{28}$. In certain embodiments, the polyethylene glycol is $PEG_{29}$. In certain embodiments, the polyethylene glycol is $PEG_{30}$. In certain embodiments, the polyethylene glycol is $PEG_{31}$. In certain embodiments, the polyethylene glycol is $PEG_{32}$. In certain embodiments, the polyethylene glycol is $PEG_{33}$. In certain embodiments, the polyethylene glycol is $PEG_{34}$. In certain embodiments, the polyethylene glycol is $PEG_{35}$. In certain embodiments, the polyethylene glycol is $PEG_{36}$. In certain embodiments, the polyethylene glycol is $PEG_{37}$. In certain embodiments, the polyethylene glycol is $PEG_{38}$. In certain embodiments, the polyethylene glycol is $PEG_{39}$. In certain embodiments, the polyethylene glycol is $PEG_{40}$. In certain embodiments, the polyethylene glycol is $PEG_{41}$. In certain embodiments, the polyethylene glycol is $PEG_{42}$. In certain embodiments, the polyethylene glycol is $PEG_{43}$. In certain embodiments, the polyethylene glycol is $PEG_{44}$. In certain embodiments, the polyethylene glycol is $PEG_{45}$. In certain embodiments, the polyethylene glycol is $PEG_{46}$. In certain embodiments, the polyethylene glycol is $PEG_{47}$. In certain embodiments, the polyethylene glycol is $PEG_{48}$. In certain embodiments, the polyethylene glycol is $PEG_{49}$. In certain embodiments, the polyethylene glycol is $PEG_{50}$. In certain embodiments, the polyethylene glycol is $PEG_{51}$. In certain embodiments, the polyethylene glycol is $PEG_{52}$. In certain embodiments, the polyethylene glycol is $PEG_{53}$. In certain embodiments, the polyethylene glycol is $PEG_{54}$. In certain embodiments, the polyethylene glycol is $PEG_{55}$. In certain embodiments, the polyethylene glycol is $PEG_{56}$. In certain embodiments, the polyethylene glycol is $PEG_{57}$. In certain embodiments, the polyethylene glycol is $PEG_{58}$. In certain embodiments, the polyethylene glycol is $PEG_{59}$. In certain embodiments, the polyethylene glycol is $PEG_{60}$. In certain embodiments, the polyethylene glycol is $PEG_{61}$. In certain embodiments, the polyethylene glycol is $PEG_{62}$. In certain embodiments, the polyethylene glycol is $PEG_{63}$. In certain embodiments, the polyethylene glycol is $PEG_{64}$. In certain embodiments, the polyethylene glycol is $PEG_{65}$. In certain embodiments, the polyethylene glycol is $PEG_{66}$. In certain embodiments, the polyethylene glycol is $PEG_{67}$. In certain embodiments, the polyethylene glycol is $PEG_{68}$. In certain embodiments, the polyethylene glycol is $PEG_{69}$. In certain embodiments, the polyethylene glycol is $PEG_{70}$. In certain embodiments, the polyethylene glycol is $PEG_{71}$. In certain embodiments, the polyethylene glycol is $PEG_{72}$. In certain embodiments, the polyethylene glycol is $PEG_{73}$. In certain embodiments, the polyethylene glycol is $PEG_{74}$. In certain embodiments, the polyethylene glycol is $PEG_{75}$. In certain embodiments, the polyethylene glycol is $PEG_{76}$. In certain embodiments, the polyethylene glycol is $PEG_{77}$. In certain embodiments, the polyethylene glycol is $PEG_{78}$. In certain embodiments, the polyethylene glycol is $PEG_{79}$. In certain embodiments, the polyethylene glycol is $PEG_{80}$. In certain embodiments, the polyethylene glycol is $PEG_{81}$. In certain embodiments, the polyethylene glycol is $PEG_{82}$. In certain embodiments, the polyethylene glycol is $PEG_{83}$. In certain embodiments, the polyethylene glycol is $PEG_{84}$. In certain embodiments, the polyethylene glycol is $PEG_{85}$. In certain embodiments, the polyethylene glycol is $PEG_{86}$. In certain embodiments, the polyethylene glycol is $PEG_{87}$. In certain embodiments, the polyethylene glycol is $PEG_{88}$. In certain embodiments, the polyethylene glycol is $PEG_{89}$. In certain embodiments, the polyethylene glycol is $PEG_{90}$. In certain embodiments, the polyethylene glycol is $PEG_{91}$. In certain embodiments, the polyethylene glycol is $PEG_{92}$.

In some embodiments, the $SP^1$ spacer is:

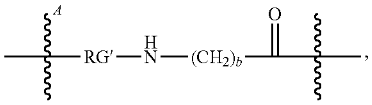

, or

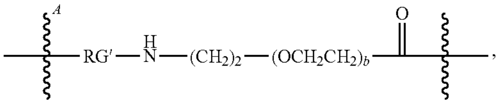

, wherein:

RG' is a reactive group residue following reaction of a reactive group RG with a binding agent;

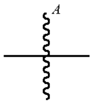

is a bond to the binding agent;

is a bond to $(AA)_n$;

n is an integer from zero to ten; and b is, independently, an integer from 1 to 92.

The reactive group RG can be any reactive group known to those of skill in the art to be capable of forming one or more bonds to the binding agent. The reactive group RG is a moiety comprising a portion in its structure that is capable of reacting with the binding agent (e.g., reacting with an antibody at its cysteine or lysine residues, or at an azide moiety, for example, a $PEG-N_3$ functionalized antibody at one or more glutamine residues; or at an amino moiety, for example, a $PEG-NH_2$ functionalized antibody at one or more glutamine residues) to form antibody-drug conjugates described herein. Following conjugation to the binding agent, the reactive group becomes the reactive group residue (RG'). Illustrative reactive groups include, but are not limited to, those that comprise haloacetyl, isothiocyanate, succinimide, N-hydroxysuccinimide, or maleimide portions that are capable of reacting with the binding agent.

The $SP^2$ spacer, when present, is a moiety that connects the $(AA)_n$ moiety to the payload. Suitable spacers include, but are not limited to, those described above as $SP^1$ spacers. Further suitable $SP^2$ spacers include, but are not limited to, those comprising alkylene or polyether, or both. The ends of the $SP^2$ spacers, for example, the portion of the spacer directly bonded to the payload or an AA, can be moieties derived from reactive moieties that are used for purposes of coupling the payload or AA to the $SP^2$ spacer during the chemical synthesis of the conjugate. In some examples, the ends of the $SP^2$ spacers, for example, the portion of the $SP^2$ spacer directly bonded to the payload or an AA, can be residues of reactive moieties that are used for purposes of coupling the payload or an AA to the spacer during the chemical synthesis of the conjugate.

In some embodiments, the $SP^2$ spacer, when present, is selected from the group consisting of $-NH-(p-C_6H_4)-CH_2-$, $-NH-(p-C_6H_4)-CH_2OC(O)-$, an amino acid, a dipeptide, a tripeptide, an oligopeptide

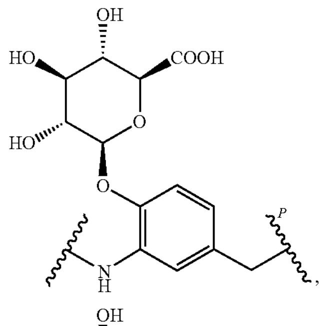

,

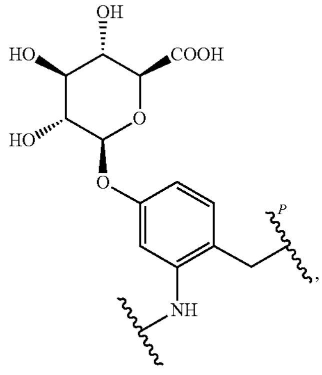

,

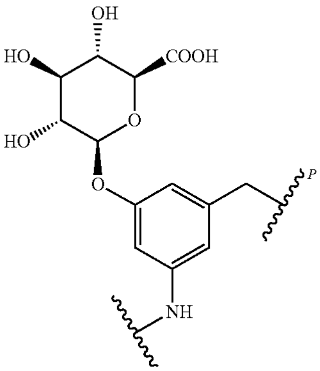

,

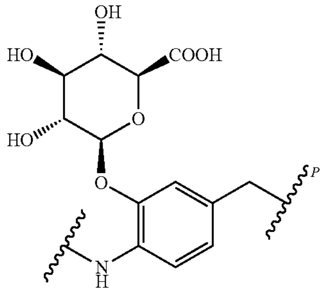

,

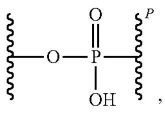

,

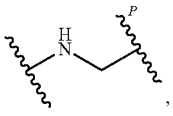

, and any combinations thereof. In certain embodiments, each

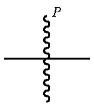

is a bond to the payload, and each

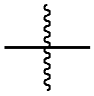

is a bond to $(AA)_n$ or absent if n=0.

In the above formulae, each $(AA)_n$ is an amino acid or, optionally, a p-aminobenzyloxycarbonyl residue (PABC). n can be 0; if so, $(AA)_n$ is absent. If PABC is present, preferably only one PABC is present. Preferably, the PABC residue, if present, is bonded to a terminal AA in the $(AA)_n$ group, proximal to the payload. Suitable amino acids for each AA include natural, non-natural, standard, non-standard, proteinogenic, non-proteinogenic, and L- or D-α-amino acids. In some embodiments, the AA comprises alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or any combinations thereof (e.g., dipeptides, tripeptides, and oligopeptides, and the like). In certain embodiments, one or more side chains of the amino acids is linked to a side chain group, described below. In some embodiments, n is two. In some embodiments, the $(AA)_n$ is valine-citrulline. In some embodiments, $(AA)_n$ is citrulline-valine. In some embodiments, $(AA)_n$ is valine-alanine. In some embodiments, $(AA)_n$ is alanine-valine. In some embodiments, $(AA)_n$ is valine-glycine. In some embodiments, $(AA)_n$ is glycine-valine. In some embodiments, the $(AA)_n$ is valine-citrulline-PABC. In some embodiments, $(AA)_n$ is citrulline-valine-PABC. In some embodiments, n is three. In some embodiments, $(AA)_n$ is glutamate-valine-citrulline. In some embodiments, $(AA)_n$ is glutamine-valine-citrulline. In some embodiments, $(AA)_n$ is lysine-valine-alanine. In some embodiments, $(AA)_n$ is lysine-valine-citrulline. In some embodiments, n is four. In some embodiments, $(AA)_n$ is glutamate-valine-citrulline-PAB. In some embodiments, $(AA)_n$ is glutamine-valine-citrulline-PABC. Those of skill will recognize PABC as a residue of p-aminobenzyloxycarbonyl with the following structure:

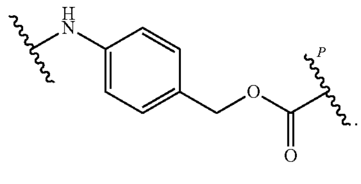

.

The PABC residue has been shown to facilitate cleavage of certain linkers in vitro and in vivo. For example, in certain embodiments, upon cleavage of PABC, the carboxylate or carboxylic acid moiety (i.e.,

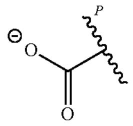

or

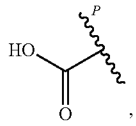

, respectively) remains intact with the remainder of the antiviral compound or payload. In certain embodiments, each

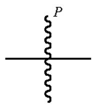

is a bond to the remainder of the antiviral compound (e.g., the payload). Those of skill will recognize PAB as a divalent residue of p-aminobenzyl (i.e., —NH-(p-$C_6H_4$)—$CH_2$— or

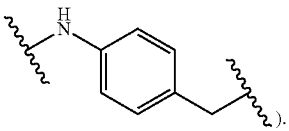 [SMILES: *Cc1ccc(N*)cc1]).

In certain embodiments, the PAB residue has been shown to facilitate cleavage of certain linkers in vitro and in vivo. For example, in certain embodiments, upon cleavage of

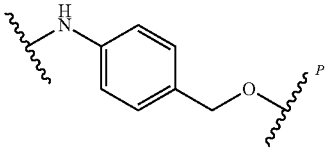

the alkoxide or hydroxyl moiety (i.e.,

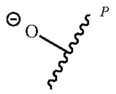 or 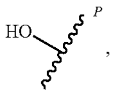, respectively) remains intact with the remainder of the antiviral compound (e.g., the payload). In certain embodiments, each

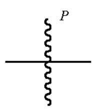

is a bond to the remainder of the antiviral compound or payload.

Linker-Payloads

In certain embodiments, linker-payloads include any specific compound or payload embraced by any one or more of Formulae I and II above, bonded to a linker, wherein the linker(s) described herein include a moiety that is reactive with an antibody or antigen binding fragment thereof described herein. In particular embodiments, the linker is bonded to the carboxyl or hydroxyl in any one or more of Formulae I and II above. In one embodiment, the linker-payload has the following structure

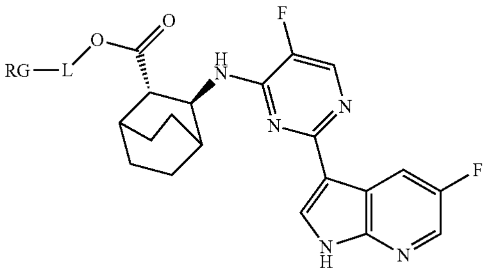 or

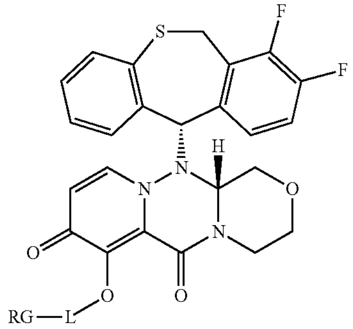

or a pharmaceutically acceptable salt thereof, wherein L is a linker, as described in any of the embodiments disclosed herein; and RG is a reactive moiety, as described in any of the embodiments disclosed herein. In one embodiment, the linker-payload is:

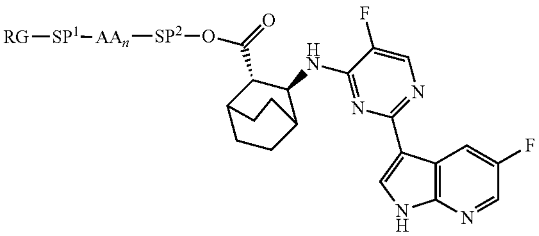 or

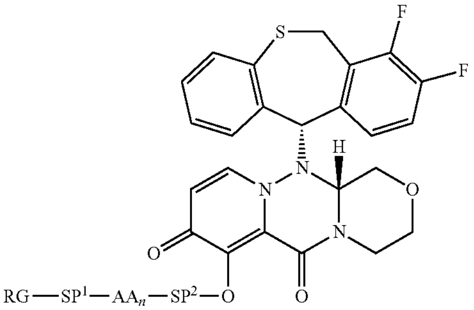

or a pharmaceutically acceptable salt thereof, wherein $SP^1$ and $SP^2$, when present, are spacer groups as described in any of the embodiments disclosed herein; RG is a moiety reactive with an antibody or an antigen binding fragment thereof as described in any of the embodiments disclosed herein; each AA is an amino acid as described in any of the embodiments disclosed herein; and n is an integer from one to ten.

In certain embodiments, provided herein are compounds (viz., linker-payloads) selected from the group consisting of:

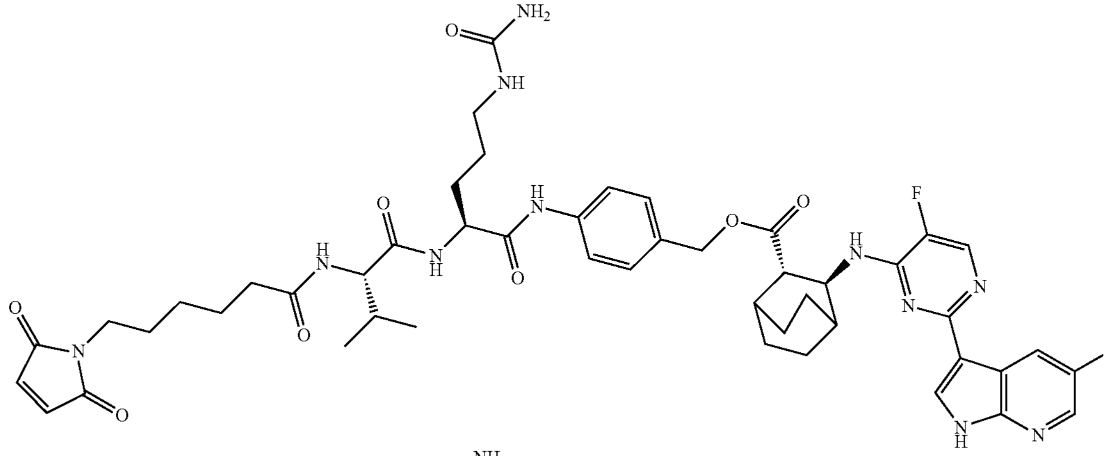

;

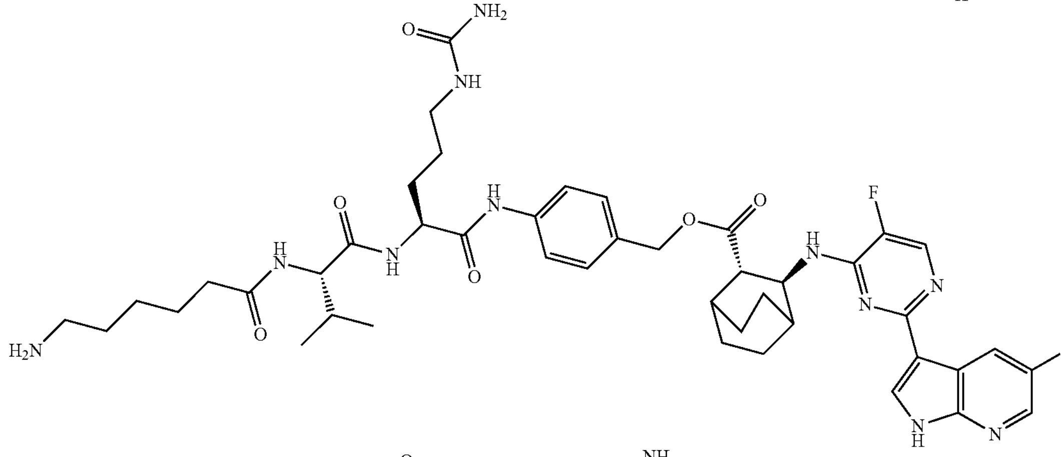

; and

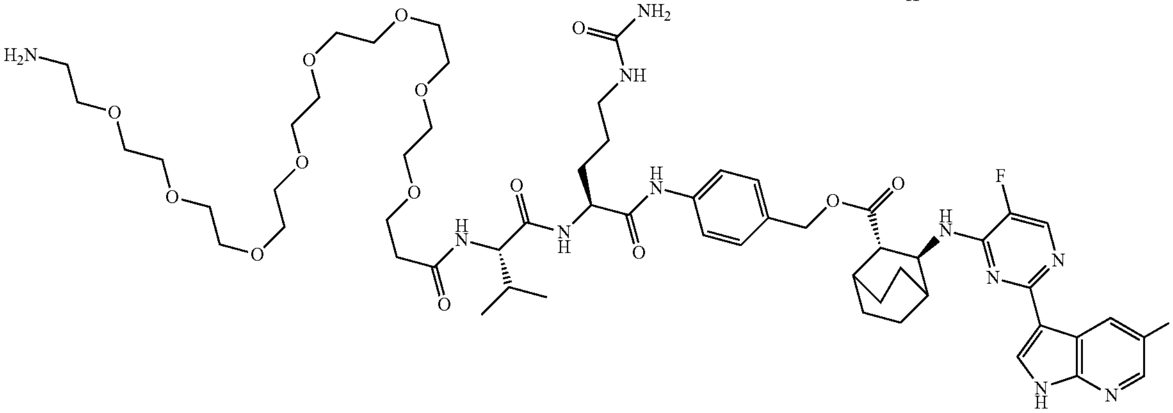

.

Conjugates/Antibody Drug Conjugates (ADCs)

Provided herein are human anti-influenza-HA monoclonal antibodies conjugated to a therapeutic moiety, such as a toxoid or an antiviral drug, to treat influenza virus infection (i.e., an ADC). The antibody may be linked to the therapeutic agent at any location along the antibody so long as the antibody is able to bind its target. In one embodiment, the therapeutic agent may be a second different antibody to Influenza-HA or ADC thereof. In certain embodiments, the antibody may be conjugated to an agent specific for a virally infected cell. The type of therapeutic moiety that may be conjugated to the anti-influenza-HA antibody and will take into account the condition to be treated and the desired therapeutic effect to be achieved. In certain embodiments, provided herein are antibodies, or an antigen binding fragment thereof, wherein the antibody is conjugated to one or more compounds of Formulae I and/or II as described herein. In one embodiment, the anti-influenza antibody or antigen-binding fragment thereof is conjugated to a payload via a linker, each as described in any of their respective embodiments disclosed herein.

In one embodiment, the antibody-drug conjugate has the following structure $$\text{Ab}-[\text{L}-\text{P}]_k$$

wherein Ab is an anti-influenza antibody or an antigen binding fragment thereof; L is a linker; and P is an antiviral compound or payload. In one embodiment, Ab is an anti-influenza antibody or an antigen binding fragment thereof; and P is an influenza inhibitor. In one embodiment, Ab is an anti-influenza antibody or an antigen binding fragment thereof; and P is a polymerase inhibitor. In one embodiment, Ab is an anti-influenza antibody or an antigen binding fragment thereof; and P is VX-787, a derivative thereof, or a residue thereof. In one embodiment, Ab is an anti-influenza antibody or an antigen binding fragment thereof; and P is baloxavir, a derivative thereof, or a residue thereof. In one embodiment, Ab is an anti-hemagglutinin antibody or an antigen binding fragment thereof; and P is an antiviral compound. In one embodiment, Ab is an anti-influenza antibody or an antigen binding fragment thereof; and P is an antiviral compound. In one embodiment, Ab is an anti-hemagglutinin antibody or an antigen binding fragment thereof; and P is an influenza inhibitor. In one embodiment, Ab is an anti-hemagglutinin antibody or an antigen binding fragment thereof; and P is a polymerase inhibitor. In any embodiment in this paragraph, Ab is an anti-influenza antibody or an antigen binding fragment thereof or an anti-hemagglutinin antibody or an antigen binding fragment thereof wherein the antibody is conjugated to a compound of Formula I, as described above. In any embodiment in this paragraph, Ab is an anti-influenza antibody or an antigen binding fragment thereof or an anti-hemagglutinin antibody or an antigen binding fragment thereof wherein the antibody is conjugated to a compound of Formula II, as described above. In one embodiment, Ab is an anti-hemagglutinin antibody or an antigen binding fragment thereof; and P is VX-787, a derivative thereof, or a residue thereof. In one embodiment, Ab is an anti-hemagglutinin antibody or an antigen binding fragment thereof; and P is baloxavir, a derivative thereof, or a residue thereof. In any of the embodiments in this paragraph, k is an integer from one to thirty. In certain embodiments, provided herein are ADCs where the antibody or antigen binding fragment thereof is conjugated to a compound of

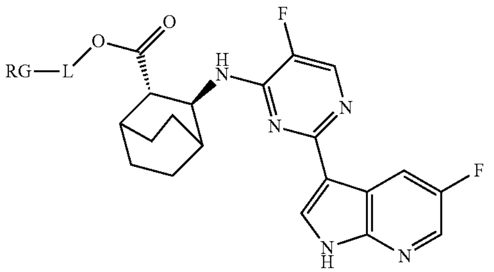

or

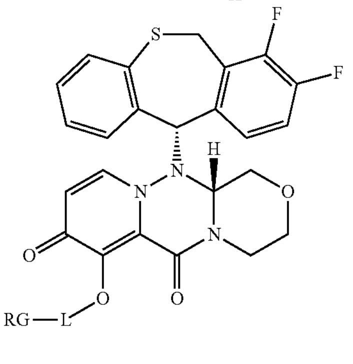

or a pharmaceutically acceptable salt thereof, wherein L is a linker described herein; and RG is a reactive moiety described herein. In certain embodiments, provided herein are ADCs wherein the conjugated compound is selected from

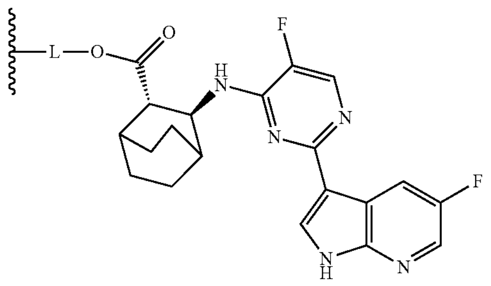

or

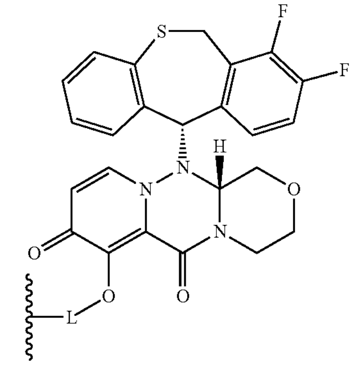

wherein L is a linker as described herein.

In certain embodiments, provided herein are ADC compounds having the following structure:

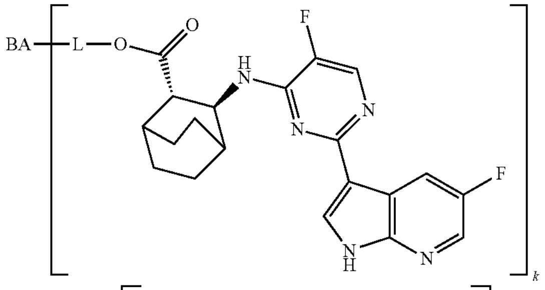

or

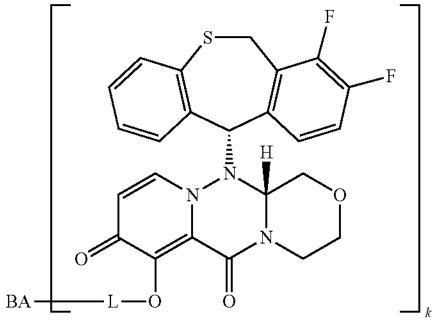

wherein L and BA are as described elsewhere herein, and k is 1, 2, 3, 4, 5, 6, 7, 8, 9, or 10. In certain embodiments, k is a range from 1-2, 1-3, 2-3, 2-4, 3-4, or 1-4. In certain embodiments, compounds conjugated to -L-BA as above include one or more compounds of Formulae I and/or II, as described above, wherein BA is a binding agent; L is a linker; and k is 1, 2, 3, 4, 5, 6, 7, 8, 9, or 10. In certain embodiments, where compounds conjugated to -L-BA as above include one or more compounds of Formulae I and/or II, as described above, wherein BA is a binding agent and L is a linker, k is a range from 1-2, 1-3, 2-3, 2-4, 3-4, or 1-4.

In one embodiment, provided herein are ADC compounds selected from the group consisting of

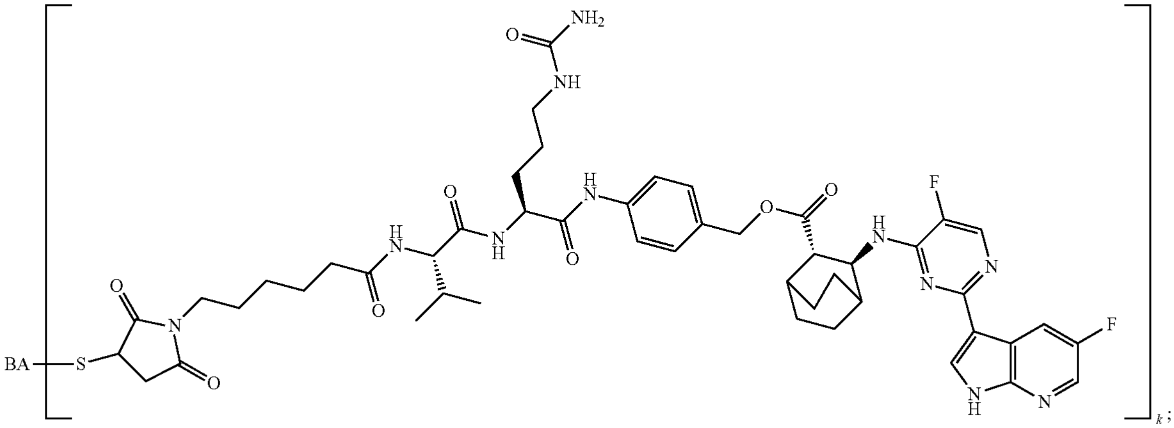

;

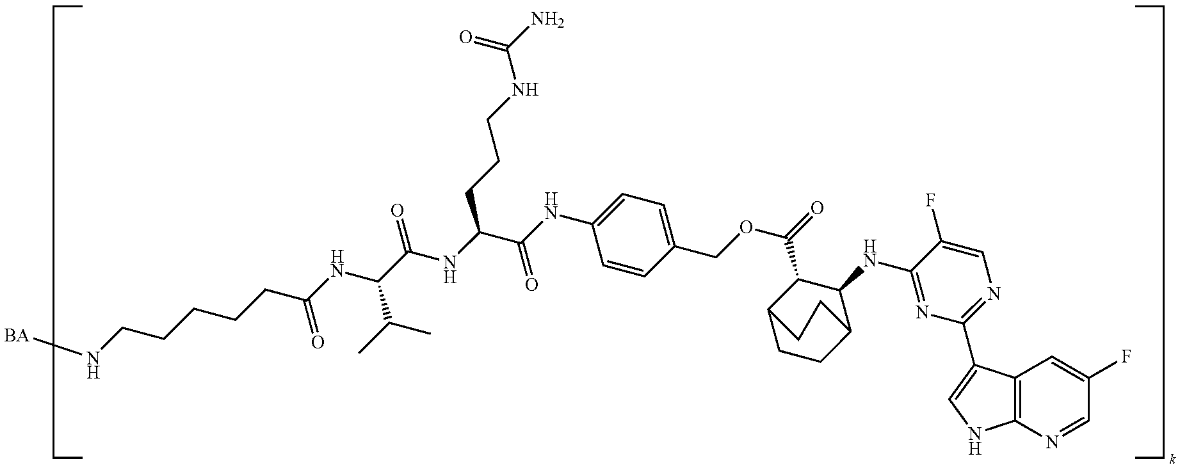

;

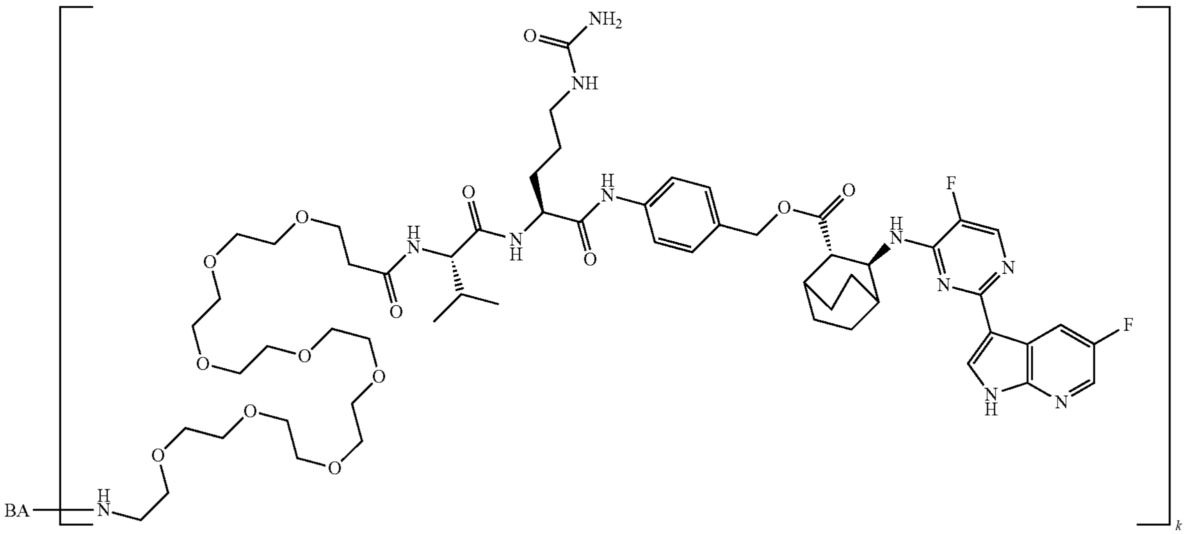

-continued

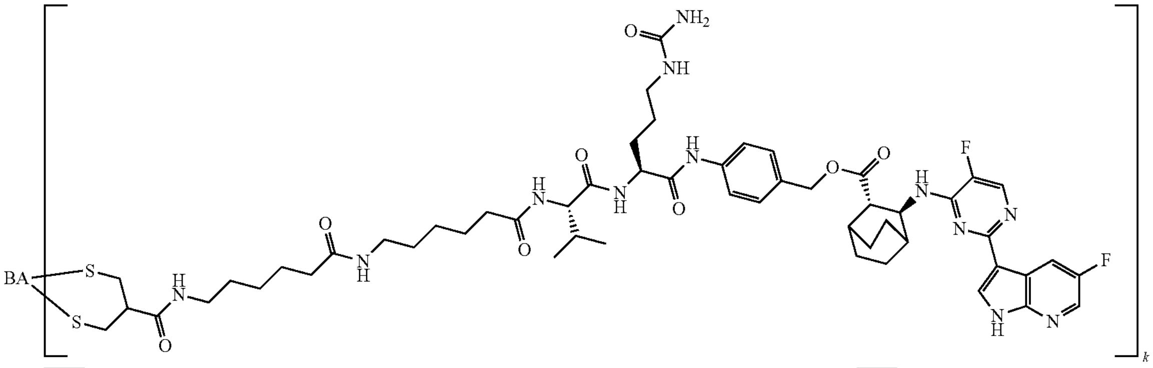

; and

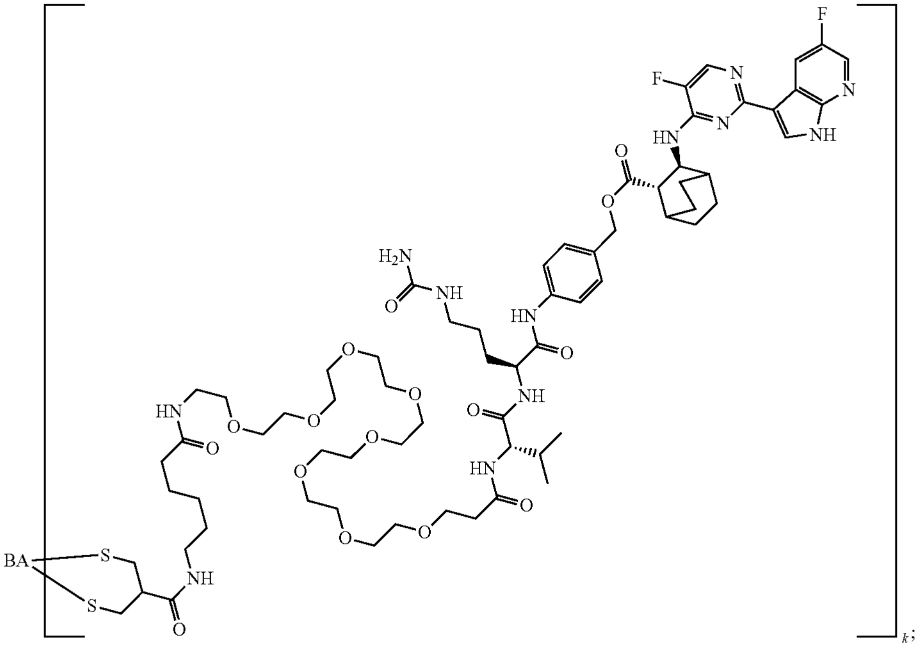

;

wherein BA is an antibody or an antigen binding fragment thereof; and k is an integer from one to thirty. In certain embodiments, k is 1, 2, 3, 4, 5, 6, 7, 8, 9, or 10. In certain embodiments, k is a range from 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10. In any of the embodiments in this paragraph, BA is contemplated to include one or more cysteine, lysine, and/or glutamine residues for conjugation to a payload and/or linker-payload, when k is greater than one. For example, the above ADC delineations contemplate a drug:antibody ratio (DAR) of one or more where one or more cysteine, lysine, and/or glutamine residues of BA accommodate a payload and/or linker-payload (e.g., when k is ≥1). The bonds from BA to —S— and/or from BA to —NH— indicate bonds from the binding agent (BA) to a cysteine or transglutaminated glutamine residue of BA, respectively. And, bonds from BA-S— and/or from BA-NH— to carbon indidcate linkage to the linker(s) as shown, or described elsewhere herein. Therefore, the sulfur from a cysteine residue of BA, and/or the nitrogen from a transglutaminated glutamine residue of BA, are within the brackets as drawn to show that BA can be conjugated with more than one payload and/or linker-payload (e.g., BA having a DAR≥1). In one embodiment, BA is an antibody or an antigen-binding fragment thereof as described herein.

In certain ADC embodiments described herein, Ab or BA is a transglutaminase-modified antibody or antigen-binding fragment thereof. In one embodiment, Ab or BA is a transglutaminase-modified antibody or antigen-binding fragment thereof comprising at least one glutamine residue used for conjugation. In one embodiment, Ab or BA is a transglutaminase-modified antibody or antigen-binding fragment thereof comprising at least two glutamine residues used for conjugation. In one embodiment, Ab or BA is a transglutaminase-modified antibody or antigen-binding fragment thereof comprising at least three glutamine residues used for conjugation. In one embodiment, Ab or BA is a transglutaminase-modified antibody or antigen-binding fragment thereof comprising at least four glutamine residues used for conjugation. In one embodiment, Ab or BA is a transglutaminase-modified antibody or antigen-binding fragment thereof comprising at least one glutamine residue available for conjugation. In one embodiment, Ab or BA is a transglutaminase-modified antibody or antigen-binding fragment thereof comprising at least two glutamine residues available for conjugation. In one embodiment, Ab or BA is a transglutaminase-modified antibody or antigen-binding fragment thereof comprising at least three glutamine residues available for conjugation. In one embodiment, Ab or BA is a transglutaminase-modified antibody or antigen-binding fragment thereof comprising at least four glutamine residues available for conjugation. In one embodiment, Ab or BA is a transglutaminase-modified antibody or antigen-binding fragment thereof, wherein conjugation is at two Q295 residues; and k is 2. In one embodiment, Ab or BA is a transglutaminase-modified antibody or antigen-binding fragment thereof, wherein conjugation is at two Q295 residues in the EU numbering system; and k is 2. In one embodiment, Ab or BA is a transglutaminase-modified antibody or antigen-binding fragment thereof comprising an antibody heavy chain, wherein conjugation is at the C-terminus of the heavy chain; and k is 2. In one embodiment, Ab or BA is a transglutaminase-modified antibody or antigen-binding fragment thereof comprising an antibody heavy chain, wherein conjugation is via a glutamine. In one embodiment, Ab or BA is a transglutaminase-modified antibody or antigen-binding fragment thereof comprising an antibody heavy chain, wherein conjugation is via a glutamine; and k is 2. In one embodiment, Ab or BA is a transglutaminase-modified antibody or antigen-binding fragment thereof comprising an antibody heavy chain, wherein conjugation is via the glutamine in a LLQGA sequence at the C-terminus of the antibody heavy chain. In one embodiment, Ab or BA is a transglutaminase-modified antibody or antigen-binding fragment thereof comprising an antibody heavy chain, wherein conjugation is via the glutamine in a LLQGA sequence at the C-terminus of the antibody heavy chain; and k is 2. In one embodiment, Ab or BA is a transglutaminase-modified antibody or antigen-binding fragment thereof, wherein conjugation is at two Q295 residues and two N297Q residues; and k is 4. In one embodiment, Ab or BA is a transglutaminase-modified antibody or antigen-binding fragment thereof, wherein conjugation is at two Q295 residues in the EU numbering system and two N297Q residues; and k is 4. In one embodiment, Ab or BA is mAb11729, as described herein.

In one embodiment, Ab or BA is a transglutaminase-modified antibody or antigen-binding fragment thereof, wherein conjugation is at two Q295 residues; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0; g) is about 1.0; or h) is about 2.0. In one embodiment, Ab or BA is a transglutaminase-modified antibody or antigen-binding fragment thereof, wherein conjugation is at two Q295 residues in the EU numbering system; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0; g) is about 1.0; or h) is about 2.0. In one embodiment, Ab or BA is a transglutaminase-modified antibody or antigen-binding fragment thereof comprising an antibody heavy chain, wherein conjugation is at the C-terminus of the heavy chain; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0; g) is about 1.0; or h) is about 2.0. In one embodiment, Ab or BA is a transglutaminase-modified antibody or antigen-binding fragment thereof comprising an antibody heavy chain, wherein conjugation is via a glutamine. In one embodiment, Ab or BA is a transglutaminase-modified antibody or antigen-binding fragment thereof comprising an antibody heavy chain, wherein conjugation is via a glutamine; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0; g) is about 1.0; or h) is about 2.0. In one embodiment, Ab or BA is a transglutaminase-modified antibody or antigen-binding fragment thereof comprising an antibody heavy chain, wherein conjugation is via the glutamine in a LLQGA sequence at the C-terminus of the antibody heavy chain. In one embodiment, Ab or BA is a transglutaminase-modified antibody or antigen-binding fragment thereof comprising an antibody heavy chain, wherein conjugation is via the glutamine in a LLQGA sequence at the C-terminus of the antibody heavy chain; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0; g) is about 1.0; or h) is about 2.0. In one embodiment, Ab or BA is a transglutaminase-modified antibody or antigen-binding fragment thereof, wherein conjugation is at two Q295 residues and two $N_{297}Q$ residues; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0 or about 3.0 or about 4.0; g) is about 1.0; h) is about 2.0; i) is about 3.0; or j) is about 4.0. In one embodiment, Ab or BA is a transglutaminase-modified antibody or antigen-binding fragment thereof, wherein conjugation is at two Q295 residues in the EU numbering system and two $N_{297}Q$ residues; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0; g) is about 1.0; or h) is about 2.0. In one embodiment, Ab or BA is a transglutaminase-modified antibody or antigen-binding fragment thereof, wherein conjugation is at two Q295 residues and two $N_{297}Q$ residues; and DAR is a) about 2.0; b) is greater than 0 to about 12.0; c) is about 0.5 to about 8.0; d) is about 0.5 to about 6.0; e) is about 1.0 to about 4.0; f) is about 1.0 or about 2.0 or about 3.0 or about 4.0; g) is about 1.0; h) is about 2.0; i) is about 3.0; or j) is about 4.0. In one embodiment, Ab or BA is mAb11729, as described herein.

In certain ADC embodiments described herein, Ab or BA is an anti-influenza antibody or antigen-binding fragment thereof. In one embodiment, Ab or BA is an anti-influenza A antibody or an antigen binding fragment thereof. In one embodiment, Ab or BA is an anti-influenza A Group 1 antibody or an antigen binding fragment thereof. In one embodiment, Ab or BA is an anti-influenza H1 antibody or an antigen binding fragment thereof. In one embodiment, Ab or BA is an anti-influenza A Group 2 antibody or an antigen binding fragment thereof. In one embodiment, Ab or BA is an anti-influenza H3 antibody or an antigen binding fragment thereof. In one embodiment, Ab or BA is an anti-influenza B antibody or an antigen binding fragment thereof. In one embodiment, an ADC includes an anti-influenza antibody or antigen-binding fragment thereof conjugated to a payload via a linker, wherein the antibody-drug conjugate binds to and/or inhibits polymerase basic protein 2 (PB2) (VX-787), polymerase acid protein (PA) (baloxavir and/or baloxavir marboxil), and/or polymerase basic protein 1 (PB1). In one embodiment, an ADC includes an anti-influenza antibody or antigen-binding fragment thereof conjugated to a payload via a linker, wherein the antibody-drug conjugate binds to and/or inhibits polymerase basic protein 2 (PB2) (VX-787) with an affinity of at least $4.0\times10^{-9}$ M, at least $3.5\times10^{-9}$ M, or at least $3.0\times10^{-9}$ M as measured by ELISA. In one embodiment, an ADC includes an anti-influenza antibody or antigen-binding fragment thereof conjugated to a payload via a linker, wherein the antibody-drug conjugate binds to and/or inhibits polymerase basic protein 1 (PB1) with an affinity of at least $4.0\times10^{-9}$ M, at least 3.5x10$^{-9}$ M, or at least 3.0x10$^{-9}$ M as measured by ELISA. In one embodiment, an ADC includes an anti-influenza antibody or antigen-binding fragment thereof conjugated to a payload via a linker, wherein the antibody-drug conjugate binds to and/or inhibits polymerase basic protein 2 (PB2) (VX-787) with an $IC_{50}$ of at least 2.5x10$^{-9}$ M, at least 2.0x10$^{-9}$ M, or at least 1.5x10$^{-9}$ M as measured by ImmunoSpot® analysis. In one embodiment, an ADC includes an anti-influenza antibody or antigen-binding fragment thereof conjugated to a payload via a linker, wherein the antibody-drug conjugate binds to and/or inhibits polymerase basic protein 1 (PB1) with an $IC_{50}$ of at least 2.5x10$^{-9}$ M, at least 2.0x10$^{-9}$ M, or at least 1.5x10$^{-9}$ M as measured by ImmunoSpot® analysis.

Methods of Preparing Compounds or Payloads, and Linker-Payloads

The compounds provided herein can be prepared, isolated, or obtained by any method apparent to those of skill in the art. Exemplary methods of preparation are described in detail in the Examples below. In certain embodiments, compounds provided herein are commercially available or can generally be prepared according to Schemes A-C:

Scheme A. Exemplary Preparation Scheme

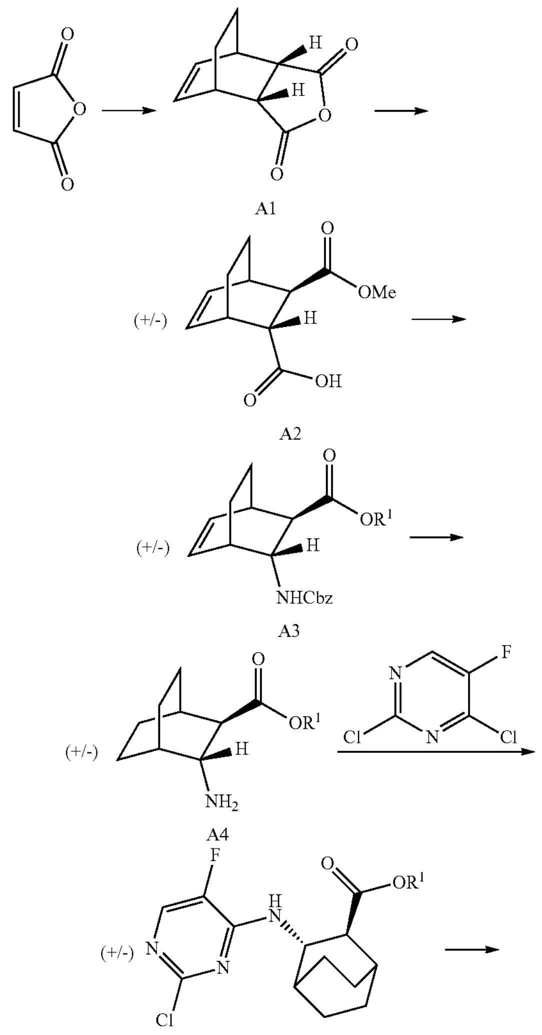

A1

A2

A3

A4

A5

-continued

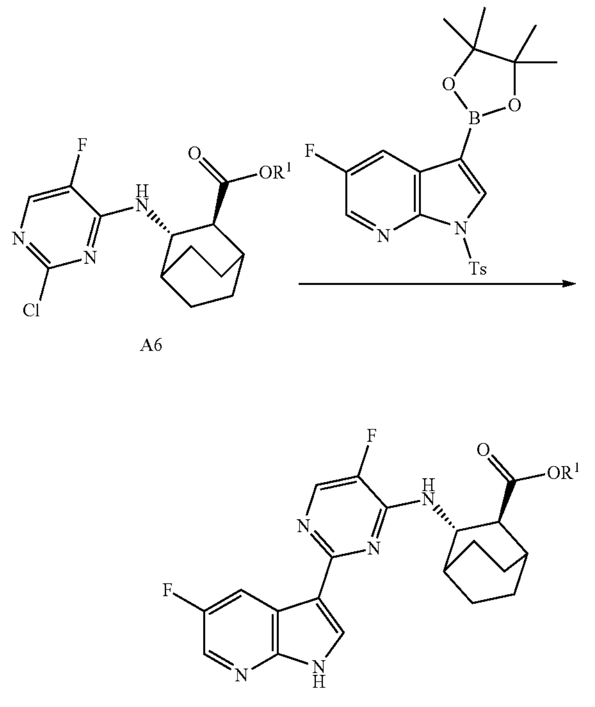

A6

VX-787 and derivatives

Scheme B1. Exemplary Preparation Scheme

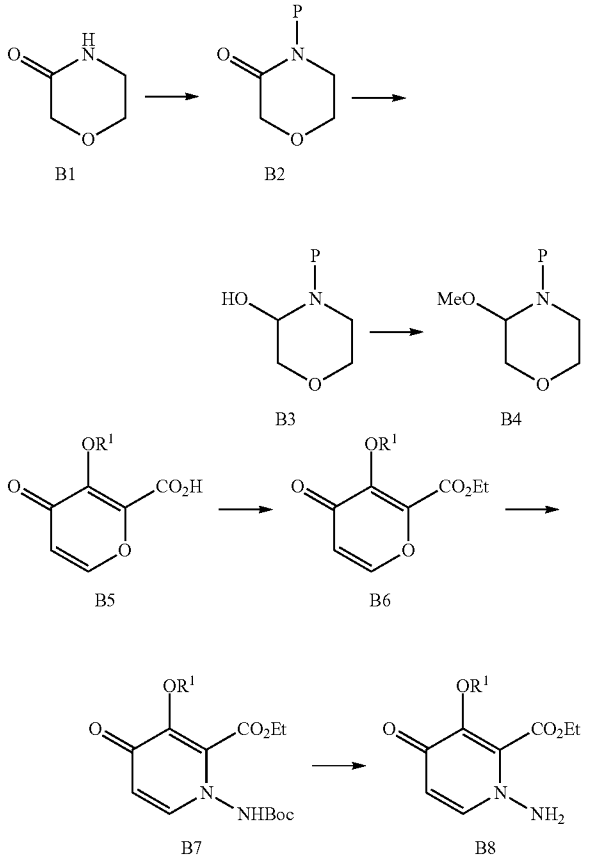

B1

B2

B3

B4

B5

B6

B7

B8

-continued
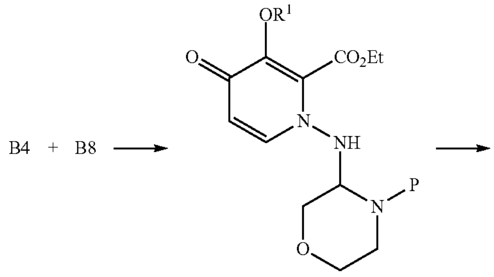
B9
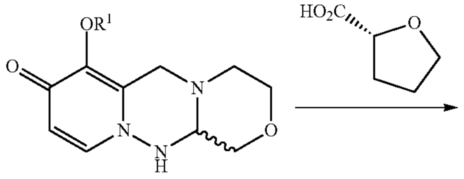
rac-B10
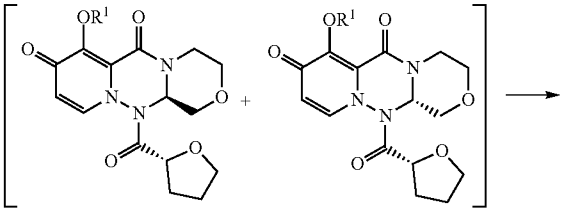
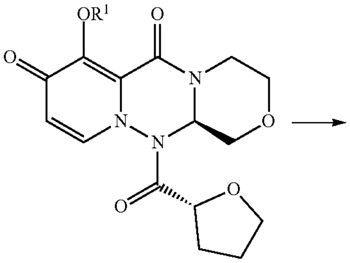
B11
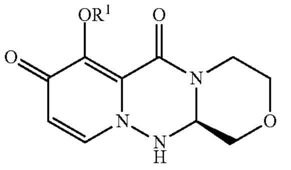
B12
Scheme B2. Exemplary Preparation Scheme
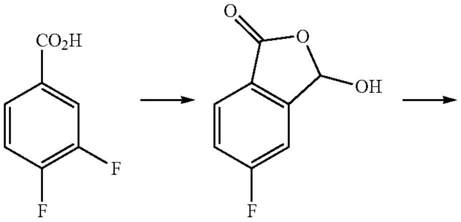
B13 B14
-continued
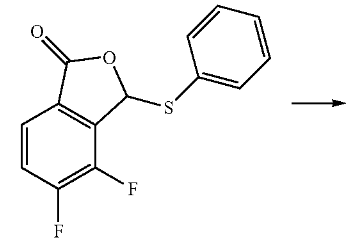
B15
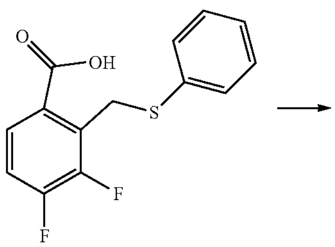
B16
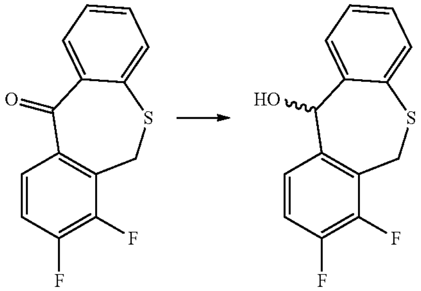
B17 B18
Scheme B3. Exemplary Preparation Scheme
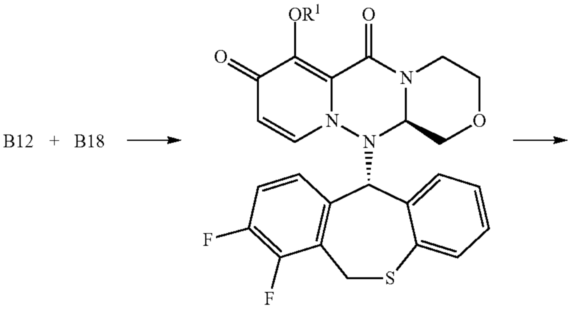
Baloxavir and derivatives -continued

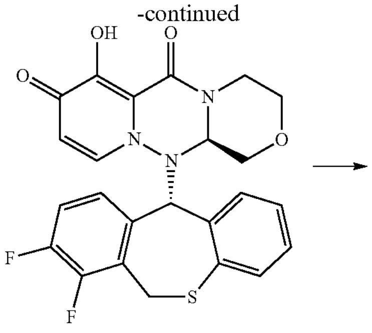

B19

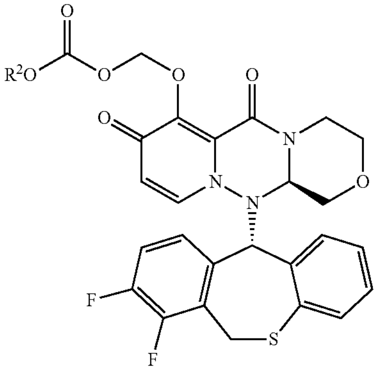

B20

In the above Exemplary Preparation Scheme A (see, *J. Med. Chem.* 2014, 57, 6668), $R^1$ is described in the context of Formula I. In Scheme A, following Diels-Alder cycloaddition with maleic anhydride and 1,3-cyclohexadiene, endo-A1 can be stirred under basic conditions to provide epimerized trans-A2. Curtius rearrangement and trapping with benzyl alcohol provides A3. Hydrogenation provides A4. Treatment with 2,4-dichloropyrimidines and chiral separation provides A6 via intermediate A5. Suzuki coupling with substituted azaindole boronate esters, followed by deprotection, yields compounds of Formula I, including VX-787 and derivatives thereof.

In the above Exemplary Preparation Schemes B1-B3 (see, *OPRD* 2019, 23, 1298), $R^1$ is described in the context of Formula II. In Scheme B1, B1 can be protected to provide B2. B2 is then reduced to provide B3, followed by substitution of hydroxyl for methoxy to provide B4. B5 can be esterified to provide B6. B6 can be treated with Boc-hydrazine to yield pyridone B7, followed by deprotection under acidic conditions to provide B8. Combination of B4 and B8 in the presence of a Lewis acid provides disubstituted hydrazine B9. Deprotection of nitrogen and Pd-mediated cyclization provides rac-B10. Separation of rac-B10 via formation of hydrazide diastereomers, followed by hydrolysis yields B12.

In Scheme B2, B13 is ortho-metalated and quenched with DMF to provide an aldehyde that intramolecularly cyclizes with the carboxylic acid to provide B14. B14 can be treated with thiophenol to provide B15. Reduction of B15 provides B16. Tricyclic sulfide B17 is provided by treatment of B16 under acidic conditions. Reduction of B17 provides B18.

In Scheme B3, combination of B12 with B18 provides baloxavir and derivatives thereof. Deprotection provides baloxavir acid B19. Baloxavir acid B19 can be realkylated to provide B20.

The linker-payloads described herein can generally be synthesized by a series of coupling steps as shown in Scheme C:

Scheme C. Exemplary Preparation Scheme

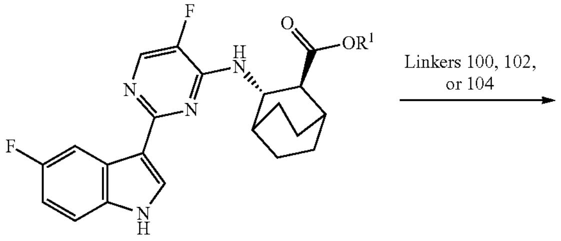

VX-787 and derivatives

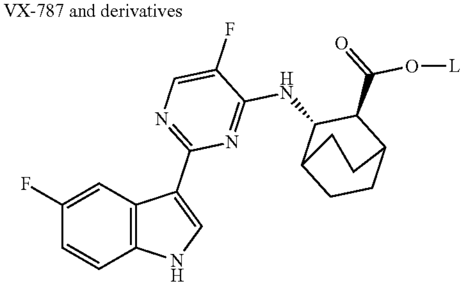

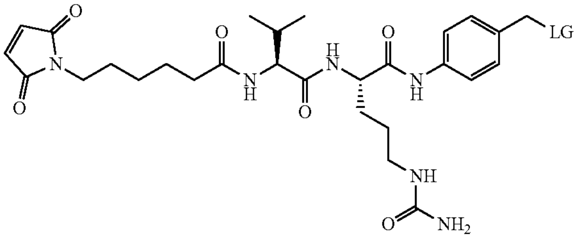

100

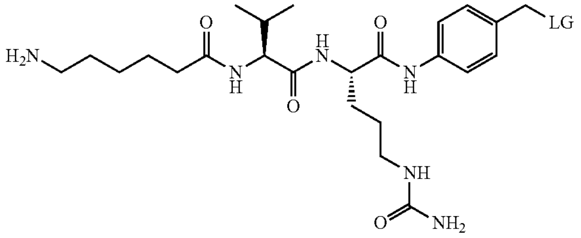

102

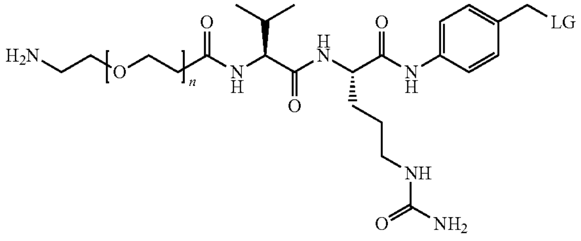

104, where n = 1-92

In the above Exemplary Preparation Scheme C, 1V is as described in the context of Formula I. In Scheme C, VX-787 and derivatives thereof are treated with Linkers bearing a leaving group (LG) to provide linker-payloads (e.g., linker-(VX-787)).

The conjugates described herein can be synthesized by coupling the linker-payloads described herein with a binding agent, for example, an antibody described herein under standard conjugation conditions (see, e.g., Doronina et al. *Nature Biotechnology* 2003, 21, 778, which is incorporated herein by reference in its entirety). When the binding agent is an antibody, the antibody may be coupled to a linker-payload via one or more cysteine or lysine residues of the antibody. Linker-payloads can be coupled to cysteine residues, for example, by subjecting the antibody to a reducing agent, for example, dithiotheritol, to cleave the disulfide bonds of the antibody, purifying the reduced antibody, for example, by gel filtration, and subsequently treating the antibody with a linker-payload containing a suitable reactive moiety, for example, a maleimido group (see, e.g., Exemplary Preparation Scheme C). Suitable solvents include, but are not limited to water, DMA, DMF, and DMSO. Linker-payloads containing a reactive group, for example, an activated ester or acid halide group, can be coupled to lysine residues of the antibody. Suitable solvents include, but are not limited to water, DMA, DMF, and DMSO. Conjugates can be purified using known protein techniques, including, for example, size exclusion chromatography, dialysis, and ultrafiltration/diafiltration.

Binding agents, for example antibodies, can also be conjugated via click chemistry reactions. In some embodiments of said click chemistry reactions, the linker-payload includes a reactive group, for example, an alkyne that is capable of undergoing a regioisomeric 1,3-cycloaddition reaction with an azide. Such suitable reactive groups are described above. The antibody includes one or more azide groups. Such antibodies include antibodies functionalized with, for example, azido-polyethylene glycol groups. In certain embodiments, such functionalized antibody is derived by treating an antibody having at least one glutamine residue, for example, heavy chain Gln295, with a primary amine compound in the presence of the enzyme transglutaminase. In certain embodiments, such functionalized antibody is derived by treating an antibody having at least one glutamine residue, for example, heavy chain Gln297, with a primary amine compound in the presence of the enzyme transglutaminase. Such antibodies include Asn297Gln (N297Q) mutants. In certain embodiments, such functionalized antibody is derived by treating an antibody having at least two glutamine residues, for example, heavy chain Gln295 and heavy chain Gln297, with a primary amine compound in the presence of the enzyme transglutaminase. Such antibodies include Asn297Gln (N297Q) mutants. In certain embodiments, the antibody has two heavy chains as described in this paragraph for a total of two or a total of four glutamine residues.

In certain embodiments, such functionalized antibody is derived by treating an antibody having at least one glutamine residue, for example, heavy chain Gln295, with a primary amine compound or peptide tag in the presence of the enzyme transglutaminase. In certain embodiments, such functionalized antibody is derived by treating an antibody having at least one glutamine residue, for example, heavy chain Gln297, with a primary amine compound or peptide tag in the presence of the enzyme transglutaminase. Such antibodies include Asn297Gln (N297Q) mutants. In certain embodiments, such functionalized antibody is derived by treating an antibody having at least two glutamine residues, for example, heavy chain Gln295 and heavy chain Gln297, with a primary amine compound or peptide tag in the presence of the enzyme transglutaminase. Such antibodies include Asn297Gln (N297Q) mutants. In certain embodiments, the antibody has two heavy chains as described in this paragraph for a total of two or a total of four glutamine residues.

In one embodiment, the functionalized antibody or antigen binding molecule includes an antibody heavy chain and further includes a peptide tag at the C-terminus of the antibody heavy chain. In one embodiment, the functionalized antibody or antigen binding molecule includes an antibody heavy chain and further includes a peptide tag at the C-terminus of the antibody heavy chain, wherein the peptide tag is the pentapeptide sequence LLQGA. In embodiment, the functionalized antibody or antigen binding molecule includes two antibody heavy chains and further includes a peptide tag at the C-terminus of each antibody heavy chain. In one embodiment, the functionalized antibody or antigen binding molecule includes two antibody heavy chains and further includes a peptide tag at the C-terminus of each antibody heavy chain, wherein the peptide tag is the pentapeptide sequence LLQGA.

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. These glutamine residues can be wild-type residues, or engineered residues. The antibodies can be prepared according to standard techniques.

Those of skill will recognize that antibodies are often glycosylated at residue N297, near residue Q295 in a heavy chain sequence. Glycosylation at residue N297 can interfere with a transglutaminase at residue Q295 (Dennler et al., supra). Accordingly, in advantageous embodiments, the antibody is not glycosylated. In certain embodiments, the antibody is deglycoslated or aglycosylated. In particular embodiments, an antibody heavy chain has an N297 mutation. Alternatively stated, the antibody is mutated to no longer have an asparagine residue at position 297. In particular embodiments, an antibody heavy chain has an N297Q mutation. Such an antibody can be prepared by site-directed mutagenesis to remove or disable a glycosylation sequence or by site-directed mutagenesis to insert a glutamine residue at a site apart from any interfering glycosylation site or any other interfering structure. Such an antibody also can be isolated from natural or artificial sources.

The antibody without interfering glycosylation is then reacted or treated with a primary amine compound. In certain embodiments, an aglycosylated antibody is reacted or treated with a primary amine compound to produce a glutaminyl-modified antibody. In certain embodiments, a deglycosylated antibody is reacted or treated with a primary amine compound to produce a glutaminyl-modified antibody.

The primary amine can be any primary amine that is capable of forming a covalent bond with a glutamine residue in the presence of a transglutaminase. Useful primary amines are described herein (see, e.g., Exemplary Preparation Scheme C). The transglutaminase can be any transglutaminase deemed suitable by those of skill in the art. In certain embodiments, the transglutaminase is an enzyme that catalyzes the formation of an isopeptide bond between a free amino group on the primary amine compound and the acyl group on the side chain of a glutamine residue. Transglutaminase is also known as protein-glutamine-γ-glutamyltransferase. In particular embodiments, the transglutaminase is classified as EC 2.3.2.13. The transglutaminase can be from any source deemed suitable. In certain embodiments, the transglutaminase is microbial. Useful transglutaminases have been isolated from *Streptomyces mobaraense, Streptomyces cinnamoneum, Streptomyces griseo-carneum, Streptomyces lavendulae*, and *Bacillus subtilis*. Non-microbial transglutaminases, including mammalian transglutaminases, can also be used, e.g., a non-microbial transglutaminase in combination with a cofactor. In certain embodiments, the transglutaminase can be produced by any technique or obtained from any source deemed suitable by the practitioner of skill. In particular embodiments, the transglutaminase is obtained from a commercial source.

In certain embodiments, the glutaminyl-modified antibody is reacted or treated with a reactive linker-payload to form an antibody-linker-payload conjugate. The reaction can proceed under conditions deemed suitable by those of skill in the art. In certain embodiments, the glutaminyl-modified antibody is contacted with the reactive linker-payload compound under conditions suitable for forming a bond between the glutaminyl-modified antibody and the linker-payload compound. Suitable reaction conditions are well known to those in the art.

Pharmaceutical Compositions and Methods of Treatment

Provided herein are methods of treating and preventing diseases, conditions, or disorders comprising administering a therapeutically or prophylactically effective amount or one or more of the compounds disclosed herein, for example, one or more of the compounds of a formula provided herein. Diseases, disorders, and/or conditions include, but are not limited to, those associated with viral infections as described herein.

The compounds described herein can be administered alone or together with one or more additional (supplementary) therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: an anti-viral drug such as a second antiviral compound or payload, an autoimmune therapeutic agent, a hormone, a biologic, or a monoclonal antibody. In some embodiments, the supplementary therapeutic agent can be selected from the group consisting of: an anti-viral drug, an anti-inflammatory drug (e.g., a corticosteroid or non-steroidal anti-inflammatory drug), an antibody that binds specifically to influenza HA, a vaccine for influenza, a dietary supplement (e.g., and anti-oxidant), and a palliative therapy to treat an influenza infection. In one embodiment, the anti-inflammatory drug is selected from the group consisting of corticosteroids and non-steroidal anti-inflammatory drugs. In one embodiment, the dietary supplement is an anti-oxidant. Suitable therapeutic agents also include, but are not limited to, any pharmaceutically acceptable salts or derivatives of an antiviral compound or payload set forth herein. In some embodiments, the supplementary therapeutic agent is administered via a different route of administration as an antibody-drug conjugate, compound, or pharmaceutical composition described herein. For example, a supplementary therapeutic agent can be administered orally. An exemplary anti-viral drug to be administered as a supplementary therapeutic agent is oseltamivir. In some embodiments, the oseltamivir is administered prior to administration of the antibody-drug conjugate, compound, or pharmaceutical composition. In some embodiments, the oseltamivir is administered concurrently with the antibody-drug conjugate, compound, or pharmaceutical composition. In some embodiments, the oseltamivir is administered after administration of the antibody-drug conjugate, compound, or pharmaceutical composition. In some embodiments, the anti-viral drug is an anti-influenza A drug or an anti-influenza B drug (e.g., an antibody or antigen-binding portion thereof), such as an antibody that binds specifically to influenza A HA or an antibody that binds specifically to influenza B HA.

In some embodiments of the methods described herein, multiple doses of a compound described herein (or a pharmaceutical composition comprising a combination of a compound described herein and any of the additional therapeutic agents mentioned herein) may be administered to a subject over a defined time course. The methods according to this embodiment of the disclosure comprise sequentially administering to a subject multiple doses of a compound described herein. The present disclosure includes methods which comprise sequentially administering to the patient a single initial dose of a compound described herein, followed by one or more secondary doses of the compound, and optionally followed by one or more tertiary doses of the compound. Exemplary doses of a compound of the present disclosure include, but are not limited to, 50 mg/kg, 49 mg/kg, 48 mg/kg, 47 mg/kg, 46 mg/kg, 45 mg/kg, 44 mg/kg, 43 mg/kg, 42 mg/kg, 41 mg/kg, 40 mg/kg, 39 mg/kg, 38 mg/kg, 37 mg/kg, 36 mg/kg, 35 mg/kg, 34 mg/kg, 33 mg/kg, 32 mg/kg, 31 mg/kg, 30 mg/kg, 29 mg/kg, 28 mg/kg, 27 mg/kg, 26 mg/kg, 25 mg/kg, 24 mg/kg, 23 mg/kg, 22 mg/kg, 21 mg/kg, 20 mg/kg, 19 mg/kg, 18 mg/kg, 17 mg/kg, 16 mg/kg, 15 mg/kg, 14 mg/kg, 13 mg/kg, 12 mg/kg, 11 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, 0.1 mg/kg, and 0.05 mg/kg.

In certain embodiments, the amount of the compound included in the initial, secondary, and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose.

The methods according to this embodiment of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this embodiment of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., antibody-drug conjugates of the compounds Formulae I and II, e.g., compositions comprising a compound described herein, a salt, stereoisomer, regioisomer, polymorph thereof, and a pharmaceutically acceptable carrier, diluent, and/or excipient. Examples of suitable carriers, diluents and excipients include, but are not limited to, buffers for maintenance of proper composition pH (e.g., citrate buffers, succinate buffers, acetate buffers, phosphate buffers, lactate buffers, oxalate buffers, and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

In certain embodiments, the compounds or payloads, linker-payloads, ADCs, or compositions thereof may be provided via alternate routes of administration. In certain embodiments, the route of administration for the composition(s) is selected from the group of subcutaneous, intradermal, intramuscular, oral, intravenous, intraperitoneal, inhalation, and intranasal. In one embodiment, the route of administration for the composition(s) is oral. In one embodiment, the route of administration for the composition(s) is intravenous. In one embodiment, the route of administration for the composition(s) is intraperitoneal. In one embodiment, the route of administration for the composition(s) is inhalation. In one embodiment, the route of administration for the composition(s) is intranasal.

In some examples, set forth herein methods for treatment, prophylaxis, reduction, or inhibition of a disease, disorder, or condition associated with an infection in a subject comprising administering to the subject an effective amount or a therapeutically effective amount of a compound of Formulae I and/or II, a linker-payload described herein, and/or an ADC described herein, combinations thereof, or a pharmaceutical composition thereof. In some embodiments, the infection is a viral infection. In some embodiments, the infection is influenza virus infection. In some embodiments, the infection is influenza A virus infection. In some embodiments, the infection is influenza B virus. In some embodiments, the infection is influenza A virus infection and influenza B virus infection. In certain embodiments, side effects associated with administration of an unconjugated payload to the subject are reduced when compared to administration of the conjugated payload or ADC to a comparable subject.

The compounds disclosed herein can also be used for treatment, prophylaxis, reduction, or inhibition of an influenza infection in a subject comprising administering to the subject an effective amount of an antibody-drug conjugate, compound, or pharmaceutical composition described herein. In some embodiments, the influenza infection is caused by influenza A virus infection. In some embodiments, the influenza infection is caused by influenza A Group 1 virus. In some embodiments, the influenza infection is caused by influenza A H1 virus. In some embodiments, the influenza infection is caused by influenza A Group 2 virus. In some embodiments, the influenza infection is caused by influenza A H3 virus. In some embodiments, the influenza infection is caused by an unknown or undetermined influenza virus. In some embodiments, the influenza infection is caused by influenza B virus infection. In some embodiments, the influenza infection is caused by influenza A virus infection and influenza B virus infection. In some embodiments, the influenza infection is caused by influenza A virus infection, influenza A Group 1 infection, influenza A H1 infection, influenza A Group 2 infection, influenza A H3 infection, an unknown or undetermined influenza virus, influenza B virus infection, or any combination thereof.

EXAMPLES

Provided herein are VX-787 and derivatives thereof, baloxavir and derivatives thereof, baloxavir marboxil and derivatives thereof, protein conjugates thereof, and methods for treating diseases, disorders, and conditions including administering VX-787, baloxavir, and baloxavir marboxil and conjugates thereof.

Example 1: Linker-Payload Synthesis

VX-787 and baloxavir were used as payloads for delivery by an anti-hemagglutinin antibody. To test the effects of different linkers in combination with VX-787 or baloxavir, linker-payloads were synthesized as indicated below (linker-(VX-787)): Compound 6 and Compound 11; linker-baloxavir: Compound 15). All the solvents used were used as is and purchased either from Sigma Aldrich or Fisher Scientific. $^1$H spectra were recorded on Varian Inova 300 MHz and 500 MHz NMR instruments. The chemical shifts (δ) were reported in ppm with respect to the NMR solvents used for analysis and were reported as s—singlet, d—doublet, t—triplet, q—quartet, dd—doublet of doublets, dt—doublet of triplets, dq—doublet of quartets, and m—multiplet. Coupling constants (J) were reported in hertz (Hz). Chromatographic purities were determined on an Agilent 1100, 1260 Infinity with 6130 Quadrupole LC/MS, or 1200 Series LC/MS systems using Chromolith® FastGradient RP-18e analytical columns (50×2 mm, Merck KGaA, P/N 1.52007.0001) and the following analytical HPLC method: injection volume 2-10 μL; flow rate 1 mL/min; 5-95% acetonitrile in water over 4 min; Agilent diode array detector at λ=254 nm; room temperature. Low resolution mass spectrometry was performed on Agilent systems using electrospray ionization sources and analyzed with either single quadrupole or ion trap mass detectors.

Compound 6 was synthesized from VX-787 as described below in Scheme 1.
Scheme 1
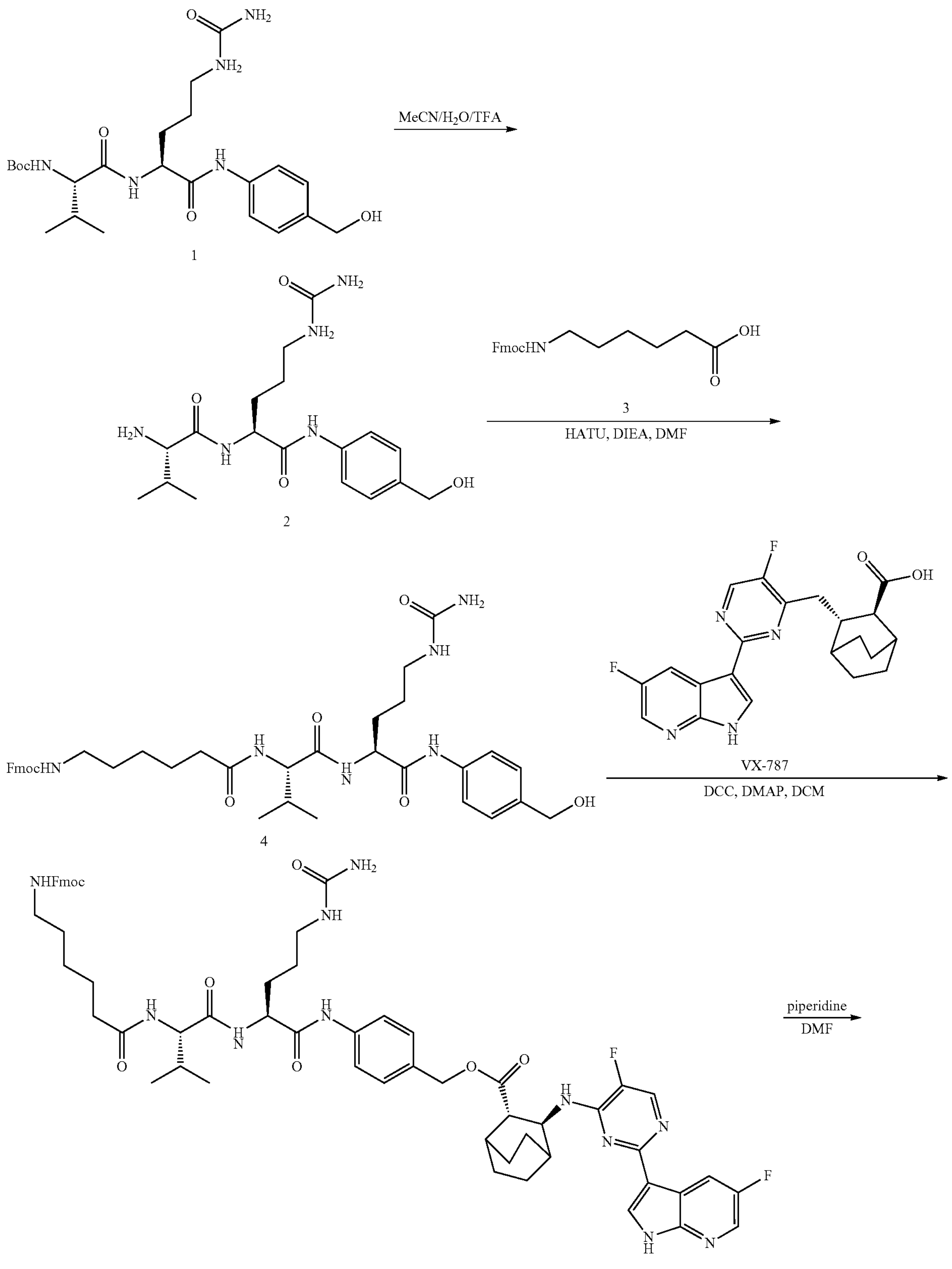
1
2
3
4
5

-continued

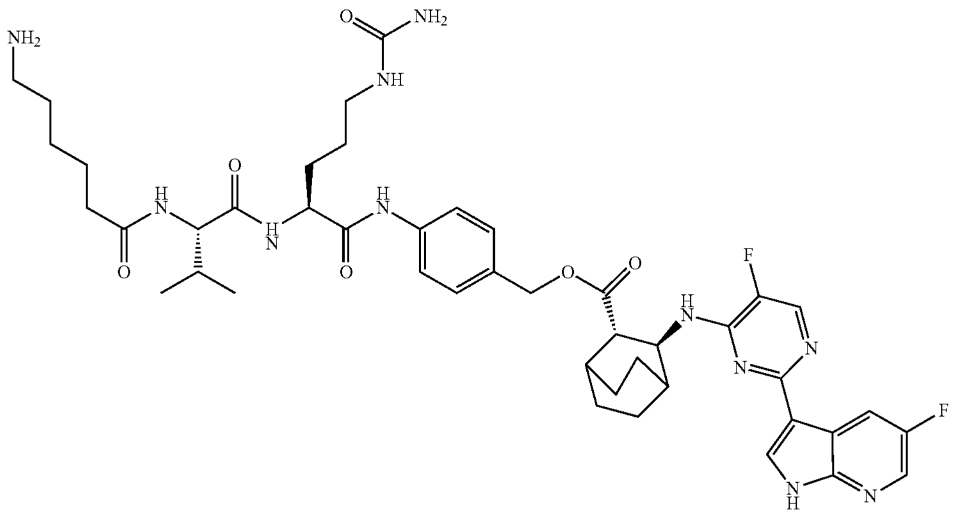

6

Compound 2: Compound 2 was prepared using PCT Int. Appl., 2014145090. tert-butyl ((S)-1-(((5)-1-((4-(hydroxymethyl)phenyl)amino)-1-oxo-5-ureidopentan-2-yl) amino)-3-methyl-1-oxobutan-2-yl)carbamate 1 (700 mg, 1.46 mmol) was dissolved in a mixture of $CH_3CN/H_2O/TFA$ (3:1:1=v/v/v, 6 mL/2 mL/2 mL). The reaction mixture was stirred at room temperature for 19 h, and monitored by LCMS. After concentration in vacuo, the crude product 2 (0.5 g salt) was used directly in the next step without further purification. MS (ESI, pos.): calculated for $C_{18}H_{29}N_5O_4$, 379.2; found 380.2 (M+H).

Compound 4: Compound 2 (100 mg, 0.263 mmol), 6-(Fmoc-amino) caprioic acid 3 (93 mg, 0.263 mmol), 1-[Bis(dimethylamino)methylene]-1H-1,2,3-triazolo[4,5-b] pyridinium 3-oxid hexafluorophosphate (HATU, 200 mg, 0.526 mmol), and 1-Hydroxy-7-azabenzotriazole (HOAt, 35 mg, 0.263 mmol) was charged to an oven-dried 2 dram vial. Anhydrous DMF (2 mL) was then added and the reaction mixture was aged for 5 min at ambient temperature, followed by dropwise addition of N,N-diisopropylethylamine (DIEA, 137 μL, 0.789 mmol) via syringe. The homogeneous yellow solution was stirred for 2 h at room temperature under nitrogen and the reaction was monitored by LC/MS for completion. The reaction mixture was purified on a 50 g C18 Aq Gold column (gradient elution: 10-95% MeCN in water, both having 0.05% acetic acid) for 20 min. The pure fractions were combined, frozen on dry ice, and lyophilized giving the title compound 4 as a white solid (120 mg, 65%). MS: calc'd for $C_{39}H_{50}N_6O_7$, 714.3; found 715.3 (M+H), 737.3 (M+Na).

Compound 5: Compound 4 (39.4 mg, 0.055 mmol) and 4-dimethylaminopyridine (DMAP, 5 mg, 0.039 mmol) were added to a stirring suspension under argon of VX-787 (22 mg, 0.055 mmol) in anhydrous THF (6 mL) at room temperature. Then a solution of N,N'-dicyclohexylcarbodiimide (DCC, 17 mg, 0.083 mmol) in anhydrous THF (2 mL) was added to the reaction mixture dropwise. After stirring for 16 h, the mixture was evaporated to dryness and the residue was dissolved in 3 mL of DMSO. The crude material was purified on a 50 g C18 Aq Gold column (gradient elution: 10-95% MeCN in water, 0.05% AcOH in both). The product fractions were combined, frozen on dry ice, and lyophilized giving the title compound 5 as a white solid (38 mg, 63%). MS (ESI, pos.): calc'd for $C_{59}H_{67}F_2N_{11}O_8$, 1095.5; found 1096.4 (M+H).

Compound 6: 5% piperidine (0.8 mL) in DMF was added to a stirred solution of compound 5 (33 mg, 0.0301 mmol) in N,N-dimethylformamide (DMF, 1 mL) under argon at ambient temperature for 30 min, and the resulting solution was stirred. LC/MS confirmed the completion of the reaction. The reaction was purified directly on a 30 g C18 Aq. Gold column via ISCO system (gradient elution: 10-95% MeCN in water, 0.05% acetic acid in both, over 30 min). The product-containing fractions were combined, frozen on dry ice, and lyophilized overnight giving the title compound 6 as an off-white solid (22 mg, 85%). MS: calc'd for $C_{44}H_{57}F_2N_{11}O_6$, 873.4; found 874.4 (M+H). $^1$H-NMR (500 MHz; DMSO-$d_6$): δ 9.97 (s, 1H), 8.50 (dd, J=9.8, 2.8 Hz, 1H), 8.28 (dd, J=2.5, 1.2 Hz, 1H), 8.20 (s, 1H), 8.16 (d, J=3.9 Hz, 1H), 8.11-8.09 (m, 1H), 7.84 (dd, J=1.6, 0.9 Hz, 1H), 7.62 (d, J=6.9 Hz, 1H), 7.54 (d, J=8.5 Hz, 2H), 7.23 (d, J=8.5 Hz, 2H), 6.02-6.00 (m, 1H), 5.43 (d, J=0.3 Hz, 2H), 5.09 (d, J=12.5 Hz, 1H), 5.00 (d, J=12.5 Hz, 1H), 4.77-4.74 (m, 1H), 4.38-4.36 (m, 1H), 4.19 (dd, J=8.5, 7.2 Hz, 1H), 3.03-2.94 (m, 4H), 2.17 (d, J=11.5 Hz, 2H), 1.99-1.95 (m, 3H), 1.85 (s, 2H), 1.81-1.78 (m, 2H), 1.73-1.71 (m, 4H), 1.50-1.47 (m, 8H), 1.39-1.34 (m, 4H), 1.26-1.23 (m, 2H), 0.85 (dd, J=12.7, 6.8 Hz, 6H).

Compound 11 was synthesized from VX-787 as described below in Scheme 2.
Scheme 2
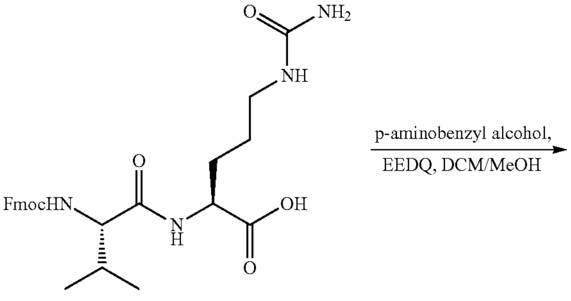
7
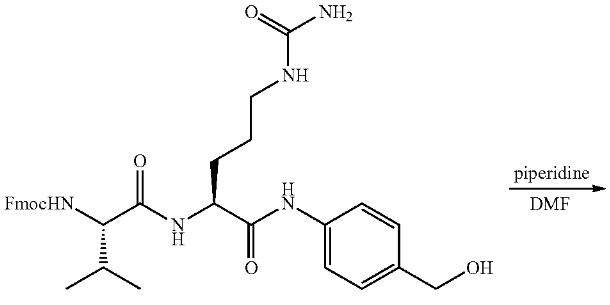
8
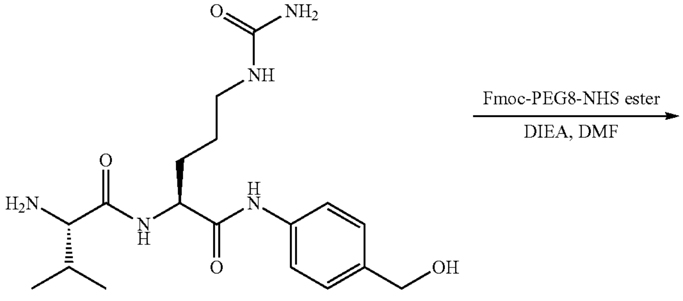
2
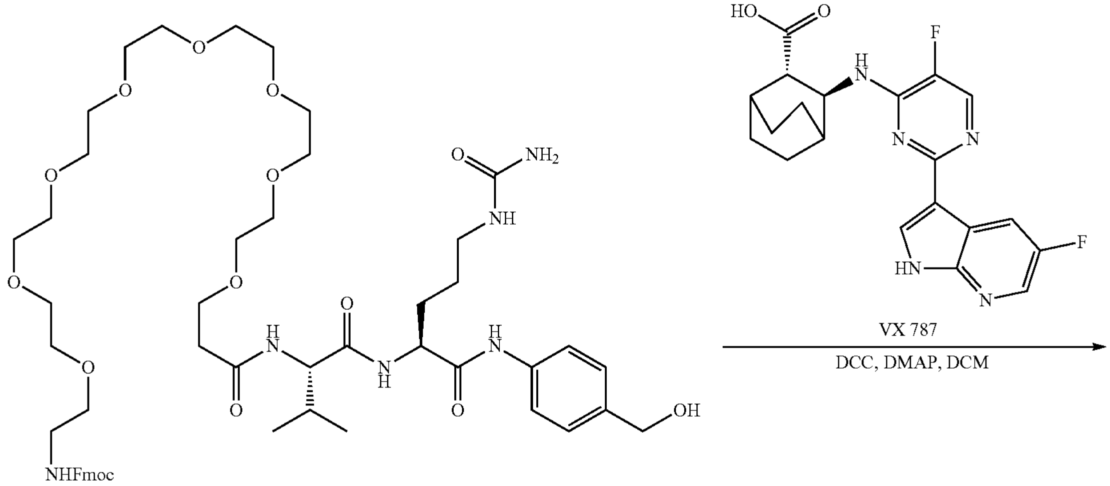
9

-continued

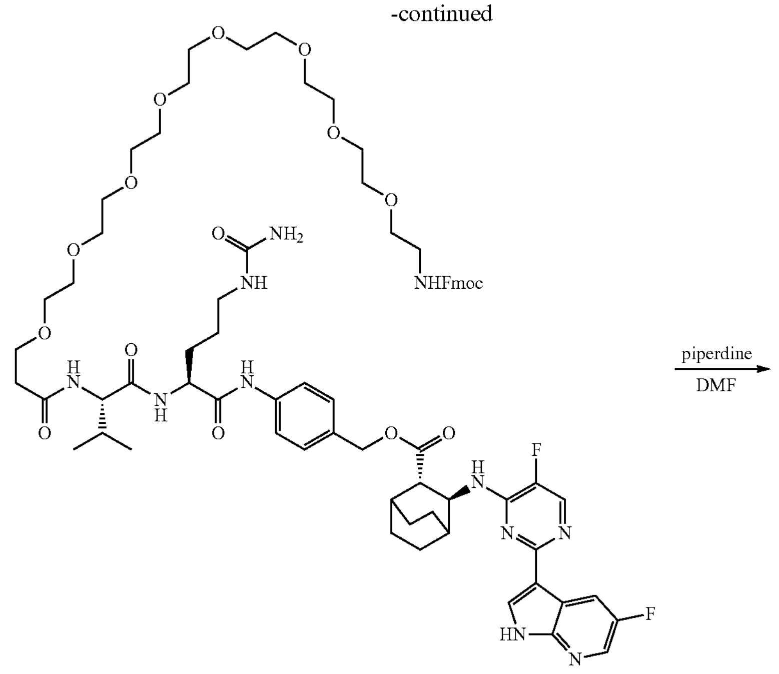

10

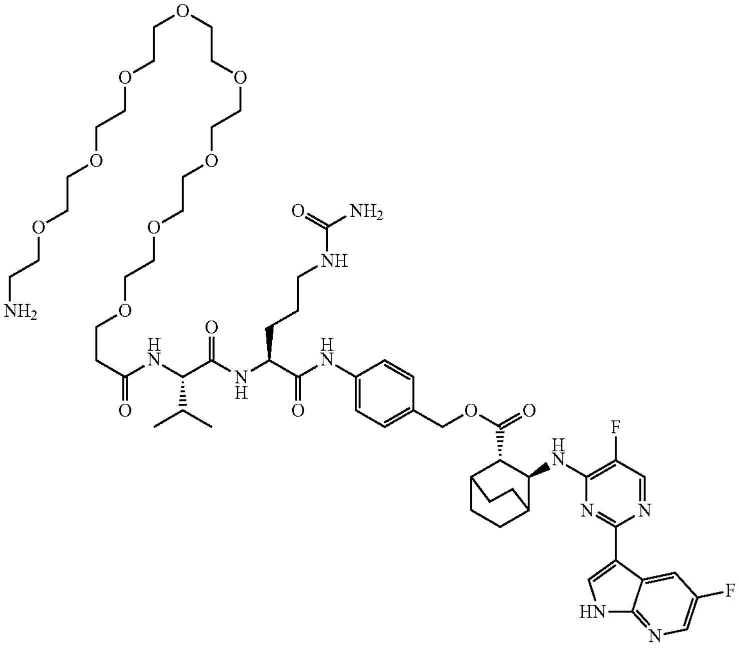

11

Compound 8: N-Ethoxycarbonyl-2-ethoxy-1,2-dihydroquinoline (EEDQ, 1.99 g, 8.05 mmol) was added to a solution of p-aminobenzyl alcohol (0.99 g, 8.05 mmol) in dichloromethane (19 mL) and methanol (7.6 mL) at room temperature. After stirring for 5 min, Fmoc-Valine-Citrulline 7 (2.0 g, 4.03 mmol) was added in one portion and the resulting solution was stirred for 18 hours. Volatiles were removed in vacuo and the residue was triturated with ether (20 mL) and washed sequentially with ether (20 mL), ethyl acetate (20 mL), and ether (20 mL) to get title compound 8 (2.2 g, 98% yield) as a light yellowish solid. MS (ESI, pos.): calc'd for $C_{33}H_{39}N_5O_6$, 601.29; found 602.3 (M+H).

Compound 2: In a 20 mL vial, Fmoc-Valine-Citrulline-PAB(OH) 8 (2.0 g, 3.33 mmol) was dissolved in 5% piperidine in DMF (10 mL) and stirred for an hour at room temperature. Precipitates were removed by filtration and the filtrate was purified on 100 g C18 Aq column using gradient elution 5-95% MeCN/$H_2O$ (both having 0.05% TFA). Pure fractions were combined, frozen, and lyophilized. Purification was repeated on the lyophilized solid to get title compound 2 (0.98 g, 61% yield) as a fluffy off-white solid. MS (ESI, pos.): calc'd for $C_{18}H_{29}N_5O_4$, 379.22; found 380.2 (M+H).

Compound 9: DIEA (40 μL, 0.22 mmol) was added to a solution of valine-citrulline-PAB(OH)*TFA salt 2 (100 mg, 0.2 mmol) and Fmoc-PEG8-NHS ester (167 mg, 0.22 mmol) in anhydrous DMF (2 mL), and stirred for 45 min. The reaction was monitored by LC/MS, and was purified on 100 g C18 Aq column using gradient elution 5-95% MeCN/$H_2O$ (both having 0.05% AcOH). Pure fractions were combined, frozen, and lyophilized to get title compound 8 (145 mg, 71%) as fluffy off-white solid. MS (ESI, pos.): calc'd for $C_{52}H_{76}N_6O_{15}$, 1024.54; found 1025.5 (M+H).

Compound 10: A room temperature solution of DCC (18.6 mg, 0.09 mmol) in dichloromethane (3 mL) was added dropwise to a suspension of Fmoc-PEG8-valine-citrulline-PAB(OH) 9 (61.8 mg, 0.06 mmol), VX-787 (24 mg, 0.06 mmol) and DMAP (7.2 mg, 0.06 mmol) in anhydrous dichloromethane (12 mL) at room temperature, and stirred for 16 h. Volatiles were removed in vacuo and the residue was purified on 50 g C18 Aq column using gradient elution 5-95% MeCN/$H_2O$ (both having 0.05% AcOH). Pure fractions were combined, frozen, and lyophilized to yield title compound 10 as fluffy off-white solid (50 mg, 51% yield). MS (ESI, pos.): calc'd for $C_{72}H_{93}F_2N_{11}O_{16}$, 1405.68; found 1406.6 (M+H).

Compound 11: 5% piperidine in DMF (0.8 mL) was added to a solution of compound 10 (50 mg, 0.035 mmol) in anhydrous DMF (1.6 mL) and stirred for 40 min before purification on a 50 g C18 Aq column using gradient elution 5-95% MeCN/$H_2O$ (both having 0.05% AcOH). Pure fractions were combined, frozen, and lyophilized to get title compound 11 (43 mg, 95% yield) as fluffy off-white solid. MS (ESI, pos.): calc'd for $C_{57}H_{83}F_2N_{11}O_{14}$, 1183.61; found 1184.6 (M+H). $^1$H-NMR (500 MHz; DMSO-$d_6$): δ 9.95 (s, 1H), 8.48 (dd, J=9.6, 2.1 Hz, 1H), 8.27 (s, 1H), 8.19 (s, 1H), 8.15 (d, J=3.6 Hz, 1H), 8.10 (d, J=7.9 Hz, 1H), 7.86 (d, J=8.3 Hz, 1H), 7.60 (dd, J=6.7, 0.5 Hz, 1H), 7.52 (d, J=8.3 Hz, 2H), 7.22 (d, J=8.4 Hz, 2H), 5.97 (t, J=4.8 Hz, 1H), 5.40 (s, 2H), 5.08 (d, J=12.7 Hz, 1H), 4.99 (d, J=12.5 Hz, 1H), 4.75 (t, J=6.1 Hz, 1H), 4.36 (q, J=6.7 Hz, 1H), 4.22 (t, J=7.9 Hz, 1H), δ 3.59 (q, J=5.6 Hz, 2H), 3.5 (s, 30H), 3.35 (t, J=5.7 Hz, 3H), 3.01-3.00 (m, 1H), 2.96-2.92 (m, 2H), 2.64 (dt, J=9.4, 4.4 Hz, 2H), 2.39-2.35 (m, 1H), 1.97-1.94 (m, 2H), 1.88 (s, 1H), 1.81-1.57 (m, 6H), 1.50-1.35 (m, 6H), 0.84 (dd, J=15.4, 6.7 Hz, 6H).

Synthesis of Compound 15 from (R)-12-((S)-7,8-difluoro-6,11-dihydrodibenzo[b,e]thiepin-11-yl)-7-hydroxy-3,4,12,12a-tetrahydro-1H-[1,4]oxazino[3,4-c]pyrido[2,1-f][1,2,4]triazine-6,8-dione 13 is described in scheme 3 below Scheme 3

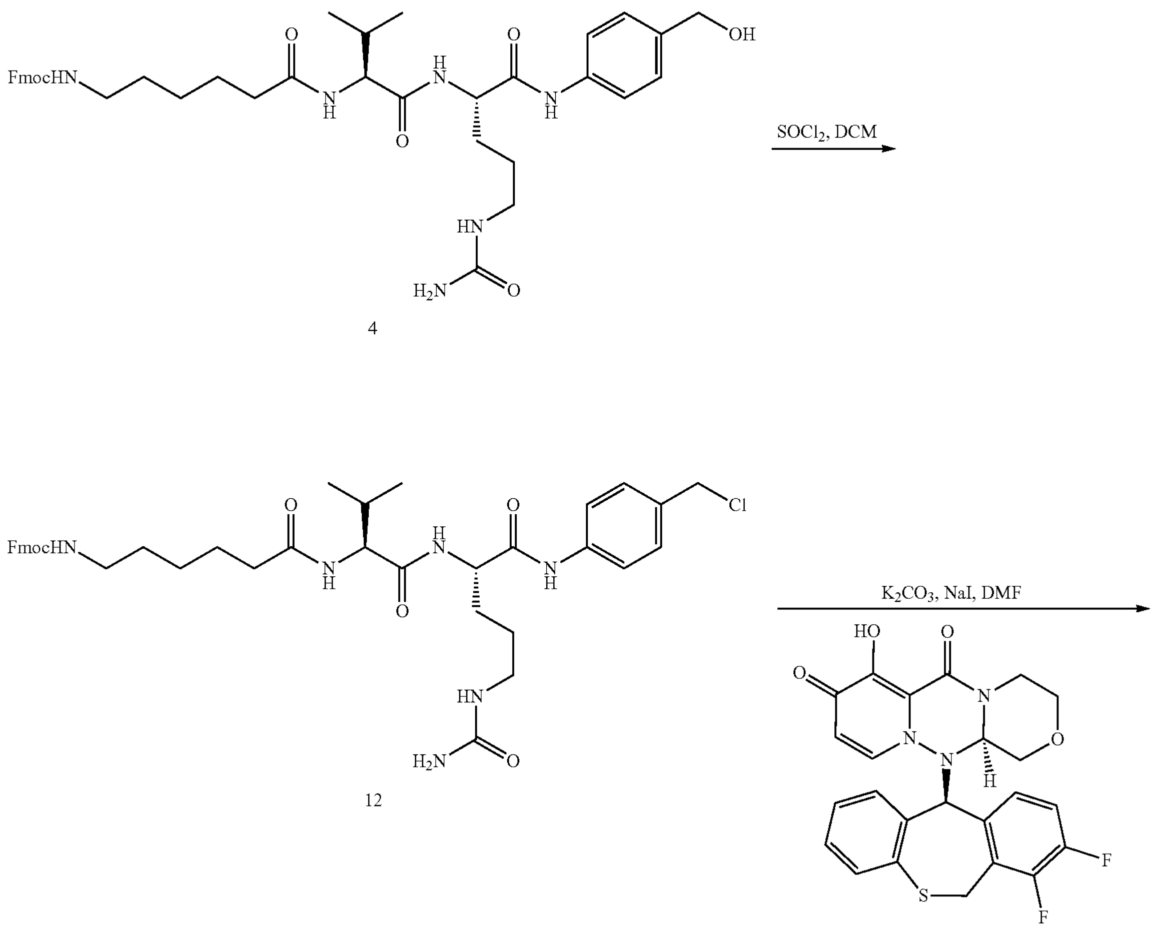

4

12

13

-continued

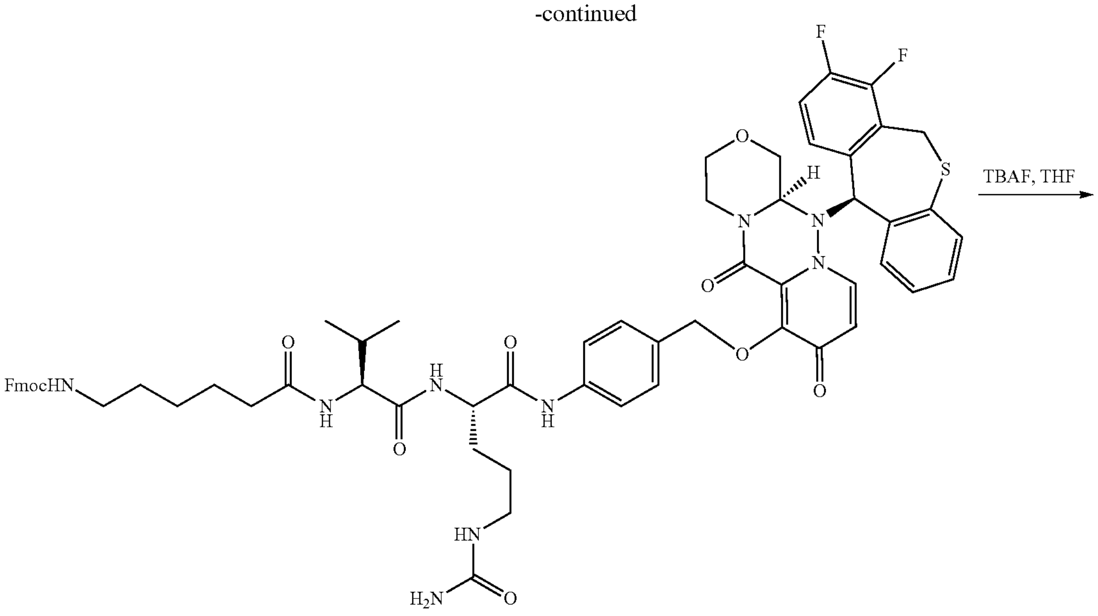

14

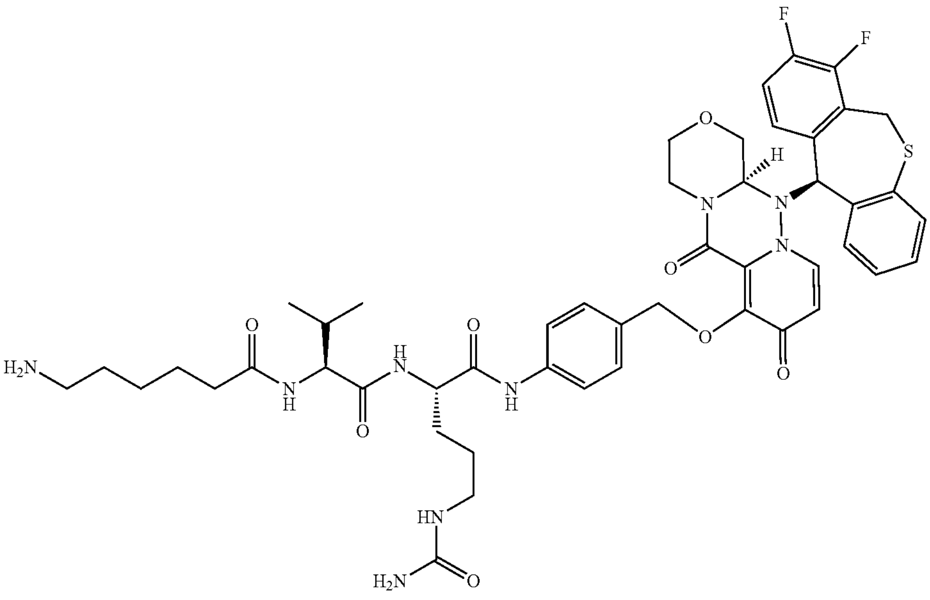

15

Compound 12: Thionyl chloride (11.8 mg, 0.1 mmol) was added to a stirred solution of Fmoc-Cap-valine-citrulline-PAB(OH) 4 (61.2 mg, 0.086 mmol) in an anhydrous dichloromethane (1 mL), at room temperature, and stirred for 1 h. After the starting material was consumed, volatiles were removed in vacuo and the residue was purified on a 30 g C18 Aq column using gradient elution 5-95% $MeCN/H_2O$ (both having 0.05% AcOH). Pure fractions were combined, frozen, and lyophilized to yield title compound 12 as a fluffy off-white solid (38 mg, 60% yield). MS (ESI, pos.): calc'd for $C_{39}H_{49}ClN_6O_6$, 732.3; found 733.3 (M+H).

Compound 14: $K_2CO_3$ (28 mg, 0.20 mmol) and NaI (6 mg, 0.041 mmol) were added to a DMF solution (1 ml) of (R)-12-((S)-7,8-difluoro-6,11-dihydrodibenzo[b,e]thiepin-11-yl)-7-hydroxy-3,4,12,12a-tetrahydro-1H-[1,4]oxazino[3,4-c]pyrido[2,1-f][1,2,4]triazine-6,8-dione 13 (20 mg, 0.041 mmol) and Fmoc-Cap-valine-citrulline-PAB-Cl (40 mg, 0.052 mmol), and the mixture was heated to 65° C. for 40 minutes. The reaction was cooled to room temperature and purified on a 30 g C18 Aq column using 5-60% $MeCN/H_2O$ (both having 0.05% acetic acid). Pure fractions were combined, frozen, and lyophilized to yield title compound 14 as a fluffy off-white solid (40 mg, 83% yield). MS (ESI, pos.): calc'd for $C_{63}H_{67}F_2N_9O_{10}S$, 1179.5; found 1180.3 (M+H).

Compound 15: A 1 M solution of TBAF in THE (21 μL, 0.021 mmol) was added dropwise to a THE (1.5 mL) solution of compound 14 (25 mg, 0.021 mmol), and stirred for 1.5 h at room temperature. Volatiles were removed in vacuo and the residue was purified on a 30 g C18 Aq column using 5-60% $MeCN/H_2O$ (both having 0.05% acetic acid). Pure fractions were combined, frozen, and lyophilized to get title compound 15 (14 mg, 70%) as a fluffy off-white solid.

MS (ESI, pos.): calc'd for $C_{48}H_{57}F_2N_9O_8S$, 957.4; found 958.3 (M+H). $^1$H-NMR (500 MHz; DMSOd$_6$): δ 10.04 (s, 1H), 8.14 (d, J=7.5 Hz, 1H), 7.85 (d, J=8.0 Hz, 1H), 7.61 (d, J=8.5 Hz, 2H), 7.48 (d, J=8.5 Hz, 2H), 7.41 (d, J=6.6 Hz, 2H), 7.20 (d, J=7.7 Hz, 1H), 7.14-7.12 (t, J=7.5 Hz, 1H), 7.07 (d, J=7.4 Hz, 1H), 6.86 (d, J=7.7 Hz, 1H), 6.75 (t, J=7.0 Hz, 1H), 6.02 (t, J=4.5 Hz, 1H), 5.71 (s, 1H), 5.67 (d, J=7.7 Hz, 1H), 5.46-5.40 (m, 3H), 5.23 (d, J=10.7 Hz, 1H), 5.05 (d, J=10.7 Hz, 1H), 4.47-4.37 (m, 3H), 4.20-4.17 (m, 1H), 4.05 (d, J=14.4 Hz, 1H), 3.96-3.94 (m, 1H), 3.66-3.63 (m, 1H), 3.21-3.15 (m, 2H), 3.03-2.88 (m, 4H), 2.20-2.09 (m, 2H), 2.00-1.96 (m, 1H), 1.72 (s, 3H), 1.62-1.54 (m, 3H), 1.51-1.41 (m, 3H), 1.38-1.27 (m, 5H), 1.26-1.21 (m, 3H), 0.94 (t, J=7.4 Hz, 2H), 0.84 (dd, J=14.1, 6.7 Hz, 6H).

Synthesis of Compound 18 from (R)-12-((S)-7,8-difluoro-6,11-dihydrodibenzo[b,e]thiepin-11-yl)-7-hydroxy-3,4,12,12a-tetrahydro-1H-[1,4]oxazino[3,4-c]pyrido[2,1-f][1,2,4]triazine-6,8-dione (13) is described in Scheme 4 below Scheme 4

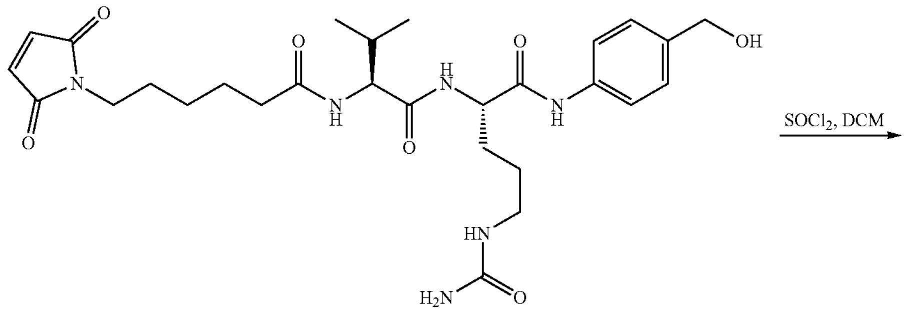

16

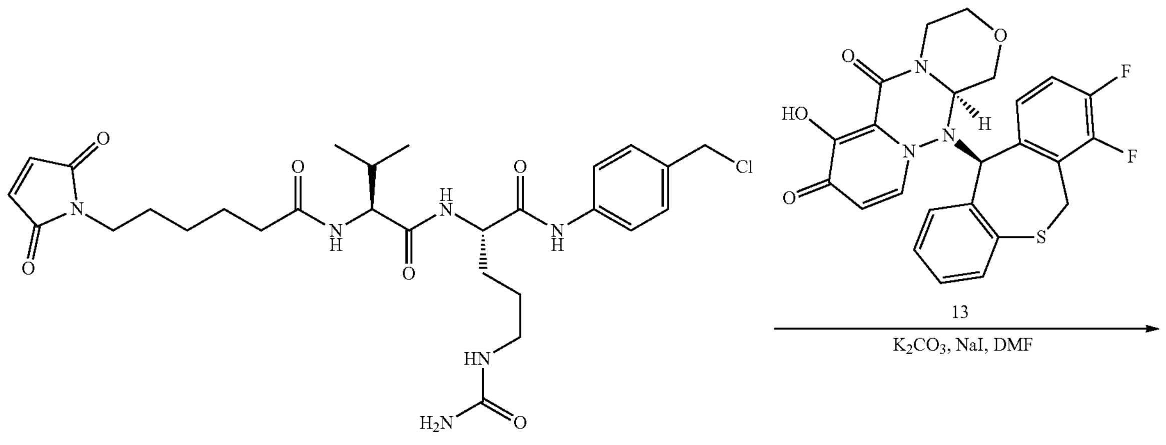

17

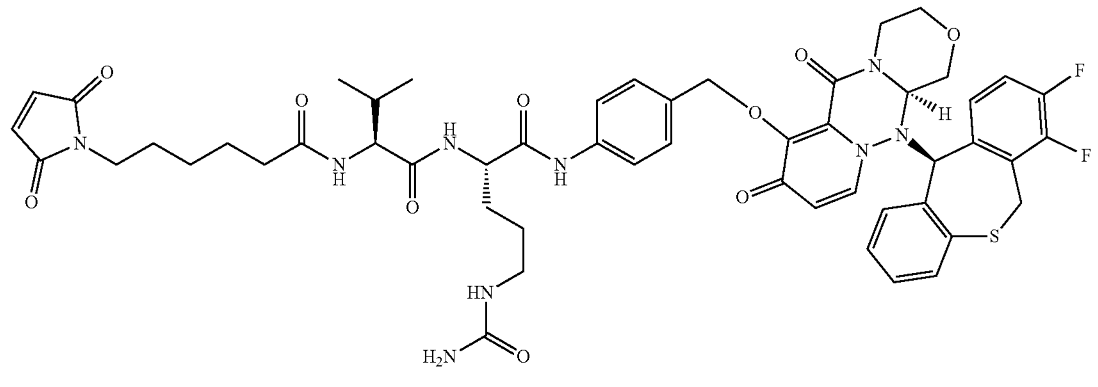

18

Compound 17: Thionyl chloride (9 μL, 0.122 mmol) was added to a suspension of Mal-cap-Val-Cit-PAB-OH (16) (35 mg, 0.061 mmol) in anhydrous DCM (3 mL), and the reaction was stirred at room temp for 1 h. The reaction was concentrated in vacuo and azeotropically dried with toluene (4 mL), then used in the next step without further purification. MS (ESI, pos.): calc'd for $C_{26}H_{39}ClN_6O_6$, 590.3; found 591.3 M+H).

Compound 18: $K_2CO_3$ (41.5 mg, 0.3 mmol) and sodium iodide (9 mg, 0.06 mmol) were added to a solution of (R)-12-((S)-7,8-difluoro-6,11-dihydrodibenzo[b,e]thiepin-11-yl)-7-hydroxy-3,4,12,12a-tetrahydro-1H-[1,4]oxazino[3,4-c]pyrido[2,1-f][1,2,4]triazine-6,8-dione (13) (23 mg, 0.048 mmol) and Mal-cap-Val-Cit-PAB-Cl (17) (35 mg, 0.06 mmol) in DMF (2 mL). The reaction was heated to 60° C. for 1 h, then cooled to room temperature and purified on 30 g C18 Aq column using 5-95% MeCN/$H_2O$ (both having 0.05% AcOH). Pure fractions were combined and lyophilized to afford compound 18 (28 mg, 57%) as a fluffy off-white solid. MS (ESI, pos.): calc'd for $C_{52}H_{57}F_2N_9O_{10}S$, 1037.4; found 1038.3 (M+H). $^1$H-NMR (300 MHz; DMSO-$d_6$): δ 10.00 (s, 1H), 8.08 (d, J=7.7 Hz, 1H), 7.80 (d, J=8.7 Hz, 1H), 7.61 (d, J=8.6 Hz, 2H), 7.49 (d, J=8.6 Hz, 2H), 7.43-7.39 (m, 2H), 7.21 (d, J=7.8 Hz, 1H), 7.13-7.06 (m, 2H), 7.01 (s, 2H), 6.87 (dd, J=7.8, 1.0 Hz, 1H), 6.76 (td, J=7.2, 1.5 Hz, 1H), 5.97 (t, J=5.6 Hz, 1H), 5.72 (s, 1H), 5.68 (d, J=7.7 Hz, 1H), 5.45-5.42 (m, 3H), 5.24 (d, J=10.8 Hz, 1H), 5.06 (d, J=10.8 Hz, 1H), 4.49-4.39 (m, 3H), 4.20 (dd, J=8.5, 6.8 Hz, 1H), 4.06 (d, J=14.3 Hz, 1H), 3.96 (dd, J=10.7, 2.5 Hz, 1H), 3.66 (dd, J=11.3, 2.6 Hz, 1H), 3.04-2.89 (m, 3H), 2.15 (dt, J=10.1, 7.3 Hz, 2H), 1.97 (q, J=6.8 Hz, 1H), 1.70-1.58 (m, 2H), 1.53-1.44 (m, 5H), 1.22 (m, 3H), 0.87-0.81 (m, 6H).

Synthesis of Compound 23 from (R)-12-((S)-7,8-difluoro-6,11-dihydrodibenzo[b,e]thiepin-11-yl)-7-hydroxy-3,4,12,12a-tetrahydro-1H-[1,4]oxazino[3,4-c]pyrido[2,1-f][1,2,4]triazine-6,8-dione (13) is shown in Scheme 5 below Scheme 5

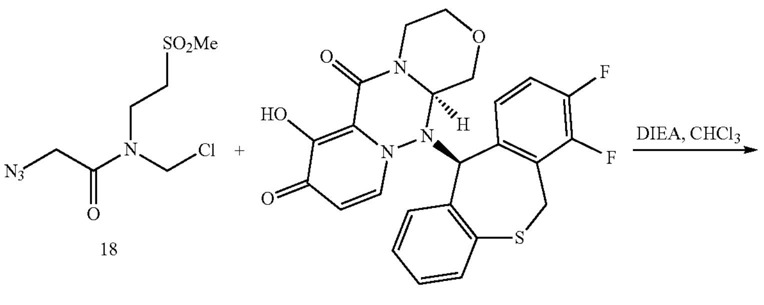

18

13

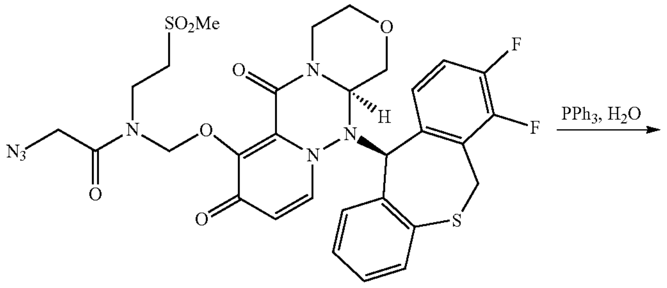

20

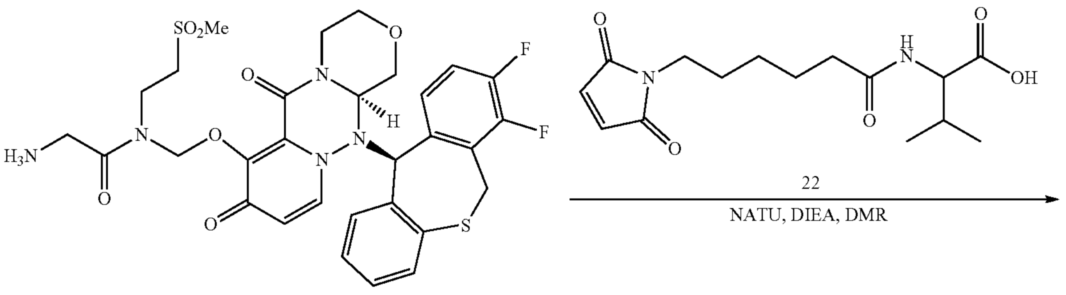

22

21

-continued

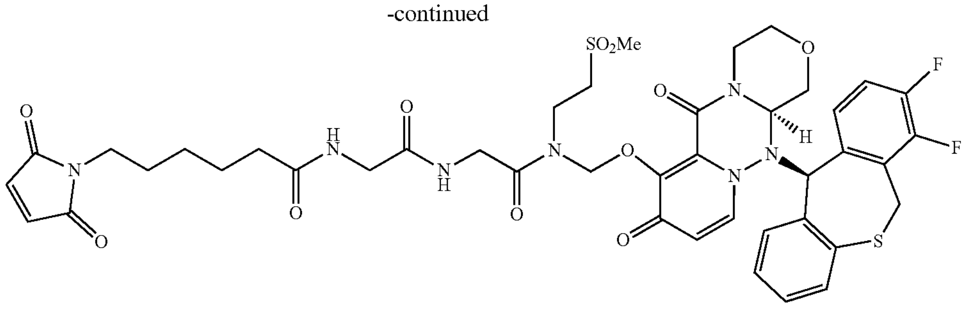

23

Compound 20: DIEA (41 μL, 0.236 mmol) was added to a chloroform (0.5 mL) solution of (R)-12-((S)-7,8-difluoro-6,11-dihydrodibenzo[b,e]thiepin-11-yl)-7-hydroxy-3,4,12,12a-tetrahydro-1H-[1,4]oxazino[3,4-c]pyrido[2,1-f][1,2,4]triazine-6,8-dione (13) (30 mg, 0.044 mmol) and compound 19 (28.5 mg, 0.059 mmol). The reaction was stirred at room temperature for 0.5 h, then was purified on 4 g silica gold column using 0-5% MeOH/DCM to obtain compound 20 (31 mg, 75%) as a colorless solid. MS (ESI, pos.): calc'd for $C_{30}H_{29}F_2N_7O_7S_2$, 701.2; found 702.1 (M+H).

Compound 21: Triphenylphosphine (28.8 mg, 0.11 mmol) was added to a solution of compound 20 (31 mg, 0.044 mmol) in 10:1 THF/$H_2O$ (0.88 mL). After stirring for 24 h at room temperature, the reaction was concentrated to dryness and purified on a 5.5 g C18 Aq column using 5-95% MeCN/$H_2O$ (both having 0.05% AcOH) to obtain compound 21 (20 mg, 68%) as a fluffy off-white solid. MS (ESI, pos.): calc'd for $C_{30}H_{31}F_2N_5O_7S_2$, 675.2; found 676.1 (M+H). Compound 23: HATU (28.5 mg, 0.075 mmol) and DIEA (13 μL, 0.075 mmol) were added to a DMF (1.0 mL) solution of compound 21 (20 mg, 0.030 mmol) and Mal-cap-Val-OH (22) (27.5 mg, 0.089 mmol). After stirring for 1 h, the reaction was purified on 30 g C18 Aq column using 5-95% MeCN/$H_2O$ (both having 0.05% AcOH). Pure fractions were combined and lyophilized to obtain compound 23 (4.5 mg, 16%) as a fluffy off-white solid. MS (ESI, pos.): calc'd for $C_{45}H_{51}F_2N_7O_{11}S_2$, 967.3; found 968.2 (M+H). $^1$H-NMR (500 MHz; acetone-$d_6$): δ 7.63 (d, J=5.0 Hz, 1H), 7.53-7.51 (m, 1H), 7.40 (d, J=7.8 Hz, 1H), 7.32 (dd, J=8.9, 8.5 Hz, 1H), 7.19 (t, J=7.3 Hz, 1H), 7.14 (t, J=7.6 Hz, 2H), 7.07 (d, J=4.6 Hz, 1H), 6.94 (t, J=7.1 Hz, 1H), 6.86 (s, 2H), 5.88 (s, 1H), 5.79 (d, J=7.7 Hz, 1H), 5.67-5.64 (m, 1H), 5.58 (d, J=10.2 Hz, 1H), 5.36 (d, J=10.3 Hz, 1H), 4.70 (dd, J=9.5, 1.8 Hz, 1H), 4.63-4.61 (m, 1H), 4.52 (dd, J=14.5, 5.1 Hz, 2H), 4.42-4.41 (m, 1H), 4.17-4.12 (m, 2H), 4.08-4.06 (m, 2H), 3.71 (t, J=10.2 Hz, 2H), 3.61-3.59 (m, 1H), 3.54-3.42 (m, 5H), 3.05 (s, 3H), 3.02-3.01 (m, 1H), 2.29 (q, J=6.7 Hz, 3H), 2.19 (m, J=6.3 Hz, 1H), 1.67-1.57 (m, 4H), 1.31 (m, 5H), 0.97 (dd, J=14.5, 6.7 Hz, 6H).

Scheme 6

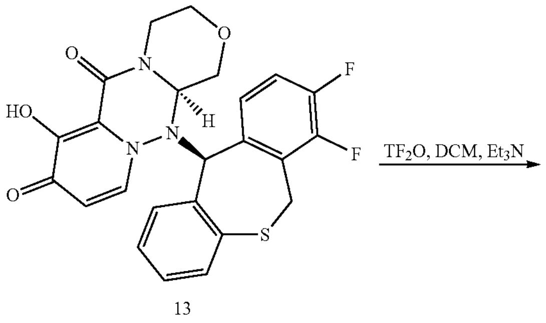

13

-continued

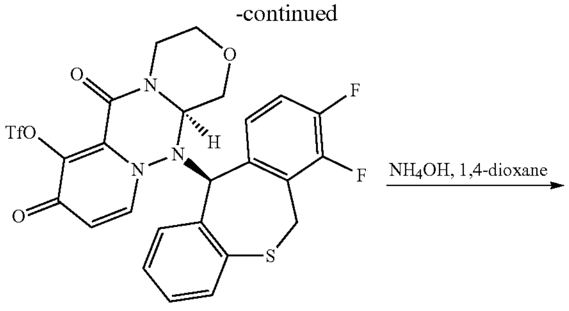

24

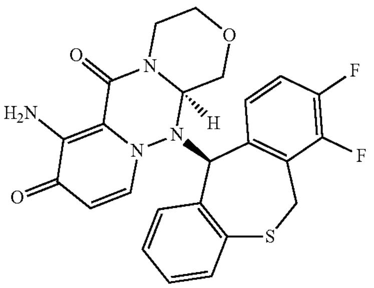

25

Compound 24: Triethylamine (17 μL, 0.12 mmol), triflic anhydride (20 μL, 0.12 mmol) and DMAP (0.7 mg, 0.006 mmol) were added to a DCM (2 mL) solution of (R)-12-((S)-7,8-difluoro-6,11-dihydrodibenzo[b,e]thiepin-11-yl)-7-hydroxy-3,4,12,12a-tetrahydro-1H-[1,4]oxazino[3,4-c]pyrido[2,1-f][1,2,4]triazine-6,8-dione (13) (29 mg, 0.06 mmol) at 0° C. After stirring for 1 h, the reaction was concentrated in vacuo and the residue was purified on 4 g silica gold column using ethyl acetate/hexanes to obtain compound 24 (24 mg, 66%) as a yellowish solid. MS (ESI, pos.): calc'd for $C_{25}H_{18}F_5N_3O_6S_2$, 615.1; found 616.0 (M+H).

Compound 25: A microwave tube was charged with triflate 24 (24 mg, 0.04 mmol) in anhydrous 1,4-dioxane (1 mL) and aqueous ammonium hydroxide (0.4 mL) was added. The reaction was heated to 80° C. for 48 h. Solvents were removed under reduced pressure and the residue was purified on a 15.5 g C18 Aq column using 5-95% MeCN/water (both having 0.05% AcOH). Pure fractions were combined and lyophilized to obtain compound 25 (18.3 mg, 75%) as a fluffy yellowish solid. MS (ESI, pos.): calc'd for $C_{24}H_{20}F_2N_4O_3S$, 482.1 found 483.1 (M+H). $^1$H-NMR (500 MHz; $CDCl_3$): δ 7.82-7.80 (m, 1H), 7.12-7.07 (m, 3H), 7.03-7.00 (m, 2H), 6.82 (td, J=7.1, 2.1 Hz, 1H), 6.70 (d, J=7.3 Hz, 1H), 6.06-6.03 (m, 1H), 5.57 (d, J=7.5 Hz, 1H), 5.38-5.35 (m, 2H), 4.68 (dd, J=13.5, 2.4 Hz, 1H), 4.52 (dd, J=10.0, 3.0 Hz, 1H), 4.07 (d, J=13.8 Hz, 1H), 3.92 (dd, J=11.0, 3.0 Hz, 1H), 3.76 (dd, J=11.7, 3.2 Hz, 1H), 3.55 (t, J=10.5 Hz, 1H), 3.44 (td, J=11.9, 2.6 Hz, 1H), 2.96-2.90 (m, 1H).

Scheme 7

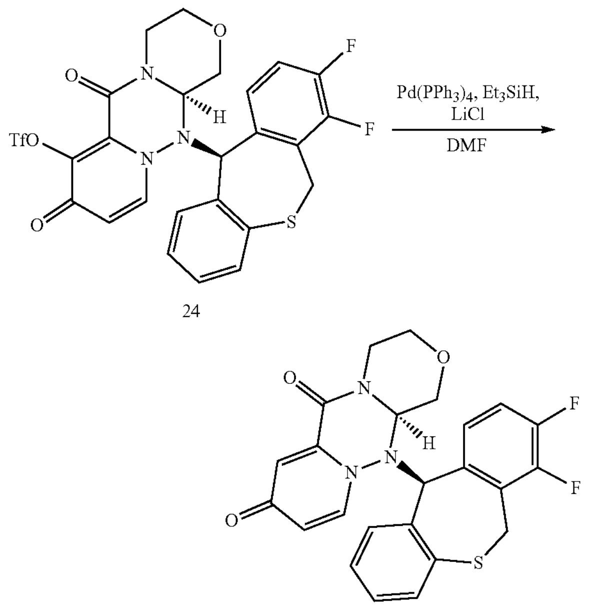

24

26

Compound 26: A vial was charged with triflate 24 (24.4 mg, 0.04 mmol) in anhydrous DMF (1 mL) under argon and LiCl (5.2 mg, 0.12 mmol), $Pd(PPh_3)_4$(2.3 mg, 0.002 mmol), and $Et_3SiH$ (19 μL, 0.12 mmol) were added. The reaction was heated to 65° C. for 2 h. Purification on 15.5 g C18 Aq column using 5-95% $MeCN/H_2O$ (both having 0.05% AcOH) afforded the title compound 26 (4.6 mg, 25%) as a fluffy off-white solid. MS (ESI, pos.): calc'd for $C_{24}H_{19}F_2N_3O_3S$, 467.1; found 468.1 (M+H). $^1$H-NMR (500 MHz; $CDCl_3$): δ 7.30 (d, J=3.1 Hz, 1H), 7.18-7.10 (m, 3H), 7.06 (d, J=7.8 Hz, 1H), 7.02 (dd, J=7.6, 4.5 Hz, 1H), 6.89 (t, J=7.3 Hz, 1H), 6.71-6.69 (m, 1H), 5.83 (dd, J=7.8, 3.0 Hz, 1H), 5.34-5.30 (m, 2H), 4.68 (dd, J=13.5, 2.1 Hz, 1H), 4.62 (dd, J=10.0, 3.0 Hz, 1H), 4.09 (d, J=13.9 Hz, 1H), 3.98 (dd, J=11.0, 2.9 Hz, 1H), 3.81 (dd, J=12.0, 3.2 Hz, 1H), 3.56 (t, J=10.6 Hz, 1H), 3.44 (td, J=11.9, 2.6 Hz, 1H), 3.01 (ddd, J=13.4, 12.0, 3.4 Hz, 1H).

Scheme 8

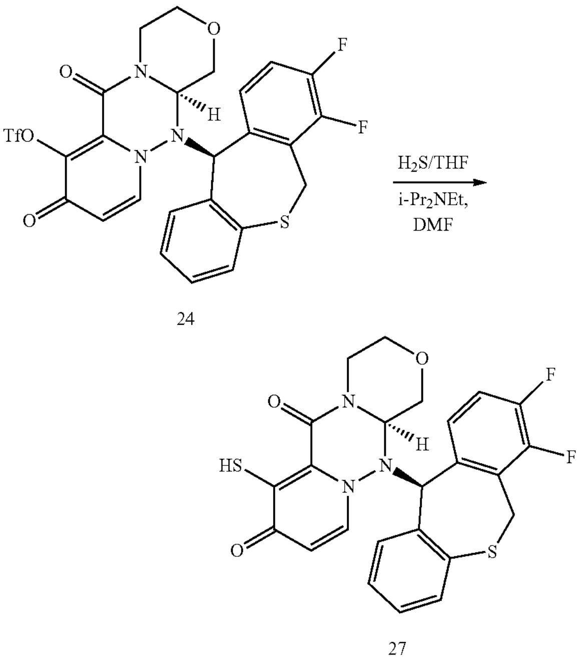

24

27

Compound 27: DIEA and 0.8 M $H_2S$ solution in THF (90 μL, 0.072 mmol) were added to a solution of triflate 24 (15 mg, 0.024 mmol) in DMF (1 mL). After stirring for 1 h, volatiles were removed in vacuo and the residue was purified on 5.5 g C18 Aq column using 5-95% $MeCN/H_2O$ (both having 0.05% AcOH). Pure fractions were combined and lyophilized to obtain the title compound 27 (7.0 mg, 58%) as a fluffy off-white solid. MS (ESI, pos.): calc'd for $C_{24}H_{19}F_2N_3O_3S_2$, 499.1; found 500.1 (M+H). $^1$H-NMR (500 MHz; $CDCl_3$): δ 7.17-7.11 (m, 4H), 7.01 (d, J=6.9 Hz, 1H), 6.88-6.83 (m, 1H), 6.65 (dd, J=28.7, 7.9 Hz, 1H), 6.28 (s, 1H), 5.81 (d, J=7.5 Hz, 1H), 5.36 (d, J=8.1 Hz, 1H), 5.29 (dd, J=28.4, 14.0 Hz, 1H), 4.74 (dd, J=12.8, 6.9 Hz, 1H), 4.65-4.60 (m, 1H), 4.11 (dd, J=13.9, 7.8 Hz, 1H), 3.99-3.96 (m, 1H), 3.81 (t, J=11.2 Hz, 1H), 3.56 (td, J=10.7, 4.4 Hz, 1H), 3.50-3.44 (m, 1H), 3.01 (t, J=12.7 Hz, 1H).

Scheme 9

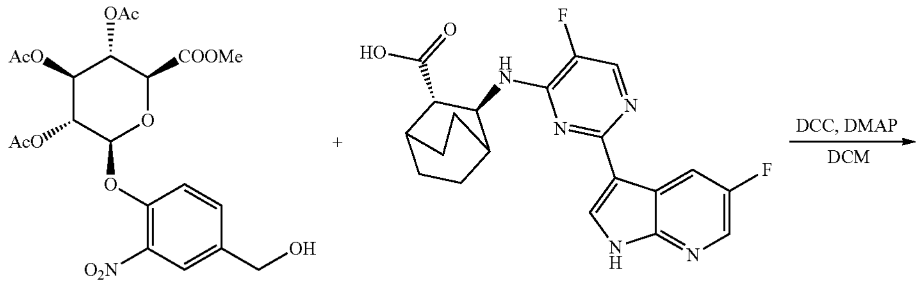

28

VX 787

-continued
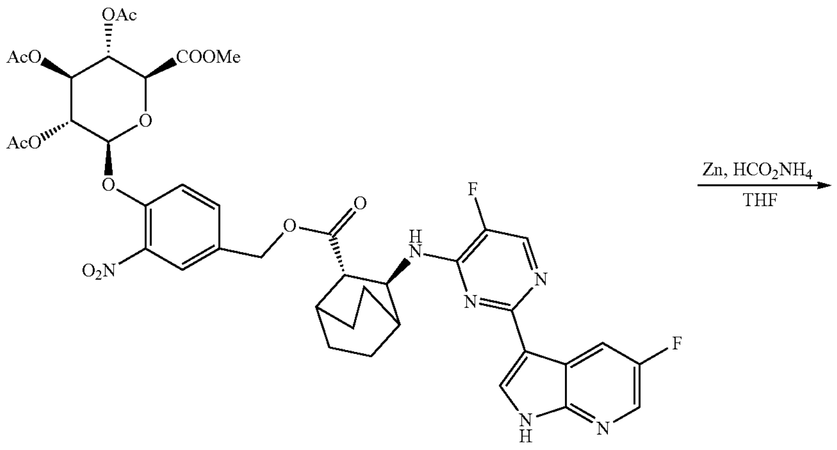
29
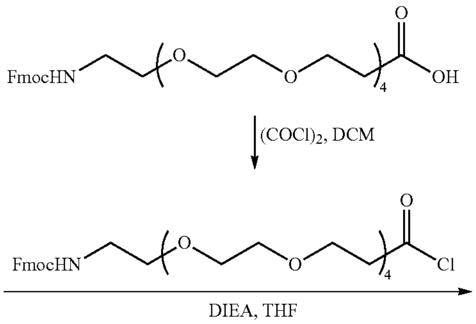
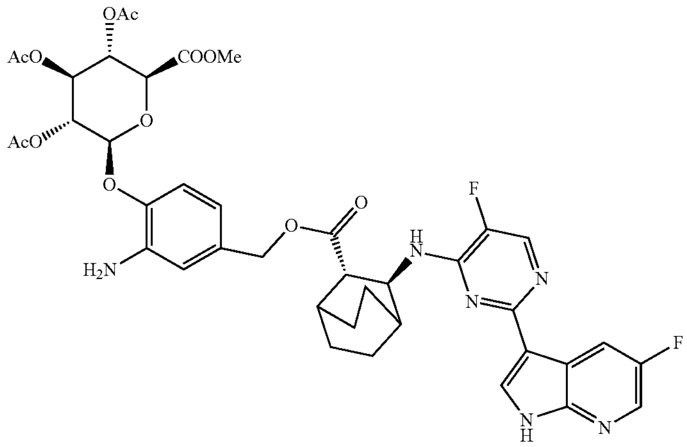
30
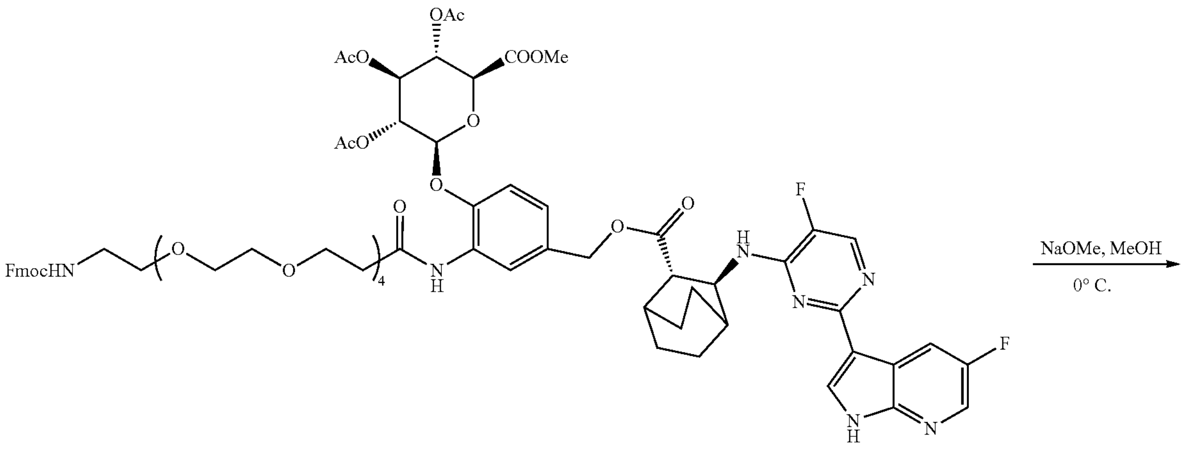
31

-continued

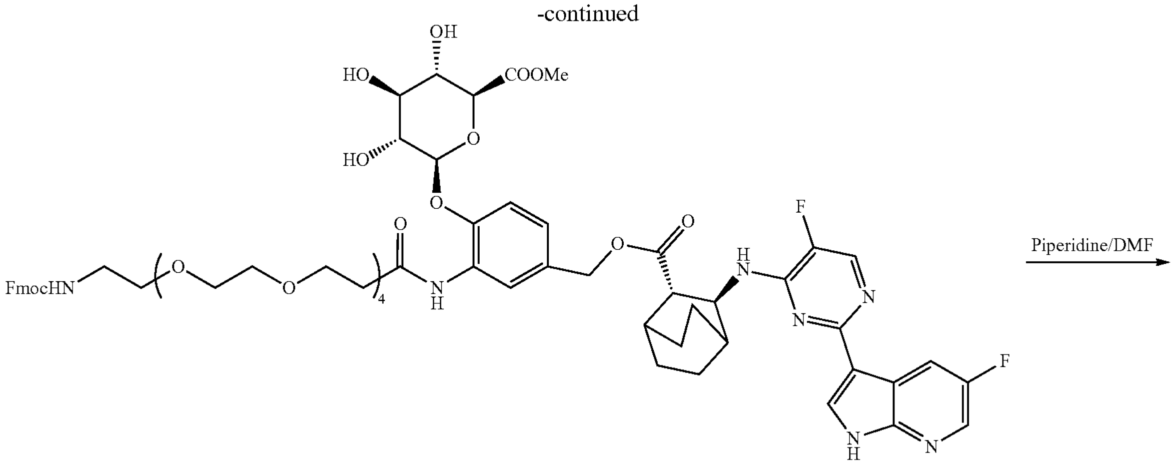

32

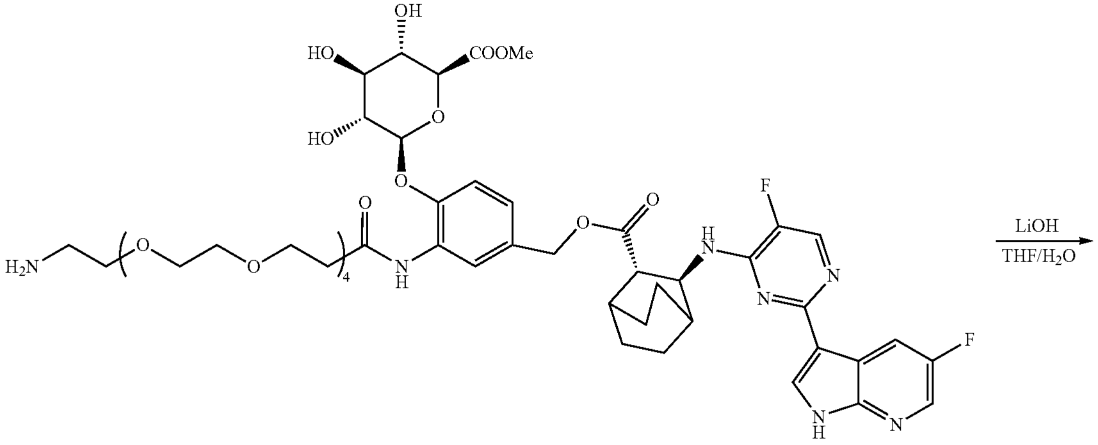

33

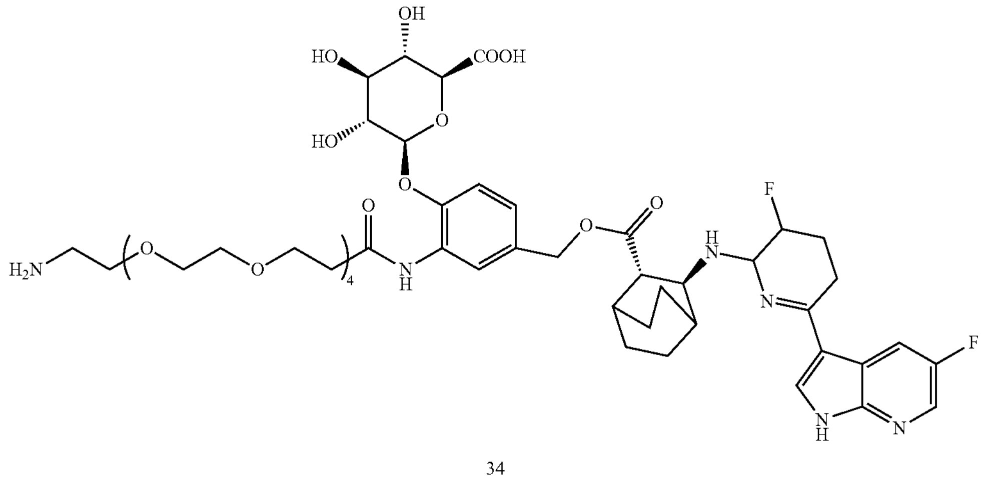

34

Compound 28 was prepared following the literature procedure from Bioconjugate Chemistry (2016), 27(10), 2549-2557.

Compound 29: DCC (57 mg, 0.227 mmol) was added to a solution of compound 28 (90 mg, 0.185 mmol), VX-787 (74 mg, 0.185 mmol) and DMAP (22 mg, 0.185 mmol) in anhydrous DCM (8 mL). The mixture was stirred for 3 h at room temperature. Solids were filtered off and the filtrate was concentrated in vacuo. The residue was purified on Teledyne ISCO with 100 g C18 Aq using 5-95% MeCN/$H_2O$ (both having 0.05% AcOH). Pure fractions were combined and lyophilized to afford the title compound 29 (120 mg, 75%) as a fluffy off-white solid. MS (ESI, pos.): calc'd for $C_{40}H_{40}F_2N_6O_{14}$, 866.3; found 867.3 (M+H).

Compound 30: A THE (10 mL) solution of compound 29 (120 mg, 0.138 mmol) was deoxygenated by bubbling nitrogen through it for 10 min. Zinc powder (180 mg, 2.76 mmol) and ammonium formate (26 mg, 0.414 mmol) were added to this solution. The reaction was deoxygenated again for 5 min and heated to 60° C. for 3.5 h. The reaction was cooled to ambient temperature, solids were removed by filtration, and the filtrate was concentrated in vacuo to obtain the title compound 30 (110 mg, 100%), which was used in the next step without further purification. MS (ESI, pos.): calc'd for $C_{40}H_{42}F_2N_6O_{12}$, 836.3; found 837.3 (M+H).

Compound 31: Oxalyl chloride (26 μL, 0.304 mmol) and DMF (2 μL) were added to a solution of Fmoc-N-amido-PEG8-acid (100 mg, 0.152 mmol) in anhydrous DCM (5 mL). After stirring for 30 mins, volatiles were removed in vacuo to obtain Fmoc-N-amido-PEG8-COCl. In a separate vial, compound 30 (110 mg, 0.138 mmol) was dissolved in an anhydrous THF (3 mL) and DIEA (53 μL, 0.304 mmol) was added followed by a THF (4 mL) solution of Fmoc-N-amido-PEG8-COCl. After 1 h, solvents were removed under reduced pressure and the residue was purified on Teledyne ISCO with 100 g C18 Aq using 5-95% $MeCN/H_2O$ (both having 0.05% AcOH). Fractions containing pure product were combined, frozen and lyophilized to obtain the title compound 31 (86 mg, 53% yield based on recovered starting material) as a fluffy off-white solid. MS (ESI, pos.): calc'd for $C_{74}H_{89}F_2N_7O_{23}$, 1481.6; found 1482.6 (M+H).

Compound 32: To a solution of compound 31 (86 mg, 0.058 mmol) in MeOH (12 mL) at 0° C., 0.1 M solution of NaOMe in MeOH (1.16 mL, 0.116 mmol) was added and the reaction was stirred at 0° C. for 1 h. The reaction was quenched by adding Dowex® Resin. The resin was filtered off and the filtrate was concentrated to afford compound 32, which was used for the next step without purification.

Compound 33: To a solution of compound 32 (0.058 mmol) in DMF (3 mL), 5% piperidine solution in DMF (1.5 mL) was added and the reaction was stirred for 45 min, then injected onto a Teledyne ISCO 50 g C18 Aq column and eluted with 5-95% $MeCN/H_2O$ (both having 0.05% AcOH as a modifier). Pure fractions were combined, frozen and lyophilized to afford the title compound 33 (32 mg, 49% over two steps) as a fluffy off-white solid. MS (ESI, pos.): calc'd for $C_{53}H_{73}F_2N_7O_{18}$, 1133.5; found 1134.4 (M+H).

Compound 34: To a solution of compound 33 (32 mg, 0.028 mmol) in THE (2 mL) and water (1 mL) at room temperature, 0.025 mM solution of LiOH in water (1.1 mL, 0.028 mmol) was added and the reaction was stirred for 2 h. Volatiles were removed under reduced pressure and the residue was purified on Teledyne ISCO with Gemini 30×150 mm column using gradient elution 5-95% $MeCN/H_2O$ (both having 0.05% AcOH as a modifier). Pure fractions were combined, frozen and lyophilized to obtain the title compound 34 (26 mg, 82%) as a fluffy off-white solid. MS (ESI, pos.): calc'd for $C_{52}H_{71}F_2N_7O_{18}$, 1119.5; found 1120.4 (M+H). $^1$H-NMR (500 MHz; DMSO-$d_6$): δ 9.19 (s, 1H), 8.47 (dd, J=9.8, 2.8 Hz, 1H), 8.26 (m, 1H), 8.16-8.13 (m, 2H), 8.07 (s, 1H), 7.60 (d, J=6.8 Hz, 1H), 7.02 (d, J=8.3 Hz, 1H), 6.93 (dd, J=8.3, 1.4 Hz, 1H), 5.60 (s, 1H), 5.02 (q, J=17.4 Hz, 3H), 4.75 (t, J=6.9 Hz, 1H), 4.60 (d, J=6.9 Hz, 1H), 3.68 (m, 2H), 3.51-3.46 (m, 32H), 2.98 (d, J=6.6 Hz, 1H), 2.89 (t, J=5.3 Hz, 2H), 2.68-2.61 (m, 2H), 2.00 (s, 1H), 1.92 (s, 1H), 1.80-1.72 (m, 4H), 1.63-1.61 (m, 1H), 1.53-1.43 (m, 5H).

Scheme 10

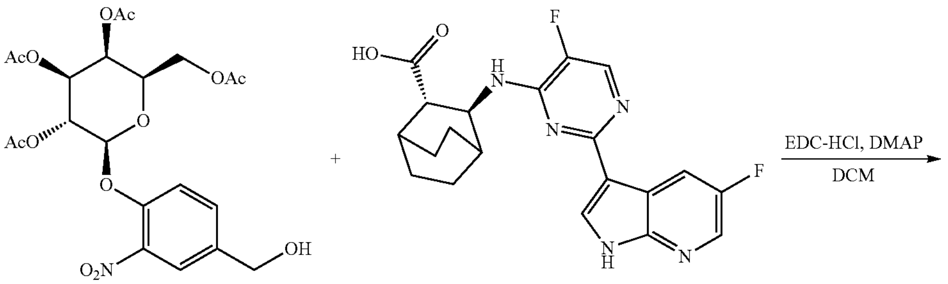

35

VX 787

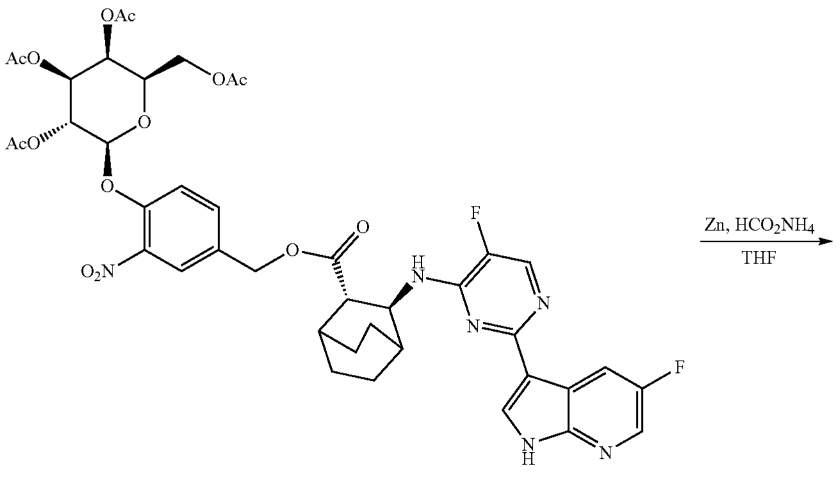

36

-continued
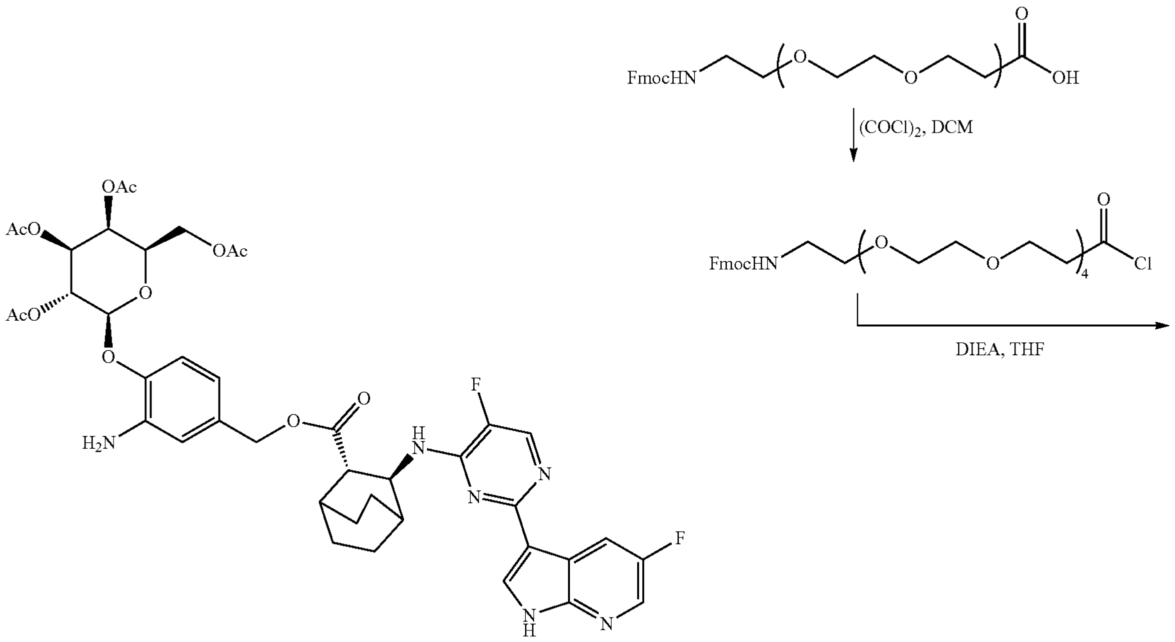
37
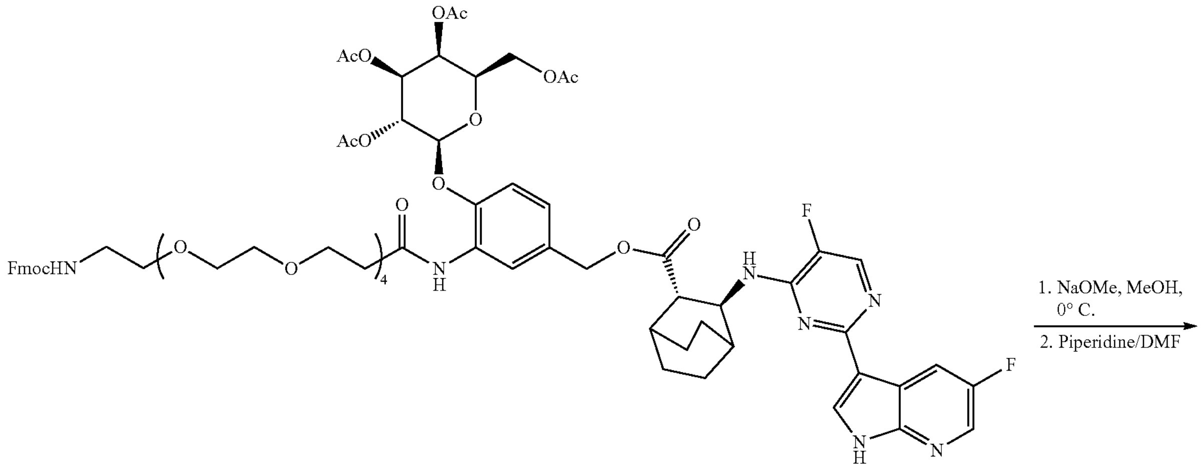
38
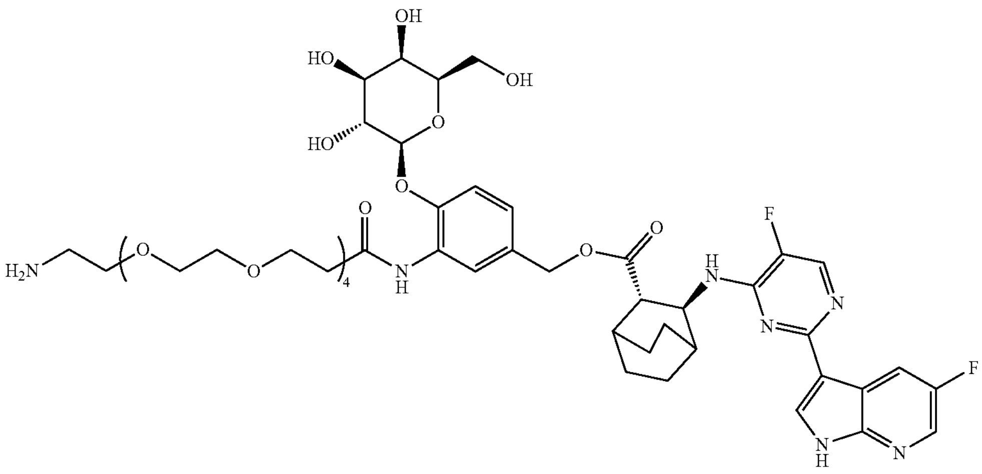
39

Compound 35 was prepared following the literature procedure from Bioconjugate Chemistry (2016), 27(10), 2549-2557.

Compound 36: EDC-HCl (67 mg, 0.350 mmol) and DMAP (34 mg, 0.278 mmol) were added to a mixture of VX-787 (100 mg, 0.250 mmol) and the alcohol 37 (125 mg, 0.250 mmol) in $CH_2Cl_2$ (16 mL). After stirring for 22 h at ambient temperature the reaction was diluted with ethyl acetate (20 mL) and washed with $H_2O$ (20 mL). The aqueous layer was extracted with three 20 mL portions of ethyl acetate. The combined organic layers were washed with 0.5N HCl (aq) solution (20 mL), then with saturated $NaHCO_3$ (aq) solution (20 mL) and finally with brine (20 mL), then were dried over $Na_2SO_4$, filtered, and concentrated in vacuo. Purification by chromatography on 12 g silica gel with 45-100% ethyl acetate in hexanes afforded compound 58b (149 mg, 67% yield, 82% purity), which was used in the next step without further purification. MS (ESI, pos.): calc'd for $C_{41}H_{42}F_2N_6O_{14}$, 880.27; found 881.30 (M+H).

Compound 37: A solution of Compound 36 (35 mg, 0.0397 mmol) in THF (1.5 mL) was deoxygenated by bubbling Argon through it for 5 min. Powdered Zn (102 mg, 1.56 mmol) was added followed by ammonium formate (12 mg, 0.0.190 mmol). Argon was bubbled through the mixture for 3 min more, then the reaction was heated under argon in a 60° C. pie block for 24 h. The reaction was filtered and the solids washed with several portions of THF. The filtrate was concentrated in vacuo then purified by chromatography on 4 g silica gel, eluting with 40-100% ethyl acetate in hexanes to afford compound 37 (14 mg, 42%) as a pale yellow solid. MS (ESI, pos.): calc'd for $C_{41}H_{44}F_2N_6O_{12}$, 850.30; found 851.30 (M+H).

Compound 38: Oxalyl chloride (8 μL, 0.0933 mol) and DMF (2 μL) were added to a solution of Fmoc-N-amido-PEG8-acid (30 mg, 0.0452 mmol) in anhydrous $CH_2Cl_2$ (1 mL). The resulting bright yellow solution was stirred at ambient temperature for 1 h then concentrated in vacuo. To the resulting residue was added three 1 mL portions of dry $CH_2Cl_2$, concentrating after each addition. In a separate vial, $iPr_2NEt$ (16 μL, 0.0918 mmol) was added to a suspension of Compound 37 (20 mg, 0.0235 mmol) in $CH_2Cl_2$ (200 μL). To this mixture was added dropwise a solution of the acid chloride (0.0452 mmol) in $CH_2Cl_2$ (400 μL). After stirring at ambient temperature for 1 h the mixture was concentrated in vacuo. The crude product was dissolved in DMSO and loaded onto a 5.5 g C18 Aq column, eluting with 20-100% MeCN in $H_2O$ with 0.05% HOAc in both solvents. Fractions containing pure product were combined and lyophilized to afford Compound 38 (7.3 mg, 21% yield) as a white solid. MS (ESI, pos.): calc'd for $C_{75}H_{91}F_2N_7O_{23}$, 1495.61; found 1496.60 (M+H).

Compound 39: 0.1 M NaOMe/MeOH solution (13 μL, 0.0013 mmol) was added to a 0° C. solution of compound 38 (2.0 mg, 0.00134 mmol) in anhydrous methanol (400 μL). After stirring in an ice bath for 4 h, the reaction was neutralized with 0.2 M HCl/MeOH solution (6.5 μL, 0.0013 mmol) and concentrated in vacuo. $CH_2Cl_2$ (0.5 mL portions) was added three times, concentrating the mixture after each addition. The resulting residue was dissolved in anhydrous DMF (0.2 mL) and treated with 10% piperidine/DMF solution (0.2 mL). After 30 min the reaction was loaded onto a 5.5 g C18 Aq column and eluted with 0-100% MeCN in $H_2O$ with 0.1% TFA in both solvents. Fractions containing clean product were combined and lyophilized to afford the TFA salt of compound 39 (1.1 mg, 71%) as a white solid. MS (ESI, pos.): calc'd for $C_{52}H_{73}F_2N_7O_{17}$, 1105.50; found 1106.50 (M+H). $^1H$ NMR (500 MHz; $CD_3OD$) δ 8.57 (dd, J=9.5, 2.8 Hz, 1H), 8.17 (s, 2H), 8.08 (d, J=1.8 Hz, 1H), 8.00 (d, J=4.0 Hz, 1H), 7.01 (d, J=8.4 Hz, 1H), 6.90-6.88 (m, 1H), 5.04 (s, 2H), 4.92 (d, J=1.9 Hz, 2H), 4.63 (d, J=7.9 Hz, 1H), 3.91 (d, J=3.2 Hz, 1H), 3.83-3.74 (m, 6H), 3.66-3.53 (m, 30H), 2.92 (dd, J=6.6, 3.7 Hz, 2H), 2.83 (d, J=7.0 Hz, 1H), 2.64 (td, J=6.4, 3.4 Hz, 2H), 2.10 (t, J=1.4 Hz, 1H), 1.96-1.81 (m, 4H), 1.74-1.64 (m, 2H), 1.55-1.50 (m, 2H).

Scheme 11

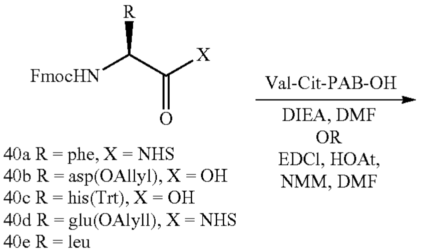

40a R = phe, X = NHS
40b R = asp(OAllyl), X = OH
40c R = his(Trt), X = OH
40d R = glu(OAlyll), X = NHS
40e R = leu
40f R = arg(Pbf)

-continued
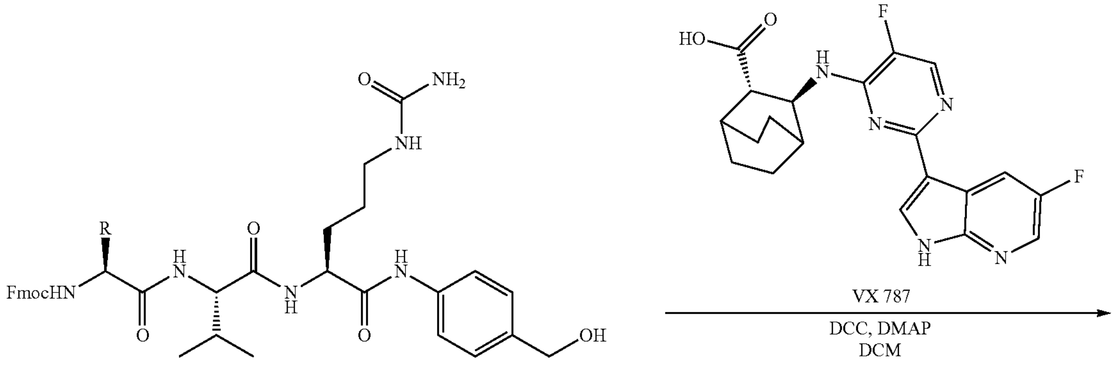
41a R = phe
41b R = asp(OAllyl)
41c R = his(Trt)
41d R = glu(OAllyl)
41e R = leu
41f R = arg(Pbf)
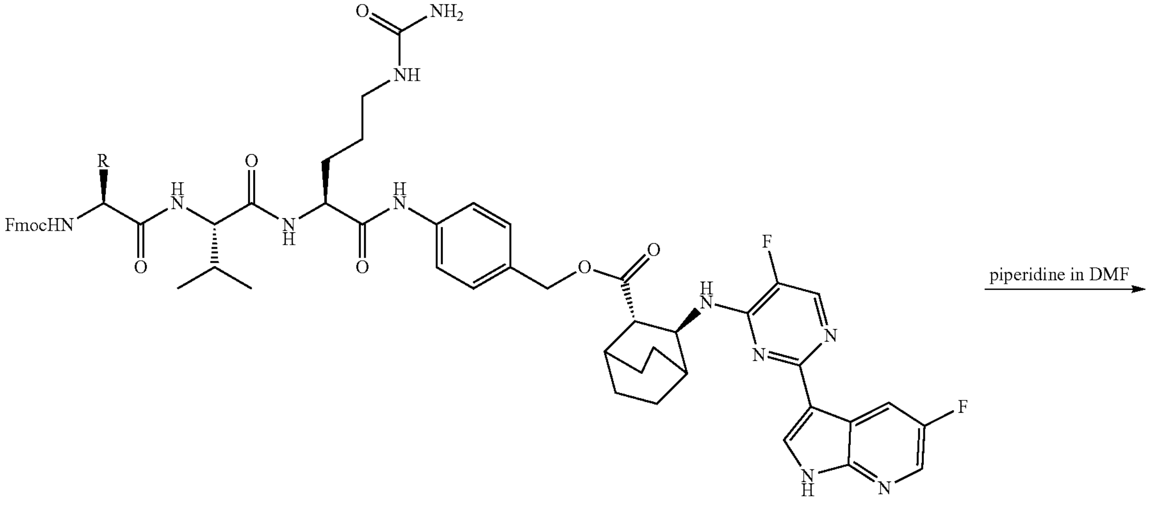
42a R = phe
42b R = asp (OAllyl)
Pd($PPh_3$)$_4$, $PhSiH_3$, THF
42b′ R = asp
42c R = his(Trt)
42d R = glu(OAllyl)
Pd($PPh_3$)$_4$, $PhSiH_3$, THF
42d′ R = glu
42e R = leu
42f R = arg(Pbf)

-continued
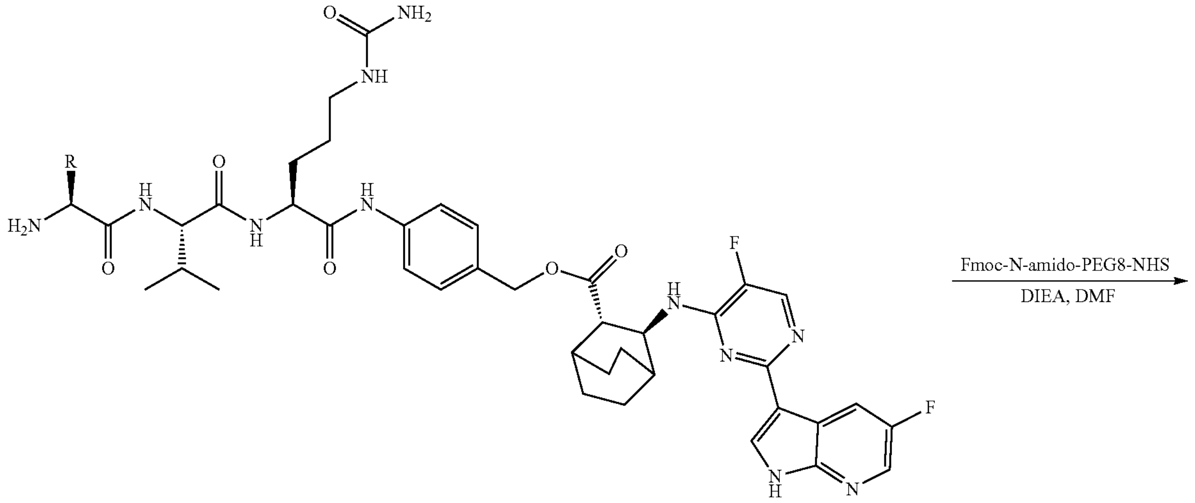
43a R = phe
43b R = asp
43c R = his(Trt)
43d R = glu
43e R = leu
43f R = arg(Pbf)
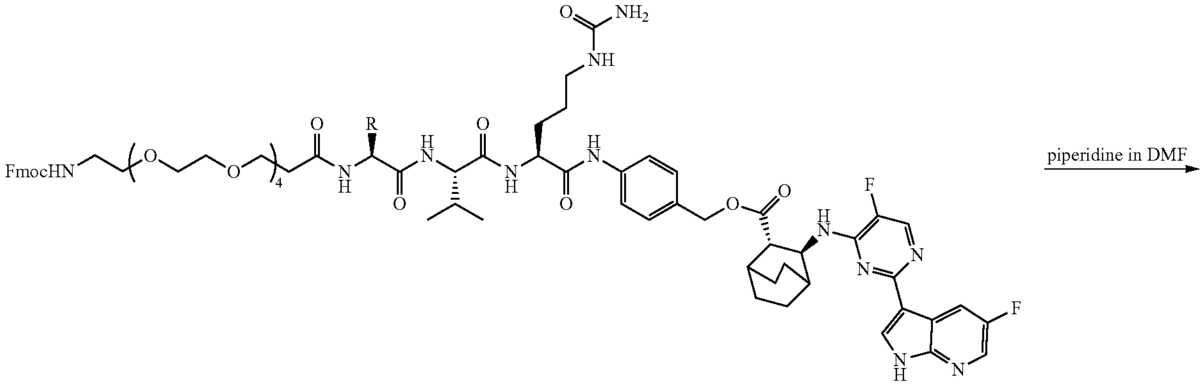
44a R = phe
44b R = asp
44c R = his(Trt)
44c' R = his
TFA/DCM
44d R = glu
44e R = leu
44f R = arg(Pbf)
44f' R = arg
$TFA/Et_3SiH/DCM$ -continued

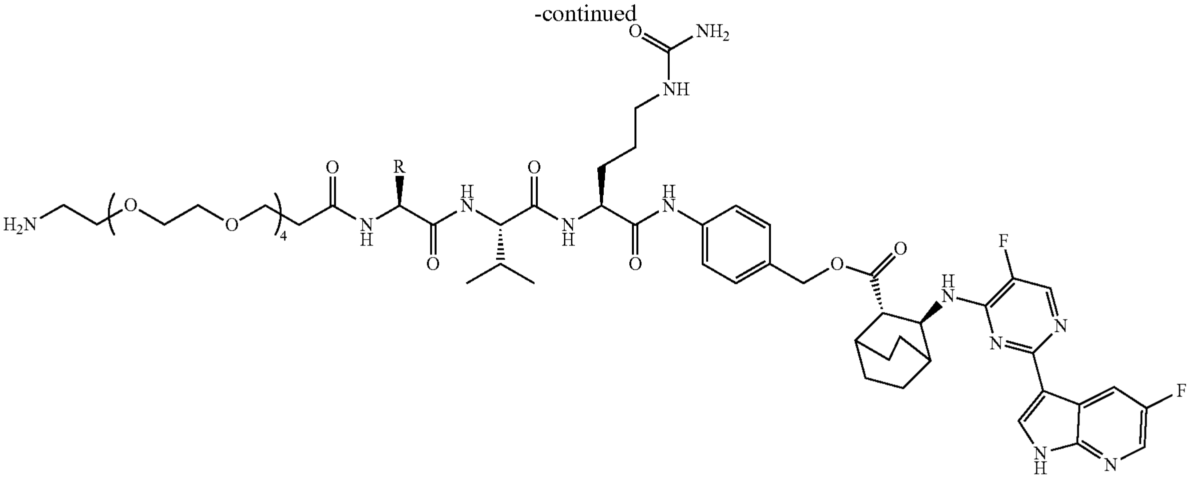

45a R = phe
45b R = asp
45c R = his
45d R = glu
45e R = leu
45f R = arg

Compound 41a: General Procedure A: To a DMF (1.5 mL) solution of Fmoc-Phe-OSu (40a) (107 mg, 0.22 mmol) and Val-Cit-PABA TFA salt (2) (99 mg, 0.2 mmol), N,N-diisopropylethylamine (105 μL, 0.6 mmol) was added. The reaction was stirred at room temperature for 30 min then injected onto a 50 g C18 Aq. column and eluted with gradient 5-95% MeCN:$H_2O$ (both having 0.05% AcOH). Pure fractions were combined, frozen and lyophilized to afford the title compound 41a (23 mg, 14%) as a fluffy off-white solid. MS (ESI, pos.): calc'd for $C_{42}H_{48}N_6O_7$, 748.4; found 749.3 (M+H).

Compound 41b: General Procedure B: To a DMF (1.5 mL) solution of Fmoc-Asp(OAllyl)-OH (40b) (83 mg, 0.21 mmol), Val-Cit-PABA.TFA salt (2) (99 mg, 0.2 mmol) and HOAt (41 mg, 0.3 mmol) were added NMM (66 μL, 0.6 mmol) and EDCI (48 mg, 0.25 mmol). The reaction was stirred at room temperature for 2 h, then was injected onto a Teledyne ISCO 30 g C18 Aq. column and eluted with 5-95% MeCN/$H_2O$ (both having 0.05% AcOH). Pure fractions were combined, frozen and lyophilized to afford the title compound 41b (85 mg, 56%) as a fluffy off-white solid. MS (ESI, pos.): calc'd for $C_{40}H_{48}N_6O_9$, 756.3; found 757.4 (M+H).

Compound 41c: Prepared by general procedure B using Fmoc-His(Trt)-OH (40c) (130 mg, 0.21 mmol). Yield=146 mg (74%) as a fluffy off-white solid. MS (ESI, pos.): calc'd for $C_{58}H_{60}N_8O_7$, 980.5; found 981.4 (M+H).

Compound 41d: Prepared by general procedure A using Fmoc-Glu(OAllyl)-OSu (40d) (51 mg, 0.1 mmol). Yield=25 mg (33%) as a fluffy off-white solid. MS (ESI, pos.): calc'd for $C_{27}H_{26}N_2O_8$, 506.2; found 507.2 (M+H).

Compound 41e: To a 0° C. solution of Val-Cit-PABA (380 mg, 1.0 mmol) in anhydrous DMA (5 mL) was added FmocLeuOH (40e) (424 mg, 1.2 mmol), HOAt (170 mg, 1.2 mmol), EDC-HCl (240 mg, 1.2 mmol) and N-methylmorpholine (220 μL, 2.0 mmol). After stirring in an ice bath for 2.5 h the reaction was diluted with $H_2O$ (35 mL). The product was collected by vacuum filtration and washed three times with $H_2O$ (5 mL portions) then with six 10-20 mL portions of ethyl acetate until LCMS analysis indicated <5% FmocLeuOH remained. After drying under vacuum overnight, the white solid was crushed into a powder and again dried under vacuum to afford compound 41e (616 mg, 86%). MS (ESI, pos.): calc'd for $C_{39}H_{50}N_6O_7$, 714.4; found 715.4 (M+H).

Compound 41f: To a 0° C. mixture of Val-Cit-PABA (200 mg, 0.527 mmol), FmocArg(Pbf)OH (40f) (410 mg, 0.632 mmol) and HOAt (86 mg, 0.632 mmol) in anhydrous DMF (5 mL) was added N-methylmorpholine (90 μL, 0.818 mmol) and EDC-HCl (120 mg, 0.626 mmol). The reaction was stirred in the ice bath for 3 h then was loaded onto a 100 g C18 column and eluted with 10-60% MeCN in $H_2O$ with 0.05% HOAc in both solvents. Fractions containing pure product were combined and lyophilized to afford compound 41f (345 mg, 65%) as a white solid. MS (ESI, pos.): calc'd for $C_{52}H_{67}N_9O_{10}S$, 1009.47; found 1010.40 (M+H).

Compound 42a: General Procedure A: VX-787 (11 mg, 0.026 mmol), DMAP (3.2 mg, 0.026 mmol) and DCC (8 mg, 0.039 mmol) were added to a DCM (3 mL) solution of Fmoc-Phe-Val-Cit-PAB-OH (41a) (20 mg, 0.026 mmol). After stirring for 5 h, additional VX-787 (4 mg) was added and the reaction was stirred for 16 h then concentrated in vacuo. The residue was dissolved in DMSO (1 mL) and purified with Teledyne ISCO on 15.5 g C18 Aq. column using gradient elution 5-95% MeCN/$H_2O$ (both having 0.05% AcOH). Pure fractions were combined, frozen and lyophilized to obtain the title compound 42a (10 mg, 50% yield based on recovered starting material) as a fluffy off-white solid. MS (ESI, pos.): calc'd for $C_{62}H_{65}F_2N_{11}O_8$, 1129.5; found 1130.4 (M+H). Unreacted 41a (7 mg) was also recovered.

Compound 42b: General Procedure B: EDCI (13.2 mg, 0.069 mmol) was added to a DCM (6 mL) solution of compound 41b (35 mg, 0.046 mmol), VX-787 (18.5 mg, 0.046 mmol) and DMAP (5.6 mg, 0.046 mmol), and the reaction was stirred for 2 h at room temperature. Additional VX-787 (6 mg) was added and the reaction was stirred overnight. Solvents were removed under reduced pressure and the residue was dissolved in DMF (1.5 mL) and purified on Teledyne ISCO with 30 g C18 Aq column using 5-95%

MeCN/$H_2O$ (both having 0.05% TFA). Pure fractions were combined and lyophilized to obtain the title compound 42b (23 mg, 44%) as a fluffy off-white solid. MS (ESI, pos.): calc'd for $C_{60}H_{65}F_2N_{11}O_{10}$, 1137.5; found 1138.4 (M+H).

Compound 42b': $Pd(PPh_3)_4$(2.4 mg, 0.002 mmol) and phenylsilane (1 drop) were added to a THE (0.8 mL):DMF (0.4 mL) solution of compound 42b (23 mg, 0.020 mmol) and the reaction was stirred for 30 min. Volatiles were removed in vacuo to obtain compound 42b', which was used in the next step without purification.

Compound 42c: Synthesized following General Procedure B using compound 41c (39 mg, 0.04 mmol) to obtain the title compound 42c (30 mg, 55%) as a fluffy off-white solid. MS (ESI, pos.): calc'd for $C_{78}H_{77}F_2N_{13}O_8$, 1361.6; found 1362.4 (M+H).

Compound 42d: Synthesized following General Procedure A using compound 41d (15.4 mg, 0.02 mmol) to obtain the title compound 42d (13 mg, 57%) as a fluffy off-white solid. MS (ESI, pos.): calc'd for $C_{61}H_{67}F_2N_{11}O_{10}$, 1151.5; found 1152.4 (M+H).

Compound 42d': $Pd(PPh_3)_4$(1.3 mg, 0.001 mmol) and phenylsilane (2 μL, 0.0165 mmol) were added to a THF (1.5 mL)/DMF (0.5 mL) solution of compound 42d (13 mg, 0.011 mmol) and the reaction was stirred for 20 min. Volatiles were removed in vacuo to obtain compound 42d' which was used in the next step without purification.

Compound 42e: Fmoc-Leu-Val-Cit-PABA (41e) (89 mg, 0.125 mmol), DMAP (30 mg, 0.245 mmol) and EDC-HCl (48 mg, 0.250 mmol) were added to a solution of VX-787 (100 mg, 0.250 mmol) in 3:1 THF:DMA (3 mL). The reaction was stirred at ambient temperature 2 h then concentrated in vacuo to remove the THF. The remaining DMA solution was loaded onto a 50 g C18 Aq column and eluted with 5-100% MeCN in $H_2O$ with 0.05% HOAc in both solvents. Product-containing fractions were lyophilized then repurified by chromatography on 30 g C18 Aq column, eluting with 50-100% MeCN in $H_2O$ with 0.05% HOAc in both solvents. After lyophilization the title compound 42e was obtained (37 mg, 24%) as a white solid that was ~90% pure by LCMS. The product was used in the next step without further purification. MS (ESI, pos.): calc'd for $C_{59}H_{67}F_2N_{11}O_8$, 1095.51; found 1096.50 (M+H).

Compound 42f: DMAP (8 mg, 0.0655 mmol) and EDC-HCl (12 mg, 0.0626 mmol) were added to a solution of compound 41f (31 mg, 0.0307 mmol) and VX-787 (25 mg, 0.0626 mmol) in 3:1 THF:DMA (760 μL). After stirring at ambient temperature for 4 h, THF was removed by concentration in vacuo. The remaining DMA solution was loaded onto a 15.5 g C18 Aq column and eluted with 0-100% MeCN in $H_2O$ with 0.05% HOAc in both solvents. Fractions containing pure product were combined and lyophilized, affording compound 42f (7 mg, 16%) as a white solid. MS (ESI, pos.): calc'd for $C_{72}H_{84}F_2N_{14}O_{11}S$, 1390.61; found 1391.45 (M+H).

General Procedure for Fmoc removal: Compound 43a: 5% piperidine in DMF (1 mL) was added to a DMF (1 mL) solution of compound 42a (10 mg, 0.01 mmol), and the reaction was stirred for 45 min. The reaction was injected onto a Teledyne ISCO 15.5 g C18 Aq column and eluted with 5-95% MeCN:$H_2O$ (both having 0.05% AcOH). Pure fractions were combined, frozen and lyophilized to obtain the title compound 43a (7 mg, 63%) as a fluffy off-white solid. MS (ESI, pos.): calc'd for $C_{47}H_{55}F_2N_{11}O_6$, 907.4; found 908.4 (M+H).

Compound 43b: General Procedure for Fmoc removal was followed. Yield=78% from crude 42b' as fluffy off-white solid. MS (ESI, pos.): calc'd for $C_{42}H_{51}F_2N_1O_8$, 875.4; found 876.4 (M+H).

Compound 43c: General Procedure for Fmoc removal was followed. Yield=53% from 42c as fluffy off-white solid. MS (ESI, pos.): calc'd for $C_{66}H_{67}F_2N_{13}O_8$, 1139.5; found 1140.4. (M+H).

Compound 43d: General Procedure for Fmoc removal was followed. Yield=59% from 42d' as fluffy off-white solid. MS (ESI, pos.): calc'd for $C_{43}H_{53}F_2N_{11}O_8$, 889.4; found 890.4 (M+H).

Compound 43e: 10% piperidine in DMF (400 μL) was added to a solution of compound 42e (20 mg, 0.0182 mmol) in anhydrous DMF (400 μL). After stirring at ambient temperature 30 min, the reaction was loaded onto a 5.5 g C18 Aq column and eluted with 5-25% MeCN in $H_2O$ with 0.1% TFA in both solvents. Pure fractions were combined and lyophilized to afford the TFA salt of compound 43e (13 mg, 72%) as a white solid. MS (ESI, pos.): calc'd for $C_{44}H_{57}F_2N_{11}O_6$, 873.45; found 874.40 (M+H).

Compound 43f: 10% piperidine/DMF solution (100 μL) was added to a solution of compound 42f (6.8 mg, 0.00489 mmol) in DMF (100 μL). After stirring at ambient temperature for 1 h, the solution was loaded onto a 5.5 g C18 Aq column and eluted with 0-100% MeCN in $H_2O$ with 0.05% HOAc in both solvents. Product-containing fractions were combined and lyophilized to afford compound 43f (5.2 mg, 91%) as a white solid. MS (ESI, pos.): calc'd for $C_{57}H_{74}F_2N_{14}O_9S$, 1168.55; found 1169.40 (M+H).

General Procedure for installing Fmoc-N-amido-PEG8: Compound 44a: To a DMF (1 mL) solution of compound 43a (7 mg, 0.008 mmol), Fmoc-N-amido-PEG8-NHS ester (7 mg, 0.009 mmol) was added followed by N,N-diisopropylethylamine (4 μL, 0.023 mmol) and the reaction was stirred for 2 h. The product was purified on Teledyne ISCO with 15.5 g C18 Aq column using gradient elution 5-95% MeCN/$H_2O$ (both having 0.05% AcOH). Pure fractions were combined, frozen and lyophilized to obtain the title compound 44a (5 mg, 42%) as a fluffy off-white solid. MS (ESI, pos.): calc'd for $C_{81}H_{102}F_2N_{12}O_{17}$, 1552.7; found 1553.7 (M+H).

Compound 44b: The general procedure for installing Fmoc-N-amido-PEG8 was followed. Yield=61% from 43b as a fluffy off-white solid. MS (ESI, pos.): calc'd for $C_{76}H_{98}F_2N_{12}O_{19}$, 1520.7; found 1521.4 (M+H).

Compound 44c: The general procedure for installing Fmoc-N-amido-PEG8 was followed. Yield=83% from 43c as a fluffy off-white solid. MS (ESI, pos.): calc'd for $C_{97}H_{114}F_2N_{14}O_{17}$, 1784.4; found 1785.6 (M+H).

Compound 44c': To a DCM (2 mL) solution of compound 44c (17 mg, 0.0073 mmol), TFA (0.2 mL) was added, After stirring for 3 h the reaction was diluted with MeOH (3 mL) and volatiles were removed in vacuo. The residue was dissolved in 1:1 MeCN:$H_2O$ (1.5 mL) and DMSO (0.2 mL) and injected onto a Teledyne ISCO 15.5 g C18 Aq column and eluted using gradient elution 5-95% MeCN:$H_2O$ (both having 10 mmol ammonium acetate as a modifier). Pure fractions were combined, frozen and lyophilized to obtain the title compound 44c' (12 mg, 82%) as a fluffy off-white solid. MS (ESI, pos.): calc'd for $C_{78}H_{100}F_2N_{14}O_{17}$, 1542.7; found 1543.8 (M+H).

Compound 44d: Prepared by following general procedure using 43d. The product 44d was used in the next step without purification.

Compound 44e: $iPr_2NEt$ (15 μL, 0.0861 mmol) was added to a solution of compound 43e-TFA salt (20 mg, 0.0206 mmol) and Fmoc-N-amido-PEG8-NHS ester (20 mg, 0.0263 mmol) in anhydrous DMA (400 µL). After stirring at ambient temperature for 2 h the reaction was loaded onto a 15.5 g C18 Aq column and eluted with 10-100% MeCN in $H_2O$ with 0.1% TFA in both solvents. Pure fractions were combined and lyophilized, affording compound 44e (13 mg, 42%) as a white solid. MS (ESI, pos.): calc'd for $C_{78}H_{104}F_2N_{12}O_{17}$, 1518.76; found 1519.70 (M+H).

Compound 44f: To a solution of compound 43f (7 mg, 0.00599 mmol) in anhydrous DMF (100 µL) was added a 10% solution of $iPr_2NEt$ in DMF (33 µL) followed by Fmoc-N-amido-PEG8-NHS ester (6 mg, 0.00789 mmol) in anhydrous DMF (100 µL). After 1 h, LCMS indicated incomplete reaction. Additional Fmoc-N-amido-PEG8-NHS ester (25 µL of a 6% solution in DMF) was added and the reaction was stirred for 2 h more to complete the reaction. Purification by chromatography on a 5.5 g C18 Aq ISCO column with 0-100% MeCN in $H_2O$ with 0.05% HOAc in both solvents, followed by lyophilization of the pure fractions afforded compound 44f (9 mg, 82%) as a white solid. MS (ESI, pos.): calc'd for $C_{91}H_{121}F_2N_{15}O_{20}S$, 1814.0; found 1815.7 (M+H).

Compound 45a: Following the general procedure for Fmoc removal, the title compound 45a was prepared from 44a in 93% yield as a fluffy off-white solid. MS (ESI, pos.): calc'd for $C_{66}H_{92}F_2N_{12}O_{15}$, 1330.7; found 1331.6 (M+H). $^1$H-NMR (500 MHz; DMSO-$d_6$): δ 10.02 (d, J=0.7 Hz, 1H), 8.48 (dd, J=9.8, 2.8 Hz, 1H), 8.26 (d, J=1.3 Hz, 1H), 8.18 (s, 1H), 8.14 (d, J=3.8 Hz, 1H), 8.08 (s, 1H), 7.85 (s, 1H) 7.60 (d, J=6.8 Hz, 1H), 7.52 (d, J=8.4 Hz, 2H), 7.23-7.18 (m, 6H), 7.18-7.14 (m, 1H), 5.99 (s, 1H), 5.42 (s, 2H), 5.07 (d, J=12.4 Hz, 1H), 4.98 (d, J=12.4 Hz, 1H), 4.74 (t, J=6.5 Hz, 1H), 4.60-4.56 (m, 1H), 4.38-4.35 (m, 1H), 4.20 (t, J=7.5 Hz, 1H), 3.48-3.47 (m, 25H), 3.41 (m, 2H), 3.39-3.34 (m, 4H), 3.02-2.96 (m, 6H), 2.77-2.74 (m, 1H), 2.65-2.62 (m, 3H), 2.37-2.33 (m, 1H), 2.28 (t, J=6.1 Hz, 2H), 1.97-1.94 (m, 3H), 1.80-1.60 (m, 6H), 1.50-1.36 (m, 6H), 0.84 (dd, J=15.0, 6.7 Hz, 6H).

Compound 45b: Following the general procedure for Fmoc removal, title compound 45b was prepared from 44b in 69% yield as a fluffy off-white solid. MS (ESI, pos.): calc'd for $C_{61}H_{88}F_2N_{12}O_{17}$, 1298.6; found 1299.5 (M+H). $^1$H-NMR (500 MHz; DMSO-$d_6$): δ 9.33 (s, 1H), 9.16 (dd, J=6.3, 0.8 Hz, 1H), 8.48 (dd, J=9.8, 2.8 Hz, 1H), 8.42-8.41 (m, 1H), 8.26 (d, J=1.3 Hz, 1H), 8.18 (s, 1H), 8.14 (d, J=3.9 Hz, 1H), 7.92 (d, J=7.6 Hz, 1H), 7.71-7.70 (m, 2H), 7.61-7.60 (m, 1H), 7.30 (s, 1H), 7.21 (d, J=8.5 Hz, 2H), 5.03 (m, 2H), 4.74-4.70 (m, 2H), 4.02 (d, J=1.0 Hz, 1H), 3.93-3.91 (m, 1H), 3.60-3.53 (m, 3H), 3.53-3.42 (m, 35H), 2.99-2.95 (m, 3H), 2.81-2.79 (m, 2H), 2.37-2.34 (m, 2H), 2.26-2.23 (m, 2H), 1.97-1.92 (m, 3H), 1.80-1.71 (m, 3H), 1.65-1.61 (m, 2H), 1.52-1.42 (m, 6H), 1.22 (d, J=0.3 Hz, 1H), 0.92 (dd, J=9.6, 7.1 Hz, 6H).

Compound 45c: Following the general procedure for Fmoc removal, title compound 45c was prepared from 44c' in 89% yield as a fluffy off-white solid. MS (ESI, pos.): calc'd for $C_{63}H_{90}F_2N_{14}O_{15}$, 1320.7; found 1322.0 (M+H). $^1$H-NMR (500 MHz; DMSO-$d_6$): δ 12.35 (d, J=0.9 Hz, 1H), 10.03 (s, 1H), 8.95 (s, 1H), 8.47 (dd, J=9.7, 2.8 Hz, 1H), 8.29 (d, J=7.6 Hz, 2H), 8.24 (dd, J=5.3, 2.3 Hz, 2H), 8.20 (d, J=4.0 Hz, 1H), 7.83 (d, J=8.3 Hz, 2H), 7.75-7.69 (m, 2H), 7.51 (d, J=8.5 Hz, 2H), 7.32 (s, 1H), 7.22 (d, J=8.6 Hz, 2H), 6.09-6.07 (m, 1H), 5.03 (m, 2H), 4.78-4.75 (m, 1H), 4.69 (q, J=7.1 Hz, 1H), 4.40-4.37 (m, 1H), 4.22-4.19 (m, 2H), 3.50 (s, 16H), 3.50 (s, 5H), 3.48 (d, J=4.2 Hz, 7H), 3.46-3.41 (m, 5H), 3.07-2.90 (m, 8H), 2.37-2.34 (m, 2H), 2.00-1.94 (m, 3H), 1.80-1.70 (m, 3H), 1.70-1.56 (m, 3H), 1.51-1.35 (m, 6H), 0.84 (dd, J=17.7, 6.8 Hz, 6H).

Compound 45d: Following the general procedure for Fmoc removal, title compound 45d was prepared from unpurified 44 in 47% yield (over two steps) as a fluffy off-white solid. MS (ESI, pos.): calc'd for $C_{62}H_{90}F_2N_{12}O_{17}$, 1312.7; found 1313.6 (M+H). $^1$H-NMR (500 MHz; DMSO-$d_6$): δ 10.01 (s, 1H), 8.56 (s, 1H), 8.49-8.47 (m, 1H), 8.30-8.26 (m, 2H), 8.18-8.14 (m, 2H), 7.90 (d, J=8.7 Hz, 1H), 7.60 (d, J=6.7 Hz, 1H), 7.53 (d, J=8.0 Hz, 2H), 7.21 (d, J=8.0 Hz, 2H), 6.65 (s, 1H), 5.68 (s, 2H), 5.02 (m, 2H), 4.74 (t, J=5.7 Hz, 1H), 4.28 (t, J=6.8 Hz, 2H), 4.18 (dd, J=8.1, 5.6 Hz, 1H), 3.51 (m, 32H), 2.95 (d, J=5.7 Hz, 4H), 2.75-2.74 (m, 2H), 2.42-2.29 (m, 3H), 2.11-2.04 (m, 3H), 1.97-1.93 (m, 2H), 1.82-1.61 (m, 8H), 1.49-1.37 (m, 6H), 1.22 (s, 3H), 0.82 (dd, J=12.6, 6.6 Hz, 6H).

Compound 45e: 10% piperidine in DMF (100 µL) was added to a solution of compound 44e (16 mg, 0.0153 mmol) in DMF (100 µL). After stirring at ambient temperature for 30 min the reaction was loaded onto a 5.5 g C18 Aq column and eluted with 5-100% MeCN in $H_2O$ with 0.1% TFA in both solvents. Clean fractions were lyophilized, affording the TFA salt of compound 45e (7 mg, 47%) as a white solid. MS (ESI, pos.): calc'd for $C_{63}H_{94}F_2N_{12}O_{15}$, 1296.69; found 1297.60 (M+H). $^1$H NMR (500 MHz; DMSO-$d_6$) δ 10.00 (br s, 1H), 8.48 (dd, J=9.8, 2.6 Hz, 1H), 8.27 (m, 1H), 8.20 (s, 1H), 8.16-8.14 (m, 1H), 8.11-8.04 (m, 2H), 7.71-7.69 (m, 1H), 7.63-7.61 (m, 1H), 7.52 (d, J=8.2 Hz, 2H), 7.22 (d, J=8.9 Hz, 2H), 6.55 (br s, 1H), 5.98-5.96 (m, 1H), 5.42 (s, 2H), 5.07 (d, J=12.3 Hz, 1H), 4.98 (d, 1H), 4.75-4.72 (d, J=12.5 Hz, 1H), 4.37-4.32 (m, 2H), 4.16 (t, J=7.7 Hz, 1H), 3.58-3.43 (m, 32H), 3.04-2.93 (m, 4H), 2.69 (t, J=5.6 Hz, 2H), 2.43-2.29 (m, 2H), 1.97-1.92 (m, 3H), 1.83-1.31 (m, 16H), 0.86-0.78 (m, 12H).

Compound 45f: To a suspension of Compound 44f (4 mg, 0.0022 mmol) in $CH_2Cl_2$ (50 µL) was added triisopropylsilane (5 µL) followed by TFA (50 µL). After stirring at ambient temperature for 90 min the reaction was concentrated in vacuo. The residue was diluted with $CH_2Cl_2$ (200 µL) and concentrated. The product was diluted three times more with $CH_2Cl_2$ (200 µL portions), concentrating each time. The resulting yellow foam (compound 44f') was treated with 5% piperidine in DMF (100 µL). After stirring at ambient temperature for 1 h, the reaction was loaded onto a 5.5 g C18 Aq column and eluted with 0-100% MeCN in $H_2O$ with 0.1% TFA in both solvents. Fractions containing pure product were combined and lyophilized to afford the TFA salt of compound 45f (1 mg, 47%) as a white solid. MS (ESI, pos.): calc'd for $C_{63}H_{95}F_2N_{15}O_{15}$, 1339.7; found 1340.5(M+H). $^1$H NMR (500 MHz; DMSO-$d_6$) δ 12.25 (br s, 1H), 10.00 (br s, 1H), 8.48 (dd, J=9.7, 2.8 Hz, 1H), 8.27 (dd, J=2.6, 1.3 Hz, 1H), 8.19 (d, J=2.7 Hz, 1H), 8.14 (d, J=3.4 Hz, 1H), 8.13 (br d, J=7 Hz, 1H), 8.09 (br d, J=7 Hz, 1H), 7.76 (br s, 2H), 7.74 (br d, J=9 Hz, 1H), 7.61 (br d J=7 Hz, 1H), 7.55-7.50 (m, 2H), 7.22 (d, J=8.5 Hz, 2H), 6.05 (br s, 1H), 5.47 (br s, 2H), 5.08 (d, J=12.5 Hz, 1H), 4.99 (d, J=12.3 Hz, 1H), 4.76-4.73 (m, 1H), 4.38-4.33 (m, 2H), 4.21-4.18 (m, 1H), 3.59-3.54 (m, 12H), 3.49 (t, J=10.5 Hz, 30H), 3.10-3.03 (m, 3H), 2.96-2.95 (m, 6H), 2.41-2.34 (m, 2H), 2.00-1.94 (m, 3H), 1.80-1.62 (m, 2H), 1.53-1.28 (m, 6H), 0.85-0.81 (m, 6H).

Example 2: Anti-Hemagglutinin Non-Cytotoxic Antibody Drug Conjugate Synthesis

Anti-hemagglutinin non-cytotoxic antibody drug conjugates were synthesized as described below.

Anti-hemagglutinin (anti-HA) monoclonal antibody mAb 11729 was mutated to introduce a consensus LLQGA pentapeptide sequence at the C-terminus of the heavy and light chain. The mutation allowed the antibodies to be enzymatically conjugated to a maximum loading of 2 on the heavy chains (one on each heavy chain). A non-HA binding mAb (derived from an immunological antigen having no relation to infectious diseases) containing the same consensus sequence at the C-terminus of the heavy chain was used as a non-binding isotype control.

Native mAb11729 and the Isotype Control antibody were deglycosylated using 400 U/mg mAb of PNGaseF (NEB P0704L) in PBS pH 7.4 at 37° C. overnight. Subsequently, the reaction mixture was buffer exchanged to PBS pH 7.4 using spin filters (Amicon, 30 kDa cut-off). This procedure allowed the antibodies to be enzymatically conjugated to a maximum loading of 2 at the Q295 site on the heavy chains.

A second anti-hemagglutinin (N3H2) monoclonal antibody mAb5385 (as described in J Virology 2014, vol 88, 7130-7144) was mutated to introduce a consensus ELQGP pentapeptide sequence at the C-terminus of the heavy chain or GGGGSGELQRP on the C-terminus of the light chain. The mutation allowed the antibodies to be enzymatically conjugated to a maximum loading of two. A non-HA binding mAb (derived from an immunological antigen having no relation to infectious diseases) containing the same consensus sequences at the C-terminus of the heavy chain or C-terminus of the light chain were used as a non-binding isotype control.

Figure 1B:
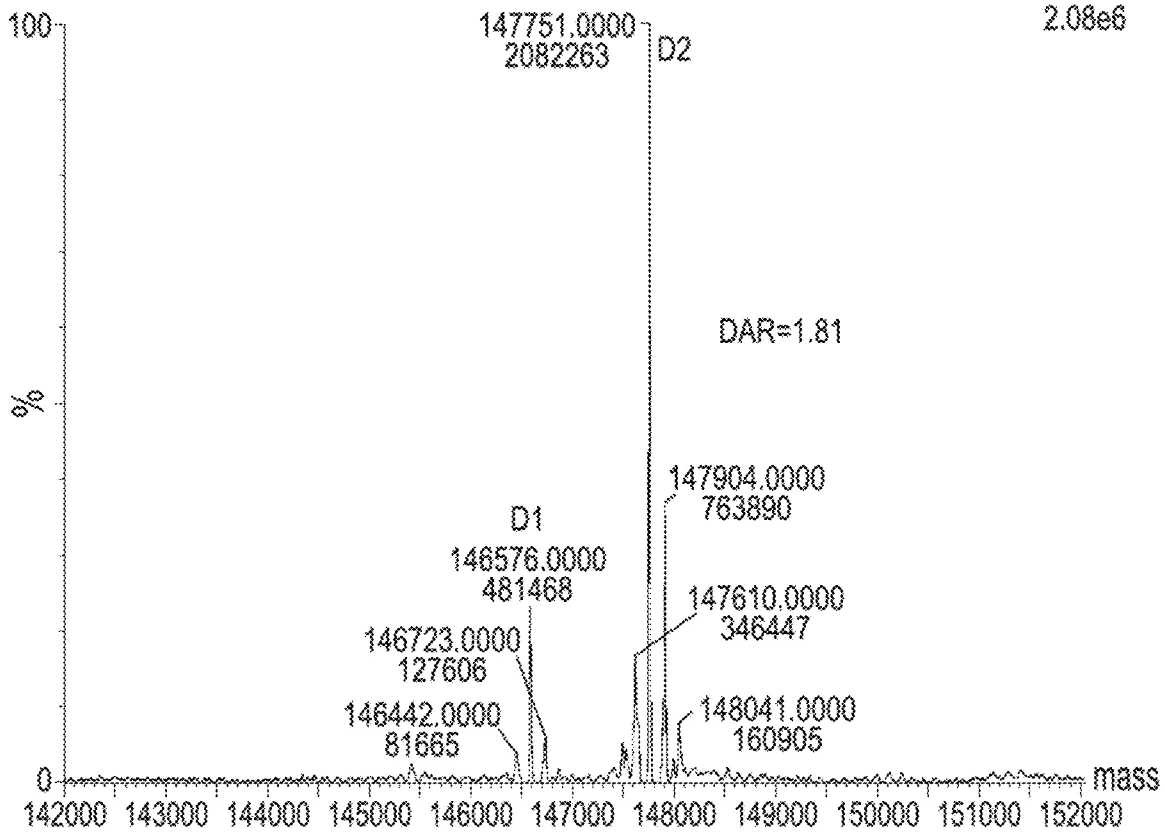
FIG. 1B shows the intensity-weighted average linker-payload (e.g., linker-antiviral compound) loadings as measured by LC-MS for Isotype Control-Q295-11.
Figure 2A:
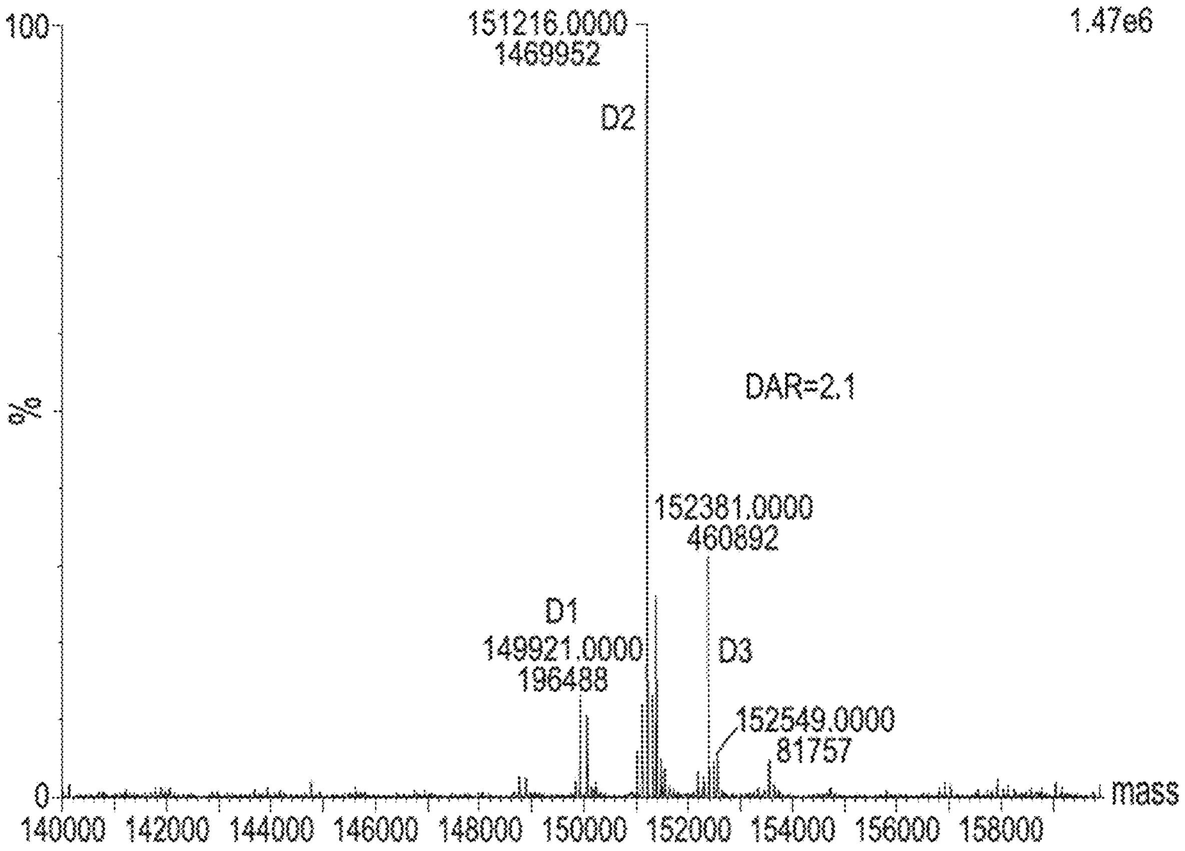
FIG. 2A shows the intensity-weighted average linker-payload (e.g., linker-antiviral compound) loadings as measured by LC-MS for 11729-HC-Cterm-11.
Figure 2B:
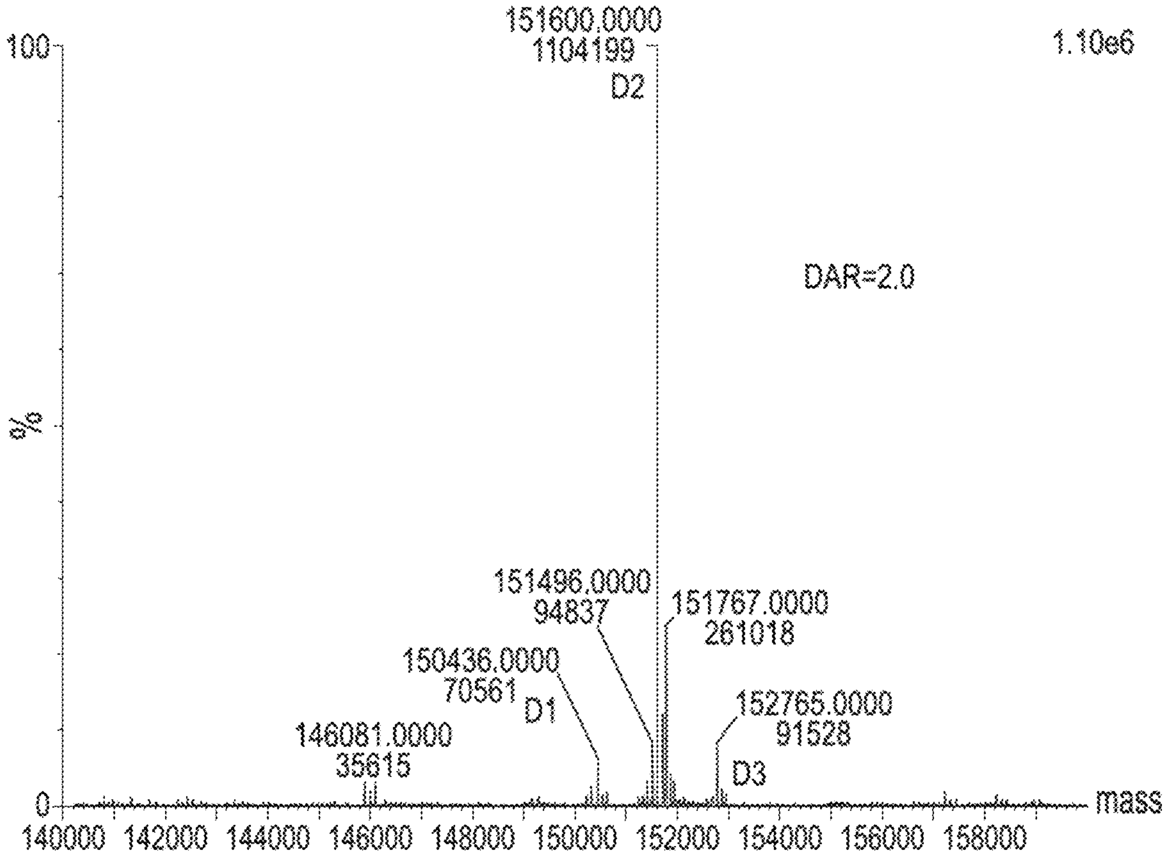
FIG. 2B shows the intensity-weighted average linker-payload (e.g., linker-antiviral compound) loadings as measured by LC-MS for Isotype Control-HC-Cterm-11.

Antibodies with a conjugation site at either the C-terminus of the heavy chain or at the Q295 site were conjugated at 1 mg/mL in PBS pH 7.4. Compound 6 or 11 (both comprising VX-787, but having different linkers) were added in a 10-40 fold molar excess over antibody and the enzymatic reaction was initiated by addition of 14 units of bacterial transglutaminase (Zedira, T1001) per mg antibody and incubated at 37° C. for 16 hours. The conjugates were purified by Protein A chromatography (Pierce Protein A Columns, ThermoScientific, product no. 20356). The conjugates were analyzed by ESI-MS for the determination of the payload:antibody ratio (DAR) using a Waters Acquity UPLC. The chromatographic separation was achieved on a C4 column (2.1×50 mm ACQUITY UPLC BEH protein C4, 1.7 um, 300 A) in a 10 min gradient (minute:percentage of mobile phase B; 0:10%, 1:10%, 5:90%, 7:90%, 7.2:10%, 10:10%). The mobile phase A was 0.1% formic acid in water, and mobile phase B was 0.1% formic acid in acetonitrile. The flow rate was set at 0.3 mL/min. The detector TOF scan was set from m/z 500-4500 with major parameters as listed (Capillary voltage 3.0 kV; Sampling Cone 80V; Source Offset at 100V; Source temperatures 150° C.; Desolvation temperature 450° C.; Cone gas 0 L/hr; Desolvation gas 800 L/hr). The spectra were deconvoluted with MaxEnt function within MassLynx software. The resulting molecular ions, which when weighted according to intensities, corresponded to the loadings listed in Table 3 and 4. The actual mass spec spectra are depicted in FIG. 1 and FIG. 2. Alternatively, to determine the loading of the payloads on the antibody, the conjugates were run on Agilent 1260 using a TSK-NPR Butyl HIC (Hydrophobic Interaction Chromatography) column using a linear gradient of 1M potassium phosphate pH 8.5 to water over 60 min. The payload loading was determined by integration of peak areas corresponding to the species of conjugated and unconjugated antibody. Payload:antibody ratios are reported in Table 5. Size-exclusion HPLC established that all conjugates were >92% monomeric (Table 5). This procedure produced a mAb11729-VX-787 non-cytotoxic antibody-drug conjugate (ncADC) with mAb 11729 conjugated to compound 11 via LLQGA pentapeptide at the antibody heavy chain C-terminus ("11729-HC-Cterm-11"), a mAb 11729-VX-787 ncADC with mAb 11729 conjugated to compound 11 via LLQGA pentapeptide at the antibody heavy chain N-terminus ("11729-HC-Nterm-11"), a mAb 11729-VX-787 ncADC with mAb 11729 conjugated to compound 11 via LLQGA pentapeptide at the antibody light chain C-terminus ("11729-LC-Cterm-11"), a mAb 11729-VX-787 ncADC with mAb 11729 conjugated to compound 11 via LLQGA pentapeptide at the antibody light chain N-terminus ("11729-LC-Nterm-11"), a mAb 11729-VX-787 ncADC with compound 11 conjugated to the Q295 site ("11729-Q295-11"), an Isotype Control antibody with compound 11 conjugated at the heavy chain C-terminus via LLQGA pentapeptide ("Isotype Control-HC-Cterm-11"), an Isotype Control antibody with compound 11 conjugated at the Q295 site ("Isotype Control-Q295-11"), a mAb11729-VX-787 ncADC with compound 6 conjugated to the Q295 site ("11729-Q295-6"), an Isotype Control antibody with compound 6 conjugated at the heavy chain C-terminus via LLQGA pentapeptide ("Isotype Control-HC-Cterm-6"), an Isotype Control antibody with compound 6 conjugated at the Q295 site ("Isotype Control-Q295-6"), a mAb 11729-baloxavir ncADC with compound 15 conjugated at the mAb 11729 heavy chain C-terminus via LLQGA pentapeptide) ("11729-HC-Cterm-15"), and an Isotype Control antibody with compound 15 conjugated at the heavy chain C-terminus ("Isotype Control-HC-Cterm-15").

Native mAb11729 and the Isotype Control antibodies (1-10 mg/mL) in 50 mM HEPES, 150 mM NaCl, pH 7.5, were treated with 1 mM dithiothreitol at 37° C. for 30 min. After gel filtration (G-25, pH 4.5 sodium acetate), the maleimido linker payload derivative compound 18 (1.2 equivalents/SH group) in DMSO (10 mg/ml) was added to the reduced antibody and the mixture adjusted to pH 7.0 with 1 M HEPES (pH 7.4). The conjugates were purified using PBS with 5% glycerol by size exclusion chromatography and sterile filtered. Protein concentrations and payload to antibody ratios were determined by UV spectral analysis. Size-exclusion HPLC established that all conjugates used were >95% monomeric. All conjugated antibodies were analyzed by mass spectroscopy for linker payload loading values. Payload to antibody ratios are reported in Table 6.

Table 3, Table 4, and Table 5 contain the loading data (ESI-MS DAR) for certain conjugates. The transglutaminase conjugated compounds 11 and 15 produced DARs approaching the theoretical value of 2. Table 6 contains a list of purity and DAR values for ncADCs.

TABLE 3

Summary of intensity-weighted average payload loadings in 11729-Q295-11 and Isotype Control-Q295-11.

| 11729-Q295-11 | | | | Isotype Control-Q295-11 | | | |
|---|---|---|---|---|---|---|---|
| Molecular Ion MW (Da) | Corresponding payload loading | Relative intensity | Intensity weighted average loading (DAR) | Molecular Ion MW (DA) | Corresponding payload loading | Relative intensity | Intensity weighted average loading (DAR) |
| 146213 | 1 | 1189372 | 1.8 | 146576 | 1 | 481468 | 1.8 |
| 147389 | 2 | 4359378 | | 147751 | 2 | 2082263 | |

TABLE 4

Summary of intensity-weighted average payload loadings in 11729-HC-Cterm-11 and Isotype Control-HC-Cterm-11.

| 11729-HC-Cterm-11 | | | | Control Isotype-HC-Cterm-11 | | | |
|---|---|---|---|---|---|---|---|
| Molecular Ion MW (Da) | Corresponding payload loading | Relative intensity | Intensity weighted average loading (DAR) | Molecular Ion MW (DA) | Corresponding payload loading | Relative intensity | Intensity weighted average loading (DAR) |
| 149921 | 1 | 149921 | 2.1 | 150436 | 1 | 70561 | 2.0 |
| 151216 | 2 | 1469952 | | 151600 | 2 | 1104199 | |
| 152381 | 3 | 460892 | | 152765 | 3 | 91528 | |

TABLE 5

Summary of intensity-weighted average payload loadings in 11729-HC-Cterm-15 and Isotype Control-HC-Cterm-15.

| 11729-HC-Cterm-15 | | | | Control Isotype-HC-Cterm-15 | | | |
|---|---|---|---|---|---|---|---|
| Molecular Ion MW (Da) | Corresponding payload loading | Relative intensity | Intensity weighted average loading (DAR) | Molecular Ion MW (DA) | Corresponding payload loading | Relative intensity | Intensity weighted average loading (DAR) |
| 150062 | 1 | 66018 | 1.9 | 150206 | 1 | 160152 | 1.9 |
| 151013 | 2 | 217666 | | 151146 | 2 | 265624 | |
| 151952 | 3 | 38052 | | 152088 | 3 | 99316 | |

TABLE 6

Purity (by SEC) and DAR of Compound 6, 11, and 15 conjugates.

| Antibody Drug Conjugate | Drag to Antibody Ratio (DAR, ESI-MS) | Drag to Antibody Ratio (DAR, HIC) | Purity (by SEC) |
|---|---|---|---|
| 11729-Q295-6 | — | 0.7 | >95% |
| Isotype Control-Q295-6 | — | 1.1 | >95% |
| 11729-Q295-11 | 1.8 | — | 92.6% |
| Isotype Control-Q295-11 | 1.8 | — | 96.4% |
| 11729-HC-Cterm-11 | 2.1 | — | 95.8% |
| Isotype Control-HC-Cterm-11 | 2.0 | — | 97.1% |
| 11729-HC-Cterm-15 | 1.9 | — | 97.8% |
| Isotype Control-HC-Cterm-15 | 1.9 | — | 94.7% |
| 11729-18 | 6.1 | — | 98% |
| Isotype Control-18 | 7.5 | — | 97% |
| 11729-HC-Cterm-34 | 2.1 | — | 97% |

TABLE 6-continued

Purity (by SEC) and DAR of Compound 6, 11, and 15 conjugates.

| Antibody Drug Conjugate | Drag to Antibody Ratio (DAR, ESI-MS) | Drag to Antibody Ratio (DAR, HIC) | Purity (by SEC) |
|---|---|---|---|
| Isotype Control-HC-Cterm-34 | 1.3 | — | 99% |
| 11729-HC-Cterm-39 | 1.5 | — | 98% |
| Isotype Control-HC-Cterm-39 | 1.0 | — | 98% |
| 11729-HC-Cterm-45a | 1.4 | — | 98% |
| Isotype Control-HC-Cterm-45a | 1.7 | — | 94% |
| 11729-HC-Cterm-45b | 1.4 | — | 96% |
| Isotype Control-HC-Cterm-45b | 1.4 | — | 95% |
| 11729-HC-Cterm-45c | 1.4 | — | 99% |
| Isotype Control-HC-Cterm-45c | 2.0 | — | 95% |
| 11729-HC-Cterm-45d | 1.1 | — | 96% |
| Isotype Control-HC-Cterm-45d | 1.0 | — | 95% |

TABLE 6-continued

Purity (by SEC) and DAR of Compound 6, 11, and 15 conjugates.

| Antibody Drug Conjugate | Drag to Antibody Ratio (DAR, ESI-MS) | Drag to Antibody Ratio (DAR, HIC) | Purity (by SEC) |
|---|---|---|---|
| F005-126-HC-Cterm-11 | 1.6 | — | >97% |
| Isotype Control-HC-Cterm-11 | 1.7 | — | >95% |
| F005-126-LC-Cterm-11 | 1.6 | — | >98% |
| Isotype Control-LC-Cterm-11 | 1.7 | — | >98% |

Example 3: Anti-HA Infected Cell Binding ELISA and Drug Antiviral Efficacy Assay MDCK London cells were seeded at 40,000 cells/well in 50 μL of infection media (DMEM (Life Technologies) containing 1% sodium pyruvate (Life Technologies), 0.21% Low IgG BSA solution (Sigma Aldrich), and 0.5% Gentamicin (Life Technologies)) in a 96-well plate. The cells were incubated at 37° C. with 5% $CO_2$ for four hours. Plates were then infected with 50 L of H1N1 A/Puerto Rico/08/1934 influenza virus at an MOI of 1.2, tapped gently, and placed back at 37° C. with 5% $CO_2$ for 20 hours. Subsequently, plates were washed once with phosphate-buffered saline (PBS, Life Technologies) and fixed with 200 μL of 4% paraformaldehyde (PFA, Alfa Aesar) in PBS and incubated for 15 minutes at room temperature. Plates were washed three times with PBS and blocked with 300 μL of StartingBlock Blocking Buffer (ThermoFisher) for one hour at room temperature. Control antibodies were tested against 11729-HC-Cterm-11, 11729-HC-Nterm-11, 11729-LC-Cterm-11, and 11729-LC-Nterm-11. The control antibodies used were unconjugated mAb111729, an unconjugated Isotype Control antibody, Isotype Control-HC-Cterm-6, Isotype Control -LC -Cterm-6, Isotype Control-HC-Cterm-45a, Isotype Control-LC-Cterm-45a, Isotype Control-HC-Cterm-34, Isotype Control-LC-Cterm-34, Isotype Control-HC-Cterm-45d, and Isotype Control-HC-Cterm-11.

The antibodies were diluted to a starting concentration of 100 μg/mL in StartingBlock Blocking Buffer and each was titrated 1:4 to a final concentration of $6.1\times10^{-3}$ μg/mL. After the plates had been incubated, the StartingBlock Blocking Buffer was removed and the diluted antibodies were added onto cells at 75 μL/well. The plates were incubated for one hour at room temperature. Following incubation, the plates were washed three times with Wash Buffer (imidazole-buffered saline and Tween® 20 diluted to 1× in Milli-Q water; KPL) and overlayed with 75 μL/well of secondary antibody (Donkey anti-Human IgG HRP-conjugated; Jackson ImmunoResearch) diluted 1:2000 in StartingBlock Blocking Buffer. This secondary solution was incubated on the plates for one hour at room temperature. Subsequently, plates were washed three times with Wash Buffer, followed by the addition of 75 μL/well of ELISA Pico Chemiluminescent Substrate in a 1:1 preparation. The plates were read immediately for luminescence on a Molecular Devices Spectramax i3x plate reader.

Figure 3:
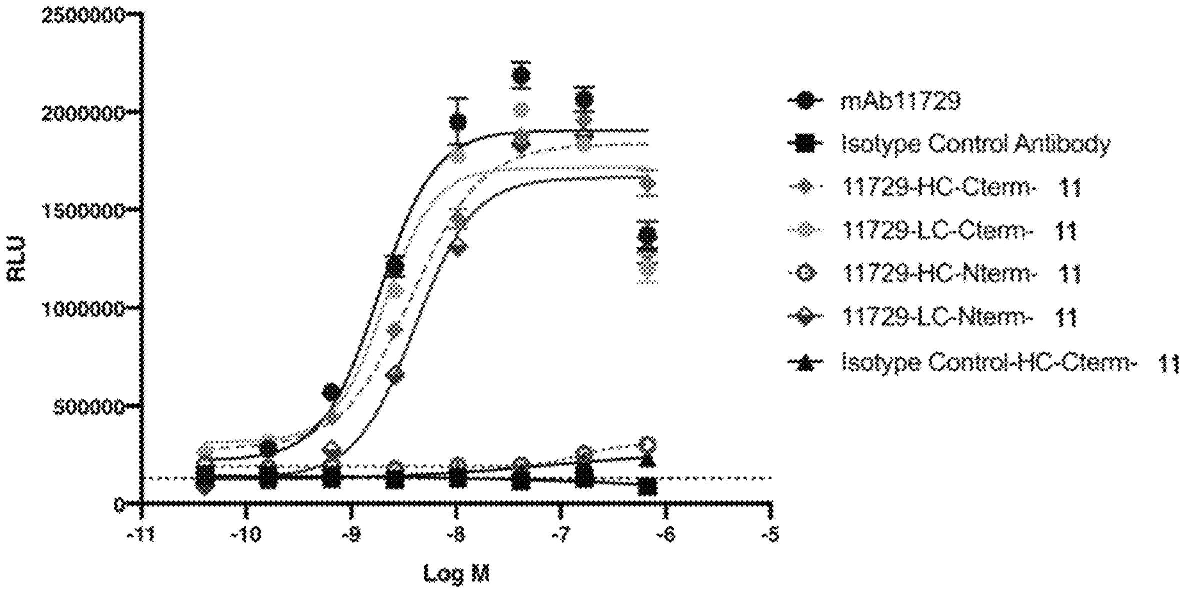
FIG. 3 shows ELISA sub-nanomolar specific binding of 11729-HC-Cterm-11, 11729-HC-Nterm-11, 11729-LC-Cterm-11, and 11729-LC-Nterm-11 to influenza A-infected cells.
Figure 11:
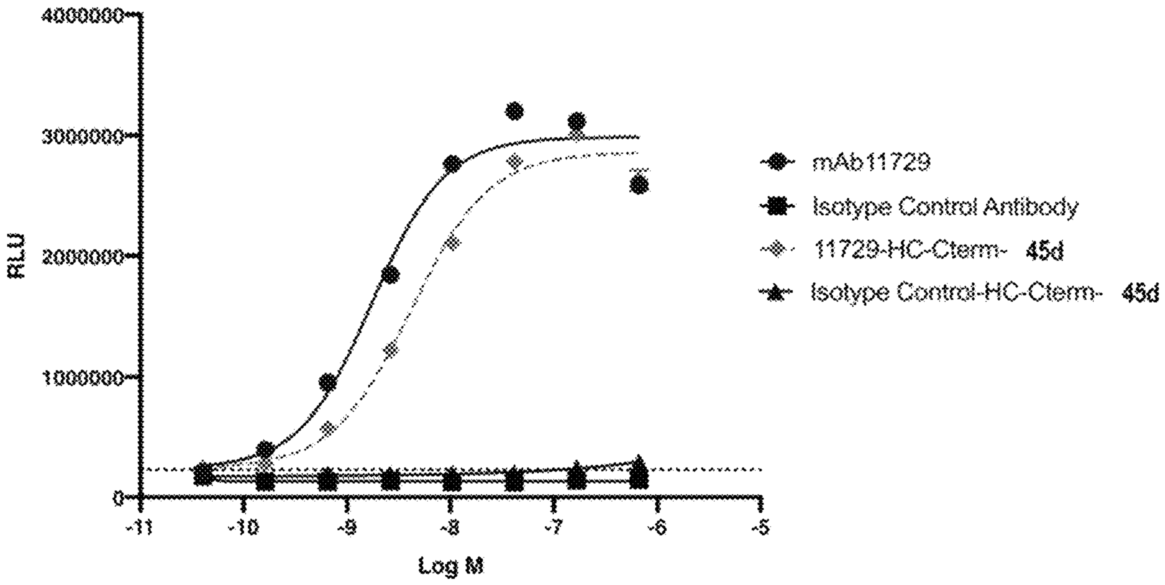
FIG. 11 shows specific binding of 11729-HC-Cterm-45d to influenza A-infected cells.

11729-HC-Cterm-11, 11729-LC-Cterm-11, and 11729-LC-Nterm-11 bound to influenza A-infected cells at sub-nanomolar concentrations, demonstrating specific binding, as shown in Table 7 and FIG. 3. Notably, this specific binding was in the same range as the unconjugated mAb 11729 antibody, indicating that addition of the payload did not have an overly deleterious effect on binding. Conjugation of the linker-payload to the N-terminus of the heavy chain resulted in reduced binding to influenza A/H1N1/PR8-infected cells, but conjugation of linker-payload to the C-terminus of the heavy chain retained binding to influenza A/H1N1/PR8-infected cells, as shown in FIG. 11.

TABLE 7

Influenza A-infected cell anti-HA binding ELISA

| Antibody | $IC_{50}$ log[M] |
|---|---|
| Unconjugated Isotype Control antibody | No Binding Detected |
| mAb11729 | $1.817 \times 10^{-9}$ |
| Isotype Control-HC-Cterm-11 | No Binding Detected |
| 11729-HC-Cterm-11 | $3.756 \times 10^{-9}$ |

To test antiviral efficacy, 11729-HC-Cterm-11 was assayed for its ability to suppress the infection of cells by influenza virus. MDCK London cells were seeded at 20,000 cells/well in 100 μL of growth media (DMEM containing 1% sodium pyruvate, 10% Fetal Bovine Serum and 0.5% Gentamicin) in a 96-well plate. The cells were incubated at 37° C. and 5% $CO_2$ for 18 hours. The following day, all antibodies were diluted to a started concentration of 500 μg/mL in Trypsin infection media (DMEM containing 1% sodium pyruvate, 0.21% Low IgGBSA solution, 1 mg/mL Trypsin TPCK-Treated and 0.5% Gentamicin) and titrated 1:3 to a final concentration of $1.143\times10^{-1}$ μg/mL. H1N1 A/Puerto Rico/08/1934 influenza virus that was engineered to express GFP in cells that it infects ("H1N1 A/Puerto Rico/08/1934-GFP") was diluted to an MOI of one in Trypsin infection media (Life Technologies) and mixed 1:1 with diluted antibody or ADC. Growth Media was removed from seeded 96-well plates and virus-antibody or virus-ADC mixture was added onto cells at 100 μL per well. Plates were lightly tapped and returned to 37° C. 5% $CO_2$ for 20 hours. Subsequently, plates were washed once with PBS and fixed with 50 μL of 4% PFA in PBS and incubated for 15 minutes at room temperature. Plates were washed twice with PBS and overlayed with 50 μL of PBS. Plates were read immediately for GFP signal on an ImmunoSpot analyzer (Cellular Technology Limited).

Figure 4:
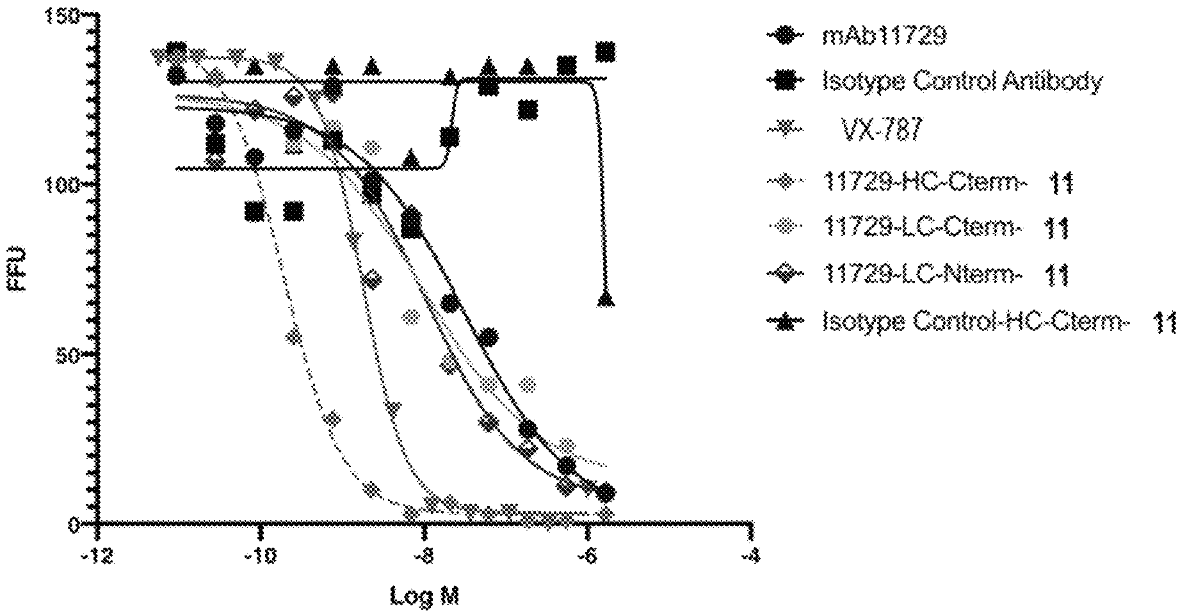
FIG. 4 shows comparative antiviral efficacy against influenza A infection between 11729-HC-Cterm-11, 11729-LC-Cterm-11, 11729-LC-Nterm-11, mAb11729, and an isotype control antibody and Isotype Control-HC-Cterm-11.
Figure 6:
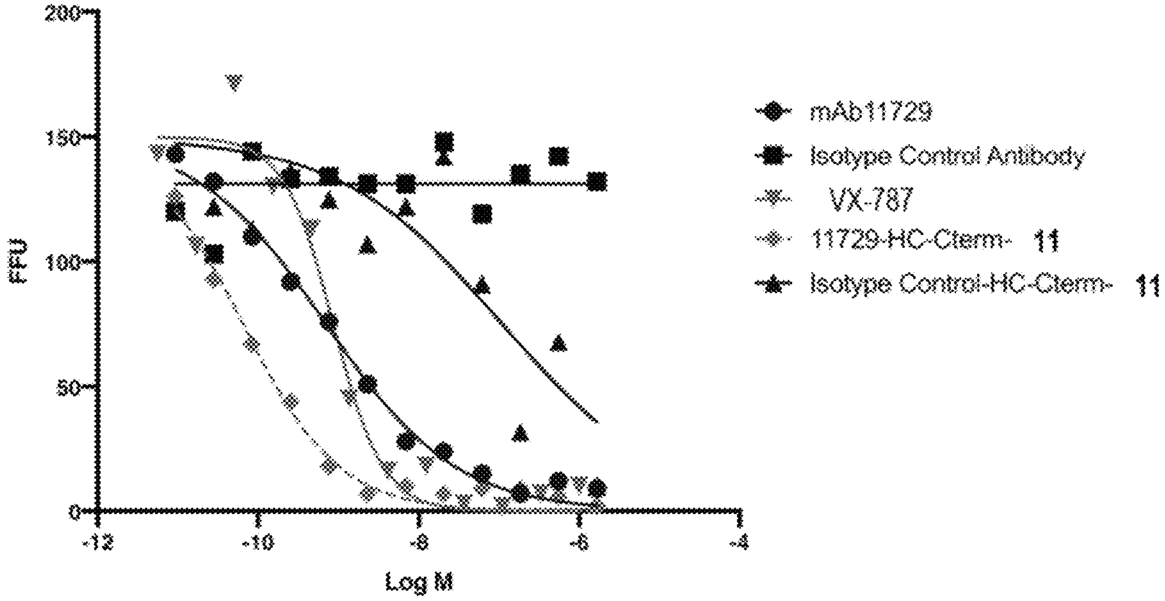
FIG. 6 shows comparative antiviral efficacy against influenza A infection between 11729-HC-Cterm-11 and an isotype control antibody and Isotype Control-HC-Cterm-11.
Figure 7:
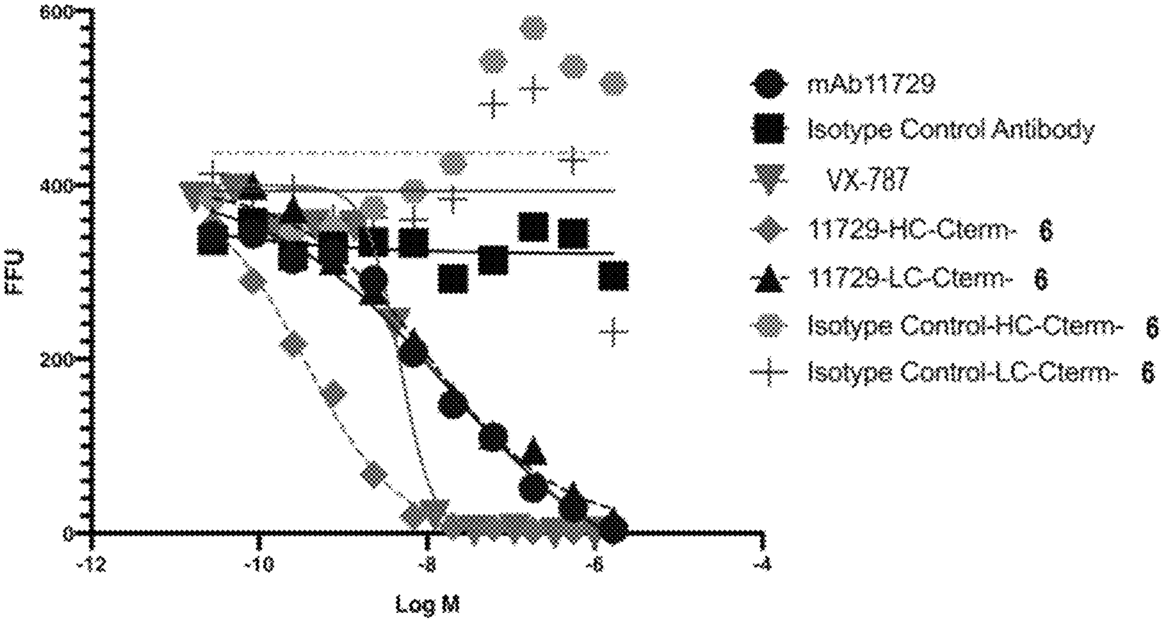
FIG. 7 shows comparative antiviral efficacy against influenza A infection between 11729-HC-Cterm-6, 11729-LC-Cterm-6, mAb11729, and an isotype control antibody, an Isotype Control-HC-Cterm-6 antibody, and an Isotype Control-LC-Cter-6 antibody.
Figure 8:
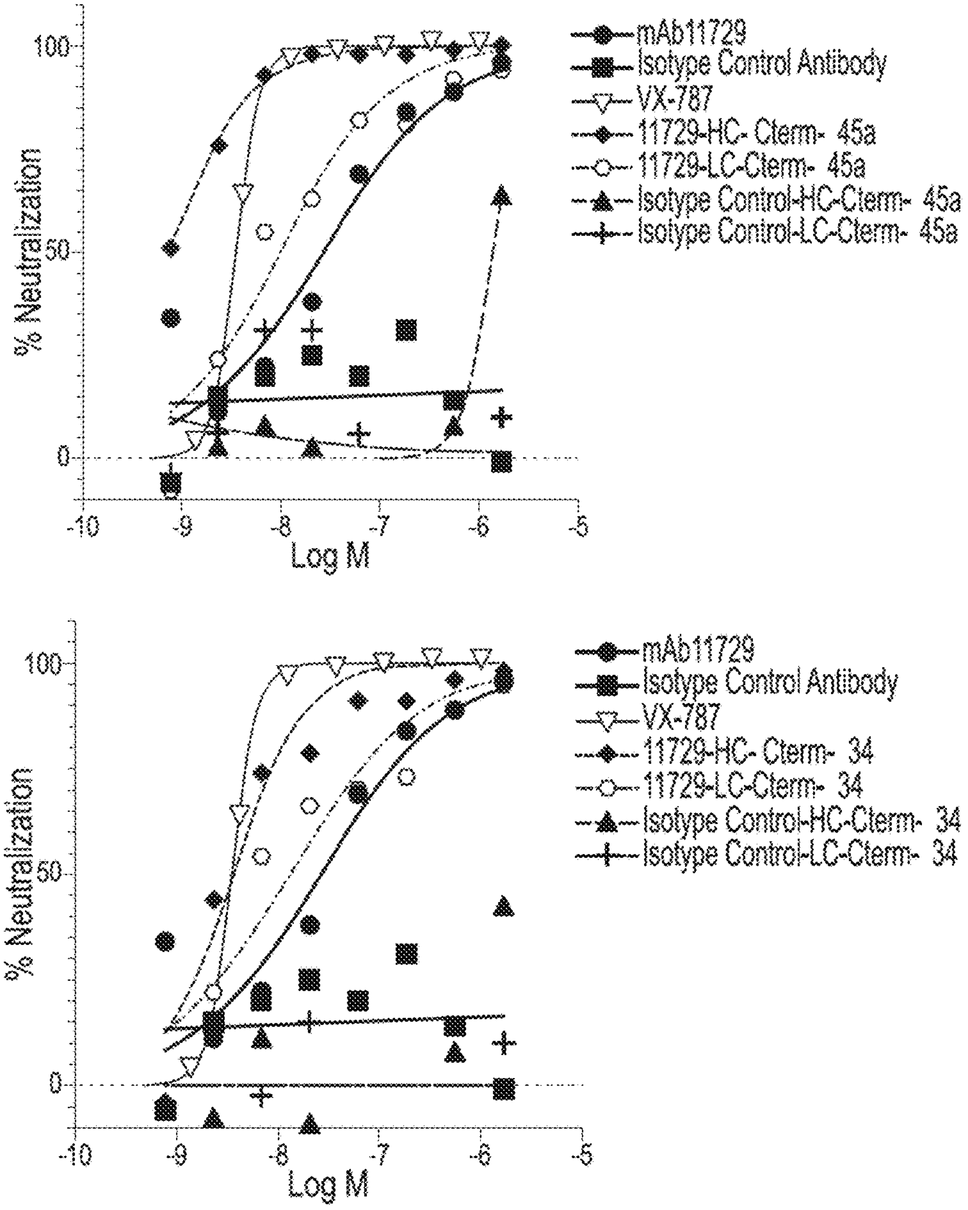
FIG. 8 shows comparative antiviral efficacy against influenza A infection between 11729-HC-Cterm-45a, 11729-LC-Cterm-45a, 11729-HC-Cterm-34, 11729-LC-Cterm-34, mAb11729, and an isotype control antibody and isotype control-antibody-drug conjugates.
Figure 9:
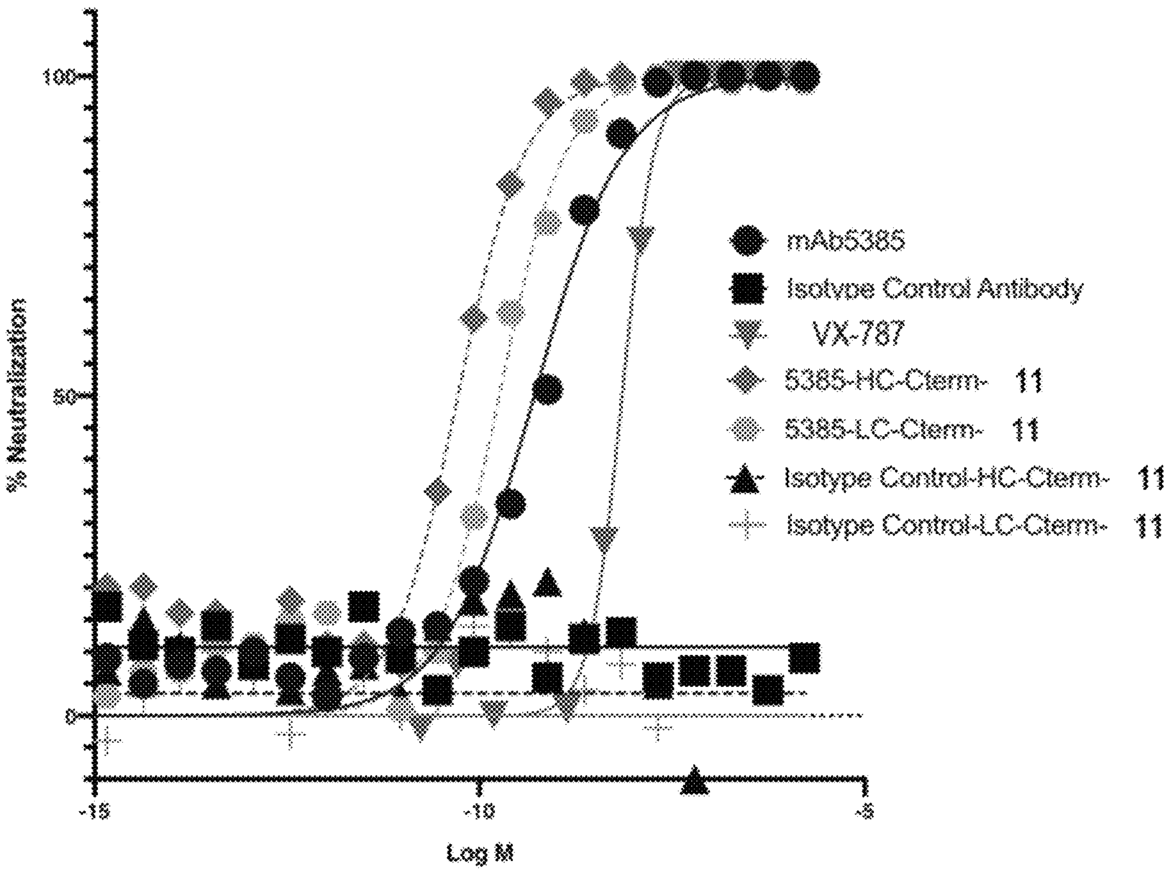
FIG. 9 shows comparative antiviral efficacy against influenza A infection between 5385-HC-Cterm-11, 5385-LC-Cterm-11, mAb11729, and an isotype control antibody and isotype control-antibody-drug conjugates.
Figure 10:
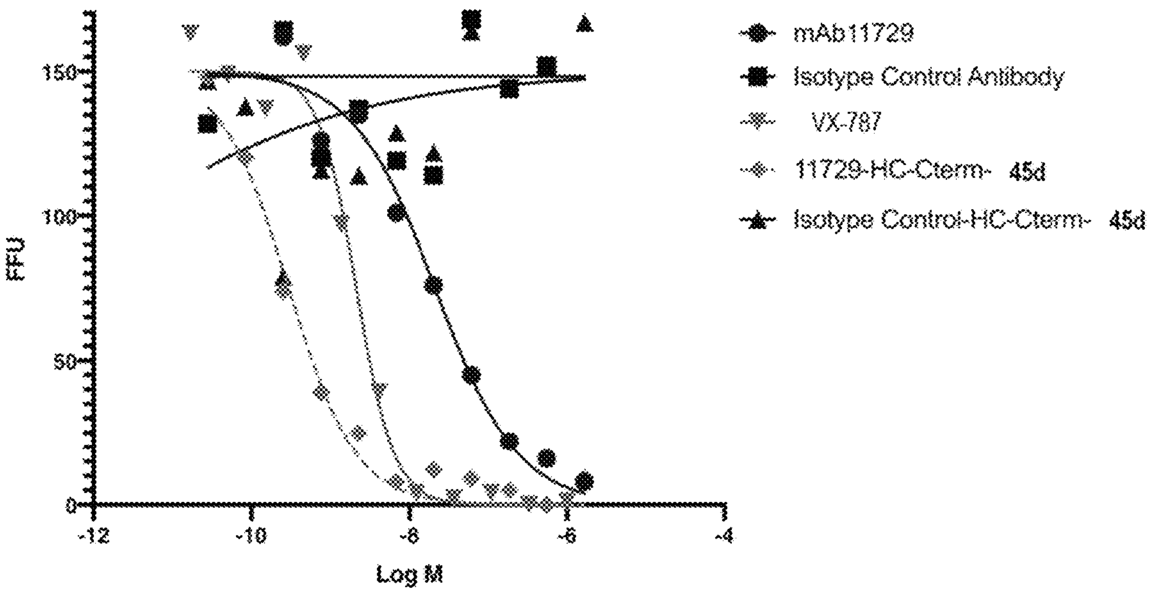
FIG. 10 shows comparative antiviral efficacy against influenza A infection between 11729-HC-Cterm-45d, mAb11729, an isotype control antibody and Isotype Control-HC-Cterm-45d.

Conjugation of linker-payload 11 to the C-terminus of the heavy chain and light chain and the N-terminus of the light chain enhanced antivital activity of antibody-drug conjugates over the parental antibody against influenza A/H1N1/Pr8 virus by 3- to 163-fold, as shown in Table 8 and FIG. 4. Conjugation of the linker-payload 11 to the C-terminus of the heavy chain increased antiviral activity of antibody-drug conjugates over the parental antibody against influenza A/H1N1/Cal09 virus by 10-fold, as shown in Table 9 and FIG. 6. Conjugation of the linker-payload 6 to the C-terminus of the heavy chain increased antiviral activity of the antibody-drug conjugates over the parental antibody against influenza A/H1N1/PR8 by 51-fold; however, conjugation of 6 to the C-terminus of the light chain did not increase antiviral activity over the parental antibody, as shown in Table 8 and FIG. 7. Conjugation of linker-payloads to the C-terminus of the heavy chain increased antiviral activity of antibody-drug conjugates over the parental antibody against influenza A/H1N1/PR8 virus by 7-fold for 11729-HC-Cterm-34 and by 35-fold for 1129-HC-Cterm-45a, but conjugation of linker-payloads to the C-terminus of the light chain did not increase antiviral activity over the parental antibody, as shown in Table 8 and FIG. 8. Conjugation of the linker-payloads to the C-terminus of the light chain and heavy increased antiviral activity of the antibody-drug conjugates over parental antibody against influenza A/H3N2/HK68X31 virus by 3- to 10-fold, as shown in Table 9 and FIG. 9. Conjugation of linker-payload to the C-terminus of the heavy chain increased viral activity of antibody-drug conjugates over parental antibody against influenza A/H1N1/PR8 by 71-fold, as shown in Table 8 and FIG. 10.

TABLE 8

Antiviral activity of antibodies against influenza A/H1N1/PR8 virus

| Antibody | $IC_{50}$ log[M] | Fold increase over parental antibody |
|---|---|---|
| Run 1 | | |
| Isotype Control antibody | No efficacy detected | N/A |
| mAb11729 | $3.136 \times 10^{-8}$ | 1.00 |
| Isotype Control-HC-Cterm-11 | No efficacy detected | N/A |
| 11729-HC-Cterm-11 | $1.914 \times 10^{-10}$ | 163.85 |
| 11729-LC-Cterm-11 | $9.457 \times 10^{-9}$ | 3.32 |
| 11279-HC-Nterm-11 | Lost binding | N/A |
| 11729-LC-Nterm-11 | $1.027 \times 10^{-8}$ | 3.05 |
| Run 2 | | |
| mAb11729 | $1.773 \times 10^{-8}$ | 1.00 |
| 11729-HC-Cterm-6 | $3.471 \times 10^{-10}$ | 51.08 |
| 11729-LC-Cterm-6 | $1.028 \times 10^{-8}$ | 1.72 |
| Isotype Control-HC-Cterm-6 | No efficacy detected | N/A |
| Isotype Control-LC-Cterm-6 | No efficacy detected | N/A |
| Run 3 | | |
| mAb11729 | $2.623 \times 10^{-8}$ | 1.00 |
| 11729-HC-Cterm-45a | $7.439 \times 10^{-10}$ | 35.26 |
| 11729-LC-Cterm-45a | $9.91 \times 10^{-9}$ | 0.08 |
| Isotype Control-HC-Cterm-45a | No efficacy detected | N/A |
| Isotype Control-LC-Cterm-45a | No efficacy detected | N/A |
| 11729-HC-Cterm-34 | $3.629 \times 10^{-9}$ | 7.23 |
| 11729-LC-Nterm-34 | $1.305 \times 10^{-8}$ | 2.01 |
| Isotype Control-HC-Cterm-34 | No efficacy detected | N/A |
| Isotype Control-LC-Cterm-34 | No efficacy detected | N/A |
| Run 4 | | |
| mAb11729 | $2.141 \times 10^{-8}$ | 1.00 |
| 11729-HC-Cterm-45d | $2.984 \times 10^{-10}$ | 71.75 |
| Isotype Control-HC-Cterm-45d | No efficacy detected | N/A |
| Isotype Control antibody | No efficacy detected | N/A |
| VX-787 | $9.457 \times 10^{-9}$ | 3.32 |

TABLE 9

Antiviral activity of antibodies against influenza A/H1N1/Cal09 virus

| Antibody | $IC_{50}$ log[M] | Fold increase over parental antibody |
|---|---|---|
| mAb11729 | $7.022 \times 10^{-10}$ | 1.00 |
| 11729-HC-Cterm-11 | $6.528 \times 10^{-11}$ | 10.76 |
| Isotype Control-HC-Cterm-11 | No efficacy detected | N/A |

TABLE 10

Antiviral activity of antibodies against influenza A/H3N2/HK68x31 virus

| Antibody | $IC_{50}$ log[M] | Fold increase over parental antibody |
|---|---|---|
| mAb5385 | $5.15 \times 10^{-10}$ | 1.00 |
| 5385-HC-Cterm-11 | $5.262 \times 10^{-11}$ | 9.78 |
| 5385-LC-Cterm-11 | $1.802 \times 10^{-10}$ | 2.86 |
| Isotype Control-HC-Cterm-11 | No efficacy detected | N/A |
| Isotype Control-LC-Cterm-11 | No efficacy detected | N/A |
| Iotype Control antibody | No efficacy detected | N/A |
| VX-787 | $7.045 \times 10^{-9}$ | N/A |

Example 4: In Vitro Plasma Stability of Anti-influenza HA mAb11729 Antibody-drug Conjugate in Monkey or IgG-depleted Human Plasma 11729-HC-Cterm-11 was incubated in vitro with plasma from different species and the DAR was evaluated.

The ncADC sample was added to fresh pooled cynomologus monkey plasma (BioReclamation, Lot CYN260056-CYN260057), or IgG-depleted human plasma (BioIVT, lot #BRH1097869), independently, to a final concentration of 50 μg/mL in Eppendorf tubes (Eppendorf, Cat #022363514), and subsequently incubated at 37° C. in a water bath for 0-72 hours. Samples were removed at time 0, 24, 48, and 72 hours, and were then stored frozen at −80° C. until analysis.

For DAR analysis, ncADC was purified from plasma samples by affinity capture using a DynaMag-2 magnetic particle processor (Life Technologies, Cat #12321D). First, biotinylated anti-human kappa antibody (Regeneron-generated reagent) was immobilized on streptavidin paramagnetic beads (Invitrogen, Cat #605602). Each plasma sample containing the ncADC was mixed at 1850 rpm with 1 mg of the beads at room temperature for 2 hours in a ThermoMixer C unit (Eppendorf, Catalog No. 2231000574). The beads were then washed three times with 600 μL of 50 mM Tris-HCl pH 7.5 buffer (diluted from 1M Tris-HCl pH 7.5 buffer, Invitrogen, Cat #15567-027) and then once with 600 μL of 10% acetonitrile (VWR Chemicals, Cat #BDH83640.100E) in water. Following the washes, the ncADC were eluted by incubating the beads with 50 μL of 1% formic acid in 25:75 acetonitrile:water (v/v) for 15 minutes at room temperature. The eluted samples were further reduced by adding 2 μL of 0.5 M TCEP (Sigma, Cat 646547-10X1ML) to each sample (19.2 mM TCEP in final solution) and incubated at 50° C. for 30 min in a ThermoMixer C unit.

The reduced ncADC samples were injected onto a 1.7 m BEH300 C4 column (Waters Corporation, Cat #186007567) coupled to a Synapt G2-Si Mass Spectrometer (Waters). The flow rate was 8 μL/min (mobile phase A: 0.1% formic acid in water; mobile phase B: 0.1% formic acid in acetonitrile), and the liquid chromatographic gradient was a 10-minute gradient with ncADC eluted during 2.1-6.5 minutes, corresponding to 26-40% of mobile phase B.

The acquired spectra were deconvoluted using MaxEntl software (Waters Corporation) with the following parameters: Mass range: 20-60 kDa m/z range: 700 Da-4000 Da; Resolution: 1.0 Da/channel; Width at half height: 1.0 Da; Minimum intensity ratios: 33%; Iteration max: 15.

Figure 5:
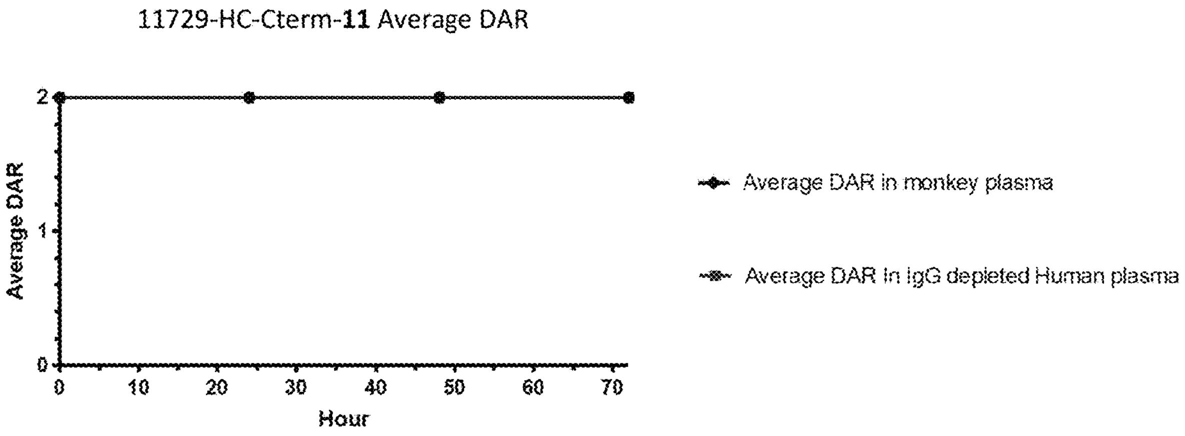
FIG. 5 shows in vitro stability (i.e., the absence of linker-payload (e.g., linker-antiviral compound) loss; or lack of DAR reduction) of 11729-HC-Cterm-11 in human plasma and monkey plasma after 72 hours.

No significant loss of linker-payloads was observed from the ncADC after the 72-hour incubation with cynomolgus monkey or IgG depleted human plasma (FIG. 5).

What is claimed is:

1. A compound selected from the group consisting of:

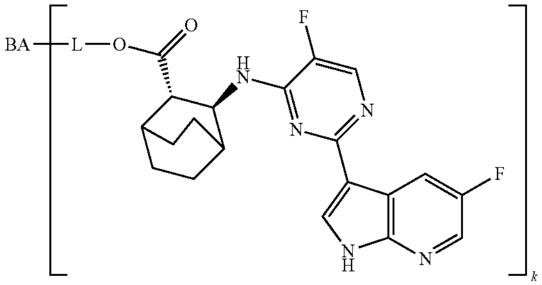

or

-continued

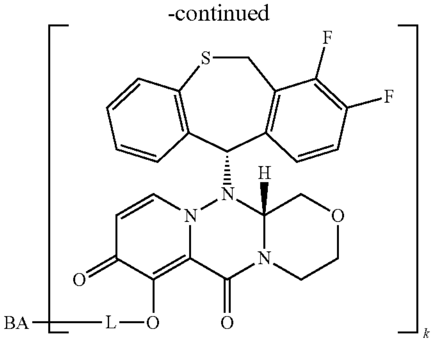

wherein:

L is a linker;

BA is a binding agent, wherein the binding agent is an antibody or an antigen binding fragment thereof; and k is an integer from one to thirty.

2. The compound of claim 1, selected from the group consisting of:
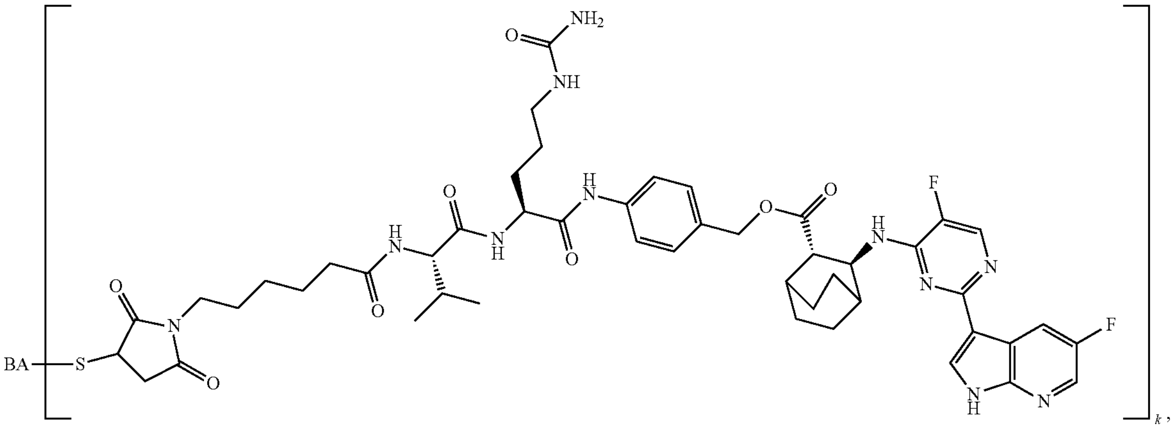
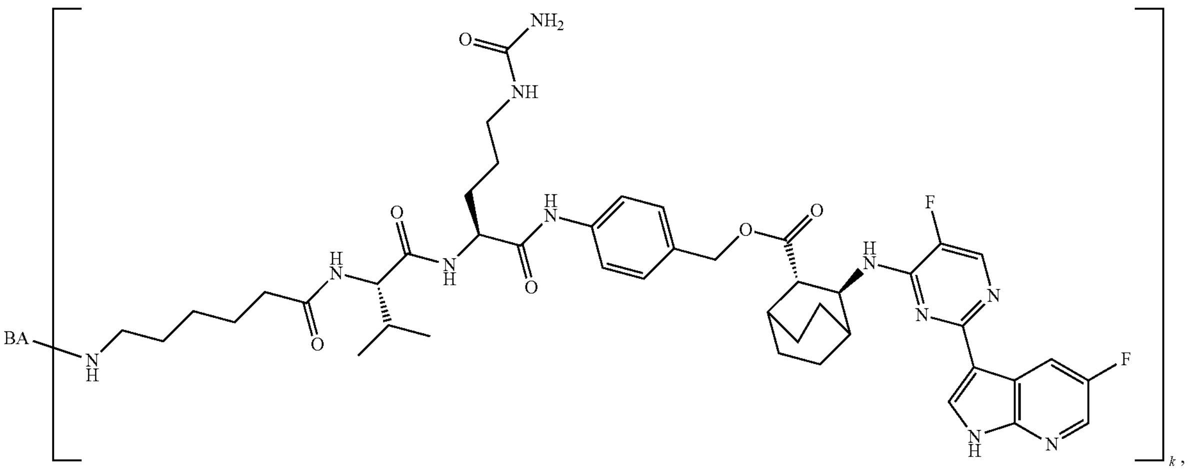
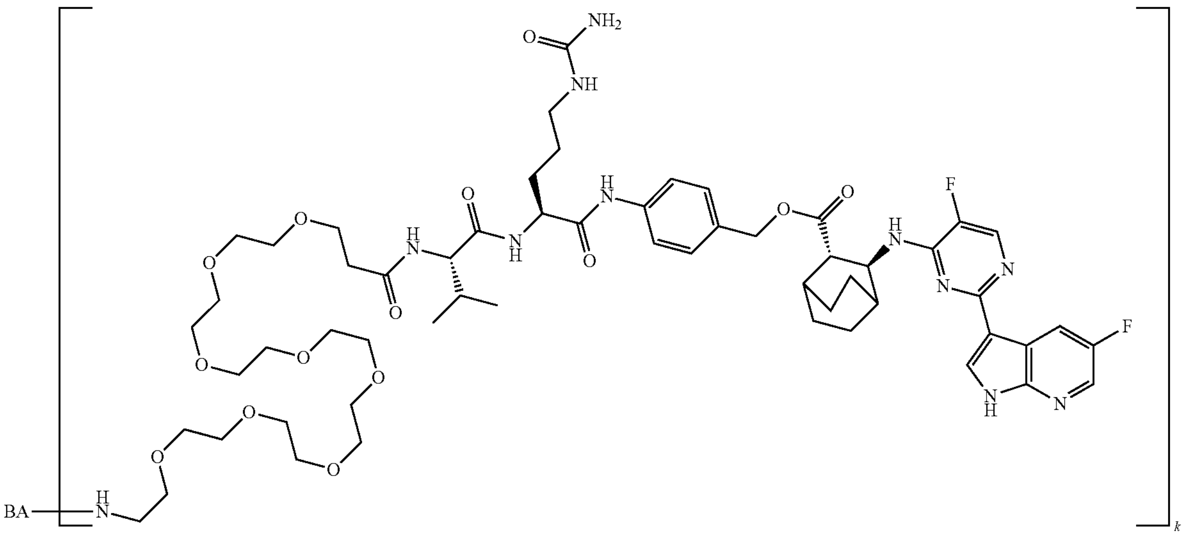

-continued

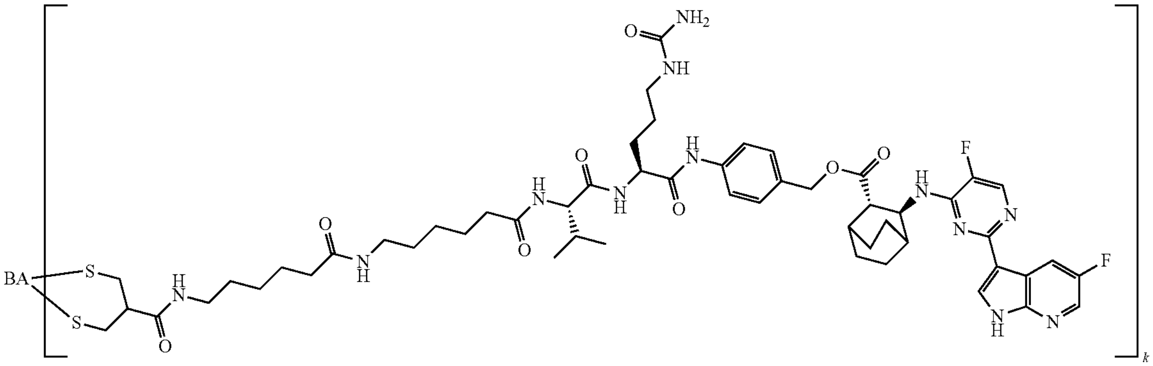

, and

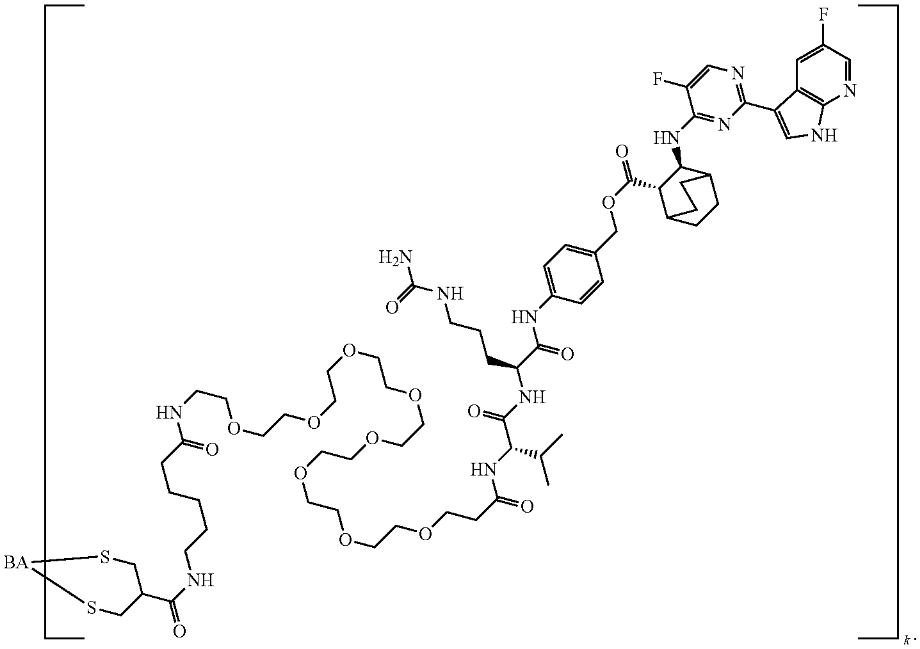

.

3. The compound of claim 1, wherein BA is mAb11729.

4. A pharmaceutical composition comprising the compound of claim 1, and a pharmaceutically acceptable excipient, carrier, or diluent.

5. A method for treatment, prophylaxis, reduction, or inhibition of a disease, disorder, or condition associated with an infection in a subject, comprising administering to the subject an effective amount of the compound of claim 1.

6. A method for treatment, prophylaxis, reduction, or inhibition of an influenza infection in a subject comprising administering to the subject an effective amount of the compound of claim 1.

7. A linker-payload compound selected from:

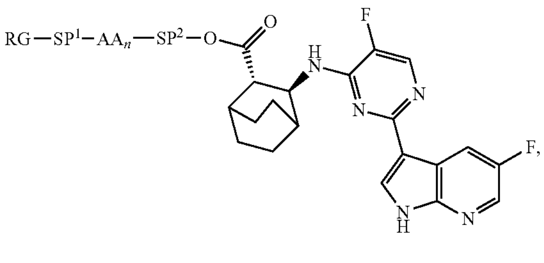

-continued

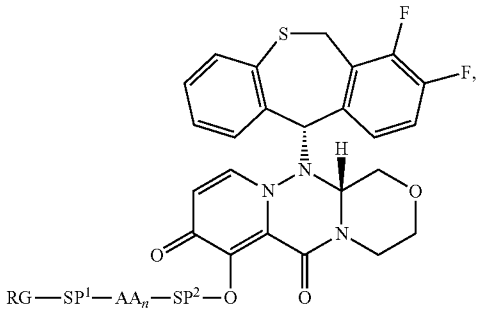

or a pharmaceutically acceptable salt thereof;

wherein:

$SP^1$ and $SP^2$, when present, are spacer groups;

RG is a reactive moiety that binds to an antibody or antigen binding fragment thereof:

each AA is an amino acid; and n is an integer from one to ten.

8. The linker-antiviral compound of claim 7, selected from the group consisting of:
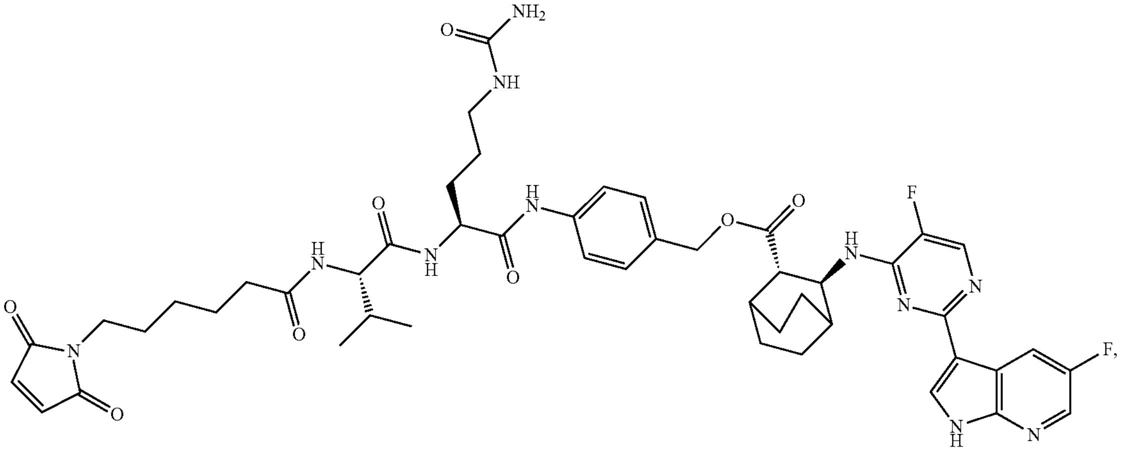
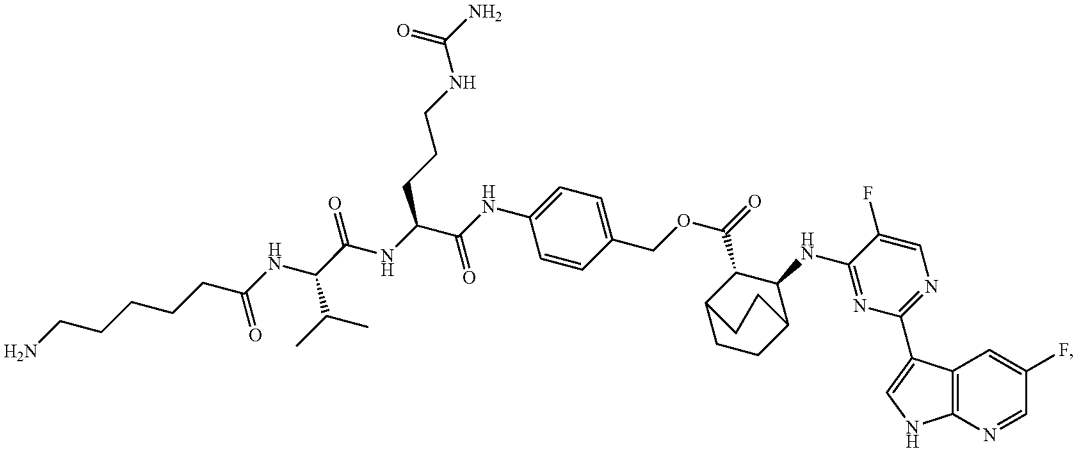
and
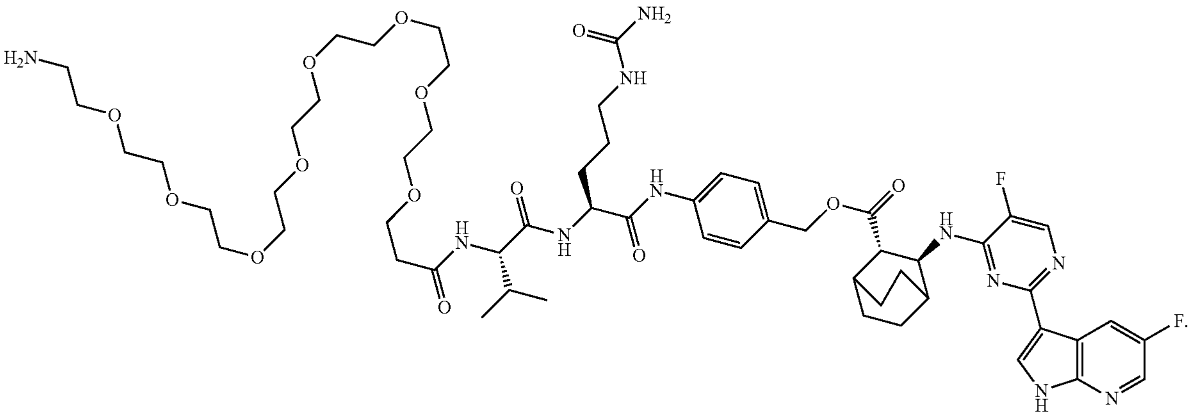

9. An antibody-drug conjugate comprising an antibody, or an antigen binding fragment thereof, where the antibody or antigen binding fragment thereof is conjugated to the linker-payload compound of claim 7.

10. The antibody-drug conjugate of claim 9, wherein the conjugated compound is selected from:

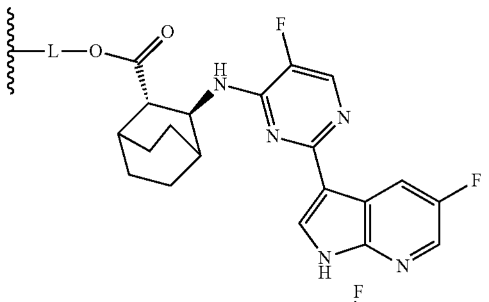

or

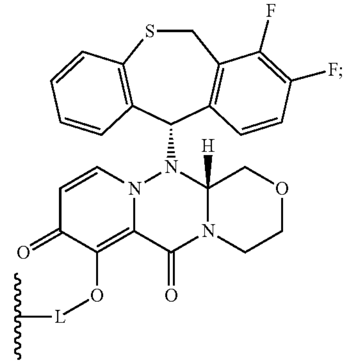

wherein:

L is a linker.

11. A method of preparing an antibody-drug conjugate comprising contacting a binding agent with a linker-payload compound of claim 7.

12. The compound of claim 1, wherein BA is an antibody or antigen binding fragment thereof comprising a LCVR further comprising an amino acid sequence set forth in SEQ ID NO: 26; and a HCVR further comprising an amino acid sequence set forth in SEQ ID NO: 18.

13. The compound of claim 1, wherein BA is an antibody or antigen binding fragment thereof comprising:

(a) a HCDR1 that comprises an amino acid sequence set forth in SEQ ID NO: 20;

(b) a HCDR2 that comprises an amino acid sequence set forth in SEQ ID NO: 22;

(c) a HCDR3 that comprises an amino acid sequence set forth in SEQ ID NO: 24;

(d) a LCDR1 that comprises an amino acid sequence set forth in SEQ ID NO: 28;

(e) a LCDR2 that comprises an amino acid sequence set forth in SEQ ID NO: 30; and (f) a LCDR3 that comprises an amino acid sequence set forth in SEQ ID NO: 32.

14. The compound of claim 1, that is:

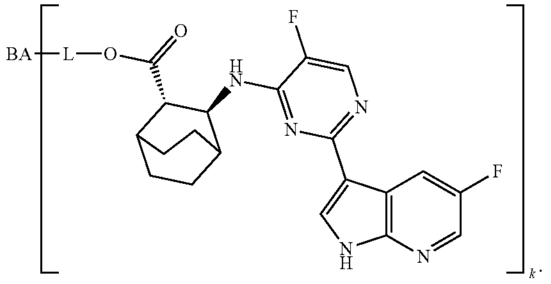

15. The compound of claim 1, that is:

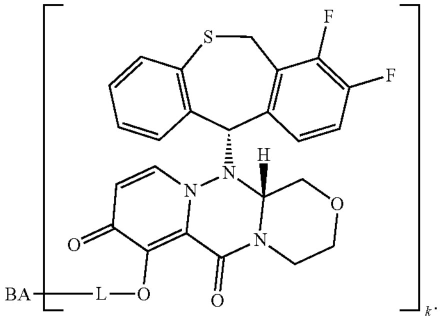

16. The compound of claim 1, wherein BA is an antiviral antibody or antigen binding fragment thereof.

17. The compound of claim 1, wherein BA is an anti-influenza antibody or antigen binding fragment thereof.

18. The compound of claim 1, wherein the antibody or antigen-binding fragment thereof is a transglutaminase-modified antibody or antigen-binding fragment thereof.

19. The compound of claim 1, wherein the antibody or antigen-binding fragment thereof is an anti-influenza antibody or antigen-binding fragment thereof.

* * * * *